US009388234B2

(12) United States Patent
Bogoch et al.

(10) Patent No.: US 9,388,234 B2

(45) Date of Patent: Jul. 12, 2016

(54) SYSTEMS AND METHODS FOR IDENTIFYING REPLIKIN SCAFFOLDS AND USES OF SAID REPLIKIN SCAFFOLDS

(71) Applicants: Samuel Bogoch, New York, NY (US); Elenore S. Bogoch, New York, NY (US); Anne-Elenore Bogoch Borsanyi, New York, NY (US); Samuel Winston Bogoch, Oakland, CA (US)

(72) Inventors: Samuel Bogoch, New York, NY (US); Elenore S. Bogoch, New York, NY (US); Anne-Elenore Bogoch Borsanyi, New York, NY (US); Samuel Winston Bogoch, Oakland, CA (US)

( * ) Notice: Subject to any disclaimer, the term of this patent is extended or adjusted under 35 U.S.C. 154(b) by 0 days.

(21) Appl. No.: 13/921,981

(22) Filed: Jun. 19, 2013

(65) Prior Publication Data

US 2014/0206556 A1 Jul. 24, 2014

Related U.S. Application Data

(63) Continuation of application No. 12/965,365, filed on Dec. 10, 2010, now Pat. No. 8,494,781, which is a (Continued)

(51) Int. Cl.

*G01N 33/50* (2006.01)

*C07K 16/10* (2006.01)

(Continued)

(52) U.S. Cl.

CPC ........... *C07K 16/1018* (2013.01); *A61K 39/015* (2013.01); *A61K 39/12* (2013.01); *A61K 39/145* (2013.01); *A61K 39/215* (2013.01); *A61K 39/42* (2013.01); *C07K 14/005* (2013.01); *G01N 33/56983* (2013.01); *A61K 2039/6081* (2013.01); *C12N 2760/16122* (2013.01); *C12N 2760/16134* (2013.01); *C12N 2760/16222* (2013.01); *C12N 2760/16234* (2013.01); *C12N 2770/20034* (2013.01); *G01N 2333/11* (2013.01); *G01N 2469/10* (2013.01); *G06F 19/22* (2013.01)

(58) Field of Classification Search

None

See application file for complete search history.

(56) References Cited

U.S. PATENT DOCUMENTS

| | | | |
|---|---|---|---|
| 4,132,769 | A | 1/1979 | Osther |
| 5,104,854 | A | 4/1992 | Schlesinger |

(Continued)

FOREIGN PATENT DOCUMENTS

| | | |
|---|---|---|
| DE | 3628658 | 3/1988 |
| EP | 0 108 564 | 5/1984 |

(Continued)

OTHER PUBLICATIONS

Brumeanu, T.M. et al., "Immunogenicity of a Contiguous T-B Synthetic Epitope of the A/PR/8/34 Influenza Virus," Journal of Virology, Jul. 1997, vol. 71, No. 7, pp. 5473-5480.

(Continued)

*Primary Examiner* — Jason Sims

(74) *Attorney, Agent, or Firm* — Daren P. Nicholson

(57) ABSTRACT

The present invention provides a new class of peptides related to rapid replication and high human mortality, and their use in diagnosing, preventing and treating disease including vaccines and therapeutics for emerging viral diseases and methods of identifying the new class of peptides and related structures.

14 Claims, 27 Drawing Sheets

Related U.S. Application Data continuation of application No. 11/355,120, filed on Feb. 16, 2006, now Pat. No. 7,894,999, which is a continuation-in-part of application No. 11/116,203, filed on Apr. 28, 2005, now Pat. No. 7,774,144, which is a continuation-in-part of application No. 10/860,050, filed on Jun. 4, 2004, now Pat. No. 7,442,761, said application No. 12/965,365 is a continuation-in-part of application No. 12/170,763, filed on Jul. 10, 2008, which is a continuation of application No. 10/860,050.

(60) Provisional application No. 60/653,083, filed on Feb. 16, 2005, provisional application No. 60/565,847, filed on Apr. 28, 2004, provisional application No. 60/531,686, filed on Dec. 23, 2003, provisional application No. 60/504,958, filed on Sep. 23, 2003, provisional application No. 60/476,186, filed on Jun. 6, 2003.

(51) Int. Cl.

| | |
|---|---|
| ***A61K 39/015*** | (2006.01) |
| ***A61K 39/145*** | (2006.01) |
| ***A61K 39/215*** | (2006.01) |
| ***C07K 14/005*** | (2006.01) |
| ***G01N 33/569*** | (2006.01) |
| ***A61K 39/42*** | (2006.01) |
| ***A61K 39/12*** | (2006.01) |
| *G06F 19/22* | (2011.01) |
| *A61K 39/00* | (2006.01) |

(56) References Cited

U.S. PATENT DOCUMENTS

| | | | |
|---|---|---|---|
| 5,231,167 | A | 7/1993 | Zanetti |
| 5,280,113 | A | 1/1994 | Rademacher |
| 5,589,174 | A | 12/1996 | Okuno |
| 5,679,352 | A | 10/1997 | Chong |
| 6,023,659 | A | 2/2000 | Seilhamer |
| 6,070,126 | A | 5/2000 | Kokolus |
| 6,090,406 | A | 7/2000 | Popescu |
| 6,242,578 | B1 | 6/2001 | Bogoch |
| 6,256,647 | B1 | 7/2001 | Toh |
| 6,470,277 | B1 | 10/2002 | Chin |
| 6,484,166 | B1 | 11/2002 | Maynard |
| 7,176,275 | B2 | 2/2007 | Bogoch |
| 7,189,800 | B2 | 3/2007 | Bogoch |
| 7,267,942 | B2 | 9/2007 | Peiris |
| 7,420,028 | B2 | 9/2008 | Bogoch |
| 7,442,761 | B2 | 10/2008 | Bogoch |
| 7,452,963 | B2 | 11/2008 | Bogoch |
| 7,674,880 | B2 | 3/2010 | Bogoch |
| 7,705,129 | B2 | 4/2010 | Bogoch |
| 7,758,863 | B2 | 7/2010 | Bogoch |
| 7,763,705 | B2 | 7/2010 | Bogoch |
| 7,774,144 | B2 | 8/2010 | Bogoch |
| 7,894,999 | B2 | 2/2011 | Bogoch |
| 8,050,871 | B2 | 11/2011 | Bogoch |
| 8,417,462 | B2 | 4/2013 | Bogoch |
| 8,494,781 | B2 | 7/2013 | Bogoch |
| 9,133,247 | B2 | 9/2015 | Bogoch |
| 9,254,315 | B2 | 2/2016 | Bogoch |
| 9,273,120 | B2 | 3/2016 | Bogoch |
| 2002/0120106 | A1 | 8/2002 | Bogoch |
| 2002/0151677 | A1 | 10/2002 | Bogoch |
| 2003/0180328 | A1 | 9/2003 | Bogoch |
| 2003/0194414 | A1 | 10/2003 | Bogoch |
| 2003/0195874 | A1 | 10/2003 | Akaboshi |
| 2005/0129715 | A1 | 6/2005 | Paterson |
| 2005/0202415 | A1 | 9/2005 | Bogoch |
| 2005/0271676 | A1 | 12/2005 | Sette |
| 2006/0024669 | A1 | 2/2006 | Bogoch |
| 2007/0128217 | A1 | 6/2007 | ter Meulen |

FOREIGN PATENT DOCUMENTS

| | | |
|---|---|---|
| EP | 0 621 339 | 10/1994 |
| EP | 0302801 | 10/1995 |
| IT | 98MI0874 | 10/1999 |
| JP | 3-503166 | 7/1991 |
| JP | 8-287088 | 11/1996 |
| JP | 9121867 | 5/1997 |
| JP | 10-212300 | 8/1998 |
| JP | 11001493 | 1/1999 |
| JP | 2000-253876 | 9/2000 |
| KR | 10-1999-0008052 | 1/1999 |
| WO | 89/07112 | 10/1989 |
| WO | 9632106 | 10/1996 |
| WO | 96/36436 | 11/1996 |
| WO | 0018351 | 4/2000 |
| WO | 00/52054 | 9/2000 |
| WO | 0104135 | 1/2001 |
| WO | 02085093 | 10/2002 |
| WO | 03005880 | 1/2003 |
| WO | 03083058 | 10/2003 |
| WO | 2005010032 | 2/2005 |
| WO | 2005004754 | 11/2005 |

OTHER PUBLICATIONS

Bucher, D. et al., "M protein (M1) of influenza virus antigenic analysis and intracellular localization with monoclonal antibodies", J Virol. Sep. 1989; 63(9): pp. 3622-3633.

Buscaglia et al., "The repetitive domain of Trypanosoma cruzi trans-sialidase enhances the immune response against the catalytic domain," Journal of Infectious Diseases, University of Chicago Press, Chicago, IL, vol. 177, No. 2, 1 Feb. 1998, pp. 431-436.

Carr C. M. et al., "A spring-loaded mechanism for the conformational change of influenza hemagglutinin," Cell, May 21, 1993, pp. 823-832, vol. 73, Cell Press, XP002059698, ISSN: 0092-8674.

Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).

Cross et al., "Studies on influenza haemagglutinin fusion peptide mutants generated by reverse genetics," The EMBO Journal vol. 20 No. 16 pp. 4432-4442, 2001.

Diggs et al. "Plasmodium falciparum: Passive immunization of Aotus lemurinus griselmembra with immune serum," Experimental Parasitology, vol. 80, Issue 2, Mar. 1995, pp. 291-296.

Gao, Identification and characterization of T helper epitopes in the nucleoprotein of influenza A virus, J. Immunol. 1989, vol. 143, pp. 3007-3014.

Gelder, C.M. et al., "Human CD4+ T-cell repertoire of response to influenza A virus hemagglutinin after recent natural infection," Journal of Virology, Dec. 1995, vol. 69, No. 12, pp. 7497-7506A.

Gerhard et al., "Identification of Eight Determinants in the Hemagglutinin Molecule of Influenza Virus A/PR/8/34 (H1N1) Which Are Recognized by Class II-Restricted T Cells from BALB/c Mice," Journal of Virology 65(1): 364-372 (1991).

Guan et al., "Emergence of multiple genotypes of H5N1 avian influenza viruses in Hong Kong SAR," PNAS vol. 99, No. 13, Jun. 25, 2002, pp. 8950-8955.

Liu et al. Science, Aug. 19, 2005; 309 (5738); 1206. Epub Jul. 6, 2005, "Highly pathogenic H5N1 influenza virus infection in migratory birds."

Margalit et al., "Prediction of Immunodominant Helper T Cell Antigenic Sites From the Primary Sequence," Jour. of Immunology, vol. 138, 2213-2229, Apr. 1, 1987.

Marra, M. et al., "The Genome Sequence of the SARS-Associated Coronavirus," Science, American Association for the Advancement of Science, US, v. 300, No. 5624, p. 1399-1404, XP002269483, ISSN: 0036-8075, May 30, 2003.

Niman et al., "Generation of protein-reactive antibodies by short peptides is an event of high frequency: Implications for the structural basis of immune recognition," PNAS USA 80:4949-4953 (1983).

O'Donnell, F.T. et al., "Epidemiology and molecular characterization of co-circulating influenza A/H3N2 virus variants in children," Epi-

(56) References Cited

OTHER PUBLICATIONS demiology and Infection, Jun. 2003, pp. 521-531, abstract, vol. 130, issue 3, The University of Texas-Houston School of Public Health, Houston, Texas. Database Medline U.S. National Library of Medicine (Bethesda, MD) Accession No. 2003:298060.

Okuno et al., "A Common Neutralizing Epitope Conserved between the Hemagglutinins of Influenza A Virus H1 and H2 Strains," Journal of Virology, vol. 67, No. 5, May 1993, p. 2552-2558.

Ostroff, "Emerging infectious diseases 1997-1998: The role of molecular epidemiology," Memorias Do Instituto Oswaldo Cruz, vol. 94, No. 1, Jan. 1999, pp. 1-3, XP002636692.

Patarroyo et al., "Induction of protective immunity against experimental infection with malaria using synthetic peptides," Nature, vol. 328, No. 6131, Aug. 13, 1987, pp. 629-632.

Patil et al., "Identification of a Talin-binding Site in the Integrin β3 Subunit Distinct from the NPLY Regulatory Motif of a Post-ligand Binding Functions," The Journal of Biological Chemistry, vol. 274, No. 1, Oct. 1, 1999, p. 28575-28583.

Simeckova-Rosenberg et al., "Protection of mice against lethal viral infection by synthetic peptides corresponding to B- and T-cell recognition sites of influenza A hemagglutinin," Vaccine, vol. 13, No. 10, pp. 927-932 (1995).

Smith et al., "Finding sequence motifs in groups of functionally related proteins," PNAS, vol. 87, pp. 826-830, Jan. 1990.

Sui, J et al., "Structural and functional bases for broad-spectrum neutralization of avian and human influenza A viruses," Nature Structural & Molecular Biology, vol. 16 No. 3 (Mar. 2009), published online Feb. 22, 2009; doi:10.1038/nsmb.1566.

Weber, E. et al., "Fine Mapping of a Peptide Sequence Containing an Antigenic Site Conserved Among Arenaviruses," Virology, vol. 164, p. 30-38 (1988).

Webster et al., "Characterization of H5N1 Influenza Viruses that Continue to Circulate in Geese in Southeastern China," 2002 Journal of Virology, 76(1):118-126.

Witteveldt, et al., "Protection of Penaeus monodon against White Spot Syndrome Virus by Oral Vaccination," Journal of Virology, Feb. 2004, p. 2057-2061 vol. 78, No. 4 (entire document, esp. p. 2060, col. 1).

Yasuko, A-O, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct. 2006.

Wikipedia, Passive Immunity, https://en.wikipedia.org/wiki/Passive_immunity (printout Sep. 28, 2015).

PCT International Preliminary Report on Patentability, PCT/US2007/069978, Mar. 14, 2009, USPTO, International Preliminary Examining Authority, Alexandria, VA, USA.

PCT International Search Report, PCT/US2002/09240, Jan. 14, 2004, USPTO, International Searching Authority, Washington DC.

PCT International Preliminary Examination Report, PCT/US2002/09240, Feb. 5, 2004, USPTO, International Preliminary Examination Authority, Alexandria, VA, USA.

PCT International Search Report, PCT/US2002/21494, May 30, 2003, USPTO, International Searching Authority, Washington DC.

PCT International Preliminary Examination Report, PCT/US2002/21494, Nov. 26, 2004, USPTO, International Searching Authority, Alexandria, VA, USA.

PCT International Search Report, PCT/US2003/08990, Dec. 7, 2005, International Searching Authority, USPTO, Alexandria, VA, USA.

PCT Written Opinion of the International Searching Authority, PCT/US2004/017936, Apr. 7, 2005, EPO, International Searching Authority, Munich, DE.

PCT International Search Report, PCT/US2004/017936, Apr. 28, 2005, EPO, International Searching Authority, Rijswijk, NL.

PCT International Preliminary Report on Patentability, PCT/US2004/017936, Apr. 13, 2007, USPTO, International Preliminary Examining Authority, Alexandria, VA, USA.

PCT International Search Report, PCT/US2005/014443, Oct. 21, 2005, EPO, International Searching Authority, Rijswijk, NL.

PCT Written Opinion of the International Searching Authority, PCT/US2005/014443, Apr. 12, 2006, EPO, International Searching Authority, Munich, DE.

PCT International Preliminary Report on Patentability, PCT/US2005/014443, Nov. 1, 2006, WIPO, International Bureau of WIPO, Geneva, Switzerland.

PCT International Search Report and Written Opinion PCT/US2006/05343, Sep. 25, 2007, USPTO, International Searching Authority, Alexandria, VA, USA.

PCT International Preliminary Report on Patentability, PCT/US2006/05343, Jul. 22, 2008, USPTO, International Preliminary Examining Authority, Alexandria, VA, USA.

PCT International Search Report and Written Opinion, PCT/US2007/069978, Jun. 10, 2008, EPO, International Searching Authority, Rijswijk, NL.

PCT International Search Report and Written Opinion, PCT/US2007/82436, Jan. 9, 2009, USPTO, International Searching Authority, Alexandria, VA, USA.

PCT International Search Report and Written Opinion, PCT/US2008/00645, Feb. 2, 2009, USPTO, International Searching Authority, Alexandria, VA, USA.

PCT International Search Report and Written Opinion, PCT/US2008/061336, Feb. 2, 2009, EPO, International Searching Authority, Rijswijk, NL.

PCT International Search Report and Written Opinion, PCT/US2009/041565, Jan. 25, 2010, EPO, Rijswijk, NL.

EP Supplementary Search 99944002, Apr. 20, 2004, EPO, Munich, DE.

EP Supplementary Search 02736514.7, Mar. 9, 2006, EPO, Munich, DE.

EP Supplementary Search 02752202.8, Mar. 10, 2006, EPO, Munich, DE.

EP Supplementary Search 03721445.9, Dec. 12, 2006, EPO, International Searching Authority, Munich, DE.

EP Supplemental Search, EP 10 01 2944, May 20, 2011, EPO, Munich, DE.

EP Supplemental Search, EP 10 01 2945.1, Jun. 9, 2011, EPO, Munich, DE.

EP Partial Search Report, EP 11 158 084.1, Oct. 7, 2011, EPO.

EP Partial Search Report, EP 11 158 093.2, Oct. 14, 2011, EPO.

NCBI accession # gi 75059 Jul. 16, 1999.

NCBI Entrez Protein AAK38298, Apr. 19, 2001, see sequence of HA (http:www.ncbi.nlm.nih.gov/entrez/viewer.fcgi?db=protein &id=13676825).

NCBI Accession No. NP 740460, residues 201-210 (removed from NCBI) (2000).

PepBank entry 42800, corresponding to UniProt database entry P15516, Apr. 1, 1990, available at http://pepbank.mgh.harvard.edu, accessed Oct. 6, 2008.

UniProt/Swiss-Prot database entry O89746 1 Influenza A virus (strain A/Chicken/Hong Kong/220/1997 H5N1 genotype Gs/Gd) Nov. 1, 1998.

NCBI Swiss-Prot Locus P33795, accessed Jul. 20, 2009.

UniProt A8DXX4 (Nov. 13, 2007).

NCBI Accession No. AAW59548 (Jan. 24, 2005).

NCBI Accession No. DQ100549 (Jul. 6, 2005).

Gen Bank Accession No. AAV74400.1 (Dec. 5, 2005).

UniProt C2W513 (Jun. 16, 2009).

NCBI Accession No. NP_052803 (May 14, 1998).

ACML 01000595 database entry (May 1, 2009).

Abrams M. B. et al., "Early Detection and Monitoring of Cancer with the Anti-Malign in Antibody Test," Cancer Detection and Prevention, XX, XX, vol. 18, No. 1, 1994, pp. 65-78, XP000673180, ISSN:0361-090X.

Aichele, P. et al., "T Cell Priming Versus T Cell Tolerance Induced by Synthetic Peptides," J. Exp. Med., vol. 182 (Jul. 1995) pp. 261-266.

Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc., XP009062995, ISSN: 0090-0877.

(56) References Cited

OTHER PUBLICATIONS

Ben-Yedidia, T. et al., "Intranasal administration of peptide vaccine protects human/mouse radiation chimera from influenza infection," International Immunology, 1999, pp. 1043-1051, XP000914818, ISSN: 0953-8178.

Betakova et al., "The Vaccinia Virus A14.5L Gene Encodes a Hydrophobic 53-Amino-Acid Virion Membrane Protein That Enhances Virulence in Mice and Is Conserved among Vertebrate Poxviruses," Journal of Virology, vol. 74., No. 9, May 2000, p. 4085-4092.

Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.

Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.

Bogoch et al., "Rapid replication and Replikintm structures: basis of the AMASRTest and CAVAXR," Cancer Detection and Prevention Online, Feb. 9, 2002, XP002350483.

Bogoch et al., "Replikins: The Chemistry of Rapid Replication," Begell House, Inc. NY, NY (2005).

Brown, L. R. et al., "Recognition of the influenza hemagglutinin by Class II MHC-restricted T lymphocytes and antibodies," Journal of Immunology, Oct. 14-15, 1991, pp. 2677-2684, vol. 147, No. 8, American Association of Immunologists, USA, XP002371257, ISSN: 0022-1767.

SPECIFICITY OF BINDING AND CYTOTOXICITY OF ANTIMALIGNIN ANTIBODY TO LEUKEMIC, BRAIN GLIOMA, AND SMALL CELL LUNG CARCINOMA CELLS

RELATION OF REPLIKIN CONCENTRATION TO PANDEMICS (P) AND EPIDEMICS (E) IN FOUR MAJOR STRAINS OF INFLUENZA VIRUS, 1902-2001

RELATION OF REPLIKIN CONCENTRATION TO PANDEMICS (P) AND EPIDEMICS (E) IN FOUR MAJOR STRAINS OF INFLUENZA VIRUS, 1902-2001

Replikin Count by Year nucleocapsid coronavirus

| Year | Accession Number - Replikin Count | No. Of Isolates per year | Mean Replikin Count per year | S.D. |
|---|---|---|---|---|
| 1962 | AAB4815713 | 1 | 3.2 | 0.0 |
| 1963 | | | | |
| 1964 | | | | |
| 1965 | | | | |
| 1967 | | | | |
| 1968 | | | | |
| 1969 | | | | |
| 1970 | P05991 21 | | | |
| 1971 | | 1 | 5.5 | 0.0 |
| 1972 | | | | |
| 1973 | | | | |
| 1974 | AAB4815714 | 1 | 3.5 | 0.0 |
| 1975 | AAB4815922 | 1 | 5.5 | 0.0 |
| 1976 | | | | |
| 1977 | | | | |
| 1978 | | | | |

FIG.10A

| | | | | |
|---|---|---|---|---|
| 1979 | | | | |
| 1980 | | | | |
| 1981 | | | | |
| 1982 | | | | |
| 1983 | A453402CAA251977CAA251987CAA254971P034162P034171P184531VHIHM11 | 8 | 1.0 | 1.3 |
| 1984 | 1010251C4AAA462202AAA464527AAA70233132AAA70235132AAA70236132AAA70237132AAA70238 132AAA70239132AAA70240132AAA70241132AAA70242132NP40829214NP040831214NP040833 214NP040834214NP 040835214NP 040836214NP 40837214NP 040838214NP 066134214NP 740 621214NP 740622214NP 740623214NP 740624214NP 740625214NP 740626214NP 740627214NP 740628214 | 38 | 3.2 | 0.5 |
| 1985 | AAA4621417AAA4622127 | 2 | 5.4 | 1.7 |
| 1986 | AAA4791421AAA4791321AAA4791621P0413421VHIHPC21 | 5 | 5.5 | 0.0 |
| 1987 | AAA429142146AAA42913146AAA42914146AAA64744146AAA66393146AAA66397146AAA66399146AAK 297381146AAK29779146AAP20417146CAAA7869717CAA7869417CAA7869917P105234P10526600IHB C4VGIHBC6 | 17 | 2.4 | 0.7 |
| 1988 | AAA427581AAA427591AAA6658323AAAB481602AAAB4816127P1264823P226541S0376221S068691VH IHAL23 | 10 | 3.7 | 2.8 |
| 1989 | A60003IIAAA4546327AAA464622CAA335212CAA335222P1513026P154222P3346911VHIV2E27 | 9 | 3.2 | 2.8 |
| 1990 | AAA464392AAA464402AAA464442AAA464452AAA464472AAA464482AAA464682AAA464692AAB4815618 B453402C453402CAA3507826CAA3985018CAA3985111CAA8084123D453402E3660723E453401F45340 1G453401H453402P184462P184472P184482P184522P184551P2441123P3292323S0803126VHIHGI22 | 30 | 2.2 | 2.5 |
| 1991 | AAB4816228CAA410669CAA450992CAA451002J011726J011744P2590911P260216P266264P3346323S 2428223VHIH7918 | 12 | 3.9 | 2.5 |
| 1992 | A4405622A4855923AAA9185530AAA9185623AAA9185720AAB2405423BAA015912CAA4724627J017252 4P36298240BI4553004700225603139 | 13 | 5.8 | 2.0 |

FIG. 10B

| | | | | |
|---|---|---|---|---|
| 1993 | A453962AAC5406818AAK38656201AAK38657201AAK38658201AAK38659201AAK38660201AAK38661201 CAA808551CAA808561CAA808571CAA808581CAA108591CAA809718J0219117J021952NP598309201NP5 98310201NP598311201NP598312201NP598333201NP598314201NP839957201NP839958201NP8399592 01NP839960201NP839961201NP839962201NP839963201NP839964201NP839965201NP83996201NP839 967201NP839968201NP8399692010029152 | 36 | 2.5 | 1.1 |
| 1994 | B495911CAA8411121D495911S4742821 | 4 | 3.8 | 2.0 |
| 1995 | AAC5708018 | 1 | 4.4 | 0.0 |
| 1996 | AAB4750214AAB4750311AAB481551VBAC0112014BAC0115610BAC0115710BAC0115313BAC0115913BAC0 116013BAC0116013BAC0116113BAC0549216BAC0349313 | 12 | 2.8 | 1.2 |
| 1997 | AAB8682170CAA7423013NP045302129NP068674129 | 4 | 2.2 | 0.9 |
| 1998 | AAC164223ACC164233AAD331042AAD390394AAD390404AAD390414AAD390424AAD390434AAD390444AAF2 387123AAF2387219AAF2387326 | 12 | 4.4 | 2.3 |
| 1999 | AAF057061AAF0635216AAF1938979AAF6892681AAF6911622AAF6912321AAF6933877AAF6934970AAF9774 311AAL4040685BAA836159BAA836169 | 12 | 3.1 | 1.8 |
| 2000 | AAF8241321AAG48597193AAG5397321NP073556193 | 4 | 3.9 | 1.2 |
| 2001 | AAK27168122AAK2716220AAK2716319AAK3160722AAK83362147AAK9379720AAL57313147CAC39121214CAC 3930717NF150083146 | 11 | 3.9 | 1.3 |
| 2002 | AAL800367AAM7700513AAM8228019AAM8228123AAM8228219AA04604819AA04604923AA04605019AA0594642 7AA05947327AA0604112AA0604127AA0604133AAC604146AA04146AA0604156XP11418016 | 16 | 5.1 | 3.6 |
| 2003 | AA05943816AAP13445188AAP13814188AAP30037AAP30714188APP3204623AAP3208323AAP37024188AAP4104 7188BAC6532822CAD676071NP828858188P5959515188AAP3204623AAP3208323AAP37024188AAP41047188BA C6532822CAD676071NP828858188P5959515 | 13 | 3.3 | 1.6 |

FIG. 10C

Amino Acid Encoding

| Amino Acid | Abbreviation | Code |
|---|---|---|
| Alanine | Ala | a |
| Arginine | Arg | r |
| Asparagine | Asn | n |
| Aspartic acid | Asp | d |
| Cysteine | Cys | c |
| Glutamine | Gln | q |
| Glutamic acid | Glu | e |
| Glycine | Gly | g |
| Histidine | His | h |
| Isoleucine | Ile | i |
| Leucine | Leu | l |
| Lysine | Lys | k |
| Methionine | Met | m |
| Phenylalanine | Phe | f |
| Proline | Pro | p |
| Serine | Ser | s |
| Threonine | Thr | t |
| Tryptophan | Trp | w |
| Tyrosine | Tyr | y |
| Valine | Val | v |

FIG.12

Cancer Protein Description

1: AAF04328. serine protease D...[gi:6137097] BLink, Links

```
LOCUS       AAF04328          422 aa              linear   PRI 20-APR-2004
DEFINITION  serine protease DESC1 [Homo sapiens].
ACCESSION   AAF04328
VERSION     AAF04328.1  GI:6137097
DBSOURCE    accession AF064819.1
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (residues 1 to 422)
  AUTHORS   Lang, J.C. and Schuller,D.E.
  TITLE     Differential expression of a novel serine protease homologue in
            squamous cell carcinoma of the head and neck
  JOURNAL   Br. J. Cancer 84 (2), 237-243 (2001)
   MEDLINE  21094880
   PUBMED   11161383
REFERENCE   2  (residues 1 to 422)
  AUTHORS   Lang, J.C. and Schuller,D.E.
  TITLE     Direct Submission
  JOURNAL   Submitted (12-MAY-1998) Otolaryngology, Ohio State University, 1248
            James Cancer Hospital, 300 West 10th Avenue, Columbus, OH 43210,
            USA
COMMENT     Method: conceptual translation.
FEATURES         Location/Qualifiers
     source      1..422
                 /organism="Homo sapiens"
                 /db_xref="taxon:9606"
                 /chromosome="4"
                 /map="4q12-q13; between D4S1619 and WI-7844; 20.21 cR from
                 WI-5548"
     Protein     1..422
                 /product="serine protease DESC1"
                 /name="expressed in normal oral epithelium, but not in
                 squamous cell tongue carcinoma or metastatic neck nodal
                 tissue"
```

FIG. 13A

```
Site        167
            /site_type="cleavage"
            /note="between arginine and isoleucine"
Site        208
            /site_type="active"
            /note="histidine; part of the catalytic triad"
Site        253
            /site_type="active"
            /note="aspartic acid; part of the catalytic triad"
Site        349
            /site_type="active"
            /note="serine; part of the catalytic triad"
CDS         1..422
            /gene="DESC1"
            /coded_by="AF064819.1:56..1324"
ORIGIN
    1 myrpdvvrar krvcwepwvi glvifisliv lavcigltvh yvrynqkkty nyystlsftt
   61 dklyaefgre asnnftemsq rlesmvknaf yksplreefv ksqvikfsqq khgvlahmll
  121 icrfhstedp etvdkivqlv lheklqdavg ppkvdphsvk ikkinktetd sylnhccgtr
  181 rsktlgqslr ivggteveeg ewpwqaslqw dgshrcgatl inatwlvsaa hcfttyknpa
  241 rwtasfgvti kpskmkrglr riivhekykh pshdydisla elsspvpytn avhrvclpda
  301 syefqpgdvm fvtgfgalkn dgysqnhlrq aqvtlidatt cnepqaynda itprmlcags
  361 legktdacqg dsggplvssd ardiwylagi vswgdecakp nkpgvytrvt alrdwitskt
  421 gi
//
```

FIG. 13B

Nucleic Acid Base – Amino Acid Correspondence.

| Nucleic Acid Base Triplets | Corresponding Amino Acid | Code |
|---|---|---|
| GCT GCC GCA GCG | Alanine | a |
| CGT CGC CGA CGG AGA AGG | Arginine | r |
| AAT AAC | Asparagine | n |
| GAT GAC | Aspartic acid | d |
| TGT TGC | Cysteine | c |
| CAA CAG | Glutamine | q |
| GAA GAG | Glutamic acid | e |
| GGT GGC GGA GGG | Glycine | g |
| CAT CAC | Histidine | h |
| ATT ATC ATA | Isoleucine | i |
| TTG TTA CTT CTC CTA CTG | Leucine | l |
| AAA AAG | Lysine | k |
| ATG | Methionine | m |
| TTT TTC | Phenylalanine | f |
| CCT CCC CCA CCG | Proline | p |
| TCT TCC TCA TCG AGT AGC | Serine | s |
| ACT ACC ACA ACG | Threonine | t |
| TGG | Tryptophan | w |
| TAT TAC | Tyrosine | y |
| GTT GTC GTA GTG | Valine | v |
| TAA TAG TGA | < stop code > | |
| | | |

FIG.14

Selected examples of Replikins in various organisms.

| Category | SEQ.ID. | Name | Replikin Pattern |
|---|---|---|---|
| Bacteria: | 10 | Mycoplasma pulmonic, chromosome replication | kkektthnk |
| | 43 | Macrophage infectivity potentiator, L. legionella | kvhffqlkk |
| Tumor Viruses: | 48 | Rous sarcoma virus tyrosine-protein kinase | kklrhek |
| | 49 | v-yes, avian sarcoma | kklrhdk |
| | 50 | c-yes, colon cancer, malignant melanoma | kklrhdk |
| | 51 | v-srcC, avian sarcoma | kklrhek |
| | 52 | c-src, colon, mammary, panrcreatic cancer | kklrhek |
| | 53 | Neuroblastoma RAS viral (v-ras) oncogene | kqahelak |
| | 54 | VPI (major capsid protein) [Polyamavirus sp.] | kthrfskh |
| | 55 | Sindbis | knlhekik |
| | 56 | EI [Human papilloamavirus type 71] | khrpllqlk |
| | 57 | v-erbB from AEV and c-erb | kspnhvk |
| | 58 | v-fms (feline sarcoma) | knihlekk |
| | 59 | c-fms (acute and chronic myelomonocytic tumors) | knihlekk |
| | 60 | large t-antigen I [Polyomavirus sp.I | kphlaqslek |
| | 61 | middle t-antigen [Polyomavirus sp,I- | kqhrelkdk |
| | 62 | small t-antigen [Polyomavirus spJ, | kqhrelkdk |
| | 63 | v-abl, murine acute leukemia | kvpvlisptlkh |
| | 64 | Human T-cell lymphotropic virus typo 2 | kslllevdkdish |
| | 65 | c-kit, GI tumors, small cell lung carcinoma | kagitimvkreyh |
| | 18 | Hepatitis C | hyppkpgcivpak |
| Trans-forming Proteins: | 66 | Transforming protein myb | ksgkhlgk |
| | 67 | Transforming protein myc, Burkitt lymphoma | krreqlkhk |
| | 68 | Ras-related GTP-binding protein | ksfevikvih |
| | 69 | Transforming protein ras (teratocarcinoma) | kkkhtvkk |
| | 70 | TRAF-associated NF•kB activator TANK | kaqkdhlsk |
| | 71 | RFP transforming protein | hlkrvkdlkk |
| | 72 | Transforming protein D (S.C.) | kygspkhrlik |
| | 73 | Papilloma virus type 11, transforming protein | klkhilgkarfik |
| | 74 | Protein tryosine kinasc (EC 2.7.1.II2slk | kgdhvkhykirk |
| | 75 | Transforming protein (axl(-)) | keklrdvmvdrhk |
| | 76 | Transforming protein (N-myc) | klqarqqqllkkieh |
| | 77 | Fibroblast growth factor 4 (Kaposi sarcoma) | kkgnrvsptmkvth |
| Cancer Cell Proteins: | 78 | Matrix metaloproteinase 7 (uterine) | keiplhfrk |
| | 79 | Transcription factor 7-like | kkkphikk |
| | 80 | Breast cancer antigen NY-BR-87 | ktrhdplak |
| | 81 | BRCA-1-Associated Ring Domain Protein (breast) | khhpkdnlik |
| | 82 | Autoantigen from a breast tumor' | khkrkkfrqk |
| | 83 | Glioma Replikin (this study) | kagvaflhkk |
| | 84 | Ovarian cancer antigen | khkrkkfrqk |
| | 85 | EE L leukemia | kkkskkhkdk |
| | 86 | Proto-oncogene tyrosine-protein kinase C-ABLE | hksekpalprk |
| | 87 | Adenomatosis polyposis coli | kkkkpsrlkgdnek |
| | 88 | Gastric cancer transforming protein | ktkkgnrvsptmkvth |
| | 89 | Transforming protein (K-RAS 2B),lung | khkekmskdgkkkkkksk |

FIG.16

Replikin Matching Code.

```
#
#   Discover a subsequence h...k...k, k...h...k, or k...k...h such that
#   (1) The distance between ks is in the range kmin..kmax.
#   (2) The distance between an h and the farthest k is in the range kmin+1..hmax.
#   (3) The fraction of k in the subsequence is percent or larger.
#
#   The sequence is searched for all possible subsequences that match,
#   and all these subsequences are returned.

set kmin 6; set kmax 10
set hmax 50
set percent 6

proc match {sequence} {
   global kmin kmax hmax percent

   set pos 0
   set L {}
   array set F {}
   foreach e [regexp -all -indices -inline k $sequence] {
      lappend L [lindex $e 0]
   }

   for {set i 1} {$i<[llength $L]} {incr i} {
      set k0 [lindex $L [expr {$i-1}]]

      # rule 1.
      for {set j $i; set wideenough 0} {!$wideenough && $j<[llength $L]} {incr j} {
         set k1 [lindex $L $j]
         if {$k1-$k0<$kmin} continue
         if {$k1-$k0>$kmax} break

         # rule 2.
         set offset [expr $k1-$hmax]
         if {$offset<0} {set offset 0}
         while 1 {
            set h [string first h $sequence $offset]
            if {$h<0 || $h>$k0+$hmax} break
            if {$h<$k0} {
               set b $h
            } else {
               set b $k0
            }
            if {$h>$k1} {
               set e $h
            } else {
               set e $k1
            }

            # rule 3.
            set subsequence [string range $sequence $b $e]
            set nk [regexp -all k $subsequence]
            if {double($nk)/double([string length $subsequence])*100>=$percent} {
               set "F($b $e)" 1
            }

            incr offset
         }
      }
   }
   lsort -integer -index 0 [array names F]
}
```

FIG.20

Replikin Scaffolding.

```
1234...............29
+------------------+
```

| Sequence | Year | Strain |
|---|---|---|
| kkgtsypklsksytnnkgkevlvlwgvhh | 1917 | H1N_ Influenza Goose Replikin |
| kkgssypklsksyvnnkgkevlvlwgvhh | 1918 | H1N1 Human Influenza Pandemic |
| kkensypklsksyvnnkgkevlvlwgvhh | 1930 | H1N1 |
| kkgdsypkltnsyvnnkgkevlvlwgvhh | 1933 | H0N1 |
| kkgtsypklsksytnnkgkevlvlwgvhh | 1976 | H1N1 |
| kkgtsypklsksytnnkgkevlvlwgvhh | 1977 | H1N1 |
| kkgnsypklsksytnnkgkevlviwgvhh | 1979 | H1N1 |
| kkgnsypklsksytnnkgkevlviwgvhh | 1980 | H1N1 |
| kkgtsypklsksytnnkgkevlvlwgvhh | 1980 | H1N1 |
| kkgnsypklsksytnnkgkevlviwgvhh | 1981 | H1N1 |
| kkgtsypklsksytnnkgkevlvlwgvhh | 1981 | H1N1 |
| kkgtsypklsksytnnkgkevlvlwgvhh | 1985 | H1N1 |
| kkgnsypklsksytnnkgkevlviwgvhh | 1991 | H1N1 |
| kkgnsypklsksytnnkgkevlviwgvhh | 1992 | H1N1 |
| kkgnsypklsksytnnkgkevlviwgvhh | 1996 | H1N1 |
| kkgdsypklsksytnnkgkevlviwgvhh | 1996 | H1N1 |
| kkgssypklsksyvnnkgkevlvlwgvhh | 1997 | H1N1 |
| kkgssypklsksyvnnkgkevlvlwgvhh | 1998 | H1N1 |
| kkgnsypklsksytnnkgkevlviwgvhh | 1999 | H1N1 |
| kkgnsypklsksytnnkgkevlviwgvhh | 2000 | H1N1 |
| kkgnsypklsksytnnkgkevlviwgvhh | 2001 | H1N1 |
| kkgnsypklsksytnnkgkevlviwgvhh | 2002 | H1N1 |
| kkgnsypkisksyinnkekevlvlwgihh | 1999 | H1N2 Influenza |
| kkgnsypklsksyinnkkkevlviwgihh | 2000 | H1N2 |
| kkgnsypklsksyinnkgkkvlvlwgihh | 2001 | H1N2 |
| kkgtsypklsksytnnkkkevlvlwgvhh | 2001 | H1N2 |
| -knglypnlsksyannkekevlvlwgvhh | 2002 | H1N2 |
| -knglypnlsksyannkekevlilwgvhh | 2002 | H1N2 |
| kkensypklrksiiinkkevklviwgihh | 1968 | H3N2 Human Influenza Pandemic |
| --------ksykntrkdpaliiwgihh | 1979-2003 | H7N7 Influenza |
| kkgpnypvakrsynntsgeqmliiwgvhh | 1957 | H2N2 Human Influenza Pandemic |
| kkgpnypvakrsynntsgeqmliiwgihh | 1957 | H2N2 Human Influenza Pandemic |
| kknnayptikrtynntnvedllilwgihh | 2002 | H5N2 Influenza |
| kknnayptikrsysntngedllvlwgihh | 1959 | H5N1 Influenza (Scotland) |
| kknnayptikrtynntniedllilwgihh | 1975 | H5N1 (Wisconsin) |
| kknnayptikrtynntnmedllilwgihh | 1981 | H5N1 (Minnesota) |
| kkgnayptikrtynntnvedllilwgihh | 1983 | H5N1 (Pennsylvania) |
| kknntyptikrsynntngedlliiwgihh | 1988 | H5N1 (Scotland) |

Residues identical to original 1917 Goose Replikin residues are shown in single underline. Amino acid substitutions in double underline and zig-zag underline.

FIG.21A

| | | |
|---|---|---|
| kknsaypt ikrsynntnqedl lvlwgihh | 1996 | H5N1 (China) |
| kknsaypt ikrsynntnqedl lvlwgihh | 1997 | H5N1 (China) |
| kknsaypt ikrsynntnqedl lvlwgihh | 1998 | H5N1 (China) |
| kknsaypt ikrsynntnqedl lvlwgihh | 1999 | H5N1 (China) |
| kknsaypt ikrsynntnqedl lvlwgihh | 2000 | H5N1 (China) |
| kknsaypt ikrsynntnqedl lvlwgihh | 2001 | H5N1 (China) |
| kknnaypt ikrsynntnqedl lvlwgihh | 2001 | H5N1 (China) |
| kknsaypt ikrsynntnqedl lvlwgihh | 2002 | H5N1 (China) |
| kknstypt ikrsynntnqedl lvlwgihh | 2002 | H5N1 (Thailand) |
| kknstypt ikrsynntnqedl lvlwgihh | 2002 | H5N1 (Vietnam) |
| kknstypt ikrsynntnqedl lvlwgihh | 2003 | H5N1 (Vietnam) |
| kknstypt ikrsynntnqedl lvlwgihh | 2003 | H5N1 (Thailand) |
| kknstypt ikrsynntnqedl lvlwgihh | 2003 | H5N1 (Sindong, China) |
| kknnaypt ikrsynntnqedl lvlwgihh | 2003 | H5N1 (China) |
| kknstypt ikrsynntnqedl lvmwgihh | 2004 | H5N1 (Vietnam, highly pathogenic) |
| kknsaypt ikrsynntnqedl lvlwgihh | 2004 | H5N1 (Vietnam,"highly pathogenic",gull) |
| kknstypt ikrsynntnqedl lvlwgihh | 2004 | H5N1 (Vietnam, highly pathogenic) |
| kknstypt ikrsynntnqedl lvlwgihh | 2004 | H5N1 (Thailand, highly pathogenic) |
| kknstypt ikrsynntnqedl lvlwgiqh | 2004 | H5N1 (Thailand, highly pathogenic) |
| kknsaypi ikrsynntnqedl lvlwgihh | 2004 | H5N1 (China,highlypathogenic) |
| kknsaypt ikrsxnntnhedl lvlwgihh | 2004 | H5N1 (China,"highly pathogenic", goose) |

Residues identical to original 1917 Goose Replikin residues are shown in single underline. Amino acid substitutions in double underline and zig-zag underline.

FIG.21B

SYSTEMS AND METHODS FOR IDENTIFYING REPLIKIN SCAFFOLDS AND USES OF SAID REPLIKIN SCAFFOLDS

This application is a continuation of U.S. application Ser. No. 12/965,365, filed Dec. 10, 2010, which is a continuation of U.S. application Ser. No. 11/355,120, filed Feb. 16, 2006, now U.S. Pat. No. 7,894,999, which claims benefit of U.S. Provisional Appln. Ser. No. 60/653,083, filed Feb. 16, 2005, and is a continuation-in-part of U.S. application Ser. No. 11/116,203, filed Apr. 28, 2005, now U.S. Pat. No. 7,774,144, which claims benefit of U.S. Provisional Appln. Ser. No. 60/565,847, filed Apr. 28, 2004, and is a continuation-in-part of U.S. application Ser. No. 10/860,050, filed Jun. 4, 2004, now U.S. Pat. No. 7,442,761. U.S. application Ser. No. 12/965,365, filed Dec. 10, 2010, is also a continuation-in-part of U.S. application Ser. No. 12/170,763, filed Jul. 10, 2008, which is a continuation of U.S. application Ser. No. 10/860, 050, filed Jun. 4, 2004, now U.S. Pat. No. 7,442,761, which claims benefit of U.S. Provisional Applns. 60/531,686, filed Dec. 23, 2003, 60/504,958, filed Sep. 23, 2003, and 60/476, 186, filed Jun. 6, 2003. Each of these applications is incorporated herein by reference in its entirety. Also incorporated herein by reference in their entireties are U.S. application Ser. No. 10/189,437, filed Jul. 8, 2002, now U.S. Pat. No. 7,452, 963, U.S. application Ser. No. 10/105,232, filed Mar. 26, 2002, now U.S. Pat. No. 7,189,800, U.S. application Ser. No. 09/984,057, filed Oct. 26, 2001, now U.S. Pat. No. 7,176,275, and U.S. Provisional Applns. 60/303,396, filed Jul. 9, 2001, and 60/278,761, filed Mar. 27, 2001.

TECHNICAL FIELD OF THE INVENTION

This invention relates generally to two newly discovered classes of peptides that share structural characteristics and the use of bioinformatics to search databases of amino acids, nucleic acids and other biological information to identify shared structural characteristics. Replikins are a newly discovered class of peptides that share structural characteristics and have been correlated with rapid replication of viruses and organisms. Replikin Scaffolds are a sub-set of the class of Replikin peptides. Exoskeleton Scaffolds are another newly discovered class of peptides that share structural characteristics and have been correlated with a decrease in replication.

BACKGROUND OF THE INVENTION

Rapid replication is characteristic of virulence in certain bacteria, viruses and malignancies, but no chemistry common to rapid replication in different organisms has been described. The inventors have found a family of conserved small protein sequences related to rapid replication, Replikins. Such Replikins offer new targets for developing effective detection methods and therapies. There is a need in the art for methods of identifying patterns of amino acids such as Replikins.

Bioinformatic Identification of Amino Acid Sequences

Identification of amino acid sequences, nucleic acid sequences and other biological structures may be aided with the implementation of bioinformatics. Publicly available databases containing amino acid and nucleic acid sequence information may be searched to identify and define Replikins, Replikin Scaffolds and Exoskeleton Scaffolds within representative proteins or protein fragments or genomes or genome fragments.

Databases of amino acids and proteins are maintained by a variety of research organizations, including, for example, the National Center for Biotechnology Information (NCBI) at the U.S. National Library of Medicine, and the Influenza Sequence Database at the Los Alamos National Laboratory. These databases are typically accessible via the Internet through web pages that provide a researcher with capabilities to search for and retrieve specific proteins.

Amino Acid Search Tools

As is known in the art, databases of proteins and amino acids may be searched using a variety of database tools and search engines. Using these publicly available tools, patterns of amino acids may be described and located in many different proteins corresponding to many different organisms. Several methods and techniques are available by which patterns of amino acids may be described. One popular format is the PROSITE pattern. A PROSITE pattern description may be assembled according to the following rules:

(1) The standard International Union of Pure and Applied Chemistry (IUPAC) one-letter codes for the amino acids are used (see FIG. 12).

(2) The symbol 'x' is used for a position where any amino acid is accepted.

(3) Ambiguities are indicated by listing the acceptable amino acids for a given position, between square parentheses '[ ]'. For example: [ALT] would stand for Alanine or Leucine or Threonine.

(4) Ambiguities are also indicated by listing between a pair of curly brackets '{ }' the amino acids that are not accepted at a given position. For example: {AM} stands for any amino acid except Alanine and Methionine.

(5) Each element in a pattern is separated from its neighbor by a '-'.

(6) Repetition of an element of the pattern can be indicated by following that element with a numerical value or a numerical range between parentheses. Examples: x(3) corresponds to x-x-x, x(2,4) corresponds to x-x or x-x-x or x-x-x-x.

(7) When a pattern is restricted to either the N- or C-terminal of a sequence, that pattern either starts with a '<' symbol or respectively ends with a '>' symbol.

(8) A period ends the pattern.

Examples of PROSITE patterns include:

PA [AC]-x-V-x(4)-{ED}. This pattern is translated as: [Alanine or Cysteine]-any-Valine-any-any-any-any-{any but Glutamic Acid or Aspartic Acid}

PA <A-x-[ST](2)-x(0,1)-V. This pattern, which must be in the N-terminal of the sequence ('<'), is translated as: Alanine-any-[Serine or Threonine]-[Serine or Threonine]-(any or none)-Valine.

Another popular format for describing amino acid sequence patterns is the regular expression format that is familiar to computer scientists. In computer science, regular expressions are typically used to describe patterns of characters for which finite automata can be automatically constructed to recognize tokens in a language. Possibly the most notable regular expression search tool is the Unix utility grep.

In the context of describing amino acid sequence patterns, a simplified set of regular expression capabilities is typically employed. Amino acid sequence patterns defined by these simple regular expression rules end up looking quite similar to PROSITE patterns, both in appearance and in result. A regular expression description for an amino acid sequence may be created according to the following rules:

(1) Use capital letters for amino acid residues and put a '-' between two amino acids (not required).

(2) Use "[ . . . ]" for a choice of multiple amino acids in a particular position. [LIVM] means that any one of the amino acids L, I, V, or M can be in that position.

(3) Use "{ . . . }" to exclude amino acids. Thus, {CF} means C and F should not be in that particular position. In some systems, the exclusion capability can be specified with a "^A" character. For example, AG would represent all amino acids except Glycine, and [^ILMV] would represents all amino acids except I, L, M, and V.

(4) Use "x" or "X" for a position that can be any amino acid.

(5) Use "(n)", where n is a number, for multiple positions. For example, x(3) is the same as "xxx".

(6) Use "(n1,n2)" for multiple or variable positions. Thus, x(1,4) represents "x" or "xx" or "xxx" or "xxxx".

(7) Use the symbol ">" at the beginning or end of the pattern to require the pattern to match the N or C terminus. For example, ">MDEL" (SEQ ID NO: 13) finds only sequences that start with MDEL (SEQ ID NO: 13). "DEL>" finds only sequences that end with DEL.

The regular expression, "[LIVM]-[VIC]-x (2)-G-[DENQTA]-x-[GAC]-x (2)-[LIVMFY](4)-x (2)-G" illustrates a 17 amino acid peptide that has: an L, I, V, or M at position 1; a V, I, or C at position 2; any residue at positions 3 and 4; a G at position 5 and so on . . . .

Other similar formats are in use as well. For example, the Basic Local Alignment Search Tool (BLAST) is a well-known system available on the Internet, which provides tools for rapid searching of nucleotide and protein databases. BLAST accepts input sequences in three formats: FASTA sequence format, NCBI Accession numbers, or GenBank sequence numbers. However, these formats are even simpler in structure than regular expressions or PROSITE patterns. An example sequence in FASTA format is:

>gi|532319|pir|TVFV2E|TVFV2E envelope protein

```
                                        (SEQ ID NO: 14)
ELRLRYCAPAGFALLKCNDADYDGFKTNCSNVSVVHCTNLMNTTV
TTGLLLNGSYSENRT

QIWQKHRTSNDSALILLNKHYNLTVTCKRPGNKTVLPVTIMAGLV
FHSQKYNLRLRQAWC

HFPSNWKGAWKEVKEEIVNLPKERYRGTNDPKRIFFQRQWGDPET
ANLWFNCHGEFFYCK

MDWFLNYLNNLTVDADHNECKNTSGTKSGNKRAPGPCVQRTYVA
CHIRSVIIWLETISKK

TYAPPREGHLECTSTVTGMTVELNYIPKNRTNVTLSPQIESIWA
AELDRYKLVEITPIGF

APTEVRRYTGGHERQKRVPFVXXXXXXXXXXXXXXXXXXXXXXV
QSQHLLAGILQQQKNL

LAAVEAQQQMLKLTIWGVK
```

Features of the BLAST system include sequence comparison algorithms that are used to search sequence databases for regions of local alignments in order to detect relationships among sequences which share regions of similarity. However, the BLAST tools are limited in terms of the structure of amino acid sequences that can be discovered and located. For example, BLAST is not capable of searching for a sequence that has "at least one lysine residue located six to ten amino acid residues from a second lysine residue," as required by a Replikin pattern, for example. Nor is BLAST capable of searching for amino acid sequences that contain a specified percentage or concentration of a particular amino acid, such as a sequence that has "at least 6% lysine residues."

Need for Replikin Search Tools

As can be seen from its definition, a Replikin pattern description cannot be represented as a single linear sequence of amino acids. Thus, PROSITE patterns and regular expressions, both of which are well suited to describing ordered strings obtained by following logical set-constructive operations such as negation, union and concatenation, are inadequate for describing Replikin patterns.

In contrast to linear sequences of amino acids, a Replikin pattern is characterized by attributes of amino acids that transcend simple contiguous ordering. In particular, the requirement that a Replikin pattern contain at least 6% lysine residues, without more, means that the actual placement of lysine residues in a Replikin pattern is relatively unrestricted. Thus, in general, it is not possible to represent a Replikin pattern description using a single PROSITE pattern or a single regular expression.

Accordingly, there is a need in the art for a system and method to scan a given amino acid sequence and identify and count all instances of a Replikin pattern. Similarly, there is a need in the art for a system and method to search protein databases and amino acid databases for amino acid sequences that match a Replikin pattern. Additionally, there is a need in the art for a generalized search tool that permits researchers to locate amino acid sequences of arbitrary specified length that includes any desired combination of the following characteristics: (1) a first amino acid residue located more than N positions and less than M positions away from a second amino acid residue; (2) a third amino acid residue located anywhere in the sequence; and (3) the sequence contains at least R percent of an amino acid residue. Finally, the shortcomings of the prior art are even more evident in research areas relating to disease prediction and treatment. There is a significant need in the art for a system to predict in advance the occurrence of disease (for example, to predict strain-specific influenza epidemics) and similarly to enable synthetic vaccines to be designed based on amino acid sequences or amino acid motifs that are discovered to be conserved over time and which have not been previously detectable by prior art methods of searching proteins and amino acid sequences.

SUMMARY OF THE INVENTION

The present invention provides a method for identifying nucleotide or amino acid sequences that include a Replikin sequence. The method is referred to herein as a 3-point-recognition method. By use of the "3-point recognition" method, peptides comprising from 7 to about 50 amino acids including (1) at least one lysine residue located six to ten amino acid residues from a second lysine residue; (2) at least one histidine residue; and (3) at least 6% lysine residues and having replication, transformation, or redox functions may be identified.

An aspect of the present invention provides a method of identifying a Replikin Scaffold in a virus or organism comprising identifying a series of Replikin Scaffold peptides comprising about 16 to about 30 amino acids comprising (1) a terminal lysine and a lysine immediately adjacent to said terminal lysine; (2) a terminal histidine and a histidine immediately adjacent to said terminal histidine, (3) a lysine within about 6 to about 10 amino acids from another lysine; and (4) at least 6% lysines.

An aspect of the invention may provide a method of identifying a Replikin Scaffold peptide in a virus or organism comprising about 16 to about 30 amino acids comprising (1) a terminal lysine and a lysine immediately adjacent to the terminal lysine; (2) a terminal histidine and a histidine immediately adjacent to the terminal histidine, (3) a lysine within about 6 to about 10 amino acids from another lysine; and (4) at least 6% lysines.

An aspect of the invention may also provide a method of making a preventive or therapeutic virus vaccine comprising identifying a Replikin Scaffold comprising about 16 to about 30 amino acids and synthesizing said Replikin Scaffold as a preventive or therapeutic virus vaccine wherein said Replikin Scaffold further comprises: (1) a terminal lysine and a lysine immediately adjacent to the terminal lysine; (2) a terminal histidine and a histidine immediately adjacent to the terminal histidine; (3) a lysine within about 6 to about 10 amino acids from another lysine; and (4) at least 6% lysines. The Replikin Scaffold may contain influenza virus peptide Replikins. A Replikin Scaffold may further comprise a group of Replikins comprising: (1) a terminal lysine and a lysine immediately adjacent to the terminal lysine; (2) a terminal histidine and a histidine immediately adjacent to the terminal histidine; (3) a lysine within about 6 to about 10 amino acids from another lysine; and (4) at least 6% lysines.

An aspect of the invention may provide a method of identifying an Exoskeleton Scaffold wherein a Replikin Scaffold is identified in a first strain of virus or organism and the Exoskeleton Scaffold is identified in a later-arising strain of said virus or organism wherein said Exoskeleton Scaffold comprises an amino acid sequence comprising the same number of amino acids as the Replikin Scaffold and further comprising (1) two terminal lysines, (2) two terminal histidines, and (3) no lysine within about 6 to about 10 amino acids from another lysine.

In an aspect of the invention an isolated or synthesized influenza virus peptide is provided with from 7 to about 50 amino acids, at least one lysine residue located six to ten residues from a second lysine residue, at least one histidine residue and at least 6% lysine residues. In a further aspect the peptide comprises a terminal lysine. In yet a further aspect the peptide is present in an emerging strain of influenza virus such as the influenza virus strain H5N1.

In another aspect of the invention an isolated or synthesized influenza virus peptide is provided comprising the H5N1 peptide KKNSTYPTIKRSYNNTNQEDLLVLWGIHH (SEQ ID NO: 15).

In another aspect of the invention, an isolated or synthesized influenza virus peptide is provided having about 16 to about 30 amino acids; a terminal lysine and a lysine immediately adjacent to the terminal lysine; a terminal histidine and a histidine immediately adjacent to the terminal histidine; a lysine within about 6 to about 10 amino acids from another lysine; and at least 6% lysines.

In another aspect of the invention, a preventive or therapeutic virus vaccine is provided having at least one isolated or synthesized peptide of influenza virus with at least one lysine residue located six to ten residues from a second lysine residue; at least one histidine residue; and at least 6% lysine residues. In a further aspect of the invention the isolated or synthesized peptide is present in an emerging strain of influenza virus or is present in an H5N1 strain of influenza virus.

In yet a further aspect of the invention, a preventive or therapeutic virus vaccine comprises the peptide KKNSTYPTIKRSYNNTNQEDLLVLWGIHH (SEQ ID NO: 15) having alternatively a synthetic UTOPE tail, an adjuvant, or a combination thereof. In yet a further aspect, the preventive or therapeutic virus vaccine comprises a pharmaceutically acceptable carrier.

In a further aspect of the invention the preventive or therapeutic virus vaccine comprises the peptide KKNSTYPTIKRSYNNTNQEDLLVLWGIHHKKKKHK (SEQ ID NO: 16)-KLH, where -KLH denotes a key limpet hemocyanin.

In yet another aspect of the invention a method of stimulating the immune system of a subject to produce antibodies to influenza virus is provided comprising administering an effective amount of at least one isolated or synthesized influenza virus Replikin peptide comprising from 7 to about 50 amino acids comprising (1) at least one lysine residue located six to ten amino acid residues from a second lysine residue; (2) at least one histidine residue; and (3) at least 6% lysine residues.

In a further aspect, in the method of stimulating the immune system the administered Replikin peptide may further comprise a pharmaceutically acceptable carrier and/or adjuvant and prevent or treat an influenza infection. The method of stimulating the immune system may further comprise an isolated or synthesized influenza virus peptide present in an emerging virus or present in an H5N1 strain of influenza virus. The method may further comprise administration of the peptide KKNSTYPTIKRSYNNTNQEDLLVLWGIHHKKKKHKKKKKHK (SEQ ID NO: 16)-KLH, where -KLH denotes a key limpet hemocyanin.

An aspect of the invention may also provide a method comprising: applying a plurality of criteria to data representing protein sequences; based on the criteria, identifying an arbitrary sub-sequence within the protein sequences; and outputting the identified sub-sequence to a data file; wherein the criteria include: a set {a} of amino acids to be included in the sub-sequence; a set {b} of amino acids to be excluded from the sub-sequence; and a minimum and a maximum permissible gap between members of sets {a} and {b}. Within the method the protein sequences may be obtained via a network. An aspect of the invention may further comprise a machine-readable medium storing computer-executable instructions to perform such a method.

An aspect of the invention may further provide a method comprising applying a plurality of criteria to data representing protein sequences; based on the criteria, identifying a sub-sequence within the protein sequences, the identified sub-sequence having a predetermined allowed range of distance between lysine amino acids thereof, and a predetermined allowed range of distance between a histidine amino acid and a farthest Lysine acid thereof; and outputting an identified sub-sequence to a data file. The protein sequences may be obtained via a network. A machine-readable medium storing computer-executable instructions may perform such a method.

BRIEF DESCRIPTION OF THE DRAWINGS

FIGS. 10A-C illustrate a chart depicting the mean Replikin count per year for nucleocapsid coronavirus isolates.

FIG. 12 is a conversion table that enables amino acids to be encoded as single alphabetic characters according to a standard supplied by the International Union of Pure and Applied Chemistry (IUPAC).

FIGS. 13A and 13B illustrate a printout of a human cancer protein (SEQ ID NO: 472) obtained by searching a protein database maintained by the National Center for Biotechnology Information (NCBI).

FIG. 14 is a conversion table illustrating a correspondence between nucleic acid base triplets and amino acids.

FIG. 15 illustrates that increasing replikin concentration ('Replikin Count') of hemagglutinin protein of H5N1 preceded three 'Bird Flu' Epidemics. In H5N1 influenza, the increasing strain-specific replikin concentration (Replikin Count, Means+/−SD) 1995 to 1997 preceded the Hong Kong H5N1 epidemic of 1997 (E1); the increase from 1999 to 2001 preceded the epidemic of 2001 (E2); and the increase from 2002 to 2004 preceded the epidemic in 2004 (E3). The decline in 1999 occurred with the massive culling of poultry in response to the E1 epidemic in Hong Kong.

FIG. 16 is a table illustrating selected examples of Replikin patterns that have been found in various organisms.

FIG. 20 is a source code listing containing a procedure for discovering Replikin patterns in a sequence of amino acids, in accordance with an aspect of the present invention.

FIGS. 21A and 21B illustrate a table illustrating Replikin Scaffolds occurring in substantially fixed amino acid positions in different proteins. FIGS. 21A and B disclose SEQ ID NOS: 473-531, respectively, in order of appearance.

DETAILED DESCRIPTION OF THE INVENTION

Definitions

Figure 1:
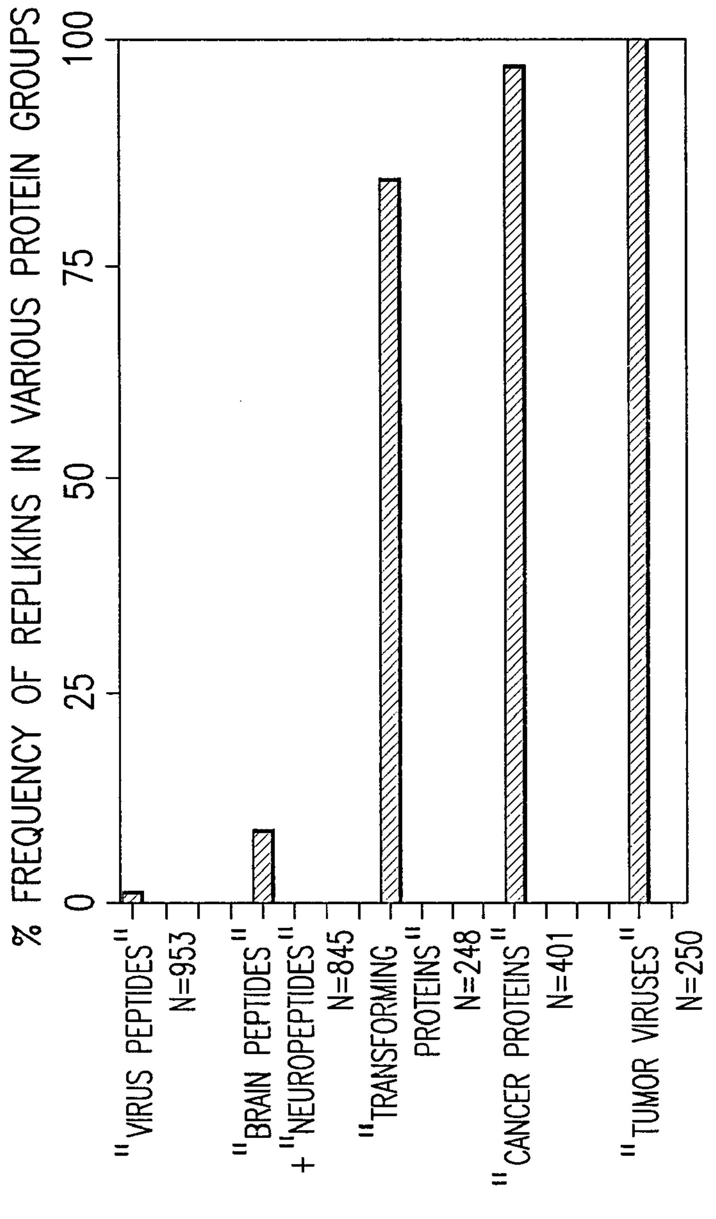
FIG. 1 is a bar graph depicting the frequency of occurrence of Replikins in various organisms.

As used herein, the term "peptide" or "protein" refers to a compound of two or more amino acids in which the carboxyl group of one is united with an amino group of another, forming a peptide bond. The term peptide is also used to denote the amino acid sequence encoding such a compound. As used herein, "isolated" or "synthesized" peptide or biologically active portion thereof refers to a peptide that is after purification substantially free of cellular material or other contaminating proteins or peptides from the cell or tissue source from which the peptide is derived, or substantially free from chemical precursors or other chemicals when chemically synthesized by any method, or substantially free from contaminating peptides when synthesized by recombinant gene techniques.

As used herein, a Replikin peptide or Replikin protein is an amino acid sequence having 7 to about 50 amino acids comprising:

(1) at least one lysine residue located six to ten amino acid residues from a second lysine residue;

(2) at least one histidine residue;

(3) at least 6% lysine residues.

Similarly, a Replikin sequence is the amino acid sequence encoding such a peptide or protein.

As used herein, an "earlier-arising" virus or organism is a specimen of a virus or organism collected from a natural source of the virus or organism on a date prior to the date on which another specimen of the virus or organism was collected. A "later-arising" virus or organism is a specimen of a virus or organism collected from a natural source of the virus or organism on a date subsequent to the date on which another specimen of the virus or organism was collected.

As used herein, "emerging strain" as used herein refers to a strain of a virus, bacterium, fungus, or other organism identified as having an increased increasing concentration of Replikin sequences in one or more of its protein sequences relative to the concentration of Replikins in other strains of such organism. The increase or increasing concentration of Replikins occurs over a period of at least about six months, and preferably over a period of at least about one year, most preferably over a period of at least about three years or more, for example, in influenza virus, but may be a much shorter period of time for bacteria and other organisms.

As used herein, "mutation" refers to change in this structure and properties of an organism caused by substitution of amino acids. In contrast, the term "conservation" as used herein, refers to conservation of particular amino acids due to lack of substitution.

As used herein, "replikin count" refers to the number of replikins per 100 amino acids in a protein or organism. A higher replikin count in a first strain of virus or organism has been found to correlate with more rapid replication of the first virus or organism as compared to a second, earlier- or later-arising strain of the virus or organism having a lower replikin count.

As used herein "Replikin Scaffold" refers to a series of conserved Replikin peptides wherein each of said Replikin peptide sequences comprises about 16 to about 30 amino acids and further comprises: (1) a terminal lysine; (2) a terminal histidine and a histidine immediately adjacent to the terminal histidine; (3) a lysine within 6 to 10 amino acid residues from another lysine; and (4) about 6% lysine. "Replikin Scaffold" peptides may comprise an additional lysine immediately adjacent to the terminal lysine. "Replikin Scaffold" also refers to an individual member or a plurality of members of a series of a "Replikin Scaffold."

Identification of Replikins

The identification of a new family of small peptides related to the phenomenon of rapid replication, referred to herein as Replikins, provides targets for detection of pathogens in a sample and developing therapies, including vaccine development. In general, knowledge of and identification of this family of peptides enables development of effective therapies and vaccines for any organism that harbors Replikins. Identification of this family of peptides also provides for the detection of viruses and virus vaccine development.

For example, identification of this family of peptides provides for the detection of influenza virus and provides new targets for influenza treatment and vaccines including treatment and vaccines for influenza H5N1. Further examples provided by the identification of this family of peptides include the detection of infectious disease Replikins, cancer immune Replikins and structural protein Replikins.

Rapid replication is characteristic of virulence in certain bacteria, viruses and malignancies, but no chemistry common to rapid replication in different organisms has been described. We have found a family of conserved small protein sequences related to rapid replication, which we have named Replikins. Such Replikins offer new targets for developing effective detection methods and therapies. The first Replikin found was the glioma Replikin, which was identified in brain glioblastoma multiforme (glioma) cell protein, called malignin.

Hydrolysis and mass spectrometry of malignin revealed the novel 16-mer peptide sequence which contains the glioma Replikin. This Replikin was not found in databases for the normal healthy human genome and therefore appeared to be derived from some source outside the body.

We have devised an algorithm to search for the glioma Replikin or homologue thereof. Homologues were not common in over 4,000 protein sequences, but were found, surprisingly, in all tumor viruses, and in the replicating proteins of algae, plants, fungi, viruses and bacteria.

We have identified that both 1) Replikin concentration (number of Replikins per 100 amino acids) and 2) Replikin composition correlate with the functional phenomenon of rapid replication. These relationships provide functional basis for the determination that Replikins are related quantitatively as well as qualitatively to the rate of replication.

The first functional basis for Replikins role to rapid replication was discovered by the Applicants in glioma replication. The fact that glioma malignin was found to be enriched ten-fold compared to the five-fold increase in cell number and membrane protein concentration in rapid replication of glioma cells suggests an integral relationship of the Replikins to replication. When the glioma Replikin was synthesized in vitro and administered as a synthetic vaccine to rabbits, abundant antimalignin antibody was produced. This establishes the antigenic basis of the antimalignin antibody in serum (AMAS) test, and provides the first potential synthetic cancer vaccine and the prototype for Replikin vaccines in other organisms. With the demonstration of this natural immune relationship of the Replikins to replication and this natural immune response to cancer Replikins, which overrides cell type, based upon the shared specificity of cancer Replikins and rapid replication, both passive augmentation of this immunity with antimalignin antibody and active augmentation with synthetic Replikin vaccines now is possible.

The relationship between the presence of antimalignin antibody and survival in patients was shown in a study of 8,090 serum specimens from cancer patients. The study showed that the concentration of antimalignin antibody increases with age, as the incidence of cancer in the population increases, and increases further two to three-fold in early malignancy, regardless of cell type. In vitro, the antimalignin antibody is cytotoxic to cancer cells at picograms (femtomoles) per cancer cell, and in vivo the concentration of antimalignin antibody relates quantitatively to the survival of cancer patients. As shown in glioma cells, the stage in cancer at which cells have only been transformed to the immortal malignant state but remain quiescent or dormant, now can be distinguished from the more active life-threatening replicating state, which is characterized by the increased concentration of Replikins. In addition, clues to the viral pathogenesis of cancer may be found in the fact that glioma glycoprotein 10B has a 50% reduction in carbohydrate residues when compared to the normal 1OB. This reduction is associated with virus entry in other instances, and so may be evidence of the attachment of virus for the delivery of virus Replikins to the 10B of glial cells as a step in the transformation to the malignant state.

Our study concerning influenza virus hemagglutinin protein sequences and influenza epidemiology over the past 100 years has provided a second functional basis for the relations of Replikins to rapid replication. Only serological hemagglutinin and antibody classification, but no strain-specific conserved peptide sequences have previously been described in influenza. Further, no changes in concentration and composition of any strain-specific peptide sequences have been described previously that correlate with epidemiologically documented epidemics or rapid replication. In this study, a four to ten-fold increase in the concentration of strain-specific influenza Replikins in one of each of the four major strains, influenza B, (A)H1N1, (A)H2N2 and, (A)H3N2 is shown to relate to influenza epidemics caused by each strain from 1902 to 2001.

We then showed that these increases in concentration are due to the reappearance of at least one specific Replikin composition from 1 to up to 64 years after its disappearance, plus the emergence of new strain-specific Replikin compositions. Previously, no strain-specific chemical structures were known with which to predict the strains that would predominate in coming influenza seasons, nor to devise annual mixtures of whole-virus strains for vaccines. The recent sharp increase in H3N2 Replikin concentration (1997 to 2000), the largest in H3N2's history, and the reappearance of specific Replikin compositions that were last seen in the high mortality H3N2 pandemic of 1968, and in the two high mortality epidemics of 1975 and 1977, but were absent for 20-25 years, together may be a warning of coming epidemics. This high degree of conservation of Replikin structures observed, whereby the identical structure can persist for 100 years, or reappear after an absence of from one to 64 years, indicate that what was previously thought to be change due to random substitution of amino acids in influenza proteins is more likely to be change due to an organized process of conservation of Replikins.

The conservation of Replikins is not unique to influenza virus but was also observed in other sources, for example in foot and mouth disease virus, type 0, HIV tat, and wheat.

A third functional basis for Replikins' role in rapid replication is seen in the increase in rapid replication in HIV. Replikin concentration was shown to be related to rapid replication in HIV. We found the Replikin concentration in the slow growing low-titre strain of HIV (NS1, "Bru"), which is prevalent in early stage infection, to be one-sixth of the Replikin concentration in the rapidly-growing high-titre strain of HIV (SI, "Lai") (prevalent in late stage HIV infection).

Further examples demonstrate the relationship of Replikins to rapid replication. In the "replicating protein," of tomato leaf curl gemini virus, which devastates tomato crops, the first 161 amino acids, the sequence that has been shown to bind to DNA, was shown to contain five Replikins. In malaria, legendary for rapid replication when trypanosomes are released from the liver in the tens of thousands from one trypanosome, multiple, novel, almost 'flamboyant' Replikin structures have been found with concentrations of up to 36 overlapping Replikins per 100 amino acids.

The conservation of any structure is critical to whether that structure provides a stable invariant target to attack and destroy or to stimulate. When a structure is tied in some way to a basic survival mechanism of the organism, the structures tend to be conserved. A varying structure provides an inconstant target, which is a good strategy for avoiding attackers, such as antibodies that have been generated specifically against the prior structure and thus are ineffective against the modified form. This strategy is used by influenza virus, for example, so that a previous vaccine may be quite ineffective against the current virulent virus.

Replikins as Stable Targets for Treatment

Both bacteria and HIV have both Replikin and non-Replikin amino acids. In HIV, for example, there has been a recent increase in drug-resistance from 9% to 13% due to mutation, that is, substitution of amino acids not essential to the definition of the Replikin structure. (See detailed analysis of TAT protein of HIV discussed herein). In bacteria, the development of 'resistant strains' is due to a similar mechanism. However, we have found that Replikin structures do not mutate or change to the same degree as non Replikin amino acids (see also discussion of foot and mouth disease virus conservation of Replikins discussed herein; further see discussion of conservation of coronavirus Replikins discussed herein). The Replikin structures, as opposed to the non-Replikin structures are conserved and thus provide new constant targets for treatment.

Certain structures too closely related to survival functions apparently cannot change constantly. Because an essential component of the Replikin structure is histidine (h), which is know for its frequent binding to metal groups in redox enzymes and probable source of energy needed for replication, and since this histidine structure remains constant, this structure remains all the more attractive a target for destruction or stimulation.

From a proteomic point of view, the inventors' construction of a template based on the newly determined glioma peptide sequence led them to the discovery of a wide class of proteins with related conserved structures and a particular function, in this case replication. Examples of the increase in Replikin concentration with virulence of a disease include, influenza, HIV, cancer and tomato leaf curl virus. This newly recognized class of structures is related to the phenomenon of rapid replication in organisms as diverse as influenza, yeast, algae, plants, the gemini curl leaf tomato virus, HIV and cancer.

Replikin concentration and composition provide new quantitative methods to detect and control the process of replication, which is central to the survival and dominance of each biological population. The sharing of immunological specificity by diverse members of the class, as demonstrated with antimalignin antibody for the glioma and related cancer Replikins, suggests that B cells and their product antibodies may recognize Replikins by means of a similar recognition language.

Examples of peptide sequences of cancer Replikins or as containing a Replikin, i.e., a homologue of the glioma peptide, kagvaflhkk (SEQ ID NO: 1), may be found in such cancers of, but not limited to, the lung, brain, liver, soft-tissue, salivary gland, nasopharynx, esophagus, stomach, colon, rectum, gallbladder, breast, prostate, uterus, cervix, bladder, eye, forms of melanoma, lymphoma, leukemia, and kidney.

Replikins provide for: 1) detection of pathogens by qualitative and quantitative determinations of Replikins; 2) treatment and control of a broad range of diseases in which rapid replication is a key factor by targeting native Replikins and by using synthetic Replikins as vaccines; and 3) fostering increased growth rates of algal and plant foods.

The first Replikin sequence to be identified was the cancer cell Replikin found in a brain cancer protein, malignin, which was demonstrated to be enriched ten-fold during rapid anaerobic replication of glioblastoma multiforme (glioma) cells. (FIG. 2) Malignin is a 10 KDa portion of the 250 KDa glycoprotein 10B, which was isolated in vivo and in vitro from membranes of glioblastoma multiforme (glioma) cells. Hydrolysis and mass spectroscopy of malignin revealed a 16-mer peptide sequence, ykagvaflhkkndide (SEQ ID NO:4), which is referred to herein as the glioma Replikin and which includes the shorter peptide, kagvaflhkk (SEQ ID NO: 1), both of which apparently are absent in the normal human genome.

TABLE 1

16-mer peptide sequence YKAGVAFLHKKNDIDE (SEQ ID NO: 4) obtained from malignin by hydrolysis and mass spectrometry

| Seq ID NO. | Fragment Identified | MH+ (mass) | Sequence | Method By Which Fragment Obtained: Auto-hydrolysis of malignin free in solution | Auto-hydrolysis of malignin immobilized on bromoacetyl cellulose | Micro-waved 5 seconds | Micro-waved 30 seconds |
|---|---|---|---|---|---|---|---|
| 19 | 1-3 | 381.21 | ()yka(g) | | | | + |
| 20 | 1-5 | 537.30 | ()ykagv(a) | | + | | |
| 21 | 2-6 | 445.28 | (y)kagva(f) | | + | | |
| 22 | 2-7 | 592.35 | (y)kagvaf(1) | | | + | |
| 23 | 4-11 | 899.55 | (a)gvaflhkk(n) | | | | + |
| 24 | 5-7 | 336.19 | (g)vaf(1) | | | | + |
| 25 | 6-7 | 237.12 | (v)af(1) | + | | | |

TABLE 1-continued 16-mer peptide sequence YKAGVAFLHKKNDIDE (SEQ ID NO: 4) obtained from malignin by hydrolysis and mass spectrometry

| Seq ID NO. | Fragment Identified | MH+ (mass) | Sequence | Method By Which Fragment Obtained: Auto-hydrolysis of malignin free in solution | Auto-hydrolysis of malignin immobilized on bromoacetyl cellulose | Micro-waved 5 seconds | Micro-waved 30 seconds |
|---|---|---|---|---|---|---|---|
| 26 | 6-10 | 615.36 | (v)aflhk(k) | | | | + |
| 27 | 6-10 | 615.36 | (v)aflhk(k) | + | | | |
| 28 | 6-12 | 857.50 | (v)aflhkkn(d) | | + | | |
| 29 | 6-12 | 857.50 | (v)afhkkn(d) | + | | | |
| 30 | 7-8 | 279.17 | (a)fl(h) | | | + | |
| 31 | 10-16 | 861.43 | (h)kkndide() | | + | | |
| 32 | 11-14 | 489.27 | (k)kndi(d) | | + | | |
| 33 | 12-15 | 476.2- | (k)ndid(e) | + | | | |

When the 16-mer glioma Replikin was synthesized and injected as a synthetic vaccine into rabbits, abundant antimalignin antibody was produced. (Bogoch et al., Cancer Detection and Prevention, 26 (Suppl. 1): 402 (2002)). The concentration of antimalignin antibody in serum in vivo has been shown to relate quantitatively to the survival of cancer patients. (Bogoch et al., Protides of Biological Fluids, 31:739-747 (1984). In vitro antimalignin antibodies have been shown to be cytotoxic to cancer cells at a concentration of picograms (femtomolar) per cancer cell. (Bogoch et al., Cancer Detection and Prevention, 26 (Suppl. 1): 402 (2002).

Studies carried out by the inventors showed that the glioma Replikin is not represented in the normal healthy human genome. Consequently, a search for the origin and possible homologues of the Replikin sequence was undertaken by analysis of published sequences of various organisms.

By using the 16-mer glioma Replikin sequence as a template and constructing a recognition proteomic system to visually scan the amino acid sequences of proteins of several different organisms, a new class of peptides, the Replikins, was identified. The present invention provides a method for identifying nucleotide or amino acid sequences that include a Replikin sequence. The method is referred to herein as a 3-point-recognition method. The three point recognition method comprises: a peptide from 7 to about 50 amino acids including (1) at least one lysine residue located six to ten amino acid residues from a second lysine residue; (2) at least one histidine residue; and (3) at least 6% lysine residues. (Replikin). These peptides or proteins constitute a new class of peptides in species including algae, yeast, fungi, amoebae, bacteria, plant, virus and cancer proteins having replication, transformation, or redox functions. Replikin peptides have been found to be concentrated in larger 'replicating' and 'transforming' proteins (so designated by their investigators, See Table 2) and cancer cell proteins. No sequences were found to be identical to the malignin 16-mer peptide.

The present invention further provides a method for identifying nucleotide or amino acid sequences that include a Replikin sequence comprising from 7 to about 50 amino acids including (1) at least one first lysine located at either terminus of the isolated or synthesized peptide, (2) a second lysine located six to ten residues from the first lysine residue; (3) at least one histidine; and (4) at least 6% lysines. In another aspect of the invention the isolated or synthesized peptides are influenza virus peptides. In yet another aspect of the invention, the isolated or synthesized peptides are H5N1 influenza virus peptides.

TABLE 2

Examples of Replikins in various organisms - prototype: Glioma Replikin* KAGVAFLHKK (SEQ ID NO: 1)

| | SEQ ID NO: | | |
|---|---|---|---|
| Algae: | 34 | *Caldophera prolifera* | kaskftkh |
| | 35 | *Isolepisprolifera* | kagaetgeikgh |
| Yeast: | 36 | *Schizosaccharomyces pombe* | ksfkypkkhk |
| | 37 | *Oryza sativa* | kkaygnelhk |
| | 2 | *Sacch. cerevisiae* replication binding protein | hsikrelgiifdk |
| Fungi: | 38 39 | *Isocitrate lyase* ICI 1,Penicillium marneffei | kvdivthqk |
| | 40 | DNA-dependent RNA polymerase 11, | kleedaayhrkk |

TABLE 2-continued

| Examples of Replikins in various organisms - prototype: Glioma Replikin* KAGVAFLHKK (SEQ ID NO: 1) | | | |
|---|---|---|---|
| | SEQ ID NO: | | |
| | | Diseula destructiva | |
| | | *Ophiostoma* novo-ulm 1, RNA in Dutch elm disease fungus | kvilplrgnikgiffkh |
| Amoeba: | 41 | Entamoeba invadens, histone H2B | klilkgdlnkh |
| Bacteria: | 42 | Pribosomal protein replication factor, *Helicobacter pylori* | ksvhaflk |
| | | Replication-associated protein *Staph. aureus* | |
| | 10 | Mycoplasma pulmonic, chromosome replication | kkektthnk |
| | 43 | Macrophage infectivity potentiator, *L. legionella* | kvhffqlkk |
| | 90 | *Bacillus anthracis* | kihlisvkk |
| | 91 | *Bacillus anthracis* | hvkkekeknk |
| | 92 | *Bacillus anthracis* | khivkievk |
| | 93 | *Bacillus anthracis* | kkkkikdiygkdallh |
| | 94 | *Bacillus anthracis* | kwekikqh |
| | 95 | *Bacillus anthracis* | kklqipppiepkkddiih |
| | 96 | *Bacillus anthracis* | hnryasnivesayllilnew-knniqsdlikk |
| | 97 | *Bacillus anthracis* | havddyagylldknqsdlv-tnskk |
| | 98 | *Bacillus anthracis* | haerlkvqknapk |
| Plants: | 44 | *Arabidopsis thaliana*, prolifera | kdhdfdgdk |
| | 45 | *Arabidopsis thaliana*, cytoplasmic ribosomal | kmkglkqkkah |
| | 46 | *Arabidopsis thaliana*, DNA binding protein | kelssttqeksh |
| Viruses: | 9 | Replication associated protein A [Maize streak virus] | kekkpskdeimrdiish |
| | 11 | Bovine herpes virus 4, DNA replication protein | hkinitngqk |
| | 12 | Meleagrid herpesvirus 1, replication binding protein | hkdlyrllmk |
| | 47 | Feline immunodeficiency | hlkdyklvk |
| | 3 | Foot and Mouth Disease (0) | hkqkivapvk |
| | 5 | HIV Type 1 | kcfncgkegh |
| | 7 | HIV Type 2 | kcwncgkegh |
| | 99 | Small Pox Virus (Variola) | khynnitwyk |
| | 100 | Small Pox Virus (Variola) | kysqtgkeliih |
| | 101 | Small Pox Virus (Variola) | hyddvrikndivvsrck |
| | 102 | Small Pox Virus (Variola) | hrfklildski |
| | 103 | Small Pox Virus (Variola) | kerghnyyfek |
| Tumor Viruses: | 48 | *Rous sarcoma* virus tyrosine-protein kinase | kklrhek |
| | 49 | v-yes, avian sarcoma | kklrhdk |
| | 50 | c-yes, colon cancer, malignant melanoma | kklrhdk |
| | 51 | v-srcC, avian sarcoma | kklrhek |
| | 52 | c-src, colon, mammary, panrcreatic cancer | kklrhek |
| | 53 | Neuroblastoma RAS viral (v-ras) oncogene | kqahelak |
| | 54 | VP1 (major capsid protein) [*Polyamavirus sp.*] | kthrfskh |
| | 55 | Sindbis | knlhekik |
| | 56 | El [Human papilloamavirus type 71] | khrpllqlk |
| | 57 | v-erbB from AEV and c-erb | kspnhvk |
| | 58 | v-fms (feline sarcoma) | knihlekk |
| | 59 | c-fms (acute and chronic myelomonocyt-ic tumors) | knihlekk |
| | 60 | large t-antigen I [Polyomavirus sp.1 | kphlaqslek |
| | 61 | middle t-antigen [Polyomavirus sp,1- | kqhrelkdk |
| | 62 | small t-antigen [Polyomavirus spJ, | kqhrelkdk |
| | 63 | v-abl, murine acute leukemia | kvpvlisptlkh |
| | 64 | Human T-cell lymphotropic virus typo 2 | kslllevdkdish |
| | 65 | c-kit, GI tumors, small cell lung carcinoma | kagitimvkreyh |
| | 18 | Hepatitis C | hyppkpgcivpak |
| Trans-Forming Proteins: | 66 | Transforming protein myb | ksgkhlgk |
| | 67 | Transforming protein myc, Burkitt lymphoma | krreqlkhk |
| | 68 | Ras-related GTP-binding protein | ksfevikvih |
| | 69 | Transforming protein ras (*teratocarcinoma*) | kkkhtvkk |
| | 70 | TRAF-associated NF•kB activator TANK | kaqkdhlsk |
| | 71 | RFP transforming protein | hlkrvkdlkk |
| | 72 | Transforming protein D (S.C.) | kygspkhrlik |
| | 73 | Papilloma virus type 11, transforming protein | klkhilgkarfik |
| | 74 | Protein tryosine kinasc (EC 2.7.1.112slk | kgdhvkhykirk |

TABLE 2-continued

Examples of Replikins in various organisms - prototype: Glioma Replikin*
KAGVAFLHKK
(SEQ ID NO: 1)

|  | SEQ ID NO: |  |  |
|---|---|---|---|
|  | 75 | Transforming protein (axl(-)) | keklrdvmvdrhk |
|  | 76 | Transforming protein (N-myc) | klqarqqq11kkieh |
|  | 77 | Fibroblast growth factor 4 (Kaposi sarcoma) | kkgnrvsptmkvth |
| Cancer | 78 | Matrix metaloproteinase 7 (uterine) | keiplhfrk |
| Cell | 79 | Transcription factor 7-like | kkkphikk |
| Proteins: | 80 | Breast cancer antigen NY-BR-87 | ktrhdplak |
|  | 81 | BRCA-1-Associated Ring Domain Protein (breast) | khhpkdnlik |
|  | 82 | 'Autoantigen from a breast tumor' | khkrkkfrqk |
|  | 83 | Glioma Replikin (this study) | kagvaflhkk |
|  | 84 | Ovarian cancer antigen | khkrkkfrqk |
|  | 85 | EE L leukemia | kkkskkhkdk |
|  | 86 | Proto-oncogene tyrosine-protein kinase C-ABLE | hksekpalprk |
|  | 87 | Adenomatosis polyposis coli | kkkkpsrlkgdnek |
|  | 88 | Gastric cancer transforming protein | ktkkgnrvsptmkvth |
|  | 89 | Transforming protein (K-RAS 2B), lung | khkekmskdgkkkkkksk |

Identification of an amino acid sequence as a Replikin or as containing a Replikin, i.e., a homologue of the glioma peptide, kagvaflhkk (SEQ ID NO: 1), requires that the three following requirements be met. According to the three point recognition system the sequences have three elements: (1) at least one lysine residue located six to ten residues from another lysine residue; (2) at least one histidine residue; and (3) a composition of at least 6% lysine within an amino acid sequence of 7 to about 50 residues. An exemplary non-limiting Replikin comprises a terminal lysine.

Databases were searched using the National Library of Medicine keyword "PubMed" descriptor for protein sequences containing Replikin sequences. Over 4,000 protein sequences were visually examined for homologues. Sequences of all individual proteins within each group of PubMed-classified proteins were visually scanned for peptides meeting the three above-listed requirements. An infrequent occurrence of homologues was observed in "virus peptides" as a whole (1.5%) (N=953), and in other peptides not designated as associated with malignant transformation or replication such as "brain peptides" and "neuropeptides" (together 8.5%) (N=845). However, surprisingly, homologues were significantly more frequently identified in large "replicating proteins," which were identified as having an established function in replication in bacteria, algae, and viruses. Even more surprising was the finding that Replikin homologues occurred in 100% of "tumor viruses" (N=250), in 97% of "cancer proteins" (N=401), and in 85% of "transforming viruses" (N=248). These results suggest that there are shared properties of cancer pathogenesis regardless of cell type and suggest a role of viruses in carcinogenesis, i.e., conversion of cells from a transformed albeit dormant state to a more virulent actively replicating state.

Homologues of the following amino acid sequence, kagvaflhkk (SEQ ID NO: 1), as defined by the three point recognition method, were found in such viruses, or viral peptides, as, but not limited to, adenovirus, lentivirus, a-virus, retrovirus, adeno-associated virus, human immunodeficiency virus, hepatitis virus, influenza virus, maize streak virus, herpes virus, bovine herpes virus, feline immunodeficiency virus, foot and mouth disease virus, small pox virus, rous sarcoma virus, neuroblastoma RAS viral oncogene, polyomavirus, sindbis, human papilloma virus, myelomonocytic tumor virus, murine acute leukemia, T-cell lymphotropic virus, and tomato leaf curl virus.

Furthermore, homologues of the amino acid sequence kagvaflhkk (SEQ ID NO: 1) are present in known classes of coronavirus, which are members of a family of enveloped viruses that replicate in the cytoplasm of host cells. Additionally, the homologue of the amino acid sequence kagvaflhkk (SEQ ID NO: 1) is present in the recently identified class of coronavirus responsible for severe acute respiratory syndrome, or SARS. The replikin is located in the nucleocapsid whole protein sequence of the SARS coronavirus. In addition, the location of the replikins is present in other members of the coronavirus class and, more specifically, are also present in the nucleocapsid protein sequences from these coronaviruses Replikins are present in such bacteria as, but not limited to, *Acetobacter, Achromobacter, Actinomyces, Aerobacter, Alcaligenes, Arthrobacter, Azotobacter, Bacillus, Brevibacterium, Chainia, Clostridium, Corynebacterium, Erwinia, Escheria, Lebsiella, Lactobacillus, Haemophilus, Flavobacterium, Methylomonas, Micrococcus, Mycobacterium, Micronomspora, Mycoplasma, Neisseria, Nocardia, Proteus, Pseudomonas, Rhizobium, Salmonella, Serratia, Staphylococcus, Streptocossus, Streptomyces, Streptosporangium, Strepto-virticillium, Vibrio* peptide, and *Xanthomas*. Replikins are present in such fungi as, but not limited to, *Penicillium, Diseula, Ophiostoma novo-ulim, Mycophycophta, Phytophthora infestans, Absidia, Aspergillus, Candida, Cephalosporium, Fusarium, Hansenula, Mucor, Paecilomyces, Pichia, Rhizopus, Torulopsis, Trichoderma*, and *Erysiphe*. Replikins are present in such yeast as, but not limited to, *Saccharomyces, Cryptococcus*, including *Cryptococcus-neoformas, Schizo-saccharomyces*, and *Oryza*. Replikins are present in algae such as, but not limited to, *Caldophera, Isolepisprolifera, Chondrus, Gracilaria, Gelidium, Caulerpa, Laurencia, Cladophexa, Sargassum, Penicillos, Halimeda, Laminaria, Fucus, Ascophyllum, Undari, Rhodymenia, Macrocystis, Eucheuma, Ahnfeltia*, and *Pteroclasia*. Replikins are present in amoeba such as, but not limited to, *Entamoeba*(including *Entamoeba invadens*), Amoebidae, *Acanthamoeba* and *Naegleria*. Replikins are present in plants such as, but not limited to, *Arabidopsis*, wheat, rice, and maize.

Auxiliary Specifications

To permit classification of subtypes of Replikins, additional or "auxiliary specifications" to the basic "3-point-recognition" requirements may be added: (a) on a structural basis, such as the common occurrence of adjacent di- and polylysines in cancer cell proteins (e.g., transforming protein P21B(K-RAS 2B), lung, Table 2, SEQ ID NO: 89), and other adjacent di-amino acids in TOLL-like receptors, or b) on a functional basis, such as exhibiting ATPase, tyrosine kinase or redox activity as seen in Table 2.

Functional Derivatives

"Functional derivatives" of the Replikins as described herein are fragments, variants, analogs, or chemical derivatives of the Replikins, which retain at least a portion of the immunological cross reactivity with an antibody specific for the Replikin. A fragment of the Replikin peptide refers to any subset of the molecule. Variant peptides may be made by direct chemical synthesis, for example, using methods well known in the art. An analog of a Replikin to a non-natural protein substantially similar to either the entire protein or a fragment thereof. Chemical derivatives of a Replikin contain additional chemical moieties not normally a part of the peptide or peptide fragment.

Replikins and Replication

Figure 2:
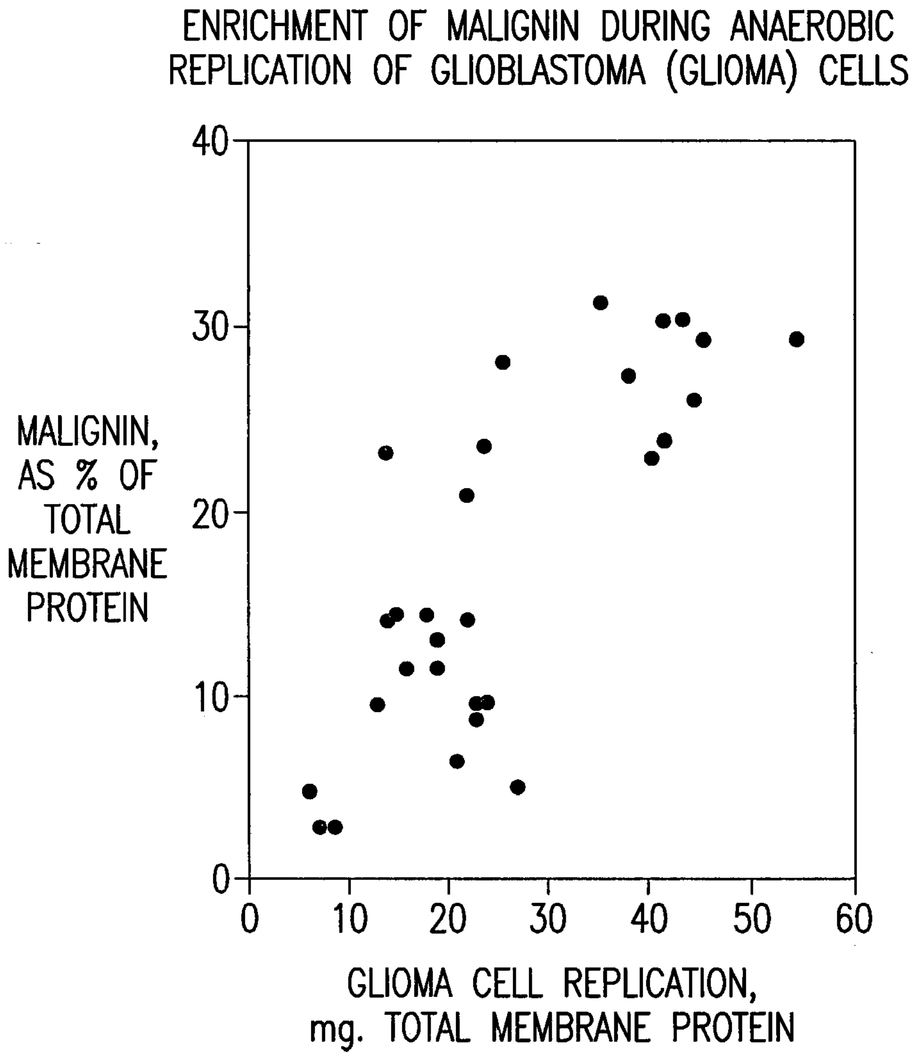
FIG. 2 is a graph depicting the percentage of malignin per milligram total membrane protein during anaerobic replication of glioblastoma cells.

As seen in FIG. 2, during anaerobic respiration when the rate of cell replication is increased, malignin is enriched. That is, malignin is found to increase not simply in proportion to the increase in cell number and total membrane proteins, but is enriched as much as ten-fold in concentration, starting with 3% at rest and reaching 30% of total membrane protein. This clear demonstration of a marked increase in Replikin concentration with glioma cell replication points to, and is consistent with, the presence of Replikins identified with the 3-point recognition method in various organisms. For example, Replikins were identified in such proteins as "Saccharomyces cerevisiae replication binding protein" (SEQ ID NO: 2) (hsikrelgiifdk); the "replication associated protein A of maize streak virus" (SEQ ID NO: 8) (kyivcareahk) and (SEQ ID NO: 9) (kekkpskdeimrdiish); the "replication-associated protein of Staphylococcus aureus" (SEQ ID NO: 10) (kkektthnk); the "DNA replication protein of bovine herpes virus 4" (SEQ ID NO: 11) (hkinitngqk); and the "Mealigrid herpes virus 1 replication binding protein" (SEQ ID NO: 12) (hkdlyrllmk). Previous studies of tomato leaf curl gemini virus show that the regulation of virus accumulation appears to involve binding of amino acids 1-160 of the "replicating protein" of that virus to leaf DNA and to other replication protein molecules during virus replication. Analysis of this sequence showed that amino acids 1-135 of this "replicating protein" contain a replikin count (concentration) as high as 20.7 (see section on tomato leaf curl Gemini virus.)

Table 2 shows that Replikin-containing proteins also are associated frequently with redox functions, and protein synthesis or elongation, as well as with cell replication. The association with metal-based redox functions, the enrichment of the Replikin-containing glioma malignin concentration during anaerobic replication, and the cytotoxicity of antimalignin at low concentrations (picograms/cell) (FIG. 4C-4F), all suggest that the Replikins are related to central respiratory survival functions, have been found less often subjected to the mutations characteristic of non-Replikin amino acids.

Replikins in Influenza Epidemics

Of particular interest, it was observed that at least one Replikin per 100 amino acids was found to be present in the hemagglutinin proteins of almost all of the individual strains of influenza viruses examined. The Replikin sequences that were observed to occur in the hemagglutinin proteins of isolates of each of the four prevalent strains of influenza virus, influenza B, H1N1, H2N2, and H3N2, for each year that amino acid sequence data are available (1902-2001), are shown in Tables 3, 4, 5 and 6.

Both the concentration and type, i.e., composition of Replikins observed, were found to relate to the occurrence of influenza pandemics and epidemics. The concentration of Replikins in influenza viruses was examined by visually scanning the hemagglutinin amino acid sequences published in the National Library of Medicine "PubMed" data base for influenza strains isolated world wide from human and animal reservoirs year by year over the past century, i.e., 1900 to 2001. These Replikin concentrations (number of Replikins per 100 amino acids, mean+/−SD) were then plotted for each strain.

Figure 7:
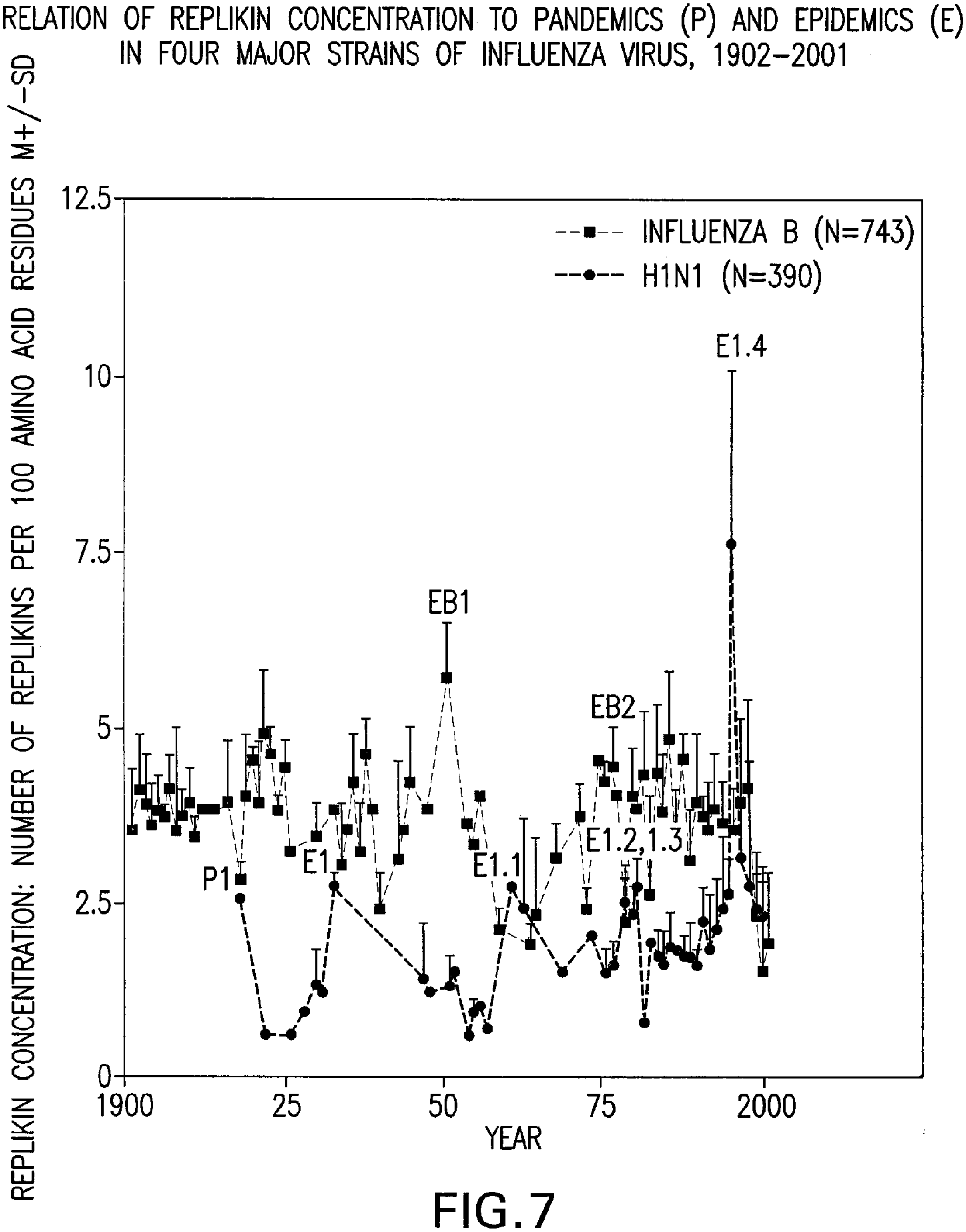
FIG. 7 is a graph showing the concentration of Replikins observed in hemagglutinin of influenza B and influenza A strain, H1N1, on a year by year basis from 1940 through 2001.
Figure 8:
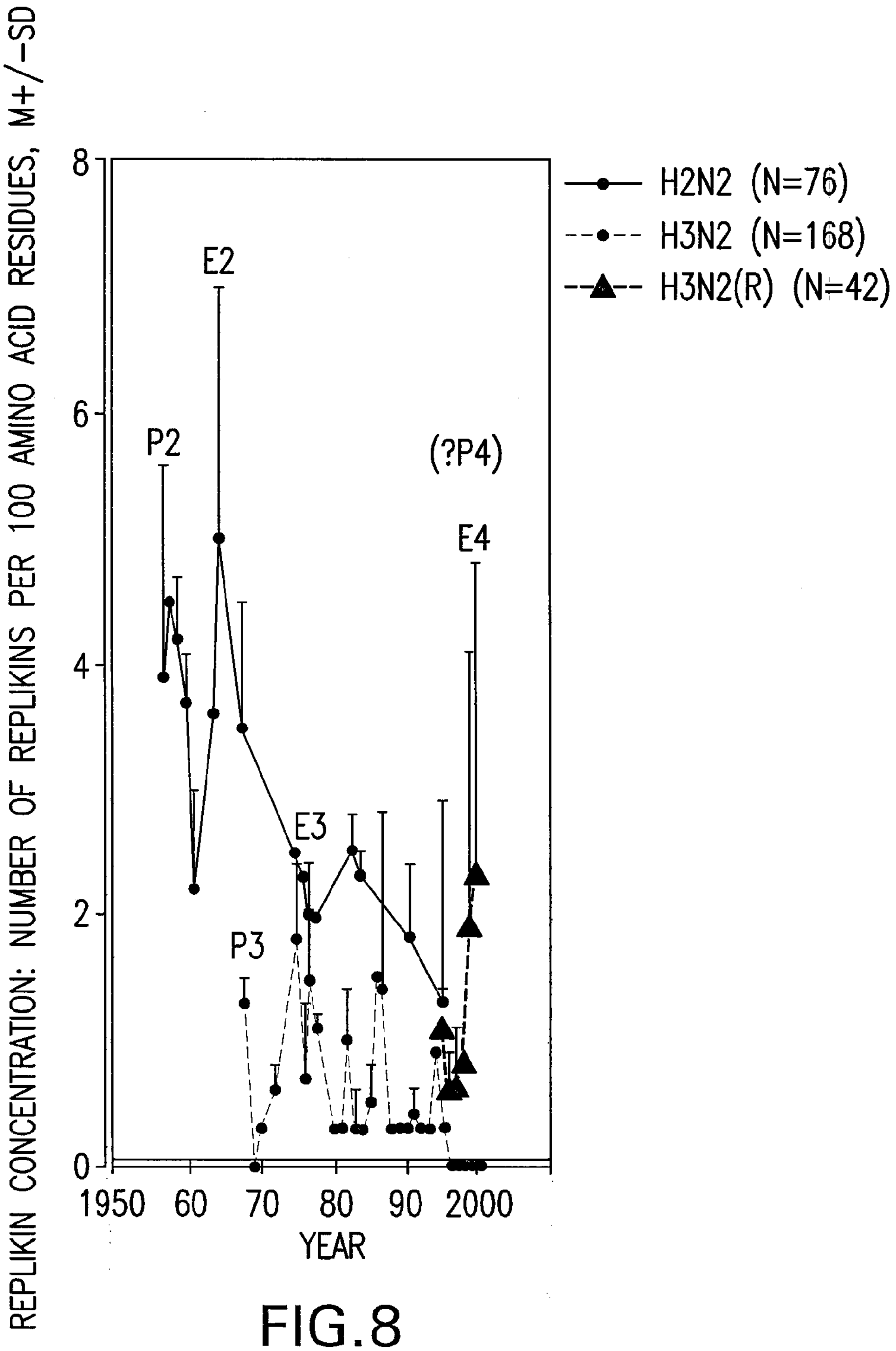
FIG. 8 is a graph of the Replikin concentration observed in hemagglutinin of influenza A strains, H2N2 and H3N2, as well as an emerging strain defined by its constituent Replikins, designated H3N2(R), on a year by year basis from 1950 to 2001.

The concentration of Replikins was found to directly relate to the occurrence of influenza pandemics and epidemics. The concentration of Replikins found in influenza B hemagglutinin and influenza A strain, H1N1, is shown in FIG. 7, and the concentration of Replikins found in the two other common influenza virus A strains, H2N2 and H3N2 is shown in FIG. 8 (H2N2, H3N2). The data in FIG. 8 also demonstrate an emerging new strain of influenza virus as defined by its constituent Replikins (H3N2(R)).

Each influenza A strain has been responsible for one pandemic: in 1918, 1957, and 1968, respectively. The data in FIGS. 7 and 8 show that at least one Replikin per 100 amino acids is present in each of the influenza hemagglutinin proteins of all isolates of the four common influenza viruses examined, suggesting a function for Replikins in the maintenance of survival levels of replication. In the 1990s, during the decline of the H3N2 strain, there were no Replikins in many isolates of H3N2, but a high concentration of new Replikins appeared in H3N2 isolates, which define the emergence of the H3N2(R) strain. See Tables 3, 4, 5 and 6.

TABLE 3

Replikin Sequences present in hemagglutinins of Influenza B viruses in each year for which amino acid sequences were available (1940-2001).
Influenza B Replikins Year Detected in Influenza B strain Peak in Figure 7: E

| | |
|---|---|
| kshfanlk (SEQ ID NO: 104) | 1940, 43, 51, 59, 75, 76, 77, 89, 90, 93, 97, 98, 99, 00, 01 |
| kshfanlkgtk (SEQ ID NO: 105) | 1940, 43, 51, 59, 75, 76, 77, 89, 90, 93, 97, 98, 99, 00, 01 |
| kshfanlkgtktrgklcpk (SEQ ID NO: 106) | 1940, 43, 51, 59, 75, 76, 77, 89, 90, 93, 97, 98, 99, 00, 01 |
| hekygglnk (SEQ ID NO: 107) | 1940, 43, 51, 59, 75, 76, 77, 89, 90, 93, 97, 98, 99, 00, 01 |
| hekygglnksk (SEQ ID NO: 108) | 1940, 43, 51, 59, 75, 76, 77, 89, 90, 93, 97, 98, 99, 00, 01 |

TABLE 3-continued

Replikin Sequences present in hemagglutinins of Influenza B viruses in each year for which amino acid sequences were available (1940-2001).

| Influenza B Replikins | Year Detected in Influenza B strain |
|---|---|
| | Peak in Figure 7: E |
| hekygglnkskpyytgehak (SEQ ID NO: 109) | 1940, 43, 51, 59, 75, 76, 77, 89, 90, 93, 97, 98, 99, 00, 01 |
| hakaigncpiwvk (SEQ ID NO: 110) | 1940, 43, 51, 59, 75, 76, 77, 89, 90, 93, 97, 98, 99, 00, 01 |
| hakaigncpiwvktplklangtk (SEQ ID NO: 111) | 1940, 43, 51, 59, 75, 76, 77, 89, 90, 93, 97, 98, 99, 00, 01 |
| hakaigncpiwvktplklangtkyrppak (SEQ ID NO: 112) | 1940, 43, 51, 59, 75, 76, 77, 89, 90, 93, 97, 98, 99, 00, 01 |
| hakaigncpiwvktplklangtkyrppakllk (SEQ ID NO: 113) | 1940, 43, 51, 59, 75, 76, 77, 89, 90, 93, 97, 98, 99, 00, 01 |
| k(a/v)silhevk (SEQ ID NO: 119) | 1940, 59, 90, 93 |
| kvwcasgrskvikgslpligeadclh (SEQ ID NO: 123) | 1940, 43, 59, 75, 76, 77, 89, 90, 98, 99, 00 |
| kpyytgehak (SEQ ID NO: 124) | 1940, 59, 89, 90, 93, 97, 98, 01 |
| hgvavaadlkstqeaink (SEQ ID NO: 128) | 1940, 59, 00 |
| hgvavaadlkstqeainkdtistqeaink (SEQ ID NO: 129) | 1940 |
| hsdneiqmvklygdsk (SEQ ID NO: 116) | |
| hsdneiqdkmvklygdskpqk (SEQ ID NO: 117) | |
| kygglnkskpyytgeh (SEQ ID NO: 122) | |
| kcmgtipsakasilhevk (SEQ ID NO: 125) | 1943, 75, 76, 77, 93 |
| klygdskpqkftssangvtth (SEQ ID NO: 130) | 1943, 75, 76, 77, 93, 97, 00 |
| hsdnetqmaklygdskpqk (SEQ ID NO: 131) | 1943, 75, 76, 77, 93 |
| hfanlkgtqtrgk (SEQ ID NO: 132) | 1959 |
| hfanlkgtktrgk (SEQ ID NO: 114) | 1976, 89, 90, 99, 00, 01 |
| hfanlkgtktrgklcpk (SEQ ID NO: 115) | 1976, 90 00, 01 |
| kprsalkckgfh (SEQ ID NO: 133) | 1988 |
| kctgtipsakasilhevk (SEQ ID NO: 121) | 1993 |
| hnvinaekapggpyk (SEQ ID NO: 126) | 1993, 97, 00 |
| hsdnetqmaklygdsk (SEQ ID NO: 127) | 1993, 97, 00 |
| hsdneiqmvklygdskpqk (SEQ ID NO: 118) | 1997, 98, 00 |
| kctgtipsakasilh (SEQ ID NO: 120) | 2000 |
| kskpyytgehakai(g/a)ncpiwvk (SEQ ID NO: 134) | 2000 |

1. Influenza B has not been responsible for any human pandemic.
2. Abbreviation for years: e.g., "43" = 1943, "01" = 2001.
3. The first year that a given Replikin appears is indicated at the beginning of the series of years in which that Replikin has been found.
4. Overlapping Replikin sequences are listed separately.
5. Return of replikins, absent for several years, in the two years before the epidemic of 1977, underlined, correlates with increased total Replikin concentration (Replikin Count = number of Replikins per 100 amino acid residues). See FIG. 7.

TABLE 4

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 E1 E1.1, 1.2, 1.3 E1.4) |
|---|---|
| **hp**(v/i)tigecp**k**yv(r/**k**)(s/t)(t/a)**k** (SEQ ID NO: 135) | 1918, 25, 28, 30, 31, 35, 47, 48, 51, 52, 55, 56, 57, 59, 63, 77, 79, 80, 81, 85, 87, 88, 89, 91, 92, 95, 96, 97, 98, 99, 00 |
| **h**dsnv**k**nly(e/g)**k**v(**k**/r)(n/s)ql(**k**/r)nna**k** (SEQ ID NO: 136) | 1918, 28, 30, 31, 77, 79, 80, 88, 91, 95, 98 |
| **h**dsnv**k**nly(e/g)**k**v(**k**/r)(n/s)ql**k** (SEQ ID NO: 137) | 1918, 28, 30, 31, 77, 79, 80, 88, 91, 95, 98 |
| **hk**c(nn/dd)(a/t/e)cmesv(r/**k**)ngtydyp**k**ysees**k**lnre(e/**k**)idgv**k** (SEQ ID NO: 138) | 1918, 30, 35, 77, 80, 98 |
| **hk**c(nn/dd)(a/t/e)cmesv(r/**k**)ngtydyp**k**ysees**k** (SEQ ID NO: 139) | 1918, 30, 35, 77, 80, 98 |
| **h**qn(e/g)qgsgyaadq**k**stqnai(d/n)gitn**k**vnsvie**k**mntqftavg**k**efn**k**le**k** (SEQ ID NO: 140) | 1918, 28, 30, 31, 35, 59, 79, 95 |
| **h**qn(e/g)qgsgyaadq**k**stqnai(d/n)gitn**k**vnsvie**k** (SEQ ID NO: 141) | 1918, 28, 30, 31, 35, 59, 79, 95 |
| **h**qn(e/g)qgsgyaadq**k**stqnai(d/n)gitn**k** (SEQ ID NO: 142) | 1918, 28, 30, 31, 35, 59, 79, 95 |
| **k**feifpktsswpn**h** (SEQ ID NO: 143) | 1918, 77 |

TABLE 4-continued

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 | | E1 | | E1.1, 1.2, 1.3 | | E1.4) | |
|---|---|---|---|---|---|---|---|---|
| kg(n/s/t)sypkl (n/s)ksy(v/t)nnk gkevlvlwgvh (SEQ ID NO: 144) | 1918, | | | 35, | 77, | | 96 | |
| ksy(v/t)nnkgkevl vlwgvh (SEQ ID NO: 145) | 1918, | | | 35, | 77, | | 96 | |
| hkcnnecmesvkngty dypkyseesklnreki dgvk (SEQ ID NO: 146) | | 1928, | 31, | | | 95 | | |
| hkcnnecmesvkngty dypkyseesk (SEQ ID NO: 147) | | 1928, | 31, | | | 95 | | |
| hkcnnecmesvkngty dypk (SEQ ID NO: 148) | | 1928, | 31, | | | 95 | | |
| hkcnnecmesvk (SEQ ID NO: 149) | | 1928, | 31, | | | 95 | | |
| hngkssfy(k/r)nll wlt(e/g)knglypnl sksyvnnkek (SEQ ID NO: 150) | | 1928, | | | | 95, | | 00 |
| hngkssfy(k/r)nll wlt(e/g)knglypnl sksyvnnk (SEQ ID NO: 151) | | 1928, | 31, | | | 95, | | 00 |
| hngkssfy(k/r)nll wlt(e/g)knglypnl sk (SEQ ID NO: 152) | | 1928, | 31, | | | 95, | | 00 |
| hngkssfy(k/r)nll wlt(e/g)k (SEQ ID NO: 153) | | 1928, | 31, | | | 95, | | 00 |

TABLE 4-continued

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 | E1 | E1.1, 1.2, 1.3 | E1.4) |
|---|---|---|---|---|
| **k**ssfy**k**nllwlte**k**ng lypnls**k**syvnn**k**e**k**e vlvlwgv**h** (SEQ ID NO: 154) | 1928, | 31, | | 95 |
| **k**nllwlte**k**nglypnl s**k**syvnn**k**e**k**evlvlw gv**h** (SEQ ID NO: 155) | 1928, | 31, | | 95 |
| **k**nglypnls**k**syvnn**k** e**k**evlvlwgv**h** (SEQ ID NO: 156) | 1928, | 31, | | 95, 96, 00 |
| ksy(v/a)nn**k**e**k**ev (l/-)(v/-)lwgv**h** (SEQ ID NO: 157) | 1928, | 31, 51, | | 95, 96, 98, 00 |
| **k**esswpnhtvt**k** (SEQ ID NO: 158) | 1928, | 31, | | 95 |
| **h**et(t/n)**k**gvtaacp yagassfyrnllwly**k** **k**ensyp**k**ls**k**syvnn**k** (SEQ ID NO: 159) | 1930, | 35 | | |
| **h**et(t/n)**k**gvtaacp yagassfyrnllwly**k** **k**ensyp**k**ls**k** (SEQ ID NO: 160) | 1930, | 35 | | |
| **k**feifp**k**tsswpnevl vlwgv**h** (SEQ ID NO: 161) | 1930 | | | |
| **k**erswp**kh** (SEQ ID NO: 162) | | 1947, 51, 52, 55, 56, | 79, 82 | |
| **k**ls**k**syvnn**k**e**k**evlv lwqv**h** (SEQ ID NO: 163) | | 1947, 51 | | |
| **k**nn**k**e**k**evlvlwqv**h** (SEQ ID NO: 164) | | 1947 | | |

TABLE 4-continued

H1N1 Replikin Sequences present in HINI hemagglutinins of Influenza viruses in each year for which amino acid sequences were available (1918-2000)
H1N1 Replikin Year Detected in Influenza
H1N1 Strain

| Peak in FIG. 7: P1 | E1 | | E1.1, 1.2, 1.3 | | E1.4) | |
|---|---|---|---|---|---|---|
| **h**(**k**/n)(g/q)**k**ssfy (r/**k**)nllwlte**k**ng (l/s)yp(n/t)ls**k** syann**k**e**k** (SEQ ID NO: 165) | 1948 | | 79, | 89, | 96 | |
| **h**(**k**/n)(g/q)**k**ssfy (r/**k**)nllwlte**k** (SEQ ID NO: 166) | 1948 | | 79, | 89, | 96 | |
| **h**a**kk**ssfy**k** (SEQ ID NO: 167) | 1951, | 57, 59 | | | | |
| **h**ng**k**lcrl**k**g**k** (SEQ ID NO: 168) | 1951, 52, 55, 56, 57, 59, | | 79, | | | |
| **h**y**k**lnn(q/g)**kk** (SEQ ID NO: 169) | 1956, | | | | | 00 |
| **h**diyrdeainnrfqiq gv**k**ltqgy**k** (SEQ ID NO: 170) | 1956 | | | | | |
| **k**gngcfeif**hk** (SEQ ID NO: 171) | 1956 | | | | | |
| **k**lnrlie**k**tnd**k**yhqi e**k** (SEQ ID NO: 172) | 1956 | | | | | |
| **k**lnrlie**k**tnd**k**y**h** (SEQ ID NO: 173) | 1956 | | | | | |
| **k**c**h**td**k**gslstt**k** (SEQ ID NO: 174) | 1956 | | | | | |
| **k**inngdya**k**lyiwgv**h** (SEQ ID NO: 175) | 1956 | | | | | |
| **h**ng**k**lcr**k**giaplqlg **k** (SEQ ID NO: 176) | 1959, | | 82 | | | |

TABLE 4-continued

H1N1 Replikin Sequences present in HINI hemagglutinins of Influenza viruses in each year for which amino acid sequences were available (1918-2000)
H1N1 Replikin Year Detected in Influenza
H1N1 Strain

| | Peak in FIG. 7: P1 | E1 | E1.1, 1.2, 1.3 | E1.4) |
|---|---|---|---|---|
| **h**etnrqvtaacpyaga nsffrnliwlv**kk**ess yp**k**ls**k** (SEQ ID NO: 177) | | | 1963, 81 | |
| **h**etnrqvtaacpyaga nsffrnliwlv**kk**ess yp**k** (SEQ ID NO: 178) | | | 1963, 81 | |
| **h**pptstdqqslyqnad ayifvgss**k**ynr**k**f**k** (SEQ ID NO: 179) | | | 1963, 81 | |
| **h**pptstdqqslyqnad ayifvgss**k**ynr**k**f**k**p eia (SEQ ID NO: 180) | | | 1963, 81 | |
| **h**diyrdeainnrfqiq gv**k**itqgy**k** (SEQ ID NO: 181) | | | 1977, 79, | 91 |
| **h**qneqgsgyaadq**k**st qnaidgitn**k**vnsvie **k**mntqftavg**k** (SEQ ID NO: 182) | | | 1977 | |
| **h**qneqgsgyaadq**k**st qnaidgitn**k**vnsvie **k** (SEQ ID NO: 183) | | | 1977 | |
| **h**qneqgsgyaadq**k**st qnaingitn**k**vnsvie **k**mntqftavg**k**efn**k**l e**k** (SEQ ID NO: 184) | | | 1979, | 91 |
| **h**ng**k**lcrl**k**giaplql g**k** (SEQ ID NO: 185) | | | 1979 | |
| **h**kcnnecmesv**k** (SEQ ID NO: 186) | | | 1979 | |

TABLE 4-continued

H1N1 Replikin Sequences present in HINI hemagglutinins of Influenza viruses in each year for which amino acid sequences were available (1918-2000)
H1N1 Replikin Year Detected in Influenza
H1N1 Strain

| | Peak in FIG. 7: P1 | E1 | E1.1, 1.2, 1.3 | E1.4) |
|---|---|---|---|---|
| kfeifpkasswpnh (SEQ ID NO: 187) | | | 1981 | |
| hdsnvknlyekvrsqlrnnak (SEQ ID NO: 188) | | | 1981 | |
| kvnsvikkmntqfaavgkefnh (SEQ ID NO: 189) | | | 1981 | |
| khngklck (SEQ ID NO: 190) | | | 1981 | |
| kkgtsypklsksythnkgkevlvlwgvh (SEQ ID NO: 191) | | | 1981 | |
| kgtsypklsksythnkgkevlvlwgvh (SEQ ID NO: 192) | | | 1981 | |
| klsksythnkgkevlvlwgvh (SEQ ID NO: 193) | | | 1981 | |
| ksythnkgkevlvlwgvh (SEQ ID NO: 194) | | | 1981 | |
| kgvtascshk (SEQ ID NO: 195) | | | 1985, 87 | |
| kgvtascshkgrssfyrnllwlteknglypnlsk (SEQ ID NO: 196) | | | 1985, 87 | |
| kgnsypklsksyvnnkekevlvlwgih (SEQ ID NO: 197) | | | 1988 | |
| kefnhlek (SEQ ID NO: 198) | | | 1988 | |

TABLE 4-continued

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 | E1 | E1.1, 1.2, 1.3 | E1.4) |
|---|---|---|---|---|
| hpptstdqqslyqnad ayvfvgsskynkkfkp eiatrpk (SEQ ID NO: 199) | | | 1988 | |
| hpptstdqqslyqnad ayvfvgsskynkkfk (SEQ ID NO: 200) | | | 1988 | |
| hegkssfyrnllwlte kegsypklknsyvnk (SEQ ID NO: 201) | | | 1991 | |
| hegkssfyrnllwlte kegsypk (SEQ ID NO: 202) | | | 1991 | |
| hkcdnecmesvrngty dypkyseesk (SEQ ID NO: 203) | | | 1991 | |
| kesswpnhtvtk (SEQ ID NO: 204) | | | 1991, 92 | |
| knllwlteknglypnl sksyvnnkekeilvlw gvh (SEQ ID NO: 205) | | | 1991, 92, 96 | |
| hngkssfy(k/m)(n/ -)llwlt(e/g)(-/ k)knglypnlsk (SEQ ID NO: 206) | | | 1991, 92, 96, | 00 |
| hngkssfyknllwltek (SEQ ID NO: 207) | | | 1991, 92, 96 | |
| htvtkgvtascshngk ssfyknllwltekngl ypnlsksyvnnkekev lvlwgvh (SEQ ID NO: 208) | | | 1995 | |

TABLE 4-continued

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 | E1 | E1.1, 1.2, 1.3 | E1.4) | |
|---|---|---|---|---|---|
| **h**tvt(**k**/g)gv(t/s) ascs**h**ngkssfy(**k**/ m)(n/-)llwlt(e/ g)**k**(-n/**k**)glypnls **k** (SEQ ID NO: 209) | | | | 1995, | 00 |
| **h**tvt**k**gvtascs**h**ng**k** ssfy**k**nllwlte**k** (SEQ ID NO: 210) | | | | 1995 | |
| **k**yvrstklrmvtglrn ipsiqsrglfgaiagf ieggwtgmidgwygy**h** (SEQ ID NO: 211) | | | | 1995 | |
| **h**qneqgsgyaadq**k**st qnaingitn**k**vnsiie **k**mntqftavg**k** (SEQ ID NO: 212) | | | | 1995 | |
| **h**qneqgsgyaadq**k**st qnaingitn**k**vnsiie **k** (SEQ ID NO: 213) | | | | 1995 | |
| **h**qneqgsgyaadq**k**st qnaingitn**k** (SEQ ID NO: 214) | | | | 1995 | |
| **h**sgarsfymllwiv**kk** gnsyp**k** (SEQ ID NO: 215) | | | | 1996 | |
| **h**sgarsfymllwiv**kk** gnsyp**k**ln**k** (SEQ ID NO: 216) | | | | 1996 | |
| **h**sgarsfymllwiv**kk** gnsyp**k**ln**k**sytnd**k** (SEQ ID NO: 217) | | | | 1996 | |

TABLE 4-continued

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 | E1 | E1.1, 1.2, 1.3 | E1.4) |
|---|---|---|---|---|
| hsgarsfymllwivkk gnsypklnksytndkg k (SEQ ID NO: 218) | | | | 1996 |
| htvskgvttscshngk (SEQ ID NO: 219) | | | | 1996 |
| katswpnhettk (SEQ ID NO: 220) | | | | 1996 |
| kqvttscshnqk (SEQ ID NO: 221) | | | | 1996 |
| kgnsypklnksytndk gkevlviwgvh (SEQ ID NO: 222) | | | | 1996 |
| klnksytndkgkevlv iwgvh (SEQ ID NO: 223) | | | | 1996 |
| ksytndkgkevlviwg vh (SEQ ID NO: 224) | | | | 1996 |
| hnqkssfyrnllwlt (e/q)knglypnlsks y(v/a)annkek (SEQ ID NO: 225) | | | | 1997, 98, 99 |
| hpitigecpkyvrsak (SEQ ID NO: 226) | | | | 1997 |
| hqneqgsgyaadqkst qnaingitnkvnsvie kmntqftavgk (SEQ ID NO: 227) | | | | 1998 |
| hqneqgsgyaadqkst qnaingitnkvnsvie k (SEQ ID NO: 228) | | | | 1998 |

TABLE 4-continued

H1N1 Replikin Sequences present in HINI hemagglutinins of Influenza viruses in each year for which amino acid sequences were available (1918-2000)
HIN1 Replikin Year Detected in Influenza
H1N1 Strain

| | Peak in FIG. 7: P1 | E1 | E1.1, 1.2, 1.3 | E1.4) |
|---|---|---|---|---|
| hngkssfyrnllwlte knglypnlsksyvnnk ek (SEQ ID NO: 229) | | | | 1998 |

1. Influenza H1N1 was responsible for the human pandemic (global distribution) of 1918.
2. Abbreviation for years: eg. "96" = 1996.
3. The first year that a given Replikin appears is indicated at the beginning of the series of years in which that Replikin has been found in this work.
4. Overlapping Replikin sequences are listed separately.
5. Increase in number of new Replikin structures occurs in years of epidemics (underlined): eg. 1918 and 1977 and correlates with increased total Replikin concentration (number of Replikins per 100 amino acid residues). See FIG. 7.

TABLE 5

Replikin Sequences present in hemagglutinins of Influenza H2N2 viruses in years 1957-2000

| Influenza H2N2 Replikins | Year Detected in Influenza H2N2 strain (Peak in FIG. 8: P2 E2) |
|---|---|
| khfekvkilpk (SEQ ID NO: 230) | 1957, 58, 59, 60, 61, 64, 65, 68, 78, 83, 84, 91 |
| khllssvkhfekvk (SEQ ID NO: 231) | 1957, 58, 59, 60, 61, 83, 84, 91 |
| ha(k/q/m)(d/n)ilekthngk (SEQ ID NO: 232) | 1957, 58, 59, 60, 61, 64, 65, 68, 78, 83, 84, 91, 95 |
| ha(k/q/m)(d/n)ilekthngklc(k/r) (SEQ ID NO: 233) | 1957, 58, 59, 60, 61, 64, 65, 68, 78, 83, 84, 91, 95 |
| hnvhpltigecpkyvksek (SEQ ID NO: 234) | 1957, 58, 59, 65, 68 |
| hpltigecpkyvksek (SEQ ID NO: 235) | 1957, 58, 59, 65, 68, 64, 65, 68, 78, 83, 84, 91 |
| khllssvkhfekvkilpk (SEQ ID NO: 236) | 1957, 58, 59, 60, 61, 64, 65, 68, 78 |
| krqssgimktegtlencetkcqtplgainttlpfhnvh (SEQ ID NO: 237) | 1957, 59, 83 |
| kgsnyp(v/i)ak(g/r)synntsgeqmliiwq(v/i)h (SEQ ID NO: 238) | 1957, 58, 59, 61, 83, 91, 95 |
| httlgqsracaysgnpsffrnmvwltekgsnypvak (SEQ ID NO: 239) | 1957 |
| khfekvk (SEQ ID NO: 240) | 1957, 59, 65 |
| kiskrgssgimktegtlencetkcqtplgainttlpfh (SEQ ID NO: 241) | 1957, 59, 65, 91 |
| krgssgimktegtlencetkcqtplgainttlpfh (SEQ ID NO: 242) | 1957, 59, 65, 91 |
| ktegtlencetkcqtplgainttlpfh (SEQ ID NO: 243) | 1957, 59, 65, 91 |
| kiskrgssgimktegtlencetkcqtplgainttlpfh (SEQ ID NO: 244) | 1957, 59, 65, 91 |
| ktegtlencetkcqtplgainttlpfhn(v/i)h (SEQ ID NO: 245) | 1957, 59, 65, 91 |
| kiskrgssgimktegtlencetkcqtplgainttlpfh (SEQ ID NO: 246) | 1957, 59, 65, 91 |
| k(e/g)snypvakgsynntsgeqmliiwgvh (SEQ ID NO: 247) | 1957, 60, 65 |
| hpltigecpkyvksek (SEQ ID NO: 248) | 1957, 60, 65 |
| kcqtplgaikttlpfh (SEQ ID NO: 249) | 1957, 65 |
| hhsndqgsgyaadkestqka(f/i)dgitnkvnsviek--mntqfeavgklf(n/s)nleklenlnkk (SEQ ID NO: 250) | 1961, 65, 68, 83, 84 |
| hsndqgsgyaadkestqka(f/i)dgitnkvnsviek--mntqfeavgklf(n/s)nleklenlnkk (SEQ ID NO: 251) | 1961, 65, 68, 83, 84 |
| hsndqgsgyaadkestqka(f/i)dgitnk (SEQ ID NO: 252) | 1961, 65, 68, 83, 84 |
| hdsnvrnlydkvrmqlrdnak (SEQ ID NO: 253) | 1964, 68, 76, 84, 91 |
| hkcddecmnsvkngtydypklnrneikgvk (SEQ ID NO: 254) | 1964, 65, 68, 76, 83, 84, 91 |
| hkcddecmnsvkngtydypklnrneik (SEQ ID NO: 255) | 1964, 65, 68, 76, 83, 84, 91 |
| hkcddecmnsvkngtydypk (SEQ ID NO: 256) | 1964, 65, 68, 76, 83, 84, 91 |

TABLE 5-continued

| Replikin Sequences present in hemagglutinins of Influenza H2N2 viruses in years 1957-2000<br>Influenza H2N2 Replikins | Year Detected in Influenza H2N2 strain<br>(Peak in FIG. 8: P2 E2) |
|---|---|
| **hk**cddecmnsv**k** (SEQ ID NO: 257) | 1964, 65, 68, 76, 83, 84, 91 |
| **k**gsnypva**k**gsynntngeqiliiwgv**h** (SEQ ID NO: 258) | 1976, 78 |
| **h**sndqgsgyaad**k**estq**k**avdgitn**k**vnsvie**k**mntqfeavg**k** (SEQ ID NO: 259) | 1976, 91 |
| **k**rgssgim**k**tegtlencet**k**cqtplgainttlpf**h** (SEQ ID NO: 260) | 1976, 78, 83, 84 |
| **h**pltigecp**k**yv**k**se**k** (SEQ ID NO: 261) | 1976 |
| **h**a**k**dile**k**thng**k**lc**k** (SEQ ID NO: 262) | 1976 |

1. Influenza H2N2 was responsible for the human pandemic (global distribution) of 1957.
2. Abbreviation for years: eg. "58" = 1958.
3. The first year that a given Replikin appears is indicated at the beginning of the series of years in which that Replikin has been found.in this work.
4. Overlapping Replikin sequences are listed separately.
5. Increase in number of new Replikin structures occurs in years of epidemics (underlined): eg. 1957 and 1965 and correlates with increased total Replikin concen tration (number of Replikins per 100 amino acid residues). See FIG. 8.

TABLE 6

H3N2 Replikin Sequences present in H3N2 hemagglutinins of Influenza viruses in each year for which amino acid sequences were available (1968-2000)

| Influenza H3N2 Replikins | Year Detected in Influenza H3N2 strain Influenza Replikins (Peak in FIG. 8: P3 E3 E4) |
|---|---|
| **h**dvyrdealnnrfqi**k**gvelksgy**k** (SEQ ID NO: 263) | 1968, 72, 75 96, 97, 98 |
| htidltdsemn**k**lfertr**k** (SEQ ID NO: 264) | 1968 |
| **k**fliqie**k** (SEQ ID NO: 265) | 1968, 72, 75, 77 96, 97, 98 |
| **k**tne**k**f**h**(g/q)ie**k** (SEQ ID NO: 266) | 1968 86 98 |
| **k**lnr(v/l)ie**k**tne**k**f**h** (SEQ ID NO: 267) | 1968, 72, 75, 77 97, 98 |
| **h**qie**k**efsevegriqdle**k**yvedt**k** (SEQ ID NO: 268) | 1968, 72, 98 |
| **k**icnnp**hk** (SEQ ID NO: 269) | 1975 |
| **k**lnrvi**kk**tne**k**f**h** (SEQ ID NO: 270) | 1975 |
| **h**d(i,v)yrdealnnrfqi**k**(g/q)ve(r/**k**)s(q/g)y**k** (SEQ ID NO: 271) | 1975, 76, 77 86 |
| **h**qie**k**efsevegriqdle**k**yvedt**k** (SEQ ID NO: 272) | 1975 |
| **k**yvedt**k**idlwsynaellvalenq**h** (SEQ ID NO: 273) | 1975 |
| **k**yv**k**qnsl**k**latgmrnvpe**k**qtrglfgaiagfiengwegmidgwygfr**h** (SEQ ID NO: 274) | 1975 |
| **k**efsevegriqdle**k**yvedt**k**idlwsynaellvalenq**h** (SEQ ID NO: 275) | 1975 2000 |
| **h**qn(s/e)(e/q)g(t/s)g(q/y)aad(l/q)**k**--stq(a/n)a (i/l)d(q/g)I(n/t)(g/n)**k**(l/v)n(r/s)vi(e/c)**k** (SEQ ID NO: 276) | 1975 2000 |
| **h**cd(g/q)f(q,r)ne**k**wdlf(v,/i)er(s/t)**k** (SEQ ID NO: 277) | 1975, 76, 77, 78, 80, 81, 82, 83, 84, 85, 86, 88, 89, 90, 91, 92, 93, 94, 95, 96, 97, 98 |
| **h**tidltdsemn**kk**lfertr**k** (SEQ ID NO: 278) | 1977, |
| ksgstypvl**k**vtmpnndnfd**k**lyiwgv**h** (SEQ ID NO: 279) | 1977 |
| **k**lnwlt**k**sgntypvinvtmpnndnfd**k**lviwgv**h** (SEQ ID NO: 280) | 1982 |
| **h**tidltdsemn**k**lfektr**k** (SEQ ID NO: 281) | 1986 |

TABLE 6-continued

H3N2 Replikin Sequences present in H3N2 hemagglutinins of Influenza viruses in each year for which amino acid sequences were available (1968-2000)

| Influenza H3N2 Replikins | Year Detected in Influenza H3N2 strain Influenza Replikins (Peak in FIG. 8: P3 E3 E4) |
|---|---|
| klnrliektnekthqtek (SEQ ID NO: 282) | 1987 |
| htgkssvmrsdapidfcnsecitpnqsipndkpfqnvnkitygacpk (SEQ ID NO: 283) | 1994 |
| htgkssvmrsdapidfcnsecitpnqsipndkpfqnvnk (SEQ ID NO: 284) | 1994 |
| hpstdsdqtslyvrasgrvtvstkrsqqtvipk (SEQ ID NO: 285) | 1994 |
| kyvedtkidlwsynaellvalenqh (SEQ ID NO: 286) | 1997, 98 |
| klfertrkqlrenaedmgngcfkiyh (SEQ ID NO: 287) | 1998 |
| krrsiksffsrinwlh (SEQ ID NO: 288) | 1998 |
| hpvtigecpky(v/r)kstk (SEQ ID NO: 289) | 2000 |
| kgnsypklsklsksyiinkkkevlviwgih (SEQ ID NO: 290) | 2000 |
| klsklsks(v/y)iinkkkevlviwgih (SEQ ID NO: 291) | 2000 |
| klsks(v/y)iinkkkevlviwgih (SEQ ID NO: 292) | 2000 |

1. Influenza H3N2 was responsible for the human pandemic (global distribution) of 1968.
2. Abbreviation for years: eg. "77" = 1977.
3. The first year that a given Replikin appears is indicated at the beginning of the series of years in which that Replikin has been found.
4. Overlapping Replikin sequences are listed separately.
5. Increase in number of new Replikin structures occurs in years of epidemics (underlined): eg. 1975 and correlates with increased total Replikin concentration (number of Replikins per 100 amino acid residues). See FIG. 8.

Several properties of Replikin concentration are seen in FIG. 7 and FIG. 8 to be common to all four influenza virus strains. First, the concentration is cyclic over the years, with a single cycle of rise and fall occurring over a period of two to thirty years. This rise and fall is consistent with the known waxing and waning of individual influenza virus strain predominance by hemagglutinin and neuraminidase classification. Second, peak Replikin concentrations of each influenza virus strain previously shown to be responsible for a pandemic were observed to relate specifically and individually to each of the three years of the pandemics. For example, for the pandemic of 1918, where the influenza virus strain, H1N1, was shown to be responsible, a peak concentration of the Replikins in H1N1 independently occurred (P1); for the pandemic of 1957, where H2N2 emerged and was shown to be responsible, a peak concentration of the Replikins in H2N2 occurred (P2); and for the pandemic of 1968, where H3N2 emerged and was shown to be the cause of the pandemic, a peak concentration of the Replikins in H3N2 occurred (P3). Third, in the years immediately following each of the above three pandemics, the specific Replikin concentration decreased markedly, perhaps reflecting the broadly distributed immunity generated in each case. Thus, this post-pandemic decline is specific for H1N1 immediately following the pandemic (P1) for which it was responsible, and is not a general property of all strains at the time. An increase of Replikin concentration in influenza B repeatedly occurred simultaneously with the decrease in Replikin concentration in H1N1, e.g., EB1 in 1951 and EB2 in 1976, both associated with influenza B epidemics having the highest mortality. (Stuart-Harris, et al., Edward Arnold Ltd. (1985). Fourth, a secondary peak concentration, which exceeded the primary peak increase in concentration, occurred 15 years after each of the three pandemics, and this secondary peak was accompanied by an epidemic: 15 years after the 1918 pandemic in an H1N1 'epidemic' year (E1); eight years after the 1957 pandemic in an H2N2 'epidemic' year (E2); and occurred seven years after the 1968 pandemic in an H3N2 'epidemic' year (E3). These secondary peak concentrations of specific Replikins may reflect recovery of the strain. Fifth, peaks of each strain's specific Replikin concentration frequently appear to be associated with declines in Replikin concentration of one or both other strains, suggesting competition between strains for host sites. Sixth, there is an apparent overall tendency for the Replikin concentration of each strain to decline over a period of 35 years (H2N2) to 60 years (influenza B). This decline cannot be ascribed to the influence of vaccines because it was evident in the case of influenza B from 1940 to 1964, prior to common use of influenza vaccines. In the case of influenza B, Replikin recovery from the decline is seen to occur after 1965, but Replikin concentration declined again between 1997 and 2000 (FIG. 7). This correlates with the low occurrence of influenza B in recent case isolates. H1N1 Replikin concentration peaked in 1978-1979 (FIG. 7) together with the reappearance and prevalence of the H1N1 strain, and then peaked in 1996 coincident with an H1N1 epidemic. (FIG. 7). H1N1 Replikin concentration also declined between 1997 and 2000, and the presence of H1N1 strains decreased in isolates obtained during these years. For H2N2 Replikins, recovery from a 35 year decline has not occurred (FIG. 8), and this correlates with the absence of H2N2 from recent isolates. For H3N2, the Replikin concentration of many isolates fell to zero during the period from 1996 to 2000, but other H3N2 isolates showed a significant, sharp increase in Replikin concentration. This indicates the emergence of a substrain of H3N2, which is designated herein as H3N2(R).

FIGS. 7 and 8 demonstrate that frequently, a one to three year stepwise increase is observed before Replikin concentration reaches a peak. This stepwise increase proceeds the occurrence of an epidemic, which occurs concurrently with the Replikin peak. Thus, the stepwise increase in concentration of a particular strain is a signal that particular strain is the most likely candidate to cause an epidemic or pandemic.

Currently, Replikin concentration in the H3N2(R) strain of influenza virus is increasing (FIG. 8, 1997 to 2000). Three similar previous peak increases in H3N2 Replikin concentration are seen to have occurred in the H3N2-based pandemic of 1968 (FIG. 8), when the strain first emerged, and in the H3N2-based epidemics of 1972 and 1975 (FIG. 8). Each of these pandemic and epidemics was associated with excess mortality. (Ailing, et al., Am J. Epidemiol., 113(1):30-43 (1981). The rapid ascent in concentration of the H3N2(R) subspecies of the H3N2 Replikins in 1997-2000, therefore, statistically represents an early warning of an approaching severe epidemic or pandemic. An H3N2 epidemic occurred in Russia in 2000 (FIG. 8, E4); and the CDC report of December 2001 states that currently, H3N2 is the most frequently isolated strain of influenza virus worldwide. (Morbidity and Mortality Weekly Reports (MMWR), Center for Disease Control; 50(48):1084-68 (Dec. 7, 2001).

In each case of influenza virus pandemic or epidemic new Replikins emerge. There has been no observation of two of the same Replikins in a given hemagglutinin in a given isolate. To what degree the emergence of a new Replikin represents mutations versus transfer from another animal or avian pool is unknown. In some cases, each year one or more of the original Replikin structures is conserved, while at the same time, new Replikins emerge. For example, in influenza virus B hemagglutinin, five Replikins were constantly conserved between 1919 and 2001, whereas 26 Replikins came and went during the same period (some recurred after several years absence). The disappearance and re-emergence years later of a particular Replikin structure suggests that the Replikins return from another virus host pool rather than through de novo mutation.

Figure 11:
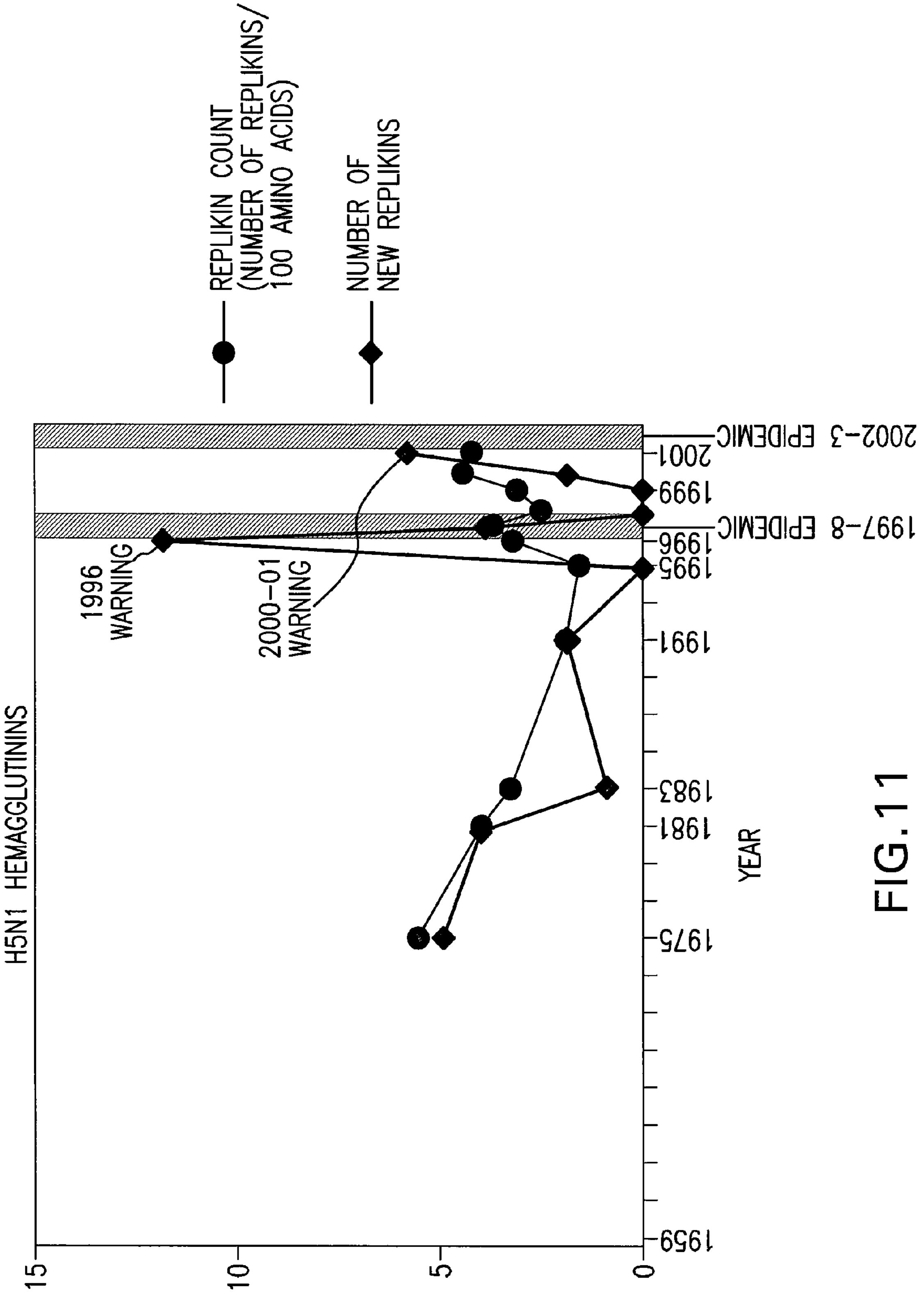
FIG. 11 is a chart depicting the Replikin count per year for H5N1 Hemagglutinins.

In the case of H1N1 Replikins, the two Replikins present in the P1 peak associated with the 1918 pandemic were not present in the recovery E1 peak of 1933, which contains 12 new Replikins Constantly conserved Replikins, therefore, are the best choice for vaccines, either alone or in combination. However, even recently appearing Replikins accompanying one year's increase in concentration frequently persist and increase further for an additional one or more years, culminating in a concentration peak and an epidemic, thus providing both an early warning and time to vaccinate with synthetic Replikins (see for example, H1N1 in the early 1990's, FIG. 7; see also, for example, H5N1 1995-2002, FIG. 11, "Replikin Count" (number of Replikins per 100 amino acids) refers to Replikin concentration) and FIG. 15).

The data in FIGS. 7, 8, 11 and 15 demonstrate a direct relationship between the presence and concentration of a particular Replikin in influenza protein sequences and the occurrence of pandemics and epidemics of influenza. Thus, analysis of the influenza virus hemagglutinin protein sequence for the presence and concentration of Replikins provides a predictor of influenza pandemics and/or epidemics, as well as a target for influenza vaccine formulation. It is worth noting again with reference to this data, previously, no strain-specific chemical structures were known with which to predict the strains that would predominate in coming influenza seasons, nor to devise annual mixtures of whole-virus strains for vaccines.

Similar to the findings of strain-specific Replikin Count increases in the influenza group one to three years prior to the occurrence of a strain-specific epidemics, the increase in Replikin Count of the coronavirus nucleocapsid protein has also been identified. Replikin Counts of the coronavirus nucleocapsid protein has increased as follows: 3.1 (±1.8) in 1999; 3.9 (±1.2) in 2000; 3.9 (±1.3) in 2001; and 5.1 (±3.6) in 2002. This pre-pandemic increase supports the finding that a coronavirus is responsible for the current (2003) SARS pandemic. (See Table 7)

Thus, monitoring Replikin structure and Replikin Count provides a means for developing synthetic strain-specific preventive vaccination and antibody therapies against the 1917-1918 Goose Replikin and its modified and accompanying Replikins as observed in both influenza and coronavirus strains.

Figure 9:
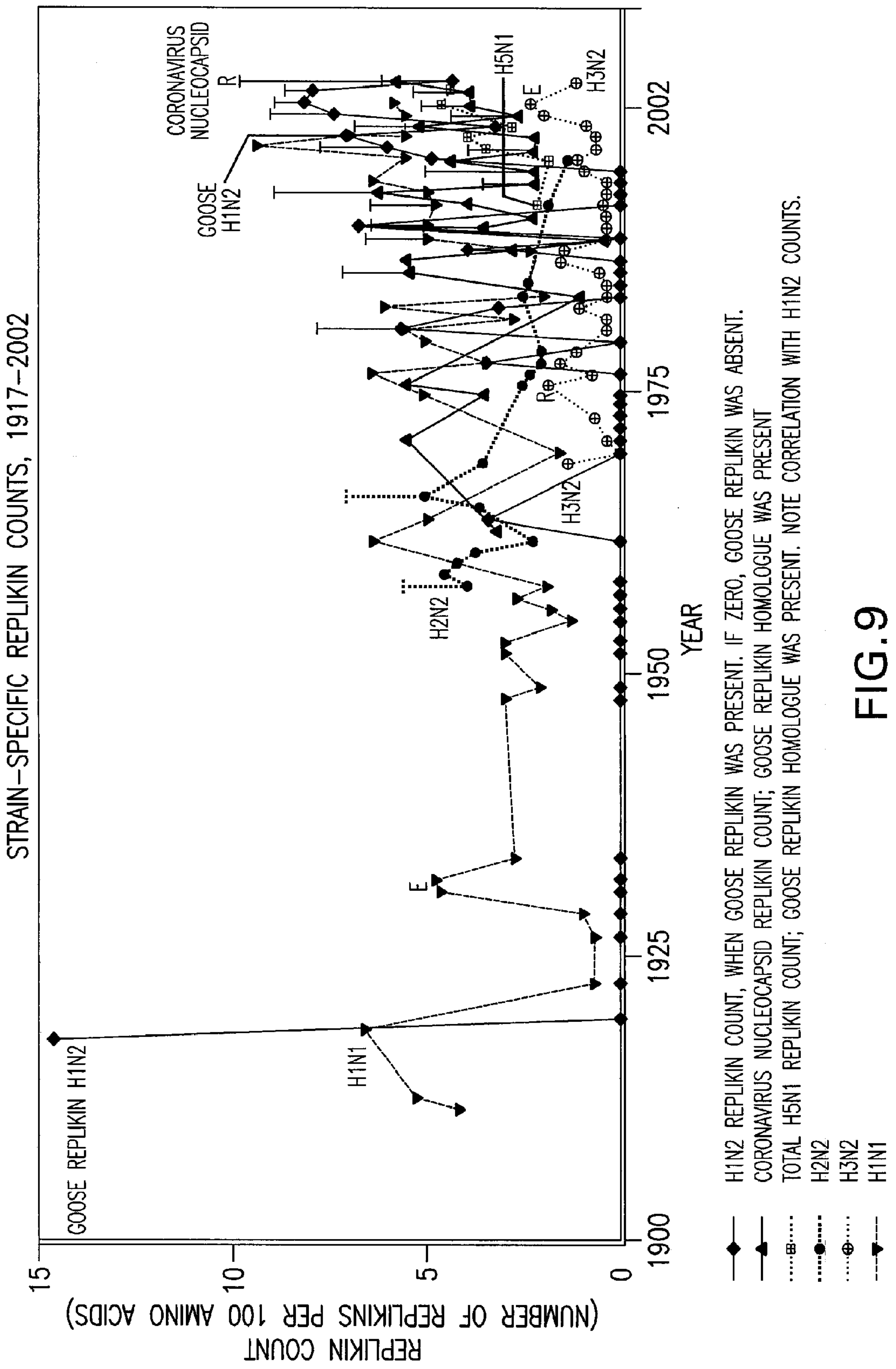
FIG. 9 is a graph depicting the Replikin count per year for several virus strains, including the coronavirus nucleocapsid Replikin, from 1917 to 2002.

FIG. 10 depicts the automated Replikin analysis of nucleocapsid coronavirus proteins for which the protein sequence is available on isolates collected from 1962 to 2003. Each individual protein is represented by an accession number and is analyzed for the presence of Replikins. The Replikin Count (number of Replikins per 100 amino acid) is automatically calculated as part of the automated Replikin analysis. For each year, the mean (±Standard deviation (S.D.)) Replikin Count per year is automatically calculated for all Replikin Counts that year. This example of early warning of increasing replication, before an epidemic, of a particular protein (the nucleocapsid protein) in a particular virus strain (the coronavirus) is comparable to the increase seen in strains of influenza virus preceding influenza epidemics and pandemics (FIGS. 7, 8, 11 and 15). It may be seen that the Replikin Count rose from 1999 to 2002, consistent with the SARS coronavirus pandemic, which emerged at the end of 2002 and has persisted into 2003. FIG. 9 provides a graph of the Replikin Counts for several virus strains, including the coronavirus nucleocapsid Replikin, from 1917 to 2002.

TABLE 7

| Replikin Sequence<br>1 2 3 4 5 6 7 8 9 10 11 12 13 14 15 16 17 18 19 20 21 22 23 24 25 26 27 28 29 | 'Multi-K' Replikins: Length | % Untreated Mortality |
|---|---|---|
| A. INFLUENZA, SARS AND OTHER CORONAVIRUSES | | |
| k k g t s y p k l s k s y t n n k g k e v l v l w g v h h | 29 | |
| k k g t s y p k l s k s y t n n k g k e v l v l w g v h h | 29 | 2.5 |
| l k e d l y p k l r k s v v h n k k k e v l v i w g i h h | 29 | |
| l k e n s y p k l r k s i i i n k k k e v l v i w g i h h | | |
| k k g t s y p k l s k s y t n n k k k e v l v l w g v h h | 29 | |
| k k n s a y p t I k r s y n n t n q e d l l v l w g i h h | >37 | |
| k k s a k t g t p k p s r n q s p a s s q t s a k s l a h | >37 | |
| k k l g v d t e k q q q r s k s k e r s n s k t r d t t p | >37 | |
| k n g l y p n l s k s y a n n k e k e v l i l w g v h h | 28 | |
| k k i N s p q p k f e g s g v p d n e n l k t s q q h | 27 | |
| k t g n a k l q r k k e k k n k r e t t l q q h | 24 | |
| k h l d a y k t f p p t e p k k d k k k k | 21 | |
| k h r e f v f k n k d g f l y v y k | 19 | |
| k e e l d k y f k n h | 11 | |
| k y r y l r h g k | 9 | |
| k k g a k l l h k | 9 | 55 |
| k h l d a y k | 7 | 55 |
| B. OTHER VIRUSES, BACTERIA, MALARIA AND CANCER REPLIKINS | | |
| h l v c g k k g l g l s g r k k | 19 | |
| k k i t n i t t k f e q l e k c c k h | 19 | |
| k k l k k s l k l l s f y h p k k | 17 | |
| k n r i e r l k k e y s s t w h | 16 | |
| k s r g i p i k k g h | 11 | |
| k s r i m p i k k g h | 11 | |
| k k f l n q f k h h | 10 | |
| k k k s k k h k d k | 10 | |
| k h h p k d n l i k | 10 | |
| k h k r k k f r q k | 10 | |
| k a g v a f l h k k | 10 | >90% |
| k i h l i s v k k | 9 | |
| k l i s i h e k | 8 | |
| k l r e e h e k | 8 | |
| k h k k q i v k | 8 | |
| k k h a t v l k | 8 | >90% |
| k k e d d e k h | 8 | |
| k h k e k m s k | 8 | >90% |
| k k l r h e k | 7 | |
| k k l r h e k | 7 | |
| k k l r h d k | 7 | |

| Replikin Sequence<br>1 2 3 4 5 6 7 8 9 10 11 12 13 14 15 16 17 18 19 20 21 22 23 24 25 26 27 28 29 | ORGANISM<br>Amino Acid position |
|---|---|

TABLE 7-continued

| | |
|---|---|
| **A. INFLUENZA, SARS AND OTHER CORONAVIRUSES** | |
| k k g t s y p k l s k s y t n n k g k e v l v l w g v h h | 1917-18 Goose Replikin (SEQ ID NO: 17) |
| k k g t s y p k l s k s y t n n k g k e v l v l w g v h h | 1918 Human Influenza (SEQ ID NO: 293) |
| l k e d l y p k l r k s v v h n k k k e v l v i w g i h h | 1919-2001 H1N1, H1N2 (SEQ ID NO: 294) |
| l k e n s y p k l r k s i i i n k k k e v l v i w g i h h | H3N2 Influenza (SEQ ID NO: 295) |
| k k g t s y p k l s k s y t n n k k k e v l v l w g v h h | 2001 H1N2 Influenza (SEQ ID NO: 296) |
| k k n s a y p t I k r s y n n t n q e d l l v l w g i h h | 1996-2001 H5N1 Influenza (SEQ ID NO: 297) |
| k k s a k t g t p k p s r n q s p a s s q t s a k s l a h | 2000 Human coronavirus 229E (SEQ ID NO: 298)[1] |
| k k l g v d t e k q q q r s k s k e r s n s k t r d t t p | 2003 Can[[c]]ine coronavirus (SEQ ID NO: 299)[2] |
| k n g l y p n l s k s y a n n k e k e v l i l w g v h h | 2002 H1N2 (SEQ ID NO: 300) |
| k k i N s p q p k f e g s g v p d n e n l k t s q q h | Avian bronchitis coronavirus (SEQ ID NO: 301) |
| k t g n a k l q r k k e k k n k r e t t l q q h | Porcine epidemic diarrhea coronavirus (SEQ ID NO: 302) |
| k h l d a y k t f p p t e p k k d k k k k | 2003 Human SARS nucleocapsid (SEQ ID NO: 303) |
| k h r e f v f k n k d g f l y v y k | 2003 Human SARS spike protein (SEQ ID NO: 304) |
| k e e l d k y f k n h | 2003 Human SARS spike protein (SEQ ID NO: 305) |
| k y r y l r h g k | 2003 Human SARS spike protein (SEQ ID NO: 306) |
| k k g a k l l h k | 2003 SARS envelope protein (SEQ ID NO: 307) |
| k h l d a y k | 2003 Human SARS nucleocapsid protein (SEQ ID NO: 308) |
| **B. OTHER VIRUSES, BACTERIA, MALARIA AND CANCER REPLIKINS** | |
| h l v c g k k g l g l s g r k k | HIV-TAT (SEQ ID NO: 309) |
| k k i t n i t t k f e q l e k c c k h | Monkeypox virus (SEQ ID NO: 310) |
| k k l k k s l k l l s f y h p k k | African swine fever virus (SEQ ID NO: 311) |
| k n r i e r l k k e y s s t w h | West Nile (SEQ ID NO: 312) |
| k s r g i p i k k g h | Nipah virus, v-protein (SEQ ID NO: 313) |
| k s r i m p i k k g h | Hendra virus, V-protein (SEQ ID NO: 314) |
| k k f l n q f k h h | Sindbis virus (SEQ ID NO: 315) |
| k k k s k k h k d k | EEL Leukemia (SEQ ID NO: 85) |
| k h h p k d n l i k | BRCA-1 Breast cancer (SEQ ID NO: 81) |
| k h k r k k f r q k | Ovarian cancer (SEQ ID NO: 84) |
| k a g v a f l h k k | Glioma Replikin (SEQ ID NO: 83) |
| k i h l i s v k k | Smallpox virus (SEQ ID NO: 316) |
| k l i s i h e k | Smallpox virus (SEQ ID NO: 317) |
| k l r e e h e k | *B. anthracis*, HATPase (SEQ ID NO: 318) |
| k h k k q i v k | *Plasm. Falciparum* ATPase (SEQ ID NO: 319) |
| k k h a t v l k | Ebola virus polymerase (SEQ ID NO: 320) |
| k k e d d e k h | *P. falciparum* blood trophozoites (SEQ ID NO: 321) |
| k h k e k m s k | (K-RAS 2B) lung cancer (SEQ ID NO: 322) |
| k k l r h e k | Rous sarcoma virus (SEQ ID NO: 48) |
| k k l r h e k | c-src, colon, breast cancer (SEQ ID NO: 52) |
| k k l r h d k | c-yes, melanoma, colon cancer (SEQ ID NO: 50) |

[1]Human coronavirus 229E 2000, SEQ ID NO: 532: kksaktgtpkpsrnqspassqtsakstarsqssetkeqkh

[2]Canine coronavirus 2003, SEQ ID NO: 533: kklgvdtekqqqrsrskskersnsktrdttpknenkh SARS and H3N2-Fujian Influenza Virus Replikins Traced Back to a 1918 Pandemic Replikin The origin of the SARS virus is as yet unknown. We report evidence that certain SARS virus peptides can be traced back through homologous peptides in several strains of influenza virus isolates from 2002 to a sequence in the strain of the 1918 influenza pandemic responsible for the deaths of over 20 million people.

By quantitative analysis of primary protein sequences of influenza virus and other microorganisms recorded through the last century we have found a new class of peptide structures rich in lysines and histidine, related to the phenomenon of rapid replication itself and to epidemics, rather than to the type of organism (eg. Table 1) and named them Replikins. We have found a new class of peptide structures with the following obligatory algorithm: at least two lysines 6 to 10 residues apart, lysine concentration 6% or greater, one histidine, in 7 to 50 amino acids. Because these peptides relate to the phenomenon of rapid replication itself and to epidemics, we named them Replikins. We have found a quantitative correlation of strain-specific replikin concentration (replikin count=number of replikins per 100 amino acids) in the hemagglutinin protein with influenza epidemics and pandemics (FIG. 7). No previous correlation of influenza epidemics with strain-specific viral protein chemistry has been reported. Conservation, condensation and concentration of replikin structure also has been found in influenza (eg. in Table 7a), HIV and malaria. The detection of replikins in SARS coronavirus, in addition to tracing its possible evolution, has permitted the synthesis of small SARS antigens for vaccines.

We have found a quantitative correlation of strain-specific replikin concentration (count) in the influenza hemagglutinin proteins with influenza epidemics and with each of the three pandemics of the last century, in 1918, 1957, and 1968. A similar course was observed for each of these three pandemics: after a strain-specific high replikin count, an immediate decline followed, then a 'rebound' increase with an accompanying epidemic occurred. Also, a 1 to 3 year warning increase in count preceded most epidemics.

We found that the replikin in the hemagglutinin of an influenza virus isolated from a goose in 1917 (which we named the Goose Replikin) appeared in the next year in the H1N1 strain of influenza responsible for the 1918 pandemic, with only two substitutions as follows: kkg(t/s)sypklsksy(t/v)nnkgkevlvlwgvhh (SEQ ID NO: 323). Table 7a shows that the influenza 1917 Goose Replikin (GR) then was essentially conserved for 85 years, despite multiple minor substitutions and apparent translocations to other influenza strains. We have found that the 1917 influenza GR demonstrated apparent mobility between several influenza strains, appearing in H1N1 (the pandemic of 1918), in H2N2 (pandemic of 1957-58), in H3N2 (pandemic of 1968, epidemic in China and Russia 2000, Fujian strain epidemic 2003) and in H5N1 (epidemic in China 1997). In 1997 its structure was restored in H1N2 exactly to its 1918 structure KKGSSYPKLSKSYVNNKGKEVLVLWGVHH (SEQ ID NO: 324).

The SARS coronavirus first appeared in the 2002-2003 influenza season. The dual origin in 2002 of SARS replikins, from influenza GR and coronavirus replikins (or from some unknown shared precursor) is suggested by the following events, all of which occurred in 2002: 1) a condensation for the first time in 85 years is seen in the GR-H1N2 Replikin sequence from 29 to 28 amino acids (Table 7a)(A similar condensation was found in H3N2 Fujian from 29 to 27 amino acids in the current epidemic (Table 7a)); 2) the replikin count of GR-H1N2 showed a marked decline consistent with GR moving out of H1N2; 3) the replikin count of coronavirus nucleocapsid proteins showed a marked increase; and 4) SARS coronavirus appeared in 2002-2003 with replikins containing the following motifs: 'kkg' and 'k-k', previously seen in GR 1918 and GR-H1N2 2001; 'k-kk', 'kk' and 'kl' seen in influenza GR-H1N2 2001; 'kk' seen in the avian bronchitis coronavirus replikin; and 'kk-kk-k' (SEQ ID NO: 325), 'kk' and 'kt' seen in the replikin of porcine epidemic diarrhea coronavirus (Table 7a) (SARS is believed to have made its first appearance in humans as the epidemic pneumonia which erupted in a crowded apartment house where there was a severe back-up of fecal sewage, which was then airborne by ventilating fans).

TABLE 7a

Goose Replikin (GR) sequences in different influenza strains from 1917 to 2003; SARS and H3N2-Fujian appearance 2002-2003.

| Replikins related to the Goose Replikin: Continuous amino acid sequences Shared motif and/or position not underlined Amino acid substitutions-underlined 'Condensed' indicates condensation of sequence length in H1N2 and H3N2-Fujian | Replikin Length (Number of amino acid) | SEQ. ID NO. | Virus or other organism containing replikin (Complete replikins except for Fujian strain) |
|---|---|---|---|
| kkgtsypklsksytnnkgkevlvlwgvhh | 326 | 29 | 1917 H1N_Influenza Goose Replikin (GR) |
| kkgssypklsksyvnnkgkevlvlwgvhh | 327 | 29 | 1918 GR in H1N1 Human Influenza |
| kkgsnypvakgsynntsgeqmliiwgvhh | 328 | 29 | 1958 GR H2N2 Influenza |
| kkgpnypvakqsynntsgeqmliiwgvhh | 329 | 29 | 1964, 1965, 1968 GR in H2N2 Influenza |
| kkgtsypklsksytnnkgkevlvlwgvhh | 330 | 29 | 1976, '77, '80, '81, '85 GR in H1N1 Influenza |
| kknsayptikrsynntnqedllvlwgihh | 331 | 29 | 1996-2001 GR in H5N1 Influenza |
| kkgdsypklsksytnnkgkevlviwgvhh | 332 | 29 | 1996 GR in H1N1 Influenza |
| kkgssypklsksyvnnkgkevlvlwgvhh | 333 | 29 | 1997, 1998 GR in H1N1 Influenza |
| kkgnsypkisksyinnkekevlvlwgihh | 334 | 29 | 1999 GR in H1N2 Influenza |
| kkgnsypklsksyinnkkkevlviwgihh | 335 | 29 | 2000 GR in H1N2 Influenza |
| kkgnsypklsksyinnkgkkvlvlwgihh | 336 | 29 | 2001 GR in H1N2 Influenza |
| kkgtsypklsksytnnkkkevlvlwgvhh | 337 | 29 | 2001 GR in H1N2 Influenza |
| knglypnlsksyannkekevlilwgvhh | 338 | 28 | 2002 GR in H1N2 Influenza (condensed) |

TABLE 7a-continued

Goose Replikin (GR) sequences in different influenza strains from 1917 to 2003; SARS and H3N2-Fujian appearance 2002-2003.

| Replikins related to the Goose Replikin: Continuous amino acid sequences Shared motif and/or position not underlined Amino acid substitutions-underlined 'Condensed' indicates condensation of sequence length in H1N2 and H3N2-Fujian | Replikin Length (Number of amino acid) | SEQ.ID NO. | Virus or other organism containing replikin (Complete replikins except for Fujian strain) |
|---|---|---|---|
| khldayktfpptepkkdkkkk | 339 | 21 | 2002-3 Human SARS nucleocapsid protein |
| kkensypklrksiiinkkkevlviwgihh | 340 | 29 | 1968-2001 GR in H3N2 Influenza (complete) |
| kleykypalnvtmpnndkfdklyiwgvhh | 341 | 29 | 1996 H3N2 Fujian Influenza (incomplete) |
| kykypalnvtmpnnekfdklyiwgvhh | 342 | 27 | 2003 H3N2 Fujian (condensed, incomplete) |
| ktgnaklqrkkekknkrettlqqh | 343 | 24 | Porcine epidemic diarrhea coronavirus |
| kkinspqpkfeqsqvpdnenlktsqqh | 344 | 27 | Avian bronchitis coronavirus |
| kknvksakqlphlkvlldvrgakqlph | 349 | 27 | 2000 shrimp white spot syndrome virus |
| kkinspqpkfeqsqvpdnenlktsqqh | 348 | 27 | Avian bronchitis coronavirus |
| khlrefvfknkdgflyvykk | 347 | 20 | 2002-3 Human SARS spike protein |
| kkgakllhkpivwh | 348 | 14 | 2002-3 Human SARS nucleocapsid protein |
| khlrefvfknkdgflyvykk | 349 | 20 | 2002-3 Human SARS spike protein |
| kkgakllhkpivwh | 350 | 14 | 2002-3 Human SARS nucleocapsid protein |
| keeldkyfknh | 351 | 11 | 2002-3 Human SARS spike protein |
| kkgakllhk | 352 | 9 | 2002-3 Human SARS envelope protein |
| kyrylrhgk | 353 | 9 | 2002-3 Human SARS spike protein |
| khldayk | 354 | 7 | 2002-3 Human SARS nucleocapsid protein |
| ksrqipikkgh | 355 | 11 | Nipah virus, v-protein |
| ksrimpikkgh | 356 | 11 | Hendra virus, v-protein |
| kkflnqfkhh | 357 | 10 | Sindbis virus |
| kkkskkhkdk | 358 | 10 | EEL leukemia |
| khhpkdnlik | 359 | 10 | BRCA-1 breast cancer |
| khkrkkfrqk | 360 | 10 | Ovarian cancer |
| kagvaflhkk | 361 | 10 | Glioma Replikin |
| kihlisvkk | 362 | 9 | Smallpox virus |
| krfilhakk | 363 | 9 | HIV TAT protein |
| klisihek | 364 | 8 | Smallpox virus |
| klreehck | 365 | 8 | B. anthracis, HATPase |
| kkhatvlk | 366 | 8 | Ebola virus polymerase |

The recent increasingly high replikin count peaks, including the presence of the 1917 Goose Replikin (FIG. 7), now in H1N2 (Table 7a), approaching the 1917 replikin count, could be a warning of a coming pandemic which may already have begun since the SARS virus and the H3N2-Fujian virus are the current carriers of the short replikin derivatives of the Goose Replikin seen in Table 7 and 7a to be associated with high mortality.

Since the Goose Replikin has at least an 85 year history involving most or all of the A-strains of influenza and SARS, it and its components are conserved vaccine candidates for pan-strain protection. Condensed short SARS replikins, 7 to 21 amino acids long, enriched in % lysine and histidine compared to the Goose Replikin, occurred in association with the higher mortality rate of SARS (10-55%) when compared to that (2.5%) of the Goose Replikin, 29 amino acids long. Short replikins here mixed with long replikins in SARS may be responsible for high mortality. This is also the case for replikins of other organisms such as the ebola and smallpox viruses and anthrax bacteria (Table 7a). These short SARS replikins showed surprising homology with short replikins of other organisms such as smallpox, anthrax, and ebola which are associated with even higher untreated mortality rates (Table 7a).

Short synthetic vaccines, besides being much more rapidly produced (days rather than months), and far less expensive, should avoid the side effects attendant on the contamination and the immunological interference engendered by multiple epitopes of thousands of undesired proteins in current whole virus vaccines in general. In any case for influenza, current whole virus vaccines are ineffective in more than half of the elderly. But would short replikins be sufficiently immunogenic? The short glioma replikin 'kagvaflhkk' (SEQ ID NO: 1) proved to be a successful basis for a synthetic anti-glioblastoma multiforme and anti-bronchogenic carcinoma vaccine. It produced anti-malignin antibody, which is cytotoxic to cancer cells at picograms/cell and relates quantitatively to the survival of cancer patients. In order to prepare for a recurrent SARS attack, which appears likely because of the surge we found in the coronavirus nucleocapsid replikin count in 2002, we synthesized four SARS short replikins, found in nucleocapsid, spike, and envelope proteins. We found that these synthetic short SARS replikins when injected into rabbits also produced abundant specific antibody. For example, the 21 amino acid SARS nucleocapsid replikin antibody binds at dilutions greater than 1 in 204,800. Because of previous unsuccessful attempts by others to achieve with various small peptides a strong immune response without the unwanted side effects obtained with a whole protein or the thousands of proteins or nucleic acids as in smallpox vaccine, the ability of small synthetic replikin antigens to achieve strong immune responses is significant for the efficacy of these SARS vaccines.

We examined the relationship of Replikin structure in influenza and SARS viruses to increased mortality, with results as shown in Table 7. The relation of high mortality to short or condensed Replikin sequences is seen in the high mortality organisms shown in Section B of Table 7, in viruses other than influenza and SARS, and in bacteria, malaria and cancer. In support of the unifying concept of Replikin structure and of the relation of Replikins to rapid replication rather than any cell type or infectious organism, in addition to the prevalence of the basic Replikin structure in a broad range of viral, bacterial, malarial and cancer organisms in which replication is crucial to propagation and virulence, the following homologous sequences have been observed: note the "k"s in positions 1 and 2, note the alignment of "k"s as they would present to DNA, RNA or other receptor or ligand for incorporation or to stimulate rapid replication, note the frequency of "double k"s and "multiple k"s, note the frequency of "g" in position 3 and the occurrence of the triplets "kkg", "hek", "hdk" and "hkk" in the most condensed shortened Replikins associated with the highest mortality organisms, cancer cells and genes as diverse as the smallpox virus, the anthrax virus, Rous sarcoma virus and glioblastome multiforme (glioma), c-src in colon and breast cancer, and c-yes in melanoma and colon cancer. Note also the almost identical Replikin structure for two recently emerging high mortality viruses in Australia and Southeast Asia, Nipah and Hendrah viruses. These two viruses are reported to have similar or identical antibodies formed against them but no structural basis has been known for this up till now, with our finding of their two almost identical Replikins, for this similar antibody.

Table 7 also shows the relationship of five SARS Replikins of 2003 which we have found both to the influenza Goose Replikin of 1917 and to two coronaviruses, the avian bronchitis coronavirus and the porcine epidemic diarrhea virus. The first 2003 human SARS Replikin in Table 7 shows certain sequence homologies to the influenza virus goose 1917 and human 1918 Replikins through an intermediary structure of influenza H1N2 in 2002 (e.g., see Replikin "k" in positions 1, 18 and 19). The 1917 Goose Replikin sequence is seen in Table 7 to have been largely conserved despite many substitutions in amino acids which are not crucial to the definition of Replikins through 1999 (substitutions are show in italics). The original 29 amino acid 1917 Replikin sequence was then found to have been almost exactly restored to its structure of 1917-1918 in the 2001 H1N2 Replikin. However, the 2002 H1N2 influenza Replikin has been shortened from 29 to 28 amino acids and the "shift to the left" of amino acids kevl(i/v)wg (v/i)hh (SEQ ID NO: 367) is clearly evident.

In 2003, one Replikin was further shortened (or compacted) to the 21 amino acid Replikin of the first listed 2003 human SARS virus. The % k of the 2003 SARS Replikin is now 38.1% (8/21) in comparison to 20.7% of the Goose Replikin and the 1918 Human Pandemic Replikin. Compared to the influenza 29 amino acid Replikin, three SARS Replikins were found to be further shortened (or compacted) to 19, 11 and 9 amino acid long sequences, respectively. In the SARS 9 amino acid sequences shown, the % k is 44.4% (4/9). With the shortening of the SARS Replikin, the SARS mortality rate in humans rose to 10% in the young and 55.5% in the elderly compared to the 2.5% mortality in the 1918 influenza pandemic.

The amino acid sequences are shown in Table 7 to emphasize the degree of homology and conservation for 85 years (1917-2002) of the influenza Replikin, for which evidence has first been observed in the 1917 Goose Replikin. No such conservation has ever been observed before. Table 7 also illustrates that the Replikins in the 2003 human SARS virus, in addition to having homologies to the influenza Replikins which first appeared as the 1917 Goose Replikin and the 1918 Human Pandemic influenza Replikin, show certain sequence homologies to both the coronavirus avian bronchitis virus Replikin (e.g. "k" in positions 1 and 2, end in "h") and to the coronavirus acute diarrhea virus Replikin (e.g. "k" in positions 1 and 11, "h" at the end of the Replikin). This evidence of relation to both influenza and coronavirus Replikins is of interest because SARS arose in Hong Kong as did several recent influenza epidemics and earlier pandemics, and the SARS virus has been classified as a new coronavirus partly because of its structure, including nucleocapsid, spike, and envelope proteins. Certain epidemiological evidence also is relevant in that SARS made its first appearance in humans as the epidemic pneumonia, which erupted, in a crowded Hong Kong apartment house where there was a severe back-up of fecal sewage, which was airborne by ventilating fans.

Composition of Replikins in Strains of Influenza Virus B: Of a total of 26 Replikins identified in this strain (Table 3), the following ten Replikins are present in every influenza B isolate examined from 1940-2001. Overlapping Replikin sequences are listed separately. Lysines and histidines are in bold type to demonstrate homology consistent with the "3-point recognition."

(SEQ ID NO: 104)
KSHFANLK (SEQ ID NO: 105)
KSHFANLKGTK (SEQ ID NO: 106)
KSHFANLKGTKTRGKLCPK (SEQ ID NO: 107)
HEKYGGLNK (SEQ ID NO: 108)
HEKYGGLNKSK (SEQ ID NO: 10)
HEKYGGLNKSKPYYTGEHAK (SEQ ID NO: 110)
HAKAIGNCPIWVK (SEQ ID NO: 111)
HAKAIGNCPIWVVKKTPLKLANGTK (SEQ ID NO: 112)
HAKAIGNCPIWVKTPLKLANGTKYRPPAK (SEQ ID NO: 113)
HAKAIGNCPIWVKTPLKLANGTKYRPPAKLLK

Tables 3 and 4 indicate that there appears to be much greater stability of the Replikin structures in influenza B hemagglutinins compared with H1N1 Replikins Influenza B has not been responsible for any pandemic, and it appears not to have an animal or avian reservoirs. (Stuart-Harris et al., Edward Arnold Ltd., London (1985)).

Replikins in Influenza Over Time

Only one Replikin "hp(v/i)tigecpkyv-(r/k)(s/t)(t/a)k" (SEQ ID NO: 135) is present in every H1N1 isolate for which sequences are available from 1918, when the strain first appeared and caused the pandemic of that year, through 2000. (Table 4). ("(v/i)" indicates that the amino acid v or i is present in the same position in different years.) Although H1N1 contains only one persistent Replikin, H1N1 appears to be more prolific than influenza B. There are 95 different Replikin structures in 82 years on H1N1 versus only 31 different Replikins in 62 years of influenza B isolates (Table 4). An increase in the number of new Replikin structures occurs in years of epidemics (Tables 3, 4, 5 and 6) and correlates with increased total Replikin concentration (FIGS. 7, 8, 11 and 15).

Influenza H2N2 Replikins: Influenza H2N2 was responsible for the human pandemic of 1957. Three of the 20 Replikins identified in that strain for 1957 were conserved in each of the H2N2 isolates available for examination on PubMed until 1995 (Table 5).

(SEQ ID NO: 232)
ha(k/q/m)(d/n)ilekthngk (SEQ ID NO: 233)
ha(k/q/m)(d/n)ilekthngklc(k/r)

(SEQ ID NO: 238)
kgsnyp(v/i)ak(g/r)synntsgeqmliiwq(v/i)h

However, in contrast to H1N1, only 13 additional Replikins have been found in H2N2 beginning in 1961. This paucity of appearance of new Replikins correlates with the decline in the concentration of the H2N2 Replikins and the appearance of H2N2 in isolates over the years. (FIG. 8).

Influenza H3N2 was responsible for the human pandemic of 1968. Five Replikins which appeared in 1968 disappeared after 1977, but reappeared in the 1990s (Table 6). The only Replikin structure which persisted for 22 years was hcd(g/q)f(q/r)nekwdlf(v/i)er(s/t)k (SEQ ID NO: 277), which appeared first in 1977 and persisted through 1998. The emergence of twelve new H3N2 Replikins in the mid 1990s (Table 6) correlates with the increase in Replikin concentration at the same time (FIG. 8), and with the prevalence of the H3N2 strain in recent isolates together with the concurrent disappearance of all Replikins from some of these isolates (FIG. 8), this suggests the emergence of the new substrain H3N2(R). The current epidemic in November-December 2003 of a new strain of H3N2 (Fujian) confirms this prediction made first in the Provisional Application U.S. 60/303,396, filed Jul. 9, 2001.

FIGS. 7, 8, 11 and 15 show that influenza epidemics and pandemics correlate with the increased concentration of Replikins in influenza virus, which is due to the reappearance of at least one Replikin from one to 59 years after its disappearance. Also, in the A strain only, there is an emergence of new strain-specific Replikin compositions (Tables 4-6, see also increase in number of new Replikins, pre-epidemic for H5N1 in FIGS. 11 and 15). Increase in Replikin concentration by repetition of individual Replikins within a single protein appears not to occur in influenza virus, but is seen in other organisms.

It has been believed that changes in the activity of different influenza strains are related to sequence changes in influenza hemagglutinins, which in turn are the products of substitutions effected by one of two poorly understood processes: i) antigenic drift, thought to be due to the accumulation of a series of point mutations in the hemagglutinin molecule, or ii) antigenic shift, in which the changes are so great that genetic reassortment is postulated to occur between the viruses of human and non-human hosts. First, the present data suggests that the change in activity of different influenza strains, rather than being related to non-specific sequence changes, are based upon, or relate to the increased concentration of strain-specific Replikins and strain-specific increases in the replication associated with epidemics. In addition, the data were examined for a possible insight into which sequence changes are due to "drift" or "shift", and which are due to conservation, storage in reservoirs, and reappearance. The data show that the epidemic-related increase in Replikin concentration is not due to the duplication of existing Replikins per hemagglutinin, but is due to the reappearance of at least one Replikin composition from 1 to up to 59 years after its disappearance, plus in the A strains only, the emergence of new strain-specific Replikin compositions (Tables 3-6). Thus the increase in Replikin concentration in the influenza B epidemics of 1951 and 1977 are not associated with the emergence of new Replikin compositions in the year of the epidemic but only with the reappearance of Replikin compositions which had appeared in previous years then disappeared (Table 3). In contrast, for the A strains, in addition to the reappearance of previously disappeared virus Replikins, new compositions appear (e.g. in H1N1 in the year of the epidemic of 1996, in addition to the reappearance of 6 earlier Replikins, 10 new compositions emerged). Since the A strains only, not influenza B, have access to non-human animal and avian reservoirs, totally new compositions probably derive from non-human host reservoirs rather than from mutations of existing human Replikins which appear to bear no resemblance to the new compositions other than the basic requirements of "3-point recognition" (Tables 2-5). The more prolific nature of H1N1 compared with B, and the fact that pandemics have been produced by the three A strains only, but not by the B strain, both may also be a function of the ability of the human A strains to receive new Replikin compositions from non-human viral reservoirs.

Some Replikins have appeared in only one year, disappeared, and not reappeared to date (Tables 3-6). Other Replikins disappear from one to up to 81 years, when the identical Replikin sequence reappears. Key Replikin 'k' and 'h' amino acids, and the spaces between them, are conserved during the constant presence of particular Replikins over many years, as shown in Tables 2 and 3-6 for the following strain-specific Replikins: ten of influenza B, the single Replikin of H1N1, and the single Replikin of H3N2 as well as for the reappearance of identical Replikins after an absence. Despite the marked replacement or substitution activity of other amino acids both inside the Replikin structure and outside it in the rest of the hemagglutinin sequences, influenza Replikin histidine (h) appears never to be, and lysine (k) is rarely replaced. Examples of this conservation are seen in the H1N1 Replikin "hp(v/i)tigecpkyv(r/k)(s/t)(t/a)k," (SEQ ID NO: 135) constant between 1918 and 2000, in the H3N2 Replikin "hcd(g/q)f(q,r)nekwdlf(v/i)er(s/t)k" (SEQ ID NO: 277) constant between 1975 and 1998 and in the H3N2 Replikin "hqn(s/e)(e/q)g(t/s)g(q/y)aad(l/q)kstq(a/n)a(i/l)d(q/g)I(n/t)(g/n)k,(l/v)n(r/s) vi(e/c)k" (SEQ ID NO: 276) which first appeared in 1975, disappeared for 25 years, and then reappeared in 2000. While many amino acids were substituted, the basic Replikin structure of 2 Lysines, 6 to 10 residues apart, one histidine, a minimum of 6% lysine in not more than approximately 50 amino acids, was conserved.

Totally random substitution would not permit the persistence of these H1N1 and H3N2 Replikins, nor from 1902 to 2001 in influenza B the persistence of 10 Replikin structures, nor the reappearance in 1993 of a 1919 18-mer Replikin after an absence of 74 years. Rather than a random type of substitution, the constancy suggests an orderly controlled process, or in the least, protection of the key Replikin residues so that they are fixed or bound in some way: lysines, perhaps bound to nucleic acids, and histidines, perhaps bound to respiratory redox enzymes. The mechanisms, which control this conservation, are at present unknown.

H5N1 Influenza Conservation of Replikin Scaffold

There is concern that the current outbreak of high mortality H5N1 "bird flu" in several countries may represent the first phase of an overdue influenza pandemic. A recent report suggests that in the first probable person-to-person transmission of H5N1, "sequencing of the viral genes identified no change in the receptor-binding site of hemagglutinin or other key features of the virus. The sequences of all eight viral gene segments clustered closely with other H5N1 sequences from recent avian isolates in Thailand." Phylogenetic analysis suggested that from the absence of evidence of "reassortment with human influenza viruses" that H5N1 is not a new variant. However, we now report three recent changes in a specific H5N1 protein sequence at sites which had not been changed in the last two H5N1 epidemics and in fact had been conserved since 1959.

Figure 15:
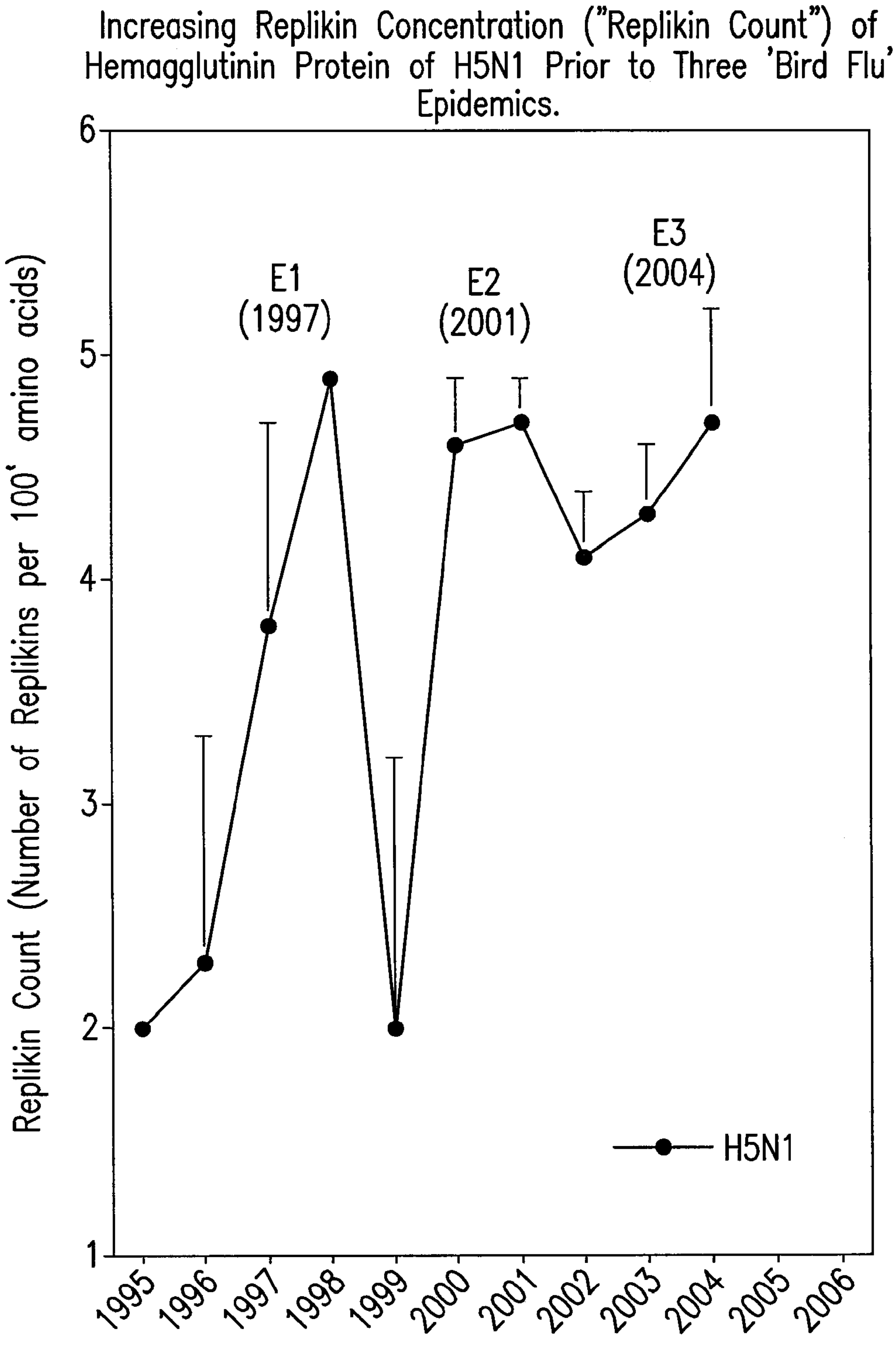
FIG. 15 is a graph illustrating a rapid increase in the concentration of Replikin patterns in the hemagglutinin protein of the H5N1 strain of influenza prior to the outbreak of three "Bird Flu" epidemics.

Previously, there has been no protein chemistry which correlated with virus epidemics and dormancy. We found that each of the three influenza pandemics of the last century, H1N1, H2N2 and H3N2, retrospectively was predicted by and correlated with an increase in the concentration of a specific class of peptides in the virus, rich in lysine and histidine, associated with rapid replication, called replikins. We have now again found the replikins to be predictive in each of the three H5N1 epidemics, in 1997, 2001, and 2003-2004 (FIG. 15). Each year that they appear in isolates, the replikins can now be counted per 100 amino acids as in FIG. 15, and their sequences analyzed and compared as in Table 9. Analysis of replikins may be accomplished manually or in a preferred aspect of the present invention automatically by software designed by the inventors for the purpose of counting replikin concentration in available sequence information.

A graph illustrating a rapid increase in the concentration of Replikin patterns in the hemagglutinin protein of the H5N1 strain of influenza prior to the outbreak of three "Bird Flu" epidemics may be seen in FIG. 15. A review of FIG. 15 illustrates that an increasing replikin concentration ('Replikin Count') in the hemagglutinin protein of H5N1 preceded three 'Bird Flu' Epidemics. For example, an increase in the Replikin Count (Means+/−SD) in 1995 to 1997 preceded the Hong Kong H5N1 epidemic of 1997 (E1). An increase in the Replikin Count from 1999 to 2001 preceded the epidemic of 2001 (E2). And an increase in Replikin Count from 2002 to 2004 preceded the epidemic in 2004 (E3). The decline in 1999 occurred with the massive culling of poultry in response to the E 1 epidemic in Hong Kong.

In addition to the total number of replikins in the virus protein, the structure of each replikin through time is informative. Table 8 shows a replikin first observed in a goose infected with influenza in 1917 (Goose Replikin). Constant length, constant lysines at the amino terminal and histidine residues at the carboxy terminal were conserved in different strains in a fixed scaffold for decades. Homologues of the Goose Replikin appeared from 1917 to 2006 in strains including each responsible for the three pandemics of 1918, 1957, and 19681, H1N1, H2N2 and H3N2, and with further substitutions between H1N2, H7N7, H5N2 and H5N1. Even certain substitutions which have occurred in the Goose Replikin tend to be selective and retained for years, rather than random. Thus despite the common assumption that amino acid substitutions should occur at random, it would appear that not all substitutions in influenza are, in fact, random. This replikin conservation over decades allows the production of synthetic influenza vaccines which rapidly and inexpensively can be prepared in advance and can be effective for more than one year.

Therefore a target for synthetic influenza vaccines is the conserved Replikin Scaffold in influenza virus. A Replikin Scaffold comprises a series of conserved peptides comprising a sequence of about 16 to about 30 amino acids and further comprising (1) a terminal lysine;

(2) a terminal histidine and another histidine in the residue portion immediately adjacent to the terminal histidine;

(3) at least one lysine within about 6 to about 10 amino acid residues from at least one other lysine; and (4) at least about 6% lysines within the 16 to about 30 amino acid peptide.

A Replikin Scaffold may further comprise a an additional lysine immediately adjacent to the terminal lysine. "Replikin Scaffold" peptides may comprise an additional lysine immediately adjacent to the terminal lysine. "Replikin Scaffold" peptide also refers to an individual member or a plurality of members of a series of a "Replikin Scaffold."

A non-limiting and preferred target for synthetic influenza vaccines may be a Replikin Scaffold in influenza virus further comprising a sequence of about 29 amino acids and a lysine immediately adjacent to the terminal lysine.

A non-preferred target for synthetic influenza may be an Exoskeleton Scaffold in a first strain of influenza virus comprising a first peptide of about 29 amino acids and (1) a terminal lysine and a lysine immediately adjacent to the terminal lysine;

(2) a terminal histidine and a histidine immediately adjacent to the terminal histidine;

(3) no lysine within 6 to 10 amino acid residues from any other lysine wherein an earlier-arising specimen of the first strain or another strain of virus comprises a Replikin Scaffold of about 29 amino acids.

In the 1997 H5N1 Hong Kong epidemic, the human mortality rate was approximately 27%. In 2004, of the fifty-two people reported to have been infected by H5N1 in Asia approximately 70% died. Most recently, nine of the eleven cases in Vietnam from Dec. 28, 2004 to Jan. 27, 2005 died. Although the virulence of the virus appears to have increased, any changes thought to be required for further spread human to human, had been thought not yet to have occurred 1. However, we now have observed recent substitutions in three H5N1 replikin amino acid residues at position numbers 18, 24 and 28 of the Goose Replikin scaffold from isolates in Vietnam, Thailand and China in 2004 (see Table 1). Substitution at site number 24 has not occurred since the appearance of H5N1 in 1959 but was present in the last two influenza pandemics caused by other strains, H2N2 in 1957 and H3N2 in 1968, together responsible for over two million human deaths, and in a recent virulent epidemic caused by H7N7 (see Table 8). While these are only hints of possible danger, these data on substitution, combined with the rising Replikin Count shown in FIG. 15, and the past correlation of such replikin data with pandemics, does not give the same reassurance as that obtained from phylogenetic analysis that the virus is unlikely to spread human to human.

With respect to the H5N1 influenza, FIG. 15 illustrates a rapid increase in the concentration of Replikins per 100 amino acids just prior to epidemics in 1997 (indicated as E1), 2001 (indicated as E2) and 2004 (indicated as E3).

TABLE 8

Replikin Scaffold showing ordered substitution in the 89 year conservation of influenza virus replikin peptides related to rapid replication, from a 1917 goose influenza replikin and the 1918 human pandemic replikin to 2006 H5N1 "Bird Flu" homologues. (SEQ ID NOS: 368-429, respectively, in order of appearance)

| [<--------------29 Amino Acids------------>] | Year | Strain |
|---|---|---|
| kkgtsypklsksytnnkgkevlvlwgvhh | 1917 | H1N_Influenza Goose Replikin |
| kkgssypklsksyvnnkgkevlvlwgvhh | 1918 | H1N1 Human Influenza Pandemic |
| kkensypklsksyvnnkgkevlvlwgvhh | 1930 | H1N1 |
| kkgdsypkltnsyvnnkgkevlvlwgvhh | 1933 | H0N1 |
| kkgtsypklsksytnnkgkevlvlwgvhh | 1976 | H1N1 |
| kkgtsypklsksytnnkgkevlvlwgvhh | 1977 | H1N1 |
| kkgnsypklsksytnnkgkevlviwgvhh | 1979 | H1N1 |
| kkgnsypklsksytnnkgkevlviwgvhh | 1980 | H1N1 |
| kkgtsypklsksytnnkgkevlvlwgvhh | 1980 | H1N1 |
| kkgnsypklsksytnnkgkevlviwgvhh | 1981 | H1N1 |
| kkgtsypklsksytnnkgkevlvlwgvhh | 1981 | H1N1 |
| kkgtsypklsksytnnkgkevlvlwgvhh | 1985 | H1N1 |
| kkgnsypklsksytnnkgkevlviwgvhh | 1991 | H1N1 |
| kkgnsypklsksytnnkgkevlviwgvhh | 1992 | H1N1 |
| kkgnsypklsksytnnkgkevlviwgvhh | 1996 | H1N1 |
| kkgdsypklsksytnnkgkevlviwgvhh | 1996 | H1N1 |
| kkgssypklsksyvnnkgkevlvlwgvhh | 1997 | H1N1 |
| kkgssypklsksyvnnkgkevlvlwgvhh | 1998 | H1N1 |
| kkgnsypklsksytnnkgkevlviwgvhh | 1999 | H1N1 |
| kkgnsypklsksytnnkgkevlviwgvhh | 2000 | H1N1 |
| kkgnsypklsksytnnkgkevlviwgvhh | 2001 | H1N1 |
| kkgnsypklsksytnnkgkevlviwgvhh | 2002 | H1N1 |
| kkgnsypkisksyinnkekevlvlwgihh | 1999 | H1N2 Influenza |
| kkgnsypklsksyinnkkkevlviwgihh | 2000 | H1N2 |
| kkgnsypklsksyinnkgkkvlvlwgihh | 2001 | H1N2 |

TABLE 8-continued

Replikin Scaffold showing ordered substitution in the 89 year conservation of influenza virus replikin peptides related to rapid replication, from a 1917 goose influenza replikin and the 1918 human pandemic replikin to 2006 H5N1 "Bird Flu" homologues. (SEQ ID NOS: 368-429, respectively, in order of appearance)

| [<--------------29 Amino Acids------------>] | Year | Strain |
|---|---|---|
| kkgtsypklsksytnnkkkevlvlwgvhh | 2001 | H1N2 |
| -knglypnlsksyannkekevlvlwgvhh | 2002 | H1N2 |
| --knglypnlsksyannkekevliilwgvhh | 2002 | H1N2 |
| kkgpnypvakrsynntsgeqmliiwgvhh | 1957 | H2N2 Human Influenza Pandemic |
| kkgpnypvakrsynntsgeqmliiwgihh | 1957 | H2N2 Human Influenza Pandemic |
| kkensypklrksiiinkkevklviwgihh | 1968 | H3N2 Human Influenza Pandemic |
| ----------ksykntrkdpaliiwgihh | 1979-2003 | H7N7 Influenza |
| kknnayptikrtynntnvedllilwgihh | 2002 | H5N2 Influenza |
| kknnayptikrsysntnqedllvlwgihh | 1959 | H5N1 Influenza (Scotland) |
| kknnayptikrtynntniedllilwgihh | 1975 | H5N1 (Wisconsin) |
| kknnayptikrtynntnmedllilwgihh | 1981 | H5N1 (Minnesota) |
| kkgnayptikrtynntnvedllilwgihh | 1983 | H5N1 (Pennsylvania) |
| kknntyptikrsynntnqedllilwgihh | 1988 | H5N1 (Scotland) |
| kknsayptikrsynntnqedllvlwgihh | 1996 | H5N1 (China) |
| kknsayptikrsynntnqedllvlwgihh | 1997 | H5N1 (China) |
| kknsayptikrsynntnqedllvlwgihh | 1998 | H5N1 (China) |
| kknsayptikrsynntnqedllvlwgihh | 1999 | H5N1 (China) |
| kknsayptikrsynntnqedllvlwgihh | 2000 | H5N1 (China) |
| kknsayptikrsynntnqedllvlwgihh | 2001 | H5N1 (China) |
| kknnayptikrsynntnqedllvlwgihh | 2001 | H5N1 (China) |
| kknsayptikrsynntnqedllvlwgihh | 2002 | H5N1 (China) |
| kknstyptikrsynntnqedllvlwgihh | 2002 | H5N1 (Thailand) |
| kknstyptikrsynntnqedllvlwgihh | 2002 | H5N1 (Vietnam) |
| kknstyptikrsynntnqedllvlwgihh | 2003 | H5N1 (Vietnam) |
| kknstyptikrsynntnqedllvlwgihh | 2003 | H5N1 (Thailand) |
| kknstyptikrsynntnqedllvlwgihh | 2003 | H5N1 (Sindong, China) |
| kknnayptikrsynntnqedllvlwgihh | 2003 | H5N1 (China) |
| kknstyptikrsynntnqedllvmwgihh | 2004 | H5N1 (Vietnam, highly pathogenic) |
| kknsayptikrsynntnqedllvlwgihh | 2004 | H5N1 (Vietnam, "highly pathogenic", gull) |
| kknstyptikrsynntnqedllvlwgihh | 2004 | H5N1Viietnam highly pathogenic |
| kknstyptikrsynntnqedllvlwgihh | 2004 | H5N1(Thailand, highly pathogenic) |
| kknstyptikrsynntnqedllvlwgiqh | 2004 | H5N1 (Thailand, highly pathogenic) |
| kknsaypiikrsynntnqedllvlwgihh | 2004 | H5N1 (China, highly pathogenic) |
| kknsayptikrsxnntnhedllvlwgihh | 2004 | H5N1 (China, "highly pathogenic", goose) |
| kknsayptikrsynntnqedllvlwgihh | 2004 | H5N1 Japan |

TABLE 8-continued

Replikin Scaffold showing ordered substitution in the 89 year conservation of influenza virus replikin peptides related to rapid replication, from a 1917 goose influenza replikin and the 1918 human pandemic replikin to 2006 H5N1 "Bird Flu" homologues.
(SEQ ID NOS: 368-429, respectively, in order of appearance)

| [<--------------29 Amino Acids------------>] | Year | Strain |
|---|---|---|
| kknnayptikrsynntnqedllvlwgihh | 2005 | H5N1 Turkey |
| kknntyptikksynntnqedllvlwgihh | 2006 | H5N1 China (Anhui) |

* Residues identical to Goose Replikin amino acids un-underlined; amino acid substitutions underlined and italicized to show scaffold pattern across years and strains.

Table 8, above, provides further support for the role of replikins in epidemics and pandemics in humans and birds. In Table 8, the history of the Goose Replikin and its homologues are tracked from 1917 to the present outbreak of avian H5N1 virus. Table 8 demonstrates conservation of the "scaffold" homology of the Goose Replikin in virulent strains of influenza.

Table 8 illustrates the history, by year or smaller time period, of the existence in the protein structure of the Goose Replikin and its homologues in other influenza Replikins. Table 8 further illustrates the history of amino acid substitutions in those homologues and the conservation of certain amino acids of the Replikin structure which are essential to the definition of a Replikin and the function of rapid replication supplied by Replikins.

A review of Table 8 illustrates that if random substitution of amino acids were to occur in virulent strains of influenza from 1917 through the present, certain framework amino acids of the Goose Replikin would not be conserved from year to year in strains in which epidemics occurred. However, contrary to what would result from random substitution, virulent strains of influenza from year to year consistently contain conserved amino acids at those positions that define a Replikin. That is, if a substitution were to occur in one of the amino acids that define a Replikin, e.g. lysine or a histidine, the definition of the Replikin would be lost. Nevertheless, the Replikin sequence is conserved over more than 85 years. Thus, since there is conservation of certain amino acids over decades, substitution cannot be said to be completely at random. The fact that substitutions do occur in amino acids that are not essential to the definition of a Replikin (i.e., amino acids other than lysines or histidines) demonstrates the importance of the Replikin in the pathogenicity of the strain.

It may be further noted from Table 8 that when substitutions do occur, they are seen to occur at certain apparently preferred positions of the Replikin Scaffold. Table 8 illustrates recurring substitutions at positions 1, 3-24 and 26-27. Further, while substitutions occur throughout these positions, a lysine continues to exist at a position 6 to 10 amino acids from the second lysine (which has not been substituted in these virulent strains).

Even when there is a substitution of a lysine position within the 29 amino acid stretch, as is seen in 1957, when K at position 11 shifts to position 10, that new position has been maintained until 2005, as have YP, AY, N (position 15), and LVLWG (SEQ ID NO: 430) to conserve the homologous structure of the Replikin Scaffold with few exceptions.

Table 8 demonstrates the integrity of the Replikin Scaffold in virulent strains of influenza. As discussed above, degeneration of the Replikin Scaffold into an Exoskeleton Scaffold is seen to decrease pathogenicity. The integrity and conservation of the Replikin Scaffold, therefore, is seen by the fact that there is generally a fixed 29 amino acid sequence that begins with two lysines and ends with two histidines.

It is important to note that an extra K has appeared in the Replikin Scaffold of a 2006 strain of H5N1 in China (Anhui). This presence of an extra K signals an increase in the Replikin count within the Replikin Scaffold. The 2006 China (Anhui) strain has a Replikin count of 6.6 (as discussed below). A Replikin count of 6.6 is the highest ever observed for an H5N1 strain and is comparable in the entire A strain of influenza only to the Replikin count of the influenza strain that caused the 1918 Pandemic. If this initial 2006 report is repeated and maintained, it may indicate that the Counts of 4.5 and 4.0 in 2004 and 2005 respectively will be substantially increased, and foretell a continuing or increased epidemic of H5N1 'Bird Flu'.

An aspect of the present invention is a combination of replikin structure and function to track the pathogenicity or rate of replication of a virus, epidemic or pandemic or to predict the occurrence of epidemics or pandemics. An example of this combination is the ability of the Replikin algorithm of the invention to be used to count increases in Replikin counts in influenza strains such as the strain of 1918 and the current H5N1 strain of H5N1. The Replikin Count of the 1918 influenza pandemic and the current outbreak of "Bird Flu" demonstrate the predictive capacity of this exemplary aspect in accordance with and made possible by the invention.

Relation of Some Shrimp White Spot Virus Replikins to Influenza Fixed Scaffold Replikin Structures The inventors have also established a relationship between virulent influenza virus and white spot virus in the Replikin Scaffold portions of the viruses. No relationship between these two viruses has been suggested previously. Although there is extensive substitution, the applicants' finding of several short Replikins of the Shrimp White Spot Syndrome Virus demonstrate significant homologies to the influenza virus Replikin sequences, especially with regard to length and key lysine (k) and histidine (h) residues (Fixed Scaffold or Replikin Scaffold), suggesting that similar mechanisms of Replikin production are used in both virus groups.

TABLE 8A

| Shrimp White Spot Scaffolding (SEQ ID NOS: 431-440, respectively, in order of appearance) | | |
|---|---|---|
| Kkgtsypklsksytnnkgkevlvlwgvhh | 1917 | H1N_Influenza goose peptide |
| Kkgnsypklsksytnnkgkevlviwgvhh | 2002 | H1N1 Swine Influenza |
| Kknvksakqlphlkvlkkldvrgakqlph | 2000 | Shrimp White Spot Syndrome Virus |
| -kvhldvkgvkqllhlkvrldvrgakqlh | 2000 | Shrimp White Spot Syndrome Virus |
| kkensypklrksiiinkkevklviwgihh | 1968 | H3N2 Human Influenza Pandemic |
| ----------ksykntrkdpaliiwgihh | 1979-2003 | H7N7 Influenza |
| kkgpnypvakrsynntsgeqmliiwgvhh | 1957 | H2N2 Human Influenza Pandemic |
| kkgpnypvakrsynntsgeqmliiwgihh | 1957 | H2N2 Human Influenza Pandemic |
| kknnayptikrtynntnvedllilwgihh | 2002 | H5N2 Influenza |
| kknnayptikrsysntnqedllvlwgihh | 1959 | H5N1 Influenza |

Residues identical to original 1917 Goose Replikin residues are shown un-underlined. Amino acid substitutions are shown underlined and in italics.

In addition, since many species, including but not limited to swine and birds, are known to provide animal "reservoirs" for human influenza infection, marine forms such as the shrimp virus can now be examined, with early warning diagnostic benefits possible for outbreaks such as swine flu and bird flu. While similarities of some influenza viruses were noted between species, and the transfer of these viruses interspecies was known, there was no previous quantitative method to gauge virus activity. It has not been possible previously to examine potential reservoirs for increased activity which might move into a different species; thus providing an advanced warning. The activity of the Replikins in each species can now be monitored constantly for evidence of increased viral replication rate and thus emergence of epidemics in that species which may then transfer to other species.

This data further supports the Replikins as a new class of peptides, with a history of its own, and a shared function of rapid replication and disease of its hosts. With the high mortality for its shrimp host, white spot syndrome virus can now have its Replikins examined as earlier forms of the virus Replikins, or as parallel morphological branches, which in either case may well act as reservoirs for bird and animal Replikins such as those in influenza viruses. The diagnostic and preventive uses of these Replikin findings in shrimp follow as they do in influenza and for other organisms containing Replikins.

Conservation of Replikin Structures

Whether Replikin structures are conserved or are subject to extensive natural mutation also was examined by scanning the protein sequences of various isolates of foot and mouth disease virus (FMDV), where mutations in proteins of these viruses have been well documented worldwide for decades. Protein sequences of FMDV isolates were visually examined for the presence of both the entire Replikin and each of the component Replikin amino acid residues observed in a particular Replikin.

Rather than being subject to extensive substitution over time as occurs in neighboring amino acids, the amino acids which comprise the Replikin structure are substituted little or not at all, that is the Replikin structure is conserved.

For example, in the protein VP1 of FMDV type 0, the Replikin (SEQ ID NO: 3) "hkqkivapvk" was found to be conserved in 78% of the 236 isolates reported in PubMed, and each amino acid was found to be conserved in individual isolates as follows: his, 95.6%; lys, 91.8%; gln 92.3%; lys, 84.1%; ile, 90.7%; val, 91.8%; ala, 97.3%; pro, 96.2%; ala, 75.4%; and lys, 88.4%. The high rate of conservation suggests structural and functional stability of the Replikin structure and provides constant targets for treatment.

Similarly, sequence conservation was found in different isolates of HIV for its Replikins, such as (SEQ ID NO: 5) "kcfncgkegh" or (SEQ ID NO: 6) "kvylawvpahk" in HIV Type 1 and (SEQ ID NO: 7) "kcwncgkegh" in HIV Type 2 (Table 2). Further examples of sequence conservation were found in the HIV tat proteins, such as (SEQ ID NO: 441) "hclvckqkkglgisygrkk," wherein the key lysine and histidine amino acids are conserved. (See Table 9).

Similarly, sequence conservation was observed in plants, for example in wheat, such as in wheat ubiquitin activating enzyme E (SEQ ID NOs. 454-456). The Replikins in wheat even provided a reliable target for stimulation of plant growth as described within. Other examples of conservation are seen in the constant presence of malignin in successive generations, over ten years of tissue culture of glioma cells, and by the constancy of affinity of the glioma Replikin for antimalignin antibody isolated by immunoadsorption from 8,090 human sera from the U.S., U.K., Europe and Asia (e.g., FIG. 5 and U.S. Pat. No. 6,242,578 B1).

Similarly, conservation was observed in trans-activator (Tat) proteins in isolates of HIV. Tat (trans-activator) proteins are early RNA binding proteins regulating lentiviral transcription. These proteins are necessary components in the life cycle of all known lentiviruses, such as the human immunodeficiency viruses (HIV). Tat is a transcriptional regulator protein that acts by binding to the trans-activating response sequence (TAR) RNA element and activates transcription Initiation and/or elongation from the LTR promoter. HIV cannot replicate without tat, but the chemical basis of this has been unknown. In the HIV tat protein sequence from 89 to 102 residues, we have found a Replikin that is associated with rapid replication in other organisms. The amino acid sequence of this Replikin is "HCLVCKQKKGLGISYGRKK." (SEQ ID NO: 441) In fact, we found that this Replikin is present in every HIV tat protein. Some tat amino acids are substituted frequently by alternate amino acids (in small size fonts lined up below the most frequent amino acid (Table 9), the percentage of conservation for the predominant Replikin "HCLVCFQKKGLGISYGRKK" (SEQ ID NO: 442)). These substitutions have appeared for most of the individual amino acids. However, the key lysine and histidine amino acids within the Replikin sequence, which define the Replikin structure, are conserved 100% in the sequence; while substitutions are common elsewhere in other amino acids, both within and outside the Replikin, none occurs on these key histidine amino acids.

As shown in Table 9 it is not the case that lysines are not substituted in the tat protein amino acid sequence. From the left side of the table, the very first lysine in the immediate neighboring sequence, but outside the Replikin sequence, and the second lysine (k) in the sequence inside the Replikin, but "extra" in that it is not essential for the Replikin formation, are both substituted frequently. However, the 3rd, 4th and 5th lysines, and the one histidine, in parentheses, which together set up the Replikin structure, are never substituted. Thus, these key amino acid sequences are 100% conserved. As observed in the case of the influenza virus Replikins, random substitution would not permit this selective substitution and selective non-substitution to occur due to chance.

This conservation makes them a constant and reliable targeted for either destruction, for example by using specific Replikins such as for influenza, FMVD or HIV vaccines as illustrated for the glioma Replikin, or stimulation.

Similarly, as provided in examples found in viruses including influenza viruses, FMDV, and HIV, where high rates of conservation in Replikins suggest that conservation is a general property of viral Replikins and thus making Replikins a constant and reliable target for destruction or stimulation, conservation of Replikin structures occurs in plants. For example, in wheat plants, Replikins are conserved and provide a reliable target for stimulation. Examples of conserved Replikins in wheat plants ubiquitin activating enzyme E include:

(SEQ ID NO: 454)
E3 HKDRLTKKVVDIAREVAKVDVPEYRRH (SEQ ID NO: 455)
E2 HKERLDRKVVDVAREVAKVEVPSYRRH (SEQ ID NO: 456)
E1 HKERLDRKVVDVAREVAKMEVPSYRRH
* *     * ** *

Similarly to conservation found in the HIV tat protein, the Replikin in the wheat ubiquitin activating enzyme E is conserved. As with the HIV tat protein, substitutions of amino acids (designated with an '*') adjacent to the Replikin variant forms in wheat ubiquitin activating enzyme E are common. The key k and h amino acids that form the Replikin structure, however, do not vary whereas the 'unessential' k that is only 5 amino acids (from the first k on the left) is substituted.

TABLE 9

% Replikin CONSERVATION of each constituent amino acid in the first 117 different isolates of HIV tat protein as reported in PubMed: (SEQ ID NOS: 443-453, respectively, in order of appearance)

| | | | | Neighboring Amino acids | | | | | | | | | | | tat Replikin | | | | | | | |
|---|---|---|---|---|---|---|---|---|---|---|---|---|---|---|---|---|---|---|---|---|---|---|
| 38 | (100) | 57 | 86 | (100) | (100) | 66 | 76 | (100) | 99 | 57 | 49 | (100) | 94 | (100) | 97 | 98 | 85 | 97 | 99 | (100) | (100) | (100)% |
| k | (c) | s | y | [(h) | (c) | l | v | (c) | f | q | k | (k) | g | (l) | g | i | s | y | g | (r) | (k) | (k)] |
| below are the amino acid substitutions observed for each amino acid above: | | | | | | | | | | | | | | | | | | | | | | |
| h | | c | f | | q | i | | | l | h | t | | | a | | | a | l | y | h | q | |
| r | | w | p | | l | l | | | | i | h | | | q | | | v | | | | | |
| y | | | s | | | s | | | | l | m | | | r | | | s | | | | | |
| i | | | | | | s | | | | m | s | | | | | | | | | | | |
| s | | | | | | r | | | | n | | | | | | | | | | | | |
| v | | | | | | | | | | | | | | | | | | | | | | |
| a | | | | | | | | | | | | | | | | | | | | | | |
| f | | | | | | | | | | | | | | | | | | | | | | |
| P | | | | | | | | | | | | | | | | | | | | | | |
| q | | | | | | | | | | | | | | | | | | | | | | |

The conservation of the Replikin structure suggests that the Replikin structure has a specific survival function for the HIV virus which must be preserved and conserved, and cannot be sacrificed to the virus 'defense' maneuver of amino acid substitution created to avoid antibody and other 'attack.' These 'defense' functions, although also essential, cannot 'compete' with the virus survival function of HIV replication.

Further conservation was observed in different isolates of HIV for its Replikins such as "kcfncgkegh" (SEQ ID NO: 5) or "kvylawvpahk" (SEQ ID NO: 6) in HIV Type 1 and "kcwncgkegh" (SEQ ID NO: 7) in HIV Type 2. The high rate of conservation observed in FMVD and HIV Replikins suggests that conservation also observed in the Replikins of influenza Replikins is a general property of viral Replikins.

Anti-Replikin Antibodies

Figure 3:
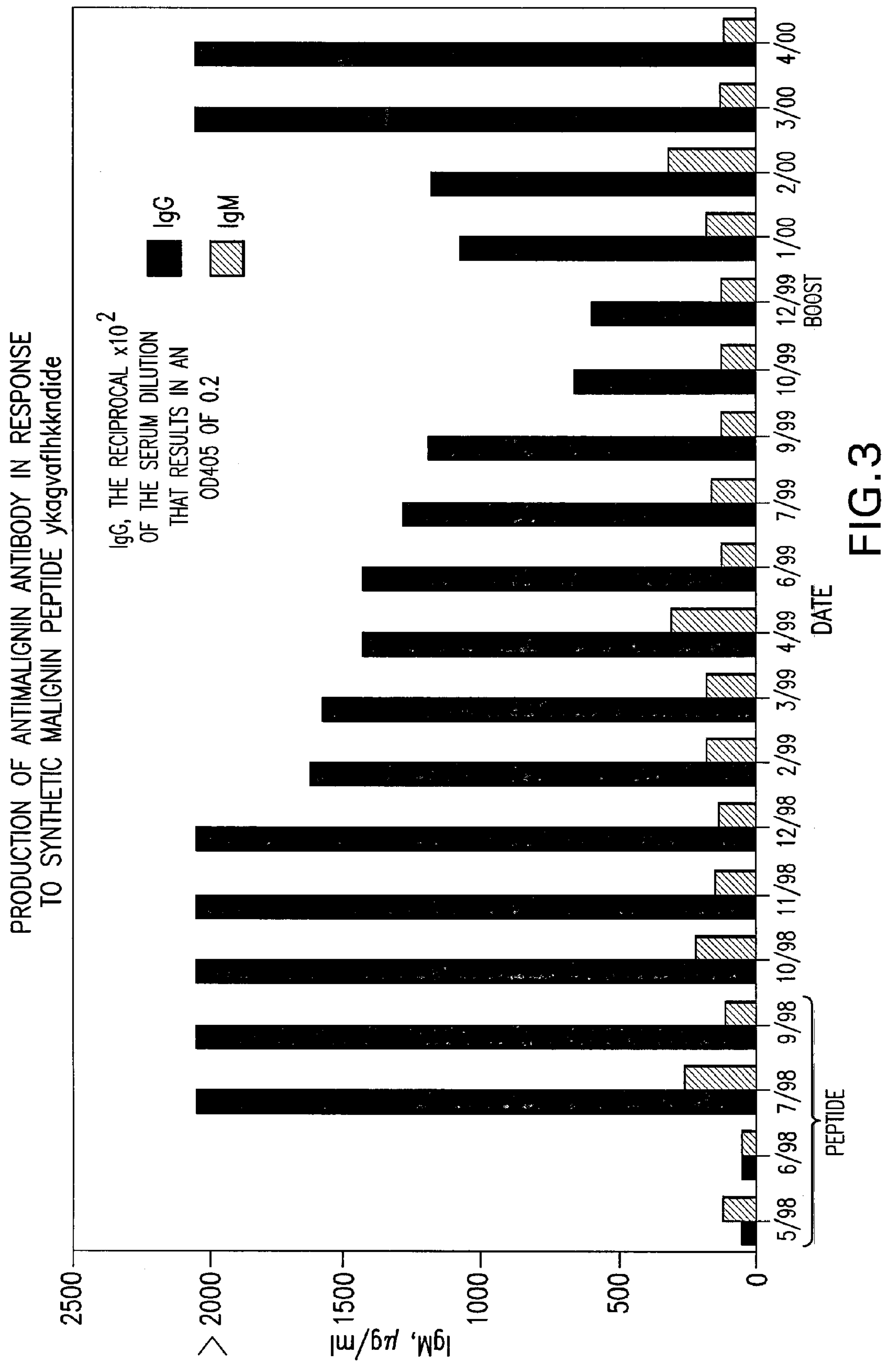
FIG. 3 is a bar graph showing amount of antimalignin antibody produced in response to exposure to the recognin 16-mer (SEQ ID NO: 4).

An anti-Replikin antibody is an antibody against a Replikin. Data on anti-Replikin antibodies also support Replikin class unity. An anti-Replikin antibody response has been quantified by immunoadsorption of serum antimalignin antibody to immobilized malignin (see Methods in U.S. Pat. No. 5,866,690). The abundant production of antimalignin antibody by administration to rabbits of the synthetic version of the 16-mer peptide whose sequence was derived from malignin, absent carbohydrate or other groups, has established rigorously that this peptide alone is an epitope, that is, provides a sufficient basis for this immune response (FIG. 3). The 16-mer peptide produced both IgM and IgG forms of the antibody. Antimalignin antibody was found to be increased in concentration in serum in 37% of 79 cases in the U.S. and Asia of hepatitis B and C, early, in the first five years of infection, long before the usual observance of liver cancer, which develops about fifteen to twenty-five years after infection. Relevant to both infectious hepatitis and HIV infections, transformed cells may be one form of safe haven for the virus: prolonging cell life and avoiding virus eviction, so that the virus remains inaccessible to anti-viral treatment.

Because administration of Replikins stimulates the immune system to produce antibodies having a cytotoxic effect, peptide vaccines based on the particular influenza virus Replikin or group of Replikins observed to be most concentrated over a given time period provide protection against the particular strain of influenza most likely to cause an outbreak in a given influenza season, e.g., an emerging strain or re-emerging strain For example, analysis of the influenza virus hemagglutinin amino acid sequence on a yearly or bi-yearly basis, provides data which are useful in formulating a specifically targeted influenza vaccine for that year. It is understood that such analysis may be conducted on a region-by-region basis or at any desired time period, so that strains emerging in different areas throughout the world can be detected and specifically targeted vaccines for each region can be formulated.

Influenza Vaccines, Treatments and Therapeutics

Currently, vaccine formulations for influenza are changed twice yearly at international WHO and CDC meetings. Vaccine formulations are based on serological evidence of the most current preponderance of influenza virus strain in a given region of the world. However, prior to the present invention there has been no correlation of influenza virus strain specific amino acid sequence changes with occurrence of influenza epidemics or pandemics.

The observations of specific Replikins and their concentration in influenza virus proteins provides the first specific quantitative early chemical correlates of influenza pandemics and epidemics and provides for production and timely administration of influenza vaccines tailored specifically to treat the prevalent emerging or re-emerging strain of influenza virus in a particular region of the world. By analyzing the protein sequences of isolates of strains of influenza virus, such as the hemagglutinin protein sequence, for the presence, concentration and/or conservation of Replikins, influenza virus pandemics and epidemics can be predicted. Furthermore, the severity of such outbreaks of influenza can be significantly lessened by administering an influenza peptide vaccine based on the Replikin sequences found to be most abundant or shown to be on the rise in virus isolates over a given time period, such as about one to about three years.

An influenza peptide vaccine of the invention may include a single Replikin peptide sequence or may include a plurality of Replikin sequences observed in influenza virus strains. Preferably, the peptide vaccine is based on Replikin sequence(s) shown to be increasing in concentration over a given time period and conserved for at least that period of time. However, a vaccine may include a conserved Replikin peptide(s) in combination with a new Replikin(s) peptide or may be based on new Replikin peptide sequences. The Replikin peptides can be synthesized by any method, including chemical synthesis or recombinant gene technology, and may include non-Replikin sequences, although vaccines based on peptides containing only Replikin sequences are preferred. Preferably, vaccine compositions of the invention also contain a pharmaceutically acceptable carrier and/or adjuvant.

The influenza vaccines of the present invention can be administered alone or in combination with antiviral drugs, such as gancyclovir; interferon; interleukin; M2 inhibitors, such as, amantadine, rimantadine; neuraminidase inhibitors, such as zanamivir and oseltamivir; and the like, as well as with combinations of antiviral drugs.

The influenza vaccine of the present invention may be administered to any animal capable of producing antibodies in an immune response. For example, the influenza vaccine of the present invention may be administered to a rabbit, a chicken, a pig or a human. Because of the universal nature of replikin sequences, an influenza vaccine of the invention may be directed at a range of strains of influenza or a specific strain of influenza.

In a non-limiting aspect in accordance with the present invention, an influenza vaccine may be directed to an immune response against animal or human strain of influenza including influenza B, (A)H1N1, (A)H2N2 and (A)H3N2, or any human variant of the virus that may arise hereafter, as well as strains of influenza predominantly in animals such as the current avian H5N1. An influenza vaccine may further be directed to a particular replikin amino acid sequence in any portion of an influenza protein.

In a non-limiting aspect in accordance with the present invention, an influenza vaccine may comprise a Replikin Scaffold of the H5N1 virus such as KKNSTYPTIKRSYNNTNQEDLLVLWGIHH (SEQ ID NO: 15). In a further non-limiting aspect, an influenza vaccine may comprise a UTOPE such as KKKKH (SEQ ID NO: 457) or KKKKH (SEQ ID NO: 458). In a further alternative, a vaccine may comprise the addition of an adjuvant such as the well known key limpet hemocyanin denoted with the abbreviation -KLH. In yet a further preferred non-limiting aspect, an influenza vaccine may comprise a Replikin Scaffold of influenza H5N1 further comprising two UTOPES and an adjuvant sequence such as KKNSTYPTIKRSYNNTNQEDLLVLWGIHHKKKKHKKKKKHK (SEQ ID NO: 16)-KLH (denoting a key limpet hemocyanin adjuvant) (Vaccine V120304U2). An aspect of the present invention may comprise the Replikin Scaffold previously constructed and shown in Table 8 as one of the Bird Flu Replikins labelled"2004 H5N1 Vietnam, highly pathogenic." With administration of 100 ug of the peptide of Vaccine V120304U2 injected subcutaneously into rabbits and chickens an antibody response was observed from unvaccinated dilutions of less than 1:50 to reach a peak in the third to fourth week after vaccination of from a dilution of 1:120,000 to greater than 1:240,000. (See Example 7.)

Repetition and Overlapping Replikin Structures

Analysis of the primary structure of a Plasmodium farciparum malaria antigen located at the merozoite surface and/or within the parasitophorous vacuole revealed that this organism, like influenza virus, also contains numerous Replikins. However, there are several differences between the observation of Replikins in Plasmodium falciparum and influenza virus isolates. For example, Plasmodium falciparum contains several partial Replikins. Another difference seen in Plasmodium falciparum is a frequent repetition of individual Replikin structures within a single protein, which was not observed with influenza virus. Repetition may occur by (a) sharing of lysine residues between Replikins, and (b) by repetition of a portion of a Replikin sequence within another Replikin sequence.

High Concentrations of Replikin Correlates with Rapid Replication

Tomato leaf curl Gemini virus has devastated tomato crops in China and in many other parts of the world. Its replikins reach high counts because of overlapping replikins as illustrated below in a virus isolated in Japan where the replikin count was 20.7

The relationship of higher Replikin concentration to rapid replication is also confirmed by analysis of HIV isolates. It was found that the slow-growing low titer strain of HIV (NSI, "Bru," which is prevalent in early stage HIV infection) has a Replikin concentration of 1.1 (+/−1.6) Replikins per 100 amino acids, whereas the rapidly-growing high titer strain of HIV (Si, "Lai", which is prevalent in late stage HIV infection) has a Replikin concentration of 6.8 (+/−2.7) Replikins per 100 amino acid residues.

Passive Immunity

In another aspect of the invention, isolated Replikin peptides may be used to generate antibodies, which may be used, for example to provide passive immunity in an individual. Passive immunity to the strain of influenza identified by the method of the invention to be the most likely cause of future influenza infections may be obtained by administering antibodies to Replikin sequences of the identified strain of influenza virus to patients in need. Similarly, passive immunity to malaria may be obtained by administering antibodies to Plasmodium falciparum Replikin(s).

Various procedures known in the art may be used for the production of antibodies to Replikin sequences. Such antibodies include but are not limited to polyclonal, monoclonal, chimeric, humanized, single chain, Fab fragments and fragments produced by an Fab expression library. Antibodies that are linked to a cytotoxic agent may also be generated. Antibodies may also be administered in combination with an antiviral agent. Furthermore, combinations of antibodies to different Replikins may be administered as an antibody cocktail.

For the production of antibodies, various host animals or plants may be immunized by injection with a Replikin peptide or a combination of Replikin peptides, including but not limited to rabbits, mice, rats, and larger mammals.

Monoclonal antibodies to Replikins may be prepared by using any technique that provides for the production of antibody molecules. These include but are not limited to the hybridoma technique originally described by Kohler and Milstein, (Nature, 1975, 256:495-497), the human B-cell hybridoma technique (Kosbor et al., 1983, Immunology Today, 4:72), and the EBV hybridoma technique (Cole et al., Monoclonal Antibodies and Cancer Therapy, Alan R. Liss, Inc., pp. 77-96). In addition, techniques developed for the production of chimeric antibodies (Morrison et al., 1984, Proc. Nat. Acad. Sci USA, 81:6851-6855) or other techniques may be used. Alternatively, techniques described for the production of single chain antibodies (U.S. Pat. No. 4,946,778) can be adapted to produce Replikin-specific single chain antibodies.

Particularly useful antibodies of the invention are those that specifically bind to Replikin sequences contained in peptides and/or polypeptides of influenza virus. For example, antibodies to any of peptides observed to be present in an emerging or re-emerging strain of influenza virus and combinations of such antibodies are useful in the treatment and/or prevention of influenza. Similarly, antibodies to any Replikins present on malaria antigens and combinations of such antibodies are useful in the prevention and treatment of malaria.

Antibody fragments which contain binding sites for a Replikin may be generated by known techniques. For example, such fragments include but are not limited to F(ab')2 fragments which can be produced by pepsin digestion of the antibody molecules and the Fab fragments that can be generated by reducing the disulfide bridges of the F(ab')2 fragments. Alternatively, Fab expression libraries can be generated (Huse et al., 1989, Science, 246:1275-1281) to allow rapid and easy identification of monoclonal Fab fragments with the desired specificity.

Figure 4A:
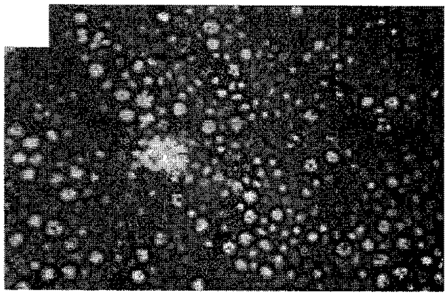
FIG. 4A is a photograph of a blood smear taken with ordinary and fluorescent light.
Figure 4B:
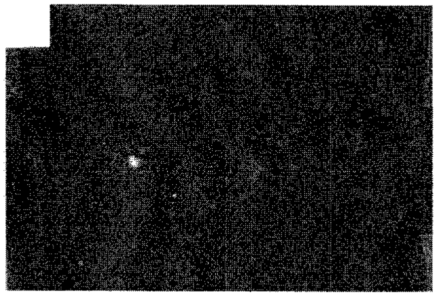
FIG. 4B is a photograph of a blood smear taken with ordinary and fluorescent light illustrating the presence of two leukemia cells.
Figure 4C:
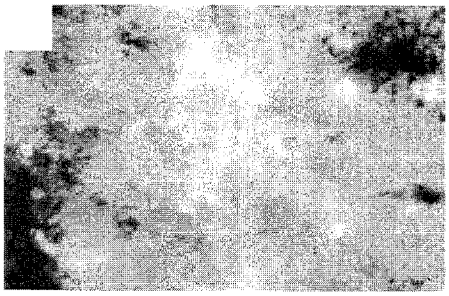
FIG. 4C is a photograph of a dense layer of glioma cells in the presence of antimalignin antibody.
Figure 4D:
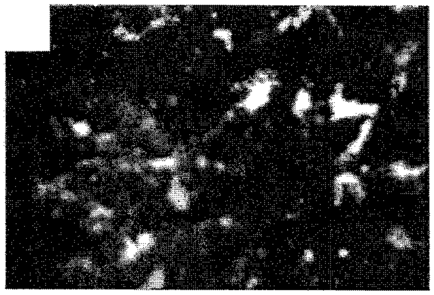
FIG. 4D and FIG. 4E are photographs of the layer of cells in FIG. 4C taken at 30 and 45 minutes following addition of antimalignin antibody.
Figure 4E:
Figure 4F:
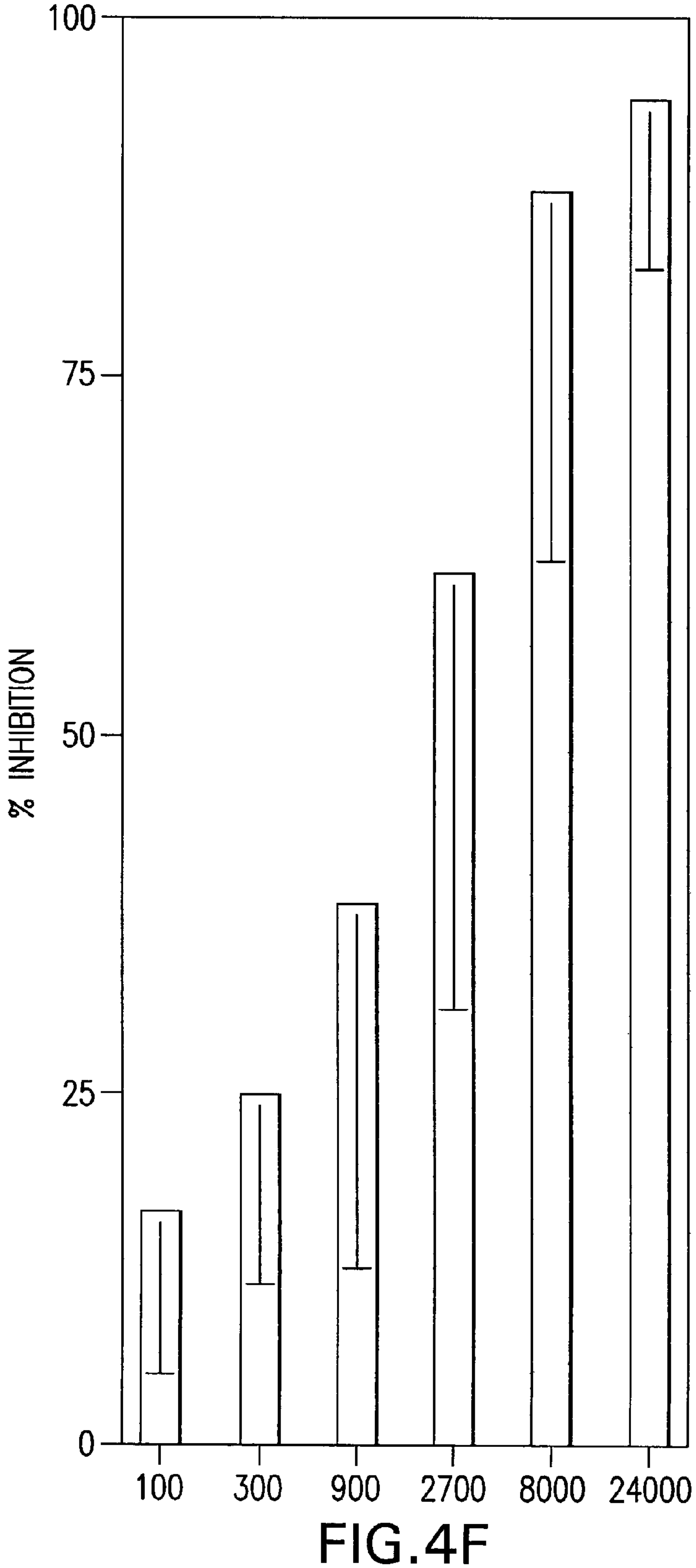
FIG. 4F is a bar graph showing the inhibition of growth of small cell lung carcinoma cells in vitro by antimalignin antibody.

The fact that antimalignin antibody is increased in concentration in human malignancy (see FIG. 5), regardless of cancer cell type, and that this antibody binds to malignant cells regardless of cell type now may be explained by the presence of the Replikin structures herein found to be present in most malignancies (FIG. 1 and Table 2). Population studies have shown that antimalignin antibody increases in concentration in healthy adults with age, and more so in high-risk families, as the frequency of cancer increases. An additional two-fold or greater antibody increase, which occurs in early malignancy, has been independently confirmed with a sensitivity of 97% in breast cancers 1-10 mm in size. Shown to localize preferentially in malignant cells in vivo, histochemically the antibody does not bind to normal cells but selectively binds to (FIG. 4A,B) and is highly cytotoxic to transformed cells in vitro (FIG. 4C-F). Since in these examples the same antibody is bound by several cell types, that is, brain glioma, hematopoietic cells (leukemia), and small cell carcinoma of lung, malignant Replikin class unity is again demonstrated.

Figure 5:
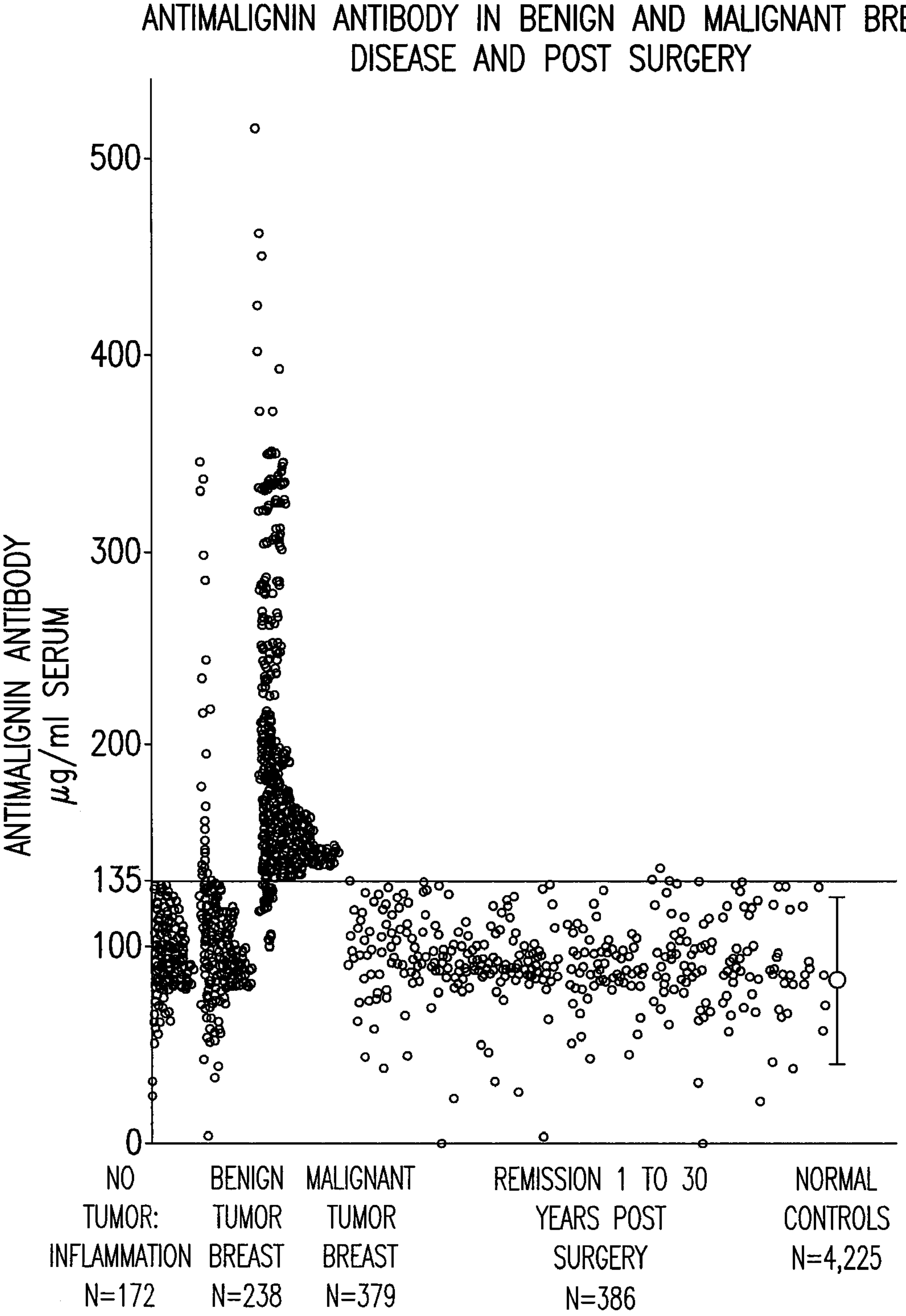
FIG. 5 is a plot of the amount of antimalignin antibody present in the serum of patients with benign or malignant breast disease pre- and post surgery.

Antimalignin does not increase with benign proliferation, but specifically increases only with malignant transformation and replication in breast in vivo and returns from elevated to normal values upon elimination of malignant cells (FIG. 5). Antimalignin antibody concentration has been shown to relate quantitatively to the survival of cancer patients, that is, the more antibody, the longer the survival. Taken together, these results suggest that anti-Replikin antibodies may be a part of a mechanism of control of cell transformation and replication. Augmentation of this immune response may be useful in the control of replication, either actively with synthetic Replikins as vaccines, or passively by the administration of anti-Replikin antibodies, or by the introduction of non-immune based organic agents, such as for example, carbohydrates, lipids and the like, which are similarly designed to target the Replikin specifically.

In another aspect of the invention, immune serum containing antibodies to one or more Replikins obtained from an individual exposed to one or more Replikins may be used to induce passive immunity in another individual or animal. Immune serum may be administered via i.v. to a subject in need of treatment. Passive immunity also can be achieved by injecting a recipient with preformed antibodies to one or more Replikins. Passive immunization may be used to provide immediate protection to individuals who have been exposed to an infectious organism. Administration of immune serum or preformed antibodies is routine and the skilled practitioner can readily ascertain the amount of serum or antibodies needed to achieve the desired effect.

Synthetic Replikin Vaccines (Active Immunity)

Synthetic Replikin vaccines, based on Replikins such as the glioma Replikin (SEQ ID NO: 1) "kagvaflhkk" or the hepatitis C Replikin (SEQ ID NO: 18) "hyppkpgcivpak", or HIV Replikins such as (SEQ ID NO: 5) "kcfncgkegh" or (SEQ ID NO: 6) "kvylawvpahk" or preferably, an influenza vaccine based on conserved and/or emerging or re-emerging Replikin(s) over a given time period may be used to augment antibody concentration in order to lyse the respective virus infected cells and release virus extracellularly where chemical treatment can then be effective. Similarly, a malaria vaccine, based on Replikins observed in Plasmodium falciparum malaria antigens on the merozoite surface or within the parasitophorous vacuole, for example, can be used to generate cytotoxic antibodies to malaria. Table 7 shows the relation of shortening or compacting of Replikin sequences to mortality rate caused by the organisms which contain these Replikins, to as short as seven amino acids. This correlation has been found by us to be a general phenomenon regardless of the type of organism. We have also found that there may be a progression over time to the shortened Replikin structure, as in influenza and SARS viruses.

There is abundant evidence that there are constant evolutionary and competitive pressures for the emergence of constantly increasing "efficacy" of each infectious organism. Based upon these observations, and by projection, it would appear that if evolutionary pressures are towards shorter and shorter Replikins, with higher and higher concentrations of lysine (k), to as high as 70% as in EEL leukemia (Table 7), then the projected theoretical ideal would be the shortest possible Replikin permitted by the algorithm which defines a Replikin, that is six amino acids (two ks six to ten amino acids apart), with the highest possible % k (see deduced Replikin "kkkkhk" (SEQ ID NO: 459), which contains 83.3% k, 5/6, and one obligatory "h"). We have therefore, so-to-speak, taken what appears to be, or might be, the next evolutionary step, not apparently as yet taken by the organisms themselves, and devised the resultant deduced Replikins to use as general vaccines.

These Replikins which we have deduced have maximum Vk's, therefore maximum potential binding capacity, plus the constituent 'h' by definition required for the Replikin, giving the potential for 'h' connection to redox energy systems. These devised Replikins are least likely to be cleaved by organisms because of their short length (proteins are cleaved to 6 to 10 amino acids long in processing for presentation to and recognition by immune cells), therefore most likely to present intact to immune-forming apparatuses in the organism to which they are administered, and, because of their high k content, they are most likely to generate a maximum immune response which mimics and may increase the maximum such response which can be generated against short homologous high mortality Replikins.

Further, we have found that high % k Replikins generate the highest antibody responses when administered to rabbits. These synthetic peptides, designed by us, are designated as Universal synthetic epitopes, or "UTOPE's", and the vaccines based upon these UTOPEs, are designated "UVAX"s. UVAXs, deduced synthetic vaccines, may be used as sole vaccines or as adjuvants when administered with more specific Replikin vaccines or other vaccines. The following are examples of deduced UTOPEs and UVAXs:

| DEVISED SYNTHETIC REPLIKIN (UTOPE OR UVAX) | SEQ ID NO: |
|---|---|
| KKKKHK | 459 |
| KKKHKK | 460 |
| KKHKKK | 461 |
| KHKKKK | 462 |
| KKKKKKH | 463 |
| KKKKKHK | 464 |
| KKKKHKK | 465 |
| KKKHKKK | 466 |
| KKHKKKK | 467 |
| KHKKKKK | 468 |
| HKKKKKK | 469 |

-continued

Recognin and/or Replikin peptides may be administered to a subject to induce the immune system of the subject to produce anti-Replikin antibodies. Generally, a 0.5 to about 2 mg dosage, preferably a 1 mg dosage of each peptide is administered to the subject to induce an immune response. Subsequent dosages may be administered if desired.

The Replikin sequence structure is associated with the function of replication. Thus, whether the Replikins of this invention are used for targeting sequences that contain Replikins for the purpose of diagnostic identification, promoting replication, or inhibiting or attacking replication, for example, the structure-function relationship of the Replikin is fundamental.

It is preferable to utilize only the specific Replikin structure when seeking to induce antibodies that will recognize and attach to the Replikin fragment and thereby cause destruction of the cell. Even though the larger protein sequence may be known in the art as having a "replication associated function," vaccines using the larger protein often have failed or proven ineffective.

Although the present inventors do not wish to be held to a single theory, the studies herein suggest that the prior art vaccines are ineffective because they are based on the use of the larger protein sequence. The larger protein sequence invariably has one or more epitopes (independent antigenic sequences that can induce specific antibody formation); Replikin structures usually comprise one of these potential epitopes. The presence of other epitopes within the larger protein may interfere with adequate formation of antibodies to the Replikin, by "flooding" the immune system with irrelevant antigenic stimuli that may preempt the Replikin antigens, See, e.g., Webster, R. G., J. Immunol., 97(2):177-183 (1966); and Webster et al., J. Infect. Dis., 134:48-58, 1976; Klenerman et al, Nature 394:421-422 (1998) for a discussion of this well-known phenomenon of antigenic primacy whereby the first peptide epitope presented and recognized by the immune system subsequently prevails and antibodies are made to it even though other peptide epitopes are presented at the same time. This is another reason that, in a vaccine formulation, it is important to present the constant Replikin peptide to the immune system first, before presenting other epitopes from the organism so that the Replikin is not preempted but lodged in immunological memory.

The formation of an antibody to a non-Replikin epitope may allow binding to the cell, but not necessarily lead to cell destruction. The presence of structural "decoys" on the C-termini of malaria proteins is another aspect of this ability of other epitopes to interfere with binding of effective anti-Replikin antibodies, since the decoy epitopes have many lysine residues, but no histidine residues. Thus, decoy epitopes may bind anti-Replikin antibodies, but may keep the antibodies away from histidine-bound respiratory enzymes. Treatment may therefore be most efficacious in two stages: 1) proteases to hydrolyze decoys, then; 2) anti-Replikin antibodies or other anti-Replikin agents.

It is well known in the art that in the course of antibody production against a "foreign" protein, the protein is first hydrolyzed into smaller fragments. Usually fragments containing from about six to ten amino acids are selected for antibody formation. Thus, if hydrolysis of a protein does not result in Replikin-containing fragments, anti-Replikin antibodies will not be produced. In this regard, it is interesting that Replikins contain lysine residues located six to ten amino acids apart, since lysine residues are known to bind to membranes.

Furthermore, Replikin sequences contain at least one histidine residue. Histidine is frequently involved in binding to redox centers. Thus, an antibody that specifically recognizes a Replikin sequence has a better chance of inactivating or destroying the cell in which the Replikin is located, as seen with anti-malignin antibody, which is perhaps the most cytotoxic anti-cancer antibody yet described, being active at picograms per cell.

One of the reasons that vaccines directed towards a particular protein antigen of a disease causing agent have not been fully effective in providing protection against the disease (such as foot and mouth vaccine which has been developed against the VP1 protein or large segments of the VP1 protein) is that the best antibodies have not been produced, that is—it is likely that the antibodies to the Replikins have not been produced. Replikins have not been produced. That is, either epitopes other than Replikins present in the larger protein fragments may interfere according to the phenomenon of antigenic primacy referred to above, and/or because the hydrolysis of larger protein sequences into smaller sequences for processing to produce antibodies results in loss of integrity of any Replikin structure that is present, e.g., the Replikin is cut in two and/or the histidine residue is lost in the hydrolytic processing. The present studies suggest that for an effective vaccine to be produced, the Replikin sequences, and no other epitope, should be used as the vaccine. For example, a vaccine of the invention can be generated using any one of the Replikin peptides identified by the three-point recognition system.

Particularly preferred peptides—for example—an influenza vaccine include peptides that have been demonstrated to be conserved over a period of one or more years, preferably about three years or more, and/or which are present in a strain of influenza virus shown to have the highest increase in concentration of Replikins relative to Replikin concentration in other influenza virus strains, e.g., an emerging strain. The increase in Replikin concentration preferably occurs over a period of at least about six months to one year, preferably at least about two years or more, and most preferably about three years or more. Among the preferred Replikin peptides for use in an influenza virus vaccine are those Replikins observed to "re-emerge" after an absence from the hemagglutinin amino acid sequence for one or more years.

The Replikin peptides of the invention, alone or in various combinations are administered to a subject, preferably by i.v. or intramuscular injection, in order to stimulate the immune system of the subject to produce antibodies to the peptide. Generally the dosage of peptides is in the range of from about 0.1 μg to about 10 mg, preferably about 10 μg to about 1 mg, and most preferably about 50 μg to about 500 ug. The skilled practitioner can readily determine the dosage and number of dosages needed to produce an effective immune response.

Quantitative Measurement Early Response(s) to Replikin Vaccines

The ability to measure quantitatively the early specific antibody response in days or a few weeks to a Replikin vaccine is a major practical advantage over other vaccines for which only a clinical response months or years later can be measured.

Adjuvants

Various adjuvants may be used to enhance the immunological response, depending on the host species, including but not limited to Freund's (complete and incomplete), mineral gels, such as aluminum hydroxide, surface active substances such as lysolecithin, pluronic polyols, polyanions, peptides, oil emulsions, key limpet hemocyanin, dintrophenol, and potentially useful human adjuvants such as BCG and *Corynebacterium parvum*. In addition to the use of synthetic UTOPEs as vaccines in themselves, UTOPEs can be used as adjuvants to other Replikin vaccines and to non-Replikin vaccines.

Replikin Nucleotide Sequences

Replikin DNA or RNA may have a number of uses for the diagnosis of diseases resulting from infection with a virus, bacterium or other Replikin encoding agent. For example, Replikin nucleotide sequences may be used in hybridization assays of biopsied tissue or blood, e.g., Southern or Northern analysis, including in situ hybridization assays, to diagnose the presence of a particular organism in a tissue sample or an environmental sample, for example. The present invention also contemplates kits containing antibodies specific for particular Replikins that are present in a particular pathogen of interest, or containing nucleic acid molecules (sense or antisense) that hybridize specifically to a particular Replikin, and optionally, various buffers and/or reagents needed for diagnosis.

Also within the scope of the invention are oligoribonucleotide sequences, that include antisense RNA and DNA molecules and ribozymes that function to inhibit the translation of Replikin- or recognin-containing mRNA. Both antisense RNA and DNA molecules and ribozymes may be prepared by any method known in the art. The antisense molecules can be incorporated into a wide variety of vectors for delivery to a subject. The skilled practitioner can readily determine the best route of delivery, although generally i.v. or i.m. delivery is routine. The dosage amount is also readily ascertainable.

Particularly preferred antisense nucleic acid molecules are those that are complementary to a Replikin sequence contained in a mRNA encoding, for example, an influenza virus polypeptide, wherein the Replikin sequence comprises from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to a Replikin present in the coding strand of the gene or to the mRNA encoding the influenza virus hemagglutinin protein, wherein the antisense nucleic acid molecule is complementary to a nucleotide sequence encoding a Replikin that has been demonstrated to be conserved over a period of six months to one or more years and/or which are present in a strain of influenza virus shown to have an increase in concentration of Replikins relative to Replikin concentration in other influenza virus strains. The increase in Replikin concentration preferably occurs over a period of at least six months, preferably about one year, most preferably about two or three years or more.

Similarly, antisense nucleic acid molecules that are complementary to mRNA those that are complementary to a mRNA encoding bacterial Replikins comprising a Replikin sequence of from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to the coding strand of the gene or to the mRNA encoding a protein of the bacteria.

Further Aspects of Replikins

In an aspect of the present invention a method of preventing or treating a virus infection comprising administering to a patient in need thereof a preventive or therapeutic virus vaccine is provided comprising at least one isolated Replikin present in a protein of an emerging strain of the virus and a pharmaceutically acceptable carrier and/or adjuvant. In a further aspect of the invention the isolated or synthesized peptides are influenza virus peptides. In yet a further aspect of the invention, the isolated or synthesized peptides are H5N1 influenza virus peptides The present invention also provides a method of making a preventive or therapeutic virus vaccine comprising:

(1) identifying a strain of a virus as an emerging strain,
(2) selecting at least one Replikin sequence present in the emerging strain as a peptide template for the virus vaccine manufacture,
(3) synthesizing peptides having the amino acid sequence of the at least one Replikin sequence selected in step (2), and
(4) combining a therapeutically effective amount of the peptides of step (3) with a pharmaceutically acceptable carrier and/or adjuvant.

In a further aspect of the method of making a preventive or therapeutic virus vaccine, the isolated Replikin is from influenza virus. In still a further aspect, the isolated Replikin is from an influenza H5N1 virus.

In another aspect, the invention is directed to a method of identifying an emerging strain of a virus for diagnostic, preventive or therapeutic purposes comprising:

(1) obtaining at least one isolate of each strain of a plurality of strains of the virus;
(2) analyzing the amino acid sequence of the at least one isolate of each strain of the plurality of strains of the virus for the presence and concentration of Replikin sequences;
(3) comparing the concentration of Replikin sequences in the amino acid sequence of the at least one isolate of each strain of the plurality of strains of the virus to the concentration of Replikin sequences observed in the amino acid sequence of each of the strains from at least one earlier time period to provide the concentration of Replikins for at least two time periods, said at least one earlier time period being within about six months to about three years prior to step (1); and
(4) identifying the strain of the virus having the highest increase in concentration of Replikin sequences during the at least two time periods.

In another aspect of the invention there is provided a process for stimulating the immune system of a subject to produce antibodies that bind specifically to a Replikin sequence, said process comprising administering to the subject an effective amount of a dosage of a composition comprising at least one Replikin peptide. A further aspect of the present invention comprises at least one peptide that is present in an emerging strain of the organism if such new strain emerges. Another aspect of the present invention comprises at least one peptide that is present in influenza H5N1.

The present invention also provides antibodies that bind specifically to a Replikin, as defined herein, as well as antibody cocktails containing a plurality of antibodies that specifically bind to Replikins. Another aspect of the present invention provides compositions comprising an antibody or antibodies that specifically bind to a Replikin and a pharmaceutically acceptable carrier.

In one aspect of the invention there are provided isolated, or separated from other proteins, recombinant, or synthesized peptides or other methods containing a viral Replikin sequence.

The present application also provides isolated, or separated from nucleocapsid proteins, amongst others, recombinant, or synthesized peptides or other methods containing a viral Replikin sequence.

In another aspect of the invention there is provided a process for stimulating the immune system of a subject to produce antibodies that bind specifically to a viral Replikin sequence, said process comprising administering to the subject an effective amount of a dosage of a composition comprising at least one Replikin peptide. Another aspect of the present invention comprises at least one peptide that is present in an emerging strain of the virus if such new strain emerges.

The present invention also provides antibodies that bind specifically to a viral Replikin, as defined herein, as well as antibody cocktails containing a plurality of antibodies that specifically bind to viral Replikins. Another aspect of the present invention provides compositions comprising an antibody or antibodies that specifically bind to a viral Replikin and a pharmaceutically acceptable carrier.

The present invention also provides therapeutic compositions comprising one or more of isolated Replikin virus peptides and a pharmaceutically acceptable carrier.

In another aspect of the invention there is provided an antisense nucleic acid molecule complementary to a virus Replikin mRNA sequence, said Replikin mRNA sequence denoting from 7 to about 50 amino acids comprising:

(1) at least one lysine residue located six to ten residues from a second lysine residue;
(2) at least one histidine residue; and
(3) at least 6% lysine residues.

In yet another aspect of the invention there is provided a method of simulating the immune system of a subject to produce antibodies to viruses, said method comprising: administering an effective amount of at least one virus Replikin peptide.

In another aspect, there is provided a method of selecting a virus peptide for inclusion in a preventive or therapeutic virus vaccine comprising:

(1) obtaining at least on isolate of each strain of a plurality of strains of said virus;
(2) analyzing the amino acid sequence of the at least one isolate of each strain of the plurality of strains of the virus for the presence and concentration of Replikin sequences;
(3) comparing the concentration of Replikin sequences in the amino acid sequence of the at least one isolate of each strain of the plurality of strains of the virus to the concentration of Replikin sequences observed in the amino acid sequence of each of the strains at least one earlier time period to provide the concentration of Replikins for at least two time periods, said at least one earlier time period being within about six months to about three years prior to step (1);
(4) identifying the strain of the virus having the highest increase in concentration of Replikin sequences during the at least two time periods; and
(5) selecting at least one Replikin sequence present in the strain of the virus peptide identified in step (4) as a peptide for inclusion in the virus vaccine.

In one aspect of the invention there are provided isolated or synthesized influenza virus peptides comprising a Replikin sequence.

In another aspect of the invention, there is provided a process for stimulating the immune system of a subject to produce antibodies that bind specifically to an influenza virus Replikin sequence, said process comprising administering to the subject an effective amount of dosage of a composition comprising at least one influenza virus Replikin peptide. A further aspect of the present invention comprises at least one Replikin peptide that is present in an emerging strain of influenza virus. Yet another aspect of the present invention comprises a composition comprising at least one influenza H5N1 Replikin peptide.

The present invention also provides antibodies that bind specifically to an influenza virus Replikin, as defined herein, as well as antibody cocktails containing a plurality of antibodies that specifically bind to influenza virus Replikins. In another aspect of the present invention, there are provided compositions comprising an antibody or antibodies that specifically bind to an influenza Replikin and a pharmaceutically acceptable carrier.

The present invention also provides therapeutic compositions comprising one or more of isolated influenza virus peptides having from 7 to about 50 amino acids comprising:

(1) at least one lysine residue located six to ten residues form a second lysine residue;

(2) at least one histidine residue; and (3) at least 6% lysine residues, and a pharmaceutical acceptable carrier.

In another aspect of the invention there is provided an antisense nucleic acid molecule complementary to an influenza virus hemagglutinin Replikin mRNA sequence, said Replikin mRNA sequence denoting from 7 to about 50 amino acids comprising:

(1) at least one lysine residue located six to ten residues from a second lysine residue;

(2) at least one histidine residue; and (3) at least 6% lysine residues.

In yet another aspect of the invention there is provided a method of simulating the immune system of a subject to produce antibodies to influenza virus comprising administering an effective amount of at least one influenza virus Replikin peptide having from 7 to about 50 amino acids comprising:

(1) at least one lysine residue located six to ten amino acid residues from a second lysine residue;

(2) at least one histidine residue; and (3) at least 6% lysine residues.

In another aspect, there is provided a method of selecting an influenza virus peptide for inclusion in a preventive or therapeutic influenza virus vaccine comprising:

(1) obtaining at least one isolate of each strain of a plurality of strains of influenza virus;

(2) analyzing the hemagglutinin amino acid sequence of the at least one isolate of each strain of the plurality of strains of influenza virus for the presence and concentration of Replikin sequences;

(3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1);

(4) identifying the strain of influenza virus having the highest increase in concentration of Replikin sequences during the at least two time periods;

(5) selecting at least one Replikin sequence present in the strain of influenza virus peptide identified in step (4) as a peptide for inclusion in an influenza virus vaccine.

The present invention also provides a method of making a preventive or therapeutic influenza virus vaccine comprising:

(1) identifying a strain of influenza virus as an emerging strain;

(2) selecting at least one Replikin sequence present in the emerging strain as a peptide template for influenza virus vaccine manufacture, (3) synthesizing peptides having the amino acid sequence of the at least one Replikin sequence selected in step (2), and (4) combining a therapeutically effective amount of the peptides of step (3) with a pharmaceutically acceptable carrier and/or adjuvant.

In another aspect, the invention is directed to a method of identifying an emerging strain of influenza virus for diagnostic, preventive or therapeutic purposes comprising:

(1) obtaining at least one isolate of each strain of a plurality of strains of influenza virus;

(2) analyzing the hemagglutinin amino acid sequence of the at least one isolate of each strain of the plurality of strains of influenza virus for the presence and concentration of Replikin sequences;

(3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1); and (4) identifying the strain of influenza virus having the highest increase in concentration of Replikin sequences during the at least two time periods.

In yet another aspect of the invention, there is provided a preventive or therapeutic influenza virus vaccine comprising at least one isolated Replikin present in the hemagglutinin protein of an emerging strain of influenza virus and a pharmaceutically acceptable carrier and/or adjuvant.

Also provided by the present invention is a method of preventing or treating influenza virus infection comprising administering to a patient in need thereof a preventive or therapeutic vaccine comprising at least one isolated Replikin present in the hemagglutinin protein of an emerging strain of influenza virus and a pharmaceutically acceptable carrier and/or adjuvant.

Computer Software for Identifying Replikins and Related Structures

Identification of Replikin structures, Replikin Scaffold structures and degenerate Exoskeleton Scaffold structures may be accomplished with the aid of bioinformatics.

Embodiments of the present invention are directed to a system and method for identifying and/or locating complex patterns in an amino acid sequence such as Replikin patterns, Replikin Scaffold structures, Exoskeleton Scaffold structures and other complex patterns in amino acid and nucleic acid sequences. According to an aspect of the present invention, techniques are provided to facilitate queries of protein databases. For protein descriptions received in response to the queries, aspects of the present invention may include a scan of the received protein descriptions to identify and locate Replikin patterns. According to an aspect of the present invention, a Replikin pattern is a sequence of from 7 to about 50 amino acids that include the following three (3) characteristics, each of which may be recognized as an aspect of the present invention: (1) the sequence has at least one lysine residue located six to ten amino acid residues from a second lysine residue; (2) the sequence has at least one histidine residue; and (3) at least 6% of the amino acids in the sequence are lysine residues. Another aspect of the present invention may identify and/or locate a complex amino acid sequence having specified length constraints, which further includes any combination of the following characteristics: (1) a first amino acid residue located more than N positions and less than M positions away from a second amino acid residue; (2) a third amino acid residue located anywhere in the sequence; and (3) at least R percent of a fourth amino acid residue. According to yet another aspect, the present invention may count occurrences of the identified amino acid sequences and may report the counted occurrences, either as raw absolute values or as ratios of the number of identified amino acid sequences per N amino acids in the protein. Still another aspect of the present invention may analyze the evolution of identified amino acid sequence patterns in variants of a given protein over time, and may also analyze the similarities and differences between instances of identified amino acid sequence patterns across a plurality of different proteins over time. As a result of the analysis, yet another aspect of the present invention may identify potential amino acid scaffolding structures that appear to be preserved over time and across different proteins, as component elements of the identified amino acid sequence patterns mutate and/or evolve.

Embodiments of the present invention will be described with reference to the accompanying drawings, wherein like parts are designated by like reference numerals throughout, and wherein the leftmost digit of each reference number refers to the drawing number of the figure in which the referenced part first appears.

Figure 17:
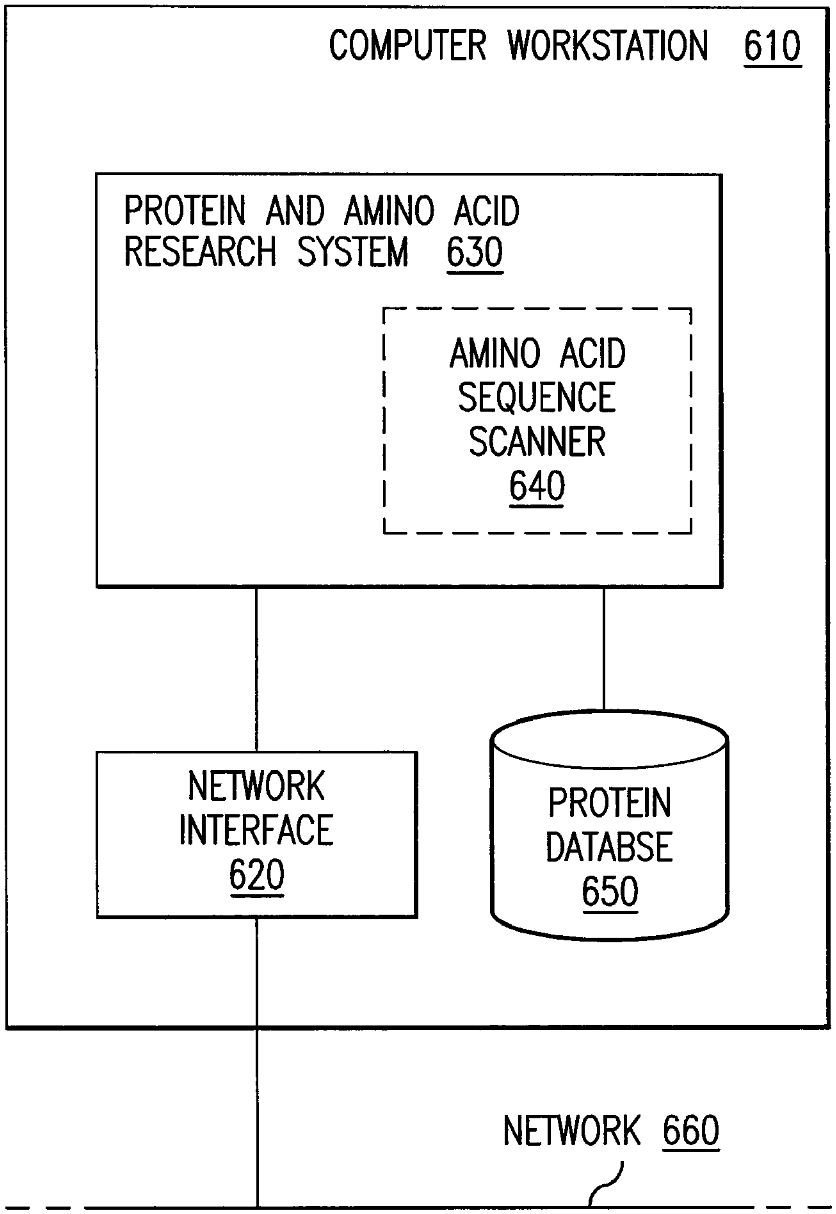
FIG. 17 is a high-level block diagram of a computer system incorporating a system and method for identifying Replikin patterns in amino acid sequences, in accordance with an aspect of the present invention.

FIG. 17 is a high-level block diagram of a computer system incorporating a system and method for identifying Replikin patterns in amino acid sequences, in accordance with an aspect of the present invention. As shown in FIG. 17, computer workstation 610 may be a computer having a processor and a memory configured to permit a researcher to search protein databases and to scan protein descriptions for selected amino acid patterns. To accomplish these functions, computer workstation 610 may include protein and amino acid research system 630, which may receive instructions from a user/researcher to conduct protein searching and amino acid scanning operations. According to an aspect, protein and amino acid research system 630 may further include amino acid sequence scanner 640 that scans and searches retrieved protein and amino acid sequences for specific patterns of amino acids, including Replikin patterns. Protein and amino acid research system 630 may communicate with network interface 620 to obtain protein sequences and amino acid sequences from resources on network 660, which may include the Internet. Alternatively, protein and amino acid research system 630 may obtain protein sequences and amino acid sequences from a local protein database 650. In addition, protein and amino acid research system 630 may obtain protein sequences and amino acid sequences directly from other input means, such as keyboard input. Protein and amino acid research system 630 may also communicate with network interface 620 to transmit results to other computers on network 660.

Automated Scanning for Replikin Patterns

Figure 18:
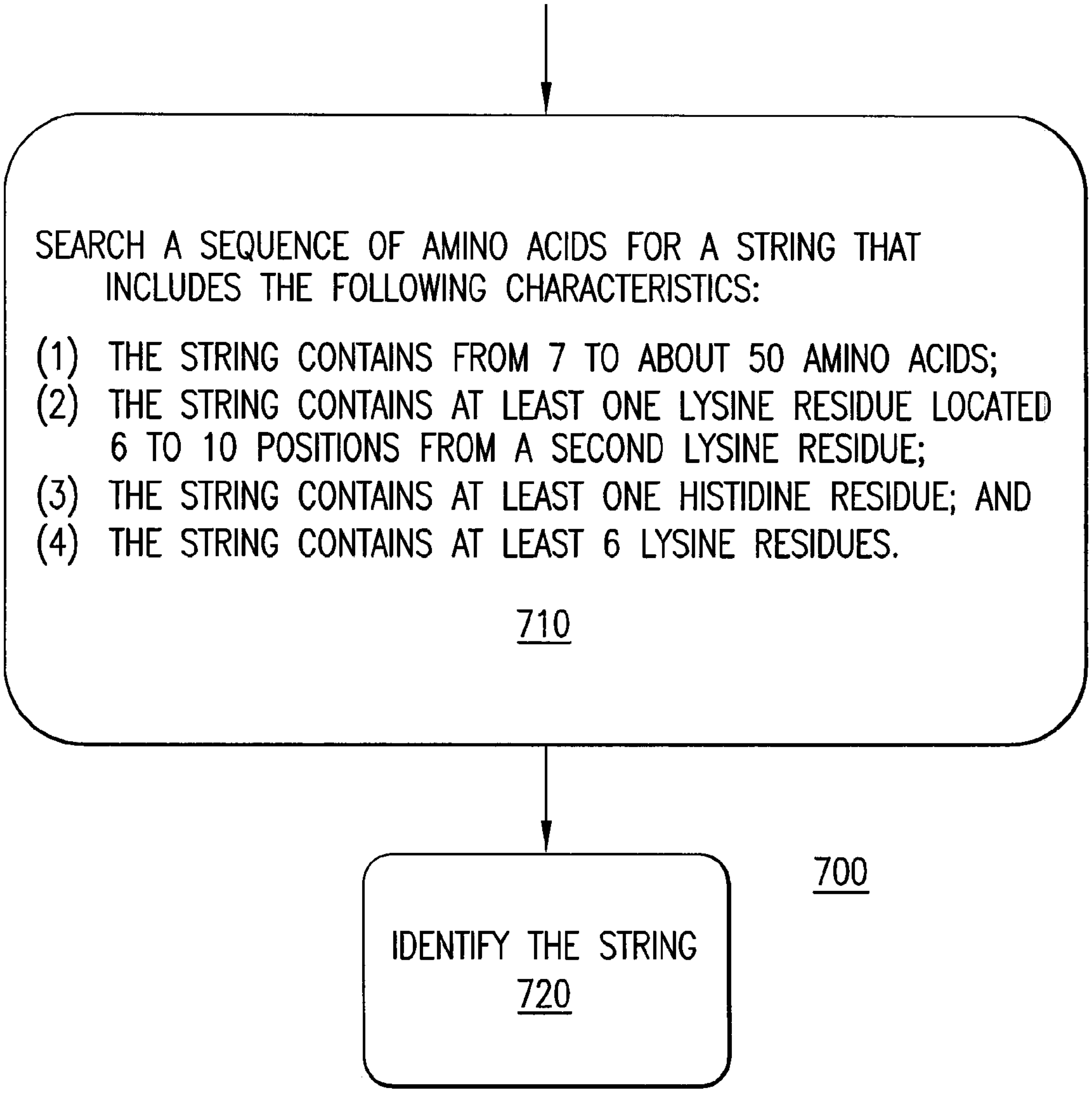
FIG. 18 is a simple flow chart illustrating a general method for locating a Replikin pattern in a sequence of amino acids, according to an aspect of the present invention.

Embodiments of the present invention may include a generalized method and system for identifying complex patterns of amino acids within proteins. For any protein definition identified or selected by protein and amino acid research system 630, the user may direct aspects of the invention to search for a variety of complex patterns of amino acids. As an example of one pattern of amino acids, the present invention provides a method for identifying nucleotide or amino acid sequences that include a Replikin pattern. FIG. 18 is a simple flow chart illustrating a general method for locating a Replikin pattern in a sequence of amino acids, according to an aspect of the present invention. The method 700 may begin after a sequence of amino acids has been obtained. Typically, the sequence of amino acids may be represented by alphabetic characters according to the code supplied in FIG. 12. However, other encodings are envisioned by the present invention as well.

Referring to FIG. 18, once a sequence of amino acids has been obtained, the sequence is searched for a Replikin pattern (710), which comprises a subsequence (or string) of amino acids that includes the following characteristics:

(1) the string contains from 7 to about 50 amino acids;

(2) the string contains at least one lysine residue located 6 to 10 positions from a second lysine residue;

(3) the string contains at least one histidine residue; and (4) the string contains at least 6% lysine residues.

Once a string of amino acids is found to match the Replikin pattern, the string may be identified or marked (720) accordingly.

A given sequence of amino acids may contain many subsequences or strings that match the Replikin pattern. Additionally, Replikin patterns may overlap each other. Thus, to locate and identify all possible Replikin patterns in a sequence of amino acids, method 700 may be invoked iteratively for each subsequence of amino acids contained within the original sequence of amino acids.

When method 700 is invoked iteratively to identify and locate all possible Replikin patterns in an amino acid sequence, an aspect of the present invention may count the number of resulting Replikin patterns. A Replikin count may be reported as an absolute number. Additionally, aspects of the invention may also determine a ratio of the number of Replikins per N amino acids in the sequence. For example, an aspect of the present invention may determine that a given protein contains a ratio of 6 Replikins for every 100 amino acids. Replikin ratios have been shown by laboratory experiment and by epidemiological evidence to correlate directly to the rate that a given protein replicates. Rapid replication of proteins may be an indication of disease. For example, the presence of relatively high ratios of Replikin patterns has been correlated to epidemics of influenza. Similarly, an increase in the count of Replikin patterns observed in a protein over time may also be an indication of future disease caused by the organism from which the protein was obtained (see, e.g., FIG. 15). Thus, the ability to detect and count Replikin patterns within sequences of amino acids is a significant advantage of the present invention.

Still referring to FIG. 18, aspects of the present invention may utilize method 700 to identify and locate other complex patterns of amino acids, which exhibit characteristics similar to Replikin patterns. That is, although some aspects of the present invention may specify exact values for: (1) distances between amino acids, (2) acceptable lengths of recognized amino acid sequences, and (3) the percentage or concentration of specific amino acids, these exact values may also be expressed as variables. Thus a researcher may employ an aspect of the present invention to identify sequences of amino acids in a protein that have the following characteristics:

(1) the sequence contains from rmin to rmax amino acids;

(2) the sequence contains at least one lysine residue located kmin to kmax amino acid residues from a second lysine residue;

(3) the sequence contains at least one histidine residue; and (4) the sequence contains at least kpercent lysine residues.

Figure 19:
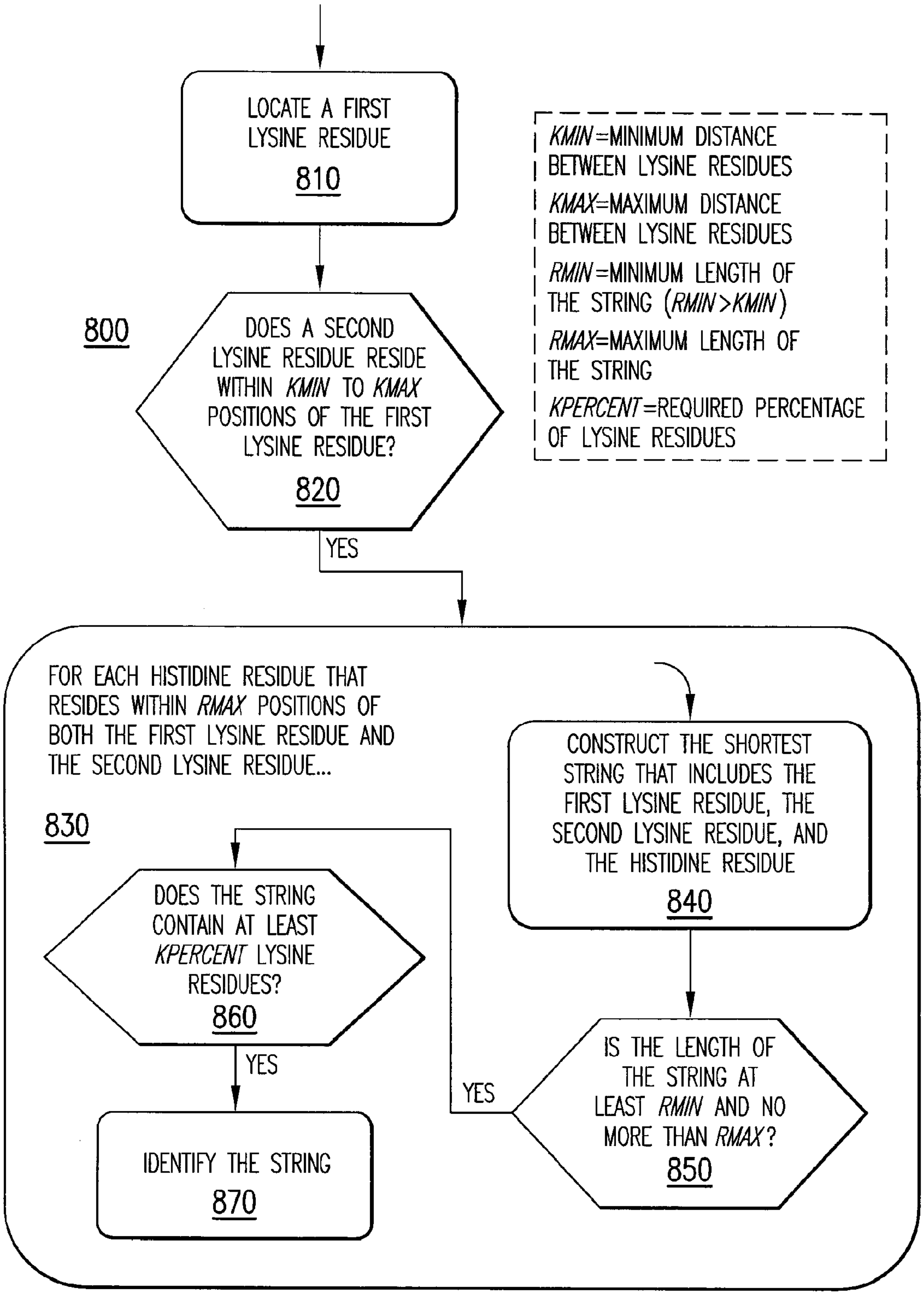
FIG. 19 is a flow chart illustrating a generalized method for locating a plurality of Replikin-like patterns in a sequence of amino acids, according to an aspect of the present invention.

FIG. 19 is a flow chart illustrating a generalized method 800 for locating a plurality of Replikin-like patterns in a given sequence of amino acids, according to an aspect of the present invention. The method 800 begins by locating a first lysine residue in the given sequence (810). Then, the method 800 may determine whether a second lysine residue resides within kmin to kmax positions of the first lysine residue (820). As indicated in FIG. 19, kmin and kmax define the limits on the distance between the first and second lysine residues. For a typical Replikin pattern, kmin will equal 6 and kmax will equal 10. However, these values may be varied by a researcher interested in discovering other similar patterns.

Once method 800 has identified two lysine residues that are close enough to each other (820), the method 800 may examine every histidine residue that resides within rmax positions of both the first and second lysine residues (830). When method 800 is employed to identify and locate typical Replikin patterns, rmax will usually be set to equal 50. For every histidine residue that resides within rmax positions of the two lysine residues identified in steps (810) and (820), method 800 will construct the shortest string of amino acid residues that includes the first lysine residue, the second lysine residue, and the identified histidine residue (840). Then, method 800 will determine whether the length of that shortest string is within the desired range—that is, whether it contains at least rmin amino acid residues and no more than rmax amino acid residues (850). Finally, if the identified string of amino acids also contains at least kpercent of lysine residues (860), the string will be identified as matching the desired Replikin-like pattern (870).

Still referring to FIG. 19, it is apparent that method 800 may identify several Replikin-like patterns from a single given amino acid sequence. This may happen because method 800 may examine more than one histidine residue that resides within rmax positions of the two identified lysine residues. Each identified histidine residue may, in combination with the two lysine residues, match the desired Replikin-like pattern.

One aspect of the method illustrated by FIG. 19 is shown in FIG. 20, which is a source code listing containing a procedure for discovering all Replikin patterns present in a given sequence of amino acids, in accordance with an aspect of the present invention. The "match" procedure shown in FIG. 20 is programmed in an interpreted shell language called "Tcl" and recognizes Replikins in a straightforward fashion. As known in the art, the "Tool Command Language" or Tcl (pronounced "tickle") is a simple interpreted scripting language that has its roots in the Unix command shells, but which has additional capabilities that are well-suited to network communication, Internet functionality and the rapid development of graphical user interfaces.

Alternative methods of recognizing Replikin patterns are also covered by the teachings of the present invention. For example, the match procedure shown in FIG. 20 could be implemented in other programming languages such as Java or C or C++. Additionally, alternative aspects of the Replikin recognizing algorithm may identify the characteristics of a Replikin pattern in any order, and may also traverse component amino acid sequences and subsequences using recursive techniques, iterative techniques, parallel processing techniques, divide-and-conquer techniques or any combination thereof.

Protein Search Engine

Returning to FIG. 17, the present invention may include a search engine to access and interact with amino acid and protein databases, either locally or over a network such as the Internet, to retrieve protein definitions. For example, protein and amino acid research system 630 may accept protein search criteria from a user, and may then access a plurality of on-line amino acid and protein database search engines to retrieve protein definitions that match the supplied search criteria. Protein database search criteria may comprise any text string that may form a valid search term in any of the on-line protein or amino acid search engines. Typically, these search criteria relate to text that may be found in the printout that describes each specific protein. For example, if the user supplied the search criteria "influenza type A," aspects of the present invention may forward this text string to a plurality of Internet protein and amino acid search engines, each of which may then return any protein descriptions found in their databases that contained the terms "influenza type A." Employing amino acid sequence scanner 640, each of the returned protein descriptions may be scanned for the presence of Replikin patterns.

Additional aspects of the present invention may permit a user to select or de-select a plurality of Internet protein search engines and to customize the search criteria and protein retrieval capabilities of the present invention for each of the selected on-line protein search engines. Moreover, aspects of the invention may also permit a user to access a local protein database 650 or to supply a specific protein definition directly, for example, by supplying a local file name containing the protein definition, or by other methods known in the art for supplying parameters to computer software.

Another aspect of the present invention may include a search engine to access and interact with amino acid and protein databases on the Internet to retrieve protein definitions or amino acid sequence definitions. After accepting protein or amino acid sequence search criteria from a user, the present invention may access a plurality of amino acid and protein database search engines, through on-line access, to retrieve protein definitions or amino acid sequence definitions that match the supplied search criteria.

Initial existing protein search criteria based on existing definitions may comprise any text string that may form a valid search term in any of the on-line protein or amino acid search engines. Typically, these search criteria relate to text that may be found in the printout that describes each specific protein. For example, if the user supplied the search criteria "influenza type A," the present invention would forward this text string to the plurality of Internet protein and amino acid search engines, each of which would then return any protein definitions in their databases that contained the terms "influenza type A."

A non-limiting aspect of the present invention comprising a protein search engine entitled "Genome Explorer" is included in Appendix A. The Tcl procedure named "GenomalEnquirer" may control the macro level operation of the protein search engine (see "proc GenomalEnquirer {database term additionalCriteria})." Within the procedure GenomalEnquirer, a series of specific on-line protein search engines may be accessed and queried using the user-supplied protein search terms and additional criteria. Additional aspects of the invention may permit a user to select or de-select a plurality of Internet protein search engines and to customize the search criteria and protein retrieval capabilities of the present invention for each of the selected on-line protein search engines. Moreover, aspects of the invention may also permit a user to access local protein databases or to supply a specific protein definition directly, for example, by supplying a local file name containing the protein definition, or by other methods known in the art for supplying parameters to computer software.

Instructions for running the Genome Explorer are included in Appendix B. Screen snapshots of the Genome Explorer application are included in Appendix C.

Replikin Analysis

Embodiments of the present invention may be employed not only to identify and locate Replikin patterns in amino acid sequences. Embodiments may also be used to discover and analyze similarities in the structure of Replikin patterns occurring in different proteins, or to analyze different Replikin patterns occurring in the same protein over time. FIG. 21 for example, is a table illustrating a Replikin Scaffold or "fixed scaffold" structure that was preserved in a "Bird Flu" influenza virus over an 87 year period from 1917 to 2004. Embodiments of the present invention may assemble a number of discovered Replikin patterns in proteins, including Replikin patterns discovered in variants of the same protein. Along with each Replikin pattern, aspects of the present invention may also associate a date when each protein was first identified. When directed by a researcher, an aspect of the present invention may include sorting and displaying a plurality of selected Replikin patterns according to content, date or other criteria, in order to reveal substantially fixed amino acid structures that have been preserved in Replikin patterns over time and which may be present in different proteins as well as variants of the same protein. Further, when directed by a researcher, an aspect of the invention may employ known methods of pattern analysis to compare a plurality of selected Replikin patterns in order to identify such fixed amino acid structures automatically. As an example, in FIG. 21, the illustrated Replikin patterns appear to demonstrate—in this case—a relatively fixed scaffold structure of (usually) 29 amino acids that begins with a pair of lysine residues (kk) at the amino terminal, ends with a pair of histidine residues (hh) at the carboxyl terminal, and contains a lysine residue in either position 8, 10 or 11. This conservation of scaffold structure over decades permits synthetic vaccines to be prepared rapidly and inexpensively. To synthesize such vaccines after a Replikin scaffolding structure has been identified, a researcher may select elements of that scaffolding structure that are conserved over time and which are also present in a current variant of a protein. A vaccine may then be prepared based on the selected elements from the scaffolding structure. Because such vaccines are based on conserved scaffolding structures, they may be effective for multiple years and may also be developed well in advance of an anticipated outbreak.

The discovery of Replikins themselves, as well as aspects of the present invention for identifying and locating Replikin patterns, provides targets for the identification of pathogens, as well as facilitates the development of anti-pathogen therapies, including vaccines. In general, knowledge of and identification of the Replikin family of peptides enables development of effective therapies and vaccines for any organism that harbors Replikins Specifically, identification of Replikins provides for the detection of viruses and virus vaccine development, including the influenza virus. Further, identification of Replikins also provides for the detection of other pathogens, such as malaria, anthrax and small pox virus, in addition to enabling the development of therapies and vaccines that target Replikin structures. Additional examples provided by the identification of Replikins include the detection of infectious disease Replikins, cancer immune Replikins and structural protein Replikins.

Embodiments of the present invention enable important Replikin patterns of amino acids to be recognized, located and analyzed in manners that are not found in the prior art. Using prior art capabilities, researchers have been limited in by existing techniques for describing sequences of amino acids. Indeed, limitations of the prior art have in some ways dampened research in this field, since heretofore it has not been possible to specify sequences of amino acids that comprise non-linear attributes. Until the development of the methods and aspects of the present invention, descriptions of amino acid sequences were limited to linear sequences containing, at most, repetitive substrings and logical constraints on substring content. Embodiments of the present invention enable a new class of amino acid sequences to be discovered, located and analyzed using tools not found in the prior art. This new class of amino acids is characterized by attributes such as specific amino acid concentration and distance relationships between specific amino acids. These attributes transcend simple contiguous ordering and thus are not easily described, discovered or located by existing methods known in the art.

For example, rather than examining strict amino acid sequence matches (homologies) as is done by other widely used programs such as BLAST, the present inventors have discovered a unique quantitative "language" related to rapid replication which defines a new class of amino acid grouping. Novel computer programs described herein detect instances of this new language.

These programs include functionality to search electronic data for amino acid sub-sequences meeting predetermined criteria. The data, which may be obtained online, may include data defining a specified group of protein sequences. The criteria may include:

i) the occurrence within a protein sequence of two amino acids, in this case Lysine (K) and histidine (H) in specific concentrations in the sequence ii) the spacing of one of these (K) to a second K in the sequence, and iii) the concentration of one or more amino acids (e.g. K) in a percentage greater than a defined percentage.

Amino acid sequences meeting the above criteria relate to a particular biological function such as rapid replication.

The programs include the capability to identify Replikin sub-sequences in genome sequences. One source of the genome sequences may be published genome sequences obtained from online, electronic databases, using search criteria provided by a user. In aspects of the invention, the databases may be NCBI (National Center for Biotechnology Information) or LANL (Los Alamos National Laboratory) databases. The programs further include the capability to search for arbitrary sub-sequences (i.e., not only Replikin sub-sequences), based on user-supplied criteria.

In one aspect, a program herein entitled "Genome Explorer" may generate a user interface to prompt a user for search terms. Genome Explorer may apply the search terms to online databases, such as NCBI or LANL databases, to obtain raw sequence data. Additional data may be further obtained, such as article names, protein source, strain, serotype and year of discovery for all the raw sequences which match the search terms. Once the raw data has been acquired, Genome Explorer may further apply additional search criteria to identify Replikin sub-sequences within the raw sequences. The search criteria can be specified by the user in such a way as to implement relatively strict, or relatively relaxed definitions of what can be included in the set of matching sub-sequences to be reported by Genome Explorer. As it identifies Replikin sub-sequences, Genome Explorer may compile ongoing statistics and display a progress bar in a user interface. When Genome Explorer completes its processing, it may save resulting statistics in a data file. For example, the data file may be an HTML file that can be opened in any word processor for inspection of results.

In another aspect, a program herein entitled "Dr. Peptide," search criteria may be applied to identify sub-sequences other than Replikin sub-sequences. With Dr. Peptide it is possible to search for, e.g., all instances of the sequence hlk . . . hlk (SEQ ID NO: 470), separated by not more than 15 amino acids, in publicly available genome databases. Such searches allow the creation of new statistical profiles and new groupings of proteins based on meeting these criteria. Dr. Peptide may include much the same functionality as Genome Explorer. For example, like Genome Explorer, Dr. Peptide may, via a user interface, prompt a user for search terms and apply the search terms to online databases, such as NCBI or LANL databases, to obtain raw sequence data. Additional data may be further obtained, such as article names, protein source, strain, serotype and year of discovery for all the raw sequences which match the search terms. Once the raw data has been acquired, Dr. Peptide may further process the data to identify arbitrary sub-sequences and present its output in a data file, for example in the form of HTML pages that can be opened in any word processor.

Below is a description of one example of a logic sequence that could be included in the Genome Explorer program. In the description, an "initial server inquiry" refers to search criteria to be applied to one or more network elements, such as server computers, storing electronic data representing protein sequences. The network elements may be included in private networks or, for example, the Internet. The data may be in the form of a "protein page," i.e., a quantum of data representing protein sequences. The character "k" represents a lysine amino acid, and the character "h" represents a histidine amino acid.

Genome Explorer Logic Sequence

Initialize user interface procedures and input fields for search parameters.

Construct user interface.

wait for user to specify search parameters.

Search parameters include:

(1) words or phrases to be matched in the initial server inquiry to obtain summaries and protein pages, (2) The allowed distance between k's, expressed as range kmin . . . kmax for a sub-sequence to qualify for a set.

(3) The allowed range of distances between an h and the farthest k, expressed as kmin+1 . . . hmax, for a sub-sequence to qualify for the set.

(4) The allowed fraction of k's in the sub-sequence, expressed as x percent or larger, for the sub-sequence to qualify for the set.

Once search parameters are specified,

Initialize output files in HTML format—these will be used to display reports.

Compare specified search parameters with previous search.

If the search parameters are identical, reuse cached protein pages as data input.

If the search parameters are not identical (cached protein pages are not relevant), Send the inquiry to the server (NCBI or LANL).

If it did not return all summaries,

Re-send the inquiry requesting all summaries.

For each summary,

Fetch and save the protein page retrieved.

For each protein page retrieved,

If from NCBI,

Parse ASN page.

Extract found sequence data (seq-data.ncbieaa).

Extract article names (descr.*.article.title.*.name).

Extract protein source (source.org.taxname).

Extract strain (subtype).

Derive year discovered.

Derive serotype.

If from LANL,

Parse HTML page for strain, definition, source, year, serotype, and raw nucleotide sequence.

Convert nucleotides to amino acids by mapping every three nucleotides in sequence to the corresponding amino acid.

Save parsed value for this protein.

For each parsed page, update user interface as to progress via progress bar, and:

For each sequence data found on the page,

Scan the amino acid sequence data for each sub-sequence matching (a) The distance between k's is in the range kmin . . . kmax as defined in parameter (2) from the user interface above.

(b) The distance between an h and the farthest k is in the range kmin+1 . . . hmax as defined in parameter (3) from the user interface above.

(c) The fraction of k units in the sub-sequence, expressed as x percent or larger as defined in parameter (4) from the user interface above.

and save the range of each matching sub-sequence, including overlaps.

Ignore sequences with no matches.

Accept the sequence with the most sub-sequence matches.

If a sequence was accepted,

Catalog each sequence by the year it was discovered.

For each additional set of criteria,

Check the additional criteria against other parsed fields.

If does not match, do not accept the page.

If the page was accepted,

Add it as a passed page.

Create an HTML page showing the full sequence and all matched sub-sequences.

If the page was not accepted,

Add it as a failed page.

For each unique matched replikin sequence,

Create an amino acid history HTML page,

Show every protein it occurs in ordered by year.

Create a statistics HTML page displaying the following:

For each year,

Show number of matched proteins and replikin sub-sequences.

Update user interface to reflect that the operation is complete;

Re-initialize input fields to allow next set of search parameters to be specified by user.

In view of the foregoing description, it may be understood that Genome Explorer implements a method including applying a plurality of criteria to data representing protein sequences, and based on the criteria, identifying a sub-sequence within the protein sequences, the identified sub-sequence having a predetermined allowed range of distance between Lysine amino acids thereof, and a predetermined allowed range of distance between a histidine amino acid and a farthest Lysine acid thereof. An identified sub-sequence may be output to a data file.

The functionality of the herein aspects may be provided on various computer platforms executing program instructions.

Figure 22:
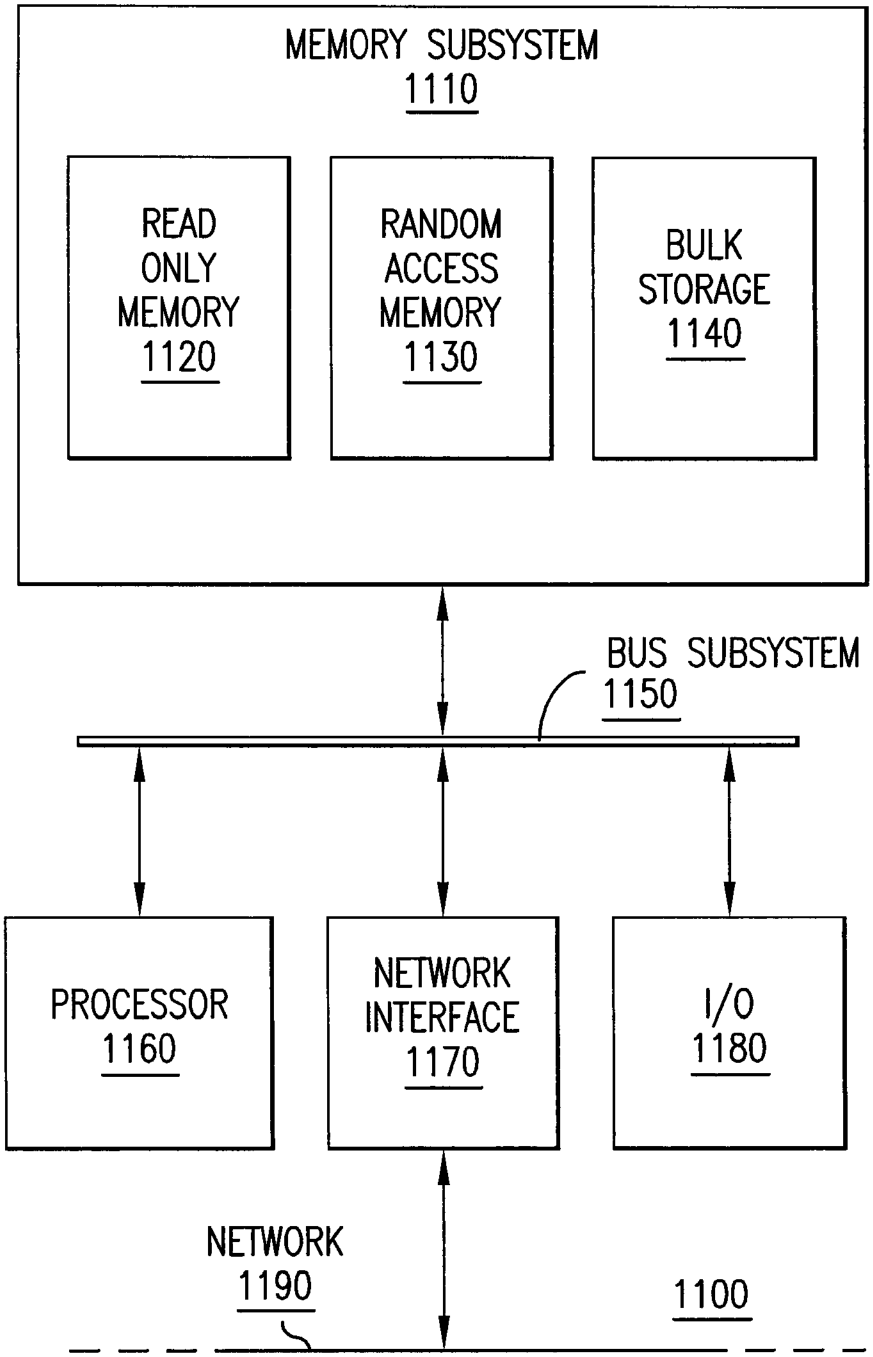
FIG. 22 is a simplified block diagram of a computer system platform useful with the present invention.

One such platform 1100 is illustrated in the simplified block diagram of FIG. 22. There, the platform 1100 is shown as being populated by a processor 1160, which communicates with a number of peripheral devices via a bus subsystem 1150. These peripheral devices typically include a memory subsystem 1110, a network interface subsystem 1170, and an input/output (I/O) unit 1180. The processor 1160 may be any of a plurality of conventional processing systems, including microprocessors, digital signal processors and field programmable logic arrays. In some applications, it may be advantageous to provide multiple processors (not shown) in the platform 1100. The processor(s) 1160 execute program instructions stored in the memory subsystem 1110. The memory subsystem 1110 may include any combination of conventional memory circuits, including electrical, magnetic or optical memory systems. As shown in FIG. 22, the memory system may include read only memories 1120, random access memories 1130 and bulk storage 1140. Memory subsystem 1110 not only stores program instructions representing the various methods described herein but also may store the data items on which these methods operate. Network interface subsystem 1170 may provide an interface to outside networks, including an interface to communications network 1190 comprising, for example, the Internet. I/O unit 1180 would permit communication with external devices, which are not shown.

Several aspects of the present invention are specifically illustrated and described herein. However, it will be appreciated that modifications and variations of the present invention are covered by the teachings of the present invention without departing from the spirit and intended scope of the invention. Additionally, the teachings of the present invention may be adaptable to other sequence-recognizing problems that have heretofore been addressed using sequential linear analyses limited to the identification of specific sequences of component elements.

Using the exemplary software contained in Appendix A, the inventors have discovered in a non-limiting aspect in accordance with the present invention that the nucleocapsid protein of the shrimp white spot virus has an exceptionally high Replikin Count as compared to all other viruses and organisms surveyed for replikins up to the present time (with the exception of malaria). While Replikins have been shown to be essential accompaniments of rapid replication in fungi, yeast, viruses, bacteria, algae, and cancer cells, the inventors have provided the first demonstration of the presence of replikins in marine organisms other than algae. And, as with algae, the presence of replikins is again related to rapid infestations. In shrimp, the white spot virus has destroyed millions of dollars of harvest of shrimp, first in eastern countries, and now in western hemisphere countries. At present, there is no effective prevention or treatment. Other examples of Replikin high mortality marine viral disease have been demonstrated by us in fish such as carp and hemorrhagic disease in salmon, and are probably widespread in marine ecology and disease.

The presence of repeat sequences of the Replikins of the nucleocapsid protein of shrimp white spot syndrome virus (WSSV) accounts for the unusually high Replikin Count of 103.8. This virus Replikin Count is much higher than the Replikin Counts of for example influenza viruses which usually range from less than 1 up to 5 or 7, and is comparable only to the record Replikin Count (so far) observed in Plasmodium Falciparum (malaria) of 111. Interestingly, while the shrimp white spot syndrome organism is a virus, and the P1. Falciparum is a trypanosome, both spend an essential part of their reproductive cycles in red blood cells, an unusual host cell whether in shrimp (white spot virus) or man (malaria), both are fulminating rapidly replicating diseases with high mortality rates of their hosts, and both appear to use the same methods of increasing their high Replikin Counts to such record highs, namely, Replikin Repeats and Replikin Overlap.

As illustrated in Table 10, examples of Replikin Repeats and Replikin Overlap were found by the applicants in the above nucleocapsid protein of the shrimp white spot syndrome virus as seen below. 497 Replikins were discovered in the white spot virus using the exemplary software provided in Appendix A. Of those 497, the replikins illustrated below in Table 10 were selected for their short sequences and high concentration of lysine which, as demonstrated throughout this application, appears to be associated with high mortality. The chosen sequences are easier and less expensive to synthesize than the longer sequences that are not included in Table 10.

Table 10 illustrates intramolecular Replikin Repeats and Replikin Overlap in shrimp white spot syndrome virus (WSSV) nucleocapsid protein (VP35) gene with a Replikin Count (number of replikins per 100 amino acids) of 103.8 (497 total replikins per 479 amino acids).

TABLE 10

Intramolecular Replikin Repeats and Replikin Overlap in shrimp white spot syndrome virus (WSSV) nucleocapsid protein (VP35) gene with Replikin Count = Number of Replikins per 100 amino acids = 497/479 = 103.8 and with thymidine kinase and thymidylate kinase activity.

| Individual Replikins at Different Positions in the same Molecule, in order of appearance in the sequence | Replikin ID Number (to be assigned) |
|---|---|
| *k24 q25 126 127 h28 129 k30* | (SEQ ID NO: 534) |
| k30 v31 h32 133 d34 v35 k36 | |
| k30 v31 h32 133 d34 v35 k36 g37 v38 *k39 q40 141 142 h43* | (SEQ ID NO: 535) |
| *k39 q 40 141 142 h43 144 k45* | (SEQ ID NO: 536) |
| k66 k67 n68 v69 k70 s71 a72 *k73 q 74 175 p76 h77* | (SEQ ID NO: 537) |
| k70 s71 a72 *k73 q 74 175 p76 h77 178 k79* | (SEQ ID NO: 538) |
| k160 k161 n162 v163 k164 s165 a166 *k167 q168 1169 p170 h171* | (SEQ ID NO: 539) |

TABLE 10-continued

Intramolecular Replikin Repeats and Replikin Overlap in shrimp white spot syndrome virus (WSSV) nucleocapsid protein (VP35) gene with Replikin Count = Number of Replikins per 100 amino acids = 497/479 = 103.8 and with thymidine kinase and thymidylate kinase activity.

| Individual Replikins at Different Positions in the same Molecule, in order of appearance in the sequence | Replikin ID Number (to be assigned) |
|---|---|
| k239 k240 n241 v242 k243 s244 a245 *k246 q247 1248 p249 h250* | (SEQ ID NO: 540) |
| k303 k304 n305 v306 k307 s308 a309 *k310 q311 1312 p313 h314* | (SEQ ID NO: 541) |
| k397 k398 n399 v400 k401 s402 a403 *k404 8405 1406 p407 h408* | (SEQ ID NO: 542) |

*Note in the shrimp virus the repeated use of identical whole Replikin sequences (underlined) and partial Replikin sequences (italicized) in different positions in the one molecule (each amino acid is numbered according to its order in the sequence).

Now that we have been able to identify these Replikins using the software described in this application, we can synthesize each of them and use them as targets for antibody and other inhibitory products and for specific synthetic vaccines against the shrimp white spot syndrome virus, specifically directed against each repeating Replikin.

The phenomenon of repeats is well known in protein structure. What is unique and specific in this case is that these are Replikin repeats. Thus while repeat of a specific Replikin sequence increases the Replikin Count within a specific molecule and is associated with more rapid replication as in the case of ATPase in P1.Falciparum in malaria, thus has apparent survival value for the molecule and the organism which contains it, at the same time it provides an increasing vulnerability, an 'Achilles Heel' so to speak. Thus the Replikin Repeat provides a higher concentration per molecule, additional target sites for attack by specific antibodies as generated by specific synthetic vaccines produced against these Replikins and other specific anti-Replikin agents. These new targets were previously unavailable because they could not be identified.

Complex Amino Acid Analysis

A further aspect of the present invention comprises a protein search engine directed to recognizing generalized amino acid and nucleic acid patterns on-line databases. Appendix D is an exemplary protein search engine directed to recognizing complex amino acid patterns such as Scaffold Exoskeletons. Appendix D is entitled "Dr. Peptide." Appendix D is an exemplary non-limiting aspect of the present invention and is designed to recognize generalized amino acid patterns in addition to the Replikin pattern.

Below is a description of one example of a logic sequence that could be included in the Dr. Peptide program. In the description, an "initial server inquiry" refers to search criteria to be applied to one or more network elements, such as server computers, storing electronic data representing protein sequences. The network elements may be included in private networks or, for example, the Internet. The data may be in the form of a "protein page," i.e., a quantum of data representing protein sequences.

Dr. Peptide Logic Sequence

Initialize user interface procedures and input fields for search parameters.

Construct user interface.

wait for user to specify search parameters, including:

(1) words or phrases to be matched in the initial server inquiry to obtain summaries and protein pages, (2) a set of specific amino acids which must be included in any sub-sequences qualifying for a set.

(3) a set of specific amino acids which must be excluded from any sub-sequences qualifying for the set.

(4) minimum m and maximum n sizes for the permissible size spacing gap which is to be applied to the set inclusion and exclusion criteria (2) and (3).

Once search parameters are specified,

Query:

If the saved protein pages are not relevant,

Send the inquiry to the server (NCBI or LANL).

If it did not return all summaries,

Re-send the inquiry requesting all summaries.

For each summary,

Fetch and save the protein page.

For each protein page,

If from NCBI,

Parse ASN page.

Extract found sequence data (seq-data.ncbieaa).

Extract article names (descr.*.article.title.*.name).

Extract protein source (source.org.taxname).

Extract strain (subtype).

Derive year discovered.

Derive serotype.

If from LANL,

Parse HTML page for strain, definition, source, year, serotype, and raw nucleotide sequence.

Convert nucleotides to amino acids by mapping every three nucleotides in sequence to the corresponding amino acid.

Save parsed value for this protein.

For each parsed page,

For each sequence data found on the page,

Scan the amino acid sequence data for each sub-sequence matching.

The match patterns are a sequence of alternative steps:

(a) An amino acid in the amino acid sequence data is in a set of specific amino acids as defined in user parameter (2) above.

(b) An amino acid in the amino acid sequence data is not in the set of specific amino acids defined in user parameter (3) above.

(c) An amino acid in the amino acid sequence data has a spacing gap of m to n amino acids from another amino acid in the amino acid sequence data as defined in user parameter (4) above.

The initial sub-sequence set is all possible terminal sequences, or "tails" of the sequence data at the first pattern step, While the set of sub-sequences is not empty, Remove one sub-sequence and record how far in the pattern string its evaluation has reached.

If the amino acid at the current pattern step

Is in a set of specific amino acids,

If the next amino acid of the sub-sequence is also in the set of amino acids,

Add the elongated sub-sequence and next pattern step to the sub-sequence set.

Is not in a set of specific amino acids.

If the next amino acid of the sub-sequence is not one of the set of amino acids, Add the elongated sub-sequences and next pattern step to the sub-sequence set.

Has a gap of m to n any amino acids.

First, elongate each sub-sequence for each possible length m through n

Then add each elongated version of the sub-sequence to the sub-sequence set

If the above pattern is exhausted,

The sub-sequence is a matched sub-sequence.

Ignore sequences with no matches.

Accept the sequence with the most matches.

If a sequence has been accepted,

Catalog each sub-sequence by the year it was discovered.

For each additional criteria,

Check the additional criteria against other parsed fields.

If it does not match, do not accept the page.

If the page was accepted,

Add it as a passed page.

Create an HTML page showing the full sequence and all matched subsequences.

If the page was not accepted,

Add it as a failed page.

In view of the foregoing description, it may be understood that Dr. Peptide implements a method including applying a plurality of criteria to data representing protein sequences, and based on the criteria, identifying arbitrary sub-sequences within the protein sequences. An identified sub-sequence may be output to a data file. The criteria may include:

a set {a} of amino acids to be included in the sub-sequence;

a set of amino acids to be excluded from the sub-sequence; and a minimum and a maximum permissible gap between members of sets {a} and {b}.

A non-limiting and exemplary aspect of the invention employs the complex amino acid analysis aspect of the invention to analyze Replikin Scaffold sequences in earlier strains of influenza that have degenerated into non-replikin sequences but maintained the scaffold structure of the Replikin Scaffold. As an example of the use of the exemplary and non-limiting software program in Appendix D to recognize generalized amino acid patterns, the inventors first discovered by visual scanning of protein sequences (now by Dr. Peptide software) that what was in earlier-arising specimens of a particular influenza species a Replikin Scaffold, was in later specimens changed as follows:

1) The length of 29 amino acids was preserved;
2) The first two amino acid positions (1 and 2) were preserved, i.e. KK;
3) The last two amino acid positions (28 and 29) were preserved, i.e. HH;
4) But there was no longer a K which was 6 to 10 amino acids from KK (needed for the definition of a Replikin).

Thus this Scaffold is no longer a Replikin Scaffold, but now is a Scaffold Exoskeleton so to speak. While Replikin Scaffolds are associated with high Replikin Counts and the occurrence of epidemics, Scaffold Exoskeletons are associated with virus dormancy and the reduction or end of the epidemic. Thus Scaffold Exoskeletons appear to be degenerative structures left as residues when Replikin Scaffolds and specific viral outbreaks are declining, thus a useful diagnostic structure for this purpose. This confirms the revelation and use of Replikin Scaffolds as 1) targets for anti-rapid replication agents such as antibodies or small inhibitory RNAs and 2) the basis of anti-viral vaccines. Software according to aspects of the present invention may comprise logic to obtain and analyze protein sequences to identify sequences having characteristics 1, 2, 3 and 4 above. For example, Scaffold Exoskeletons can now be detected and counted in any protein sequence by the exemplary software in Appendix D.

Another non-limiting aspect in accordance with the present invention is a method of identifying a Replikin Scaffold comprising identifying a series of peptides comprising about 17 to about 30 amino acids and further comprising (1) identifying a terminal lysine;
(2) identifying a terminal histidine and another histidine in the residue portion immediately adjacent to the terminal histidine;
(3) identifying at least one lysine within about 6 to about 10 amino acid residues from at least one other lysine; and
(4) identifying at least about 6% lysines.

In a non-limiting aspect in accordance with the present invention the method of identifying a Replikin Scaffold may comprise identifying a single or plurality of individual members of the series of a Replikin Scaffold.

In a preferred non-limiting aspect in accordance with the present invention the method of identifying a Replikin Scaffold further comprises the identification of a second lysine immediately adjacent to the terminal lysine. Software according to aspects of the present invention may comprise logic to obtain and analyze protein sequences to identify sequences using steps 1, 2, 3 and 4 above.

The Tcl Programming Language

Tcl (the "Tool Command Language," pronounced "tickle") is a simple interpreted scripting language that has its roots in the Unix command shells, but which has additional capabilities that are well-suited to network communication, Internet functionality and the rapid development of graphical user interfaces. Tcl was created by John K. Ousterhout at the University of California at Berkeley in 1988. Originally conceived as a reusable, embeddable language core for various software tools, it is now widely used in applications including web scripting, test automation, network and system management, and in a variety of other fields.

In aspects, Genome Explorer and Dr. Peptide may be coded in Tcl/Tk, a scripting programming language that includes powerful facilities for internet access, user interface design, and string manipulation. Because Tcl/Tk has been ported to nearly all available computer architectures and is familiar to those skilled in the art, programs written in Tcl/Tk can be run on nearly any operating system. Source code for specific implementations of Genome Explorer and Dr. Peptide are provided in Appendices A and D. The specific implementations are provided by way of illustration and example only, and the present invention is not in any way limited to the specific implementations illustrated.

Other Uses of the Three Point Recognition Method

Since "3-point-recognition" is a proteomic method that specifies a particular class of proteins, using three or more different recognition points for other peptides similarly should provide useful information concerning other protein classes. Further, the "3-point-recognition" method is applicable to other recognins, for example to the TOLL 'innate' recognition of lipopolyssacharides of organisms. The three point recognition method may also be modified to identify other useful compounds of covalently linked organic molecules, including other covalently linked amino acids, nucleotides, carbohydrates, lipids or combinations thereof. In this aspect of the invention a sequence is screened for subsequences containing three or more desired structural characteristics. In the case of screening compounds composed of covalently linked amino acids, lipids or carbohydrates the subsequence of 7 to about 50 covalently linked units should contain (1) at least one first amino acid, carbohydrate or lipid residue located seven to ten residues from a second of the first amino acid, carbohydrate or lipid residue; (2) encoding at least one second amino acid, lipid or carbohydrate residue; and (3) at least 6% of the first amino acid, carbohydrate or lipid residue. In the case of screening nucleotide sequences, the subsequence of about 21 to about 150 nucleotides should contain (1) at least one codon encoding a first amino acid located within eighteen to thirty nucleotides from a second codon encoding the first amino acid residue; (2) at least one second amino acid residue; and (3) encodes at least 6% of said first amino acid residue.

Several aspects of the present invention are specifically illustrated and described herein. However, it will be appreciated that modifications and variations of the present invention are encompassed by the above teachings and within the purview of the appended claims without departing from the spirit and intended scope of the invention.

Example 1

Process for Extraction, Isolation and Identification of Replikins and the Use of Replikins to Target, Label or Destroy Replikin-Containing Organisms a) Algae The following algae were collected from Bermuda water sites and either extracted on the same day or frozen at −20 degrees C. and extracted the next day. The algae were homogenized in a cold room (at 0 to 5 degrees C.) in 1 gram aliquots in neutral buffer, for example 100 cc. of 0.005M phosphate buffer solution, pH 7 ("phosphate buffer") for 15 minutes in a Waring blender, centrifuged at 3000 rpm, and the supernatant concentrated by perevaporation and dialyzed against phosphate buffer in the cold to produce a volume of approximately 15 ml. The volume of this extract solution was noted and an aliquot taken for protein analysis, and the remainder was fractionated to obtain the protein fraction having a pK range between 1 and 4.

The preferred method of fractionation is chromatography as follows: The extract solution is fractionated in the cold room (4° C.) on a DEAE cellulose (Cellex-D) column 2.5×11.0 cm, which has been equilibrated with 0.005M phosphate buffer. Stepwise eluting solvent changes are made with the following solutions:

- Solution 1—4.04 g. NaH2PO4 and 0.5 g NaH2PO4 are dissolved in 15 liters of distilled water (0.005 molar, pH 7);
- Solution 2—8.57 g. NaH2PO4 is dissolved in 2,480 ml. of distilled water;
- Solution 3—17.1 g. of NaH2PO4 is dissolved in 2480 ml of distilled water (0.05 molar, pH 4.7);
- Solution 4—59.65 g. of NaH2PO4 is dissolved in 2470 ml distilled water (0.175 molar);
- Solution 5—101.6 g. of NaH2PO4 is dissolved in 2455 ml distilled water (pH 4.3);
- Solution 6—340.2 g. of NaH2PO4 is dissolved in 2465 of distilled water (1.0 molar, pX-i 4.1);
- Solution 7-283.63 g. of 80% phosphoric acid (H3P04) is made up in 2460 ml of distilled water (1.0 molar, pH 1.0).

The extract solution, in 6 to 10 ml volume, is passed onto the column and overlayed with Solution 1, and a reservoir of 300 ml of Solution 1 is attached and allowed to drip by gravity onto the column. Three ml aliquots of eluant are collected and analyzed for protein content at OD 280 until all of the protein to be removed with Solution 1 has been removed from the column. Solution 2 is then applied to the column, followed in succession by Solutions 3, 4, 5, 6 aid 7 until all of the protein which can, be removed with each Solution is removed from the column. The eluates from Solution 7 are combined, dialyzed against phosphate buffer, the protein content determined of both dialysand and dialyzate, and both analyzed by gel electrophoresis. One or two bands of peptide or protein of molecular weight between 3,000 and 25,000 Daltons are obtained in Solution 7. For example the algae *Caulerpa mexicana, Laurencia obtura, Cladophexa prolifera, Sargassum natans, Caulerpa verticillata, Halimeda tuna*, and *Penicillos capitatus*, after extraction and treatment as above, all demonstrated in Solution 7 eluates sharp peptide bands in this molecular weight region with no contaminants. These Solution 7 proteins or their eluted bands are hydrolyzed, and the amino acid composition determined. The peptides so obtained, which have a lysine composition of 6% or greater are Replikin precursors. These Replikin peptide precursors are then determined for amino acid sequence and the Replikins are determined by hydrolysis and mass spectrometry as detailed in U.S. Pat. No. 6,242,578 B1. Those that fulfill the criteria defined by the "3-point-recognition" method are identified as Replikins. This procedure can also be applied to obtain yeast, bacterial and any plant Replikins.

b) Virus

Using the same extraction and column chromatography separation methods as above in a) for algae, Replikins in virus-infected cells are isolated and identified.

c) Tumor Cells In Vivo and In Vitro Tissue Culture

Using the same extraction and column chromatography separation methods as above in a) for algae, Replikins in tumor cells are isolated and identified. For example, Replikin precursors of Astrocytin isolated from malignant brain tumors, Malignin (Aglyco 10B) isolated from glioblastoma tumor cells in tissue culture, MCF7 mammary carcinoma cells in tissue culture, and P3J Lymphoma cells in tissue culture each treated as above in a) yielded Replikin precursors with lysine content of 9.1%, 6.7%, 6.7%, and 6.5% respectively. Hydrolysis and mass spectrometry of Aglyco10B as described in Example 10 U.S. Pat. No. 6,242,578 B1 produced the amino acid sequence, ykagvaflhkkndiide (SEQ ID NO: 471) the 16-mer Replikin.

Example 2

As an example of diagnostic use of Replikins: Aglyco 1OB or the 16-mer Replikin may be used as antigen to capture and quantify the amount of its corresponding antibody present in serum for diagnostic purposes are as shown in FIGS. 2, 3, 4 and 7 of U.S. Pat. No. 6,242,578 B1.

As an example of the production of agents to attach to Replikins for labeling, nutritional or destructive purposes: Injection of the 16-mer Replikin into rabbits to produce the specific antibody to the 16-mer Replikin is shown in Example 6 and FIGS. 9A and 9B of U.S. Pat. No. 6,242,578 B1.

As an example of the use of agents to label Replikins: The use of antibodies to the 16-mer Replikin to label specific cells which contain this Replikin is shown in FIG. 5 and Example 6 of U.S. Pat. No. 6,242,578 B1.

Figure 6:
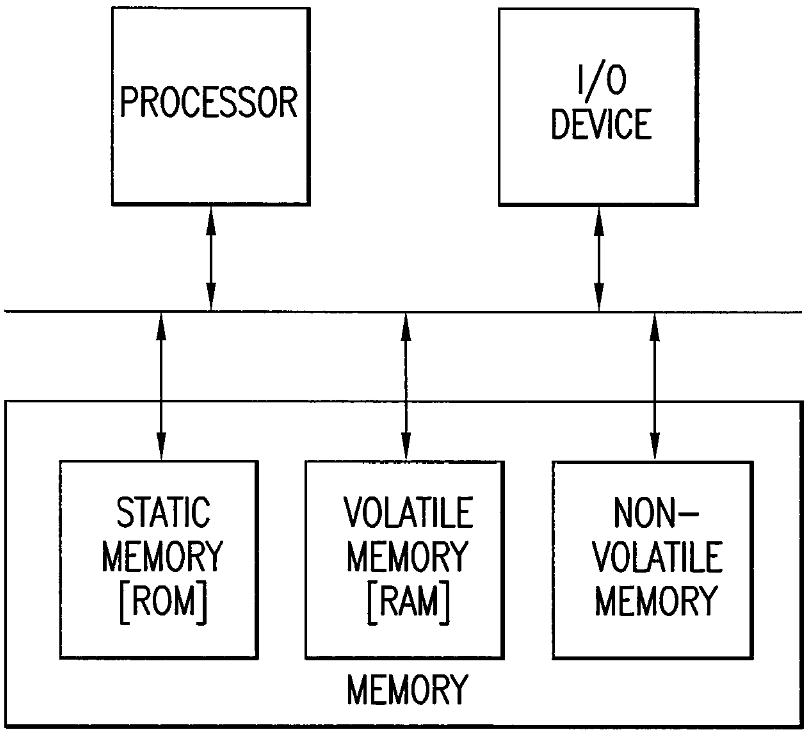
FIG. 6 is a box diagram depicting an aspect of the invention wherein a computer is used to carry out the 3-point-recognition method of identifying Replikin sequences.

As an example of the use of agents to destroy Replikins: The use of antibodies to the 16-mer Replikin to inhibit or destroy specific cells which contain this Replikin is shown in FIG. 6 of U.S. Pat. No. 6,242,578 B1.

Example 3

Analysis of sequence data of isolates of influenza virus hemagglutinin protein or neuraminidase protein for the presence and concentration of Replikins is carried out by visual scanning of sequences or through use of a computer program based on the 3-point recognition system described herein. Isolates of influenza virus are obtained and the amino acid sequence of the influenza hemagglutinin and/or neuraminidase protein is obtained by any art known method, such as by sequencing the hemagglutinin or neuraminidase gene and deriving the protein sequence therefrom. Sequences are scanned for the presence of new Replikins, conservation of Replikins over time and concentration of Replikins in each isolate. Comparison of the Replikin sequences and concentrations to the amino acid sequences obtained from isolates at an earlier time, such as about six months to about three years earlier, provides data that are used to predict the emergence of strains that are most likely to be the cause of influenza in upcoming flu seasons, and that form the basis for seasonal influenza peptide vaccines or nucleic acid based vaccines. Observation of an increase in concentration, particularly a stepwise increase in concentration of Replikins in a given strain of influenza virus for a period of about six months to about three years or more is a predictor of emergence of the strain as a likely cause of influenza epidemic or pandemic in the future.

Peptide vaccines or nucleic acid-based vaccines based on the Replikins observed in the emerging strain are generated. An emerging strain is identified as the strain of influenza virus having the highest increase in concentration of Replikin sequences within the hemagglutinin and/or neuraminidase sequence during the time period. Preferably, the peptide or nucleic acid vaccine is based on or includes any Replikin sequences that are observed to be conserved in the emerging strain. Conserved Replikins are preferably those Replikin sequences that are present in the hemagglutinin or neuraminidase protein sequence for about two years and preferably longer. The vaccines may include any combination of Replikin sequences identified in the emerging strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 mg to about 10 mg.

The influenza vaccine is preferably administered to a patient in need thereof prior to the onset of "flu season." Influenza flu season generally occurs in late October and lasts through late April. However, the vaccine may be administered at any time during the year. Preferably, the influenza vaccine is administered once yearly, and is based on Replikin sequences observed to be present, and preferably conserved in the emerging strain of influenza virus. Another preferred Replikin for inclusion in an influenza vaccine is a Replikin demonstrated to have re-emerged in a strain of influenza after an absence of one or more years.

Example 4

Analysis of sequence data of isolates of coronavirus nucleocapsid, or spike, or envelope, or other protein for the presence and concentration of Replikins is carried out by visual scanning of sequences or through use of a computer program based on the 3-point recognition method described herein. Isolates of coronavirus are obtained and the amino acid sequence of the coronavirus protein is obtained by any method known in the art, such as by sequencing the protein's gene and deriving the protein sequence therefrom. Sequences are scanned for the presence of new Replikins, conservation of Replikins over time and concentration of Replikins in each isolate. Comparison of the Replikin sequences and concentrations to the amino acid sequences obtained from isolates at an earlier time, such as about six months to about three years earlier, provides data that are used to predict the emergence of strains that are most likely to be the cause an outbreak or pandemic, and that form the basis for coronavirus peptide vaccines or nucleic acid based vaccines. Observation of an increase in concentration, particularly a stepwise increase in concentration of Replikins in a given class, or strain, of coronavirus for a period of about six months to about three years or more is a predictor of emergence of the strain as a likely cause of an epidemic or pandemic, such as SARS, in the future.

Peptide vaccines or nucleic acid-based vaccines based on the Replikins observed in the emerging strain of coronaviruses are generated. An emerging strain is identified as the strain of coronavirus having the highest increase in concentration of Replikin sequences within the nucleocapsid sequence during the time period. Preferably, the peptide or nucleic acid vaccine is based on or includes any Replikin sequences that are observed to be conserved in the strain. Conserved Replikins are preferably those Replikin sequences which are present in the nucleocapsid protein sequence for about two years and preferably longer. The vaccines may include any combination of Replikin sequences identified in the emerging strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 mg to about 10 mg.

The coronavirus vaccine may be administered to a patient at any time of the year. Preferably, the coronavirus vaccine is administered once and is based on Replikin sequences observed to be present, and preferably conserved, in the classes of coronavirus.

Example 5

Analysis of sequence data of isolates of Plasmodium falciparum antigens for the presence and concentration of Replikins is carried out by visual scanning of sequences or through use of a computer program based on the 3-point recognition method described herein. Isolates of Plasmodium falciparum are obtained and the amino acid sequence of the protein is obtained by any art known method, such as by sequencing the gene and deriving the protein sequence therefrom. Sequences are scanned for the presence of Replikins, conservation of Replikins over time and concentration of Replikins in each isolate. This information provides data that are used to form the basis for anti-malarial peptide vaccines or nucleic acid based vaccines.

Peptide vaccines or nucleic acid-based vaccines based on the Replikins observed in the malaria causing organism are generated. Preferably, the peptide or nucleic acid vaccine is based on or includes any Replikin sequences that are observed to be present on a surface antigen of the organism. The vaccines may include any combination of Replikin sequences identified in the malaria causing strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 mg to about 10 mg.

Then malaria vaccine is preferably administered to a patient in need thereof at any time during the year, and particularly prior to travel to a tropical environment.

Another aspect includes an antisense nucleic acid molecule complementary to the coding strand of the gene or the mRNA encoding organism for the replikins in organisms including, but not limited to, viruses, trypanosomes, bacteria, fungi, algae, amoeba, and plants, wherein said antisense nucleic acid molecules is complementary to a nucleotide sequence of a replikin containing organism.

Example 6

Amino acid sequences of five short SARS Replikins found in nucleocapsid, spike, and envelope proteins of the SARS coronavirus were synthesized and tested on rabbits to test immune response to Replikin sequences in the SARS coronavirus. The following Replikin sequences were tested: (1) 2003 Human SARS nucleocapsid (SEQ ID NO: 303); (2) 2003 Human SARS spike protein (SEQ ID NO: 304); (3) 2003 Human SARS spike protein (SEQ ID NO: 305); 2003 Human SARS spike protein; (SEQ ID NO: 306); (4) 2003 SARS envelope protein (SEQ ID NO: 307); and (5) 2003 Human SARS nucleocapsid protein (SEQ ID NO: 308). Each synthesized peptide was injected subcutaneously into a rabbit. The tested rabbits produced measurable specific antibody to each of the five sequences that bound at dilutions of greater than 1 in 10,0000. The 21 amino acid SARS nucleocapsid replikin antibody (SEQ. ID NO: 303) was demonstrated to bind at dilutions greater than 1 in 204,800. Because of previous unsuccessful attempts by others to achieve with various small peptides a strong immune response without the unwanted side effects obtained with a whole protein or the thousands of proteins or nucleic acids as in smallpox vaccine, the ability of small synthetic replikin antigens to achieve strong immune responses was shown to be significant for the efficacy of SARS vaccines.

Example 7

A 41 amino acid replikin sequence KKNSTYPTIKRSYNNTNQEDLLVLWGIHHKKKKHKKKKKHK (SEQ ID NO: 16)-KLH with the addition of a key limpet hemocyanin adjuvant on the C-terminal end (denoted as -KLH) was designated Vaccine V120304U2. The vaccine was designed by the inventors from the 29 amino acid replikin Scaffold of H5N1 "Bird Flu" Influenza Replikins labeled "2004 H5N1 Vietnam, highly pathogenic" in Table 8 with the addition of two UTOPE units (KKKKHK) (SEQ ID NO: 459) on the C-terminal end of the H5N1 scaffold and an additional adjuvant (key limpet hemocyanin adjuvant (denoted-KLH)) covalently linked on the C-terminal end of the two UTOPE units. 100 μg of Vaccine V120304U2 was injected subcutaneously into rabbits and chickens. The antibody response was measured before vaccination and at from one week after injection to eight weeks after injection. An antibody response was noted at one week and reached a peak in the third to fourth week after vaccination. Peak antibody responses ranged from a dilution of 1:120,000 to a dilution of greater than 1:240,000. Antibody titers were determined with an enzyme linked immunosorbent assay (ELISA) with Peptide-GGG (goat gamma globulin) bound in solid phase (0.1 μg/100 μl/well) on high binding 96 well plates. The serum was first diluted 50 fold and then further diluted in 2-fold serial dilutions. The ELISA titer result was determined from the estimated dilution factor that resulted from an optical density at 405 nm of 0.2 and derived from nonlinear regression analysis of the serial dilution curve. Detection was obtained using a horse radish peroxidase conjugated secondary antibody and ABTS substrate (ABTS is a registered trademark of Boehringer Mannheim. GmbH). Results from tests on two chickens and two rabbits are provided in Table 11. Individual well results from the test on rabbit D4500 are provided in Table 12. In combination with the results reported in Example 6, in a total of six tests of Replikin sequences for antibody responses in rabbit or chicken, all six sequences provided a measurable antibody response and have proved antigenic.

TABLE 11

| Animal | Bleed Day | ELISA Titer |
|---|---|---|
| Chickens injected with 100 μg V120304U2 on day 1<br>ELISA titer of antibody production on day 18 | | |
| U0682 (Control) | Prior to administration of vaccine | <50 |
| u0682 | 18 days after administration | >204,800 |
| U0683 (Control) | Prior to administration of vaccine | <50 |
| u0683 | 18 days after administration | >204,800 |
| Rabbits injected with 100 μg V120304U2 on day 1.<br>ELISA titer of antibody production on day 20 | | |
| D4500 (Control) | Prior to vaccine administration | <50 |
| d4500 | 20 days after administration | >204,800 |
| D4501 (Control) | Prior to vaccine administration | 100 |
| d4501 | 20 days after administration | >204,800 |

TABLE 12

Rabbits injected with 100 μg V120304U2 on day 1. OD450 results for titers on days 7, 20 and 28 in individual wells

| Animal | Test Day | Well 1 | Well 2 | Well 3 | Well 4 | Well 5 | Well 6 |
|---|---|---|---|---|---|---|---|
| d4500 | Day 7 | 0.11 | 0.10 | 0.09 | 0.08 | 0.07 | 0.07 |
| | Day 20 | 0.49 | 0.38 | 0.23 | 0.19 | 0.22 | 0.17 |
| | Day 28 | 2.77 | 1.41 | 0.92 | 0.56 | 0.43 | 0.42 |
| | | Well 7 | Well 8 | Well 9 | Well 10 | Well 11 | Well 12 |
| d4500 | Day 7 | 0.06 | 0.06 | 0.06 | 0.06 | 0.6 | 0.6 |
| | Day 20 | 0.02 | 0.16 | 0.17 | 0.15 | 0.19 | 0.28 |
| | Day 28 | 0.17 | 0.14 | 0.12 | 0.11 | 0.11 | 0.10 |

TABLE 12-continued

Rabbits injected with 100 μg V120304U2 on day 1. OD450 results for titers on days 7, 20 and 28 in individual wells

| | | Well 1 | Well 2 | Well 3 | Well 4 | Well 5 | Well 6 |
|---|---|---|---|---|---|---|---|
| d4501 | Day 7 | 0.25 | 0.18 | 0.15 | 0.11 | 0.09 | 0.08 |
| | Day 20 | 0.50 | 0.23 | 0.20 | 0.16 | 0.18 | 0.18 |
| | Day 28 | 1.75 | 0.84 | 0.61 | 0.50 | 0.34 | 0.35 |
| | | Well 7 | Well 8 | Well 9 | Well 10 | Well 11 | Well 12 |
| d4501 | Day 7 | 0.07 | 0.07 | 0.07 | 0.06 | 0.06 | 0.06 |
| | Day 20 | 0.16 | 0.18 | 0.16 | 0.17 | 0.17 | 0.25 |
| | Day 28 | 0.20 | 0.14 | 0.12 | 0.12 | 0.11 | 0.13 |

What is claimed is:

1. A method of providing passive immunity in a subject comprising administering an effective amount of at least one antibody that specifically binds to an influenza virus peptide sequence consisting of 16 to 30 amino acids and comprising a terminal lysine and a lysine immediately adjacent to the terminal lysine, a terminal histidine and a histidine immediately adjacent to the terminal histidine, and at least a lysine residue at position 8, 10, or 11 of the peptide sequence.

2. The method of claim 1, wherein said influenza virus peptide sequence is comprised within a peptide of influenza virus or a polypeptide of influenza virus.

3. The method of claim 2, wherein said peptide of influenza virus or said polypeptide of influenza virus is from a hemagglutinin protein.

4. The method of claim 1, wherein said influenza virus peptide sequence consists of 29 amino acids.

5. The method of claim 1, wherein said isolated antibody specifically binds to a fragment of said influenza virus peptide sequence that is a functional derivative of said influenza virus peptide sequence.

6. The method of claim 1, wherein the influenza virus peptide sequence is present in an emerging strain of influenza virus.

7. The method of claim 1, wherein homologues of said influenza virus peptide sequence are present in a plurality of different specimens of influenza virus, wherein said homologues consist of 16 to 30 amino acids and comprise:

(1) a terminal lysine and a lysine immediately adjacent to said terminal lysine;

(2) a terminal histidine and a histidine immediately adjacent to said terminal histidine;

(3) a lysine within 6 to 10 amino acids from another lysine; and (4) at least 6% lysines.

8. The method of claim 7, wherein said influenza virus peptide sequence consists of 29 amino acids and said homologues of said influenza virus peptide sequence consist of 29 amino acids.

9. The method of claim 1, wherein said isolated antibody is a single chain antibody or an antibody fragment.

10. The method of claim 1, wherein said isolated antibody is a monoclonal antibody.

11. The method of claim 1, wherein said at least one antibody is comprised with an antibody cocktail comprising a plurality of isolated antibodies of claim 1.

12. The method of claim 1, wherein said at least one antibody is comprised within a composition comprising: the antibody of claim 1 and a pharmaceutically acceptable carrier and/or adjuvant.

13. The method of claim 11, wherein said at least one antibody is comprised within a composition comprising: the antibody cocktail of claim 11 and a pharmaceutically acceptable carrier and/or adjuvant.

14. The method of claim 13, wherein at least one antibody specifically binds to an influenza virus peptide sequence present in an emerging strain of influenza virus.

* * * * *

SEQUENCE LISTING

```
<160> NUMBER OF SEQ ID NOS: 542

<210> SEQ ID NO 1
<211> LENGTH: 10
<212> TYPE: PRT
<213> ORGANISM: Homo sapiens

<400> SEQUENCE: 1

Lys Ala Gly Val Ala Phe Leu His Lys Lys
1               5                   10


<210> SEQ ID NO 2
<211> LENGTH: 13
<212> TYPE: PRT
<213> ORGANISM: Saccharomyces cervisiae

<400> SEQUENCE: 2

His Ser Ile Lys Arg Glu Leu Gly Ile Ile Phe Asp Lys
1               5                   10


<210> SEQ ID NO 3
<211> LENGTH: 10
<212> TYPE: PRT
<213> ORGANISM: Foot and Mouth Disease virus type O

<400> SEQUENCE: 3

His Lys Gln Lys Ile Val Ala Pro Val Lys
1               5                   10


<210> SEQ ID NO 4
<211> LENGTH: 16
<212> TYPE: PRT
<213> ORGANISM: Homo sapiens

<400> SEQUENCE: 4

Tyr Lys Ala Gly Val Ala Phe Leu His Lys Lys Asn Asp Ile Asp Glu
1               5                   10                  15


<210> SEQ ID NO 5
<211> LENGTH: 10
<212> TYPE: PRT
<213> ORGANISM: Human immunodeficiency virus type 1

<400> SEQUENCE: 5

Lys Cys Phe Asn Cys Gly Lys Glu Gly His
1               5                   10
```

-continued

<210> SEQ ID NO 6
<211> LENGTH: 11
<212> TYPE: PRT
<213> ORGANISM: Human immunodeficiency virus type 1

<400> SEQUENCE: 6

Lys Val Tyr Leu Ala Trp Val Pro Ala His Lys
1               5                   10

<210> SEQ ID NO 7
<211> LENGTH: 10
<212> TYPE: PRT
<213> ORGANISM: Human immunodeficiency virus type 2

<400> SEQUENCE: 7

Lys Cys Trp Asn Cys Gly Lys Glu Gly His
1               5                   10

<210> SEQ ID NO 8
<211> LENGTH: 11
<212> TYPE: PRT
<213> ORGANISM: Maize streak virus

<400> SEQUENCE: 8

Lys Tyr Ile Val Cys Ala Arg Glu Ala His Lys
1               5                   10

<210> SEQ ID NO 9
<211> LENGTH: 17
<212> TYPE: PRT
<213> ORGANISM: Maize streak virus

<400> SEQUENCE: 9

Lys Glu Lys Lys Pro Ser Lys Asp Glu Ile Met Arg Asp Ile Ile Ser
1               5                   10                  15

His

<210> SEQ ID NO 10
<211> LENGTH: 9
<212> TYPE: PRT
<213> ORGANISM: Staphylococcus aureas

<400> SEQUENCE: 10

Lys Lys Glu Lys Thr Thr His Asn Lys
1               5

<210> SEQ ID NO 11
<211> LENGTH: 10
<212> TYPE: PRT
<213> ORGANISM: Bovine herpes virus 4

<400> SEQUENCE: 11

His Lys Ile Asn Ile Thr Asn Gly Gln Lys
1               5                   10

<210> SEQ ID NO 12
<211> LENGTH: 10
<212> TYPE: PRT
<213> ORGANISM: Meleagrid herpesvirus 1

<400> SEQUENCE: 12

His Lys Asp Leu Tyr Arg Leu Leu Met Lys
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Met Asp Glu Leu
1

<210> SEQ ID NO 14
<211> LENGTH: 379
<212> TYPE: PRT
<213> ORGANISM: Simian immunodeficiency virus
<220> FEATURE:
<221> NAME/KEY: MOD_RES
<222> LOCATION: (322)..(343)
<223> OTHER INFORMATION: Variable amino acid

<400> SEQUENCE: 14

```
Glu Leu Arg Leu Arg Tyr Cys Ala Pro Ala Gly Phe Ala Leu Leu Lys
1               5                   10                  15

Cys Asn Asp Ala Asp Tyr Asp Gly Phe Lys Thr Asn Cys Ser Asn Val
            20                  25                  30

Ser Val Val His Cys Thr Asn Leu Met Asn Thr Thr Val Thr Thr Gly
        35                  40                  45

Leu Leu Leu Asn Gly Ser Tyr Ser Glu Asn Arg Thr Gln Ile Trp Gln
    50                  55                  60

Lys His Arg Thr Ser Asn Asp Ser Ala Leu Ile Leu Leu Asn Lys His
65                  70                  75                  80

Tyr Asn Leu Thr Val Thr Cys Lys Arg Pro Gly Asn Lys Thr Val Leu
                85                  90                  95

Pro Val Thr Ile Met Ala Gly Leu Val Phe His Ser Gln Lys Tyr Asn
            100                 105                 110

Leu Arg Leu Arg Gln Ala Trp Cys His Phe Pro Ser Asn Trp Lys Gly
        115                 120                 125

Ala Trp Lys Glu Val Lys Glu Glu Ile Val Asn Leu Pro Lys Glu Arg
    130                 135                 140

Tyr Arg Gly Thr Asn Asp Pro Lys Arg Ile Phe Phe Gln Arg Gln Trp
145                 150                 155                 160

Gly Asp Pro Glu Thr Ala Asn Leu Trp Phe Asn Cys His Gly Glu Phe
                165                 170                 175

Phe Tyr Cys Lys Met Asp Trp Phe Leu Asn Tyr Leu Asn Asn Leu Thr
            180                 185                 190

Val Asp Ala Asp His Asn Glu Cys Lys Asn Thr Ser Gly Thr Lys Ser
        195                 200                 205

Gly Asn Lys Arg Ala Pro Gly Pro Cys Val Gln Arg Thr Tyr Val Ala
    210                 215                 220

Cys His Ile Arg Ser Val Ile Ile Trp Leu Glu Thr Ile Ser Lys Lys
225                 230                 235                 240

Thr Tyr Ala Pro Pro Arg Glu Gly His Leu Glu Cys Thr Ser Thr Val
                245                 250                 255

Thr Gly Met Thr Val Glu Leu Asn Tyr Ile Pro Lys Asn Arg Thr Asn
            260                 265                 270

Val Thr Leu Ser Pro Gln Ile Glu Ser Ile Trp Ala Ala Glu Leu Asp
        275                 280                 285
```

-continued

```
Arg Tyr Lys Leu Val Glu Ile Thr Pro Ile Gly Phe Ala Pro Thr Glu
    290                 295                 300

Val Arg Arg Tyr Thr Gly Gly His Glu Arg Gln Lys Arg Val Pro Phe
305                 310                 315                 320

Val Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Val Gln Ser Gln His Leu Leu Ala Gly
            340                 345                 350

Ile Leu Gln Gln Gln Lys Asn Leu Leu Ala Ala Val Glu Ala Gln Gln
        355                 360                 365

Gln Met Leu Lys Leu Thr Ile Trp Gly Val Lys
    370                 375


<210> SEQ ID NO 15
<211> LENGTH: 29
<212> TYPE: PRT
<213> ORGANISM: Influenza A virus

<400> SEQUENCE: 15

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 16
<211> LENGTH: 41
<212> TYPE: PRT
<213> ORGANISM: Influenza A virus

<400> SEQUENCE: 16

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His Lys Lys Lys
            20                  25                  30

Lys His Lys Lys Lys Lys Lys His Lys
        35                  40


<210> SEQ ID NO 17
<211> LENGTH: 29
<212> TYPE: PRT
<213> ORGANISM: Influenza virus

<400> SEQUENCE: 17

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25


<210> SEQ ID NO 18
<211> LENGTH: 13
<212> TYPE: PRT
<213> ORGANISM: Hepatitis C virus

<400> SEQUENCE: 18

His Tyr Pro Pro Lys Pro Gly Cys Ile Val Pro Ala Lys
1               5                   10


<210> SEQ ID NO 19
<211> LENGTH: 4
<212> TYPE: PRT
```

<213> ORGANISM: Homo sapiens

<400> SEQUENCE: 19

Tyr Lys Ala Gly
1

<210> SEQ ID NO 20
<211> LENGTH: 6
<212> TYPE: PRT
<213> ORGANISM: Homo sapiens

<400> SEQUENCE: 20

Tyr Lys Ala Gly Val Ala
1 5

<210> SEQ ID NO 21
<211> LENGTH: 7
<212> TYPE: PRT
<213> ORGANISM: Homo sapiens

<400> SEQUENCE: 21

Tyr Lys Ala Gly Val Ala Phe
1 5

<210> SEQ ID NO 22
<211> LENGTH: 8
<212> TYPE: PRT
<213> ORGANISM: Homo sapiens

<400> SEQUENCE: 22

Tyr Lys Ala Gly Val Ala Phe Leu
1 5

<210> SEQ ID NO 23
<211> LENGTH: 10
<212> TYPE: PRT
<213> ORGANISM: Homo sapiens

<400> SEQUENCE: 23

Ala Gly Val Ala Phe Leu His Lys Lys Asn
1 5 10

<210> SEQ ID NO 24
<211> LENGTH: 5
<212> TYPE: PRT
<213> ORGANISM: Homo sapiens

<400> SEQUENCE: 24

Gly Val Ala Phe Leu
1 5

<210> SEQ ID NO 25
<211> LENGTH: 4
<212> TYPE: PRT
<213> ORGANISM: Homo sapiens

<400> SEQUENCE: 25

Val Ala Phe Leu
1

<210> SEQ ID NO 26
<211> LENGTH: 7
<212> TYPE: PRT
<213> ORGANISM: Homo sapiens

<400> SEQUENCE: 26

Val Ala Phe Leu His Lys Lys
1 5

<210> SEQ ID NO 27
<211> LENGTH: 7
<212> TYPE: PRT
<213> ORGANISM: Homo sapiens

<400> SEQUENCE: 27

Val Ala Phe Leu His Lys Lys
1 5

<210> SEQ ID NO 28
<211> LENGTH: 9
<212> TYPE: PRT
<213> ORGANISM: Homo sapiens

<400> SEQUENCE: 28

Val Ala Phe Leu His Lys Lys Asn Asp
1 5

<210> SEQ ID NO 29
<211> LENGTH: 8
<212> TYPE: PRT
<213> ORGANISM: Homo sapiens

<400> SEQUENCE: 29

Val Ala Phe His Lys Lys Asn Asp
1 5

<210> SEQ ID NO 30
<211> LENGTH: 4
<212> TYPE: PRT
<213> ORGANISM: Homo sapiens

<400> SEQUENCE: 30

Ala Phe Leu His
1

<210> SEQ ID NO 31
<211> LENGTH: 8
<212> TYPE: PRT
<213> ORGANISM: Homo sapiens

<400> SEQUENCE: 31

His Lys Lys Asn Asp Ile Asp Glu
1 5

<210> SEQ ID NO 32
<211> LENGTH: 6
<212> TYPE: PRT
<213> ORGANISM: Homo sapiens

<400> SEQUENCE: 32

Lys Lys Asn Asp Ile Asp
1 5

<210> SEQ ID NO 33
<211> LENGTH: 6
<212> TYPE: PRT
<213> ORGANISM: Homo sapiens

<400> SEQUENCE: 33

Lys Asn Asp Ile Asp Glu
1 5

<210> SEQ ID NO 34
<211> LENGTH: 8
<212> TYPE: PRT
<213> ORGANISM: Caldophera prolifera

<400> SEQUENCE: 34

Lys Ala Ser Lys Phe Thr Lys His
1 5

<210> SEQ ID NO 35
<211> LENGTH: 12
<212> TYPE: PRT
<213> ORGANISM: Isolepis prolifera

<400> SEQUENCE: 35

Lys Ala Gln Ala Glu Thr Gly Glu Ile Lys Gly His
1 5 10

<210> SEQ ID NO 36
<211> LENGTH: 10
<212> TYPE: PRT
<213> ORGANISM: Schizosaccharomyces pombe

<400> SEQUENCE: 36

Lys Ser Phe Lys Tyr Pro Lys Lys His Lys
1 5 10

<210> SEQ ID NO 37
<211> LENGTH: 10
<212> TYPE: PRT
<213> ORGANISM: Oryza sativa

<400> SEQUENCE: 37

Lys Lys Ala Tyr Gly Asn Glu Leu His Lys
1 5 10

<210> SEQ ID NO 38
<211> LENGTH: 9
<212> TYPE: PRT
<213> ORGANISM: Penicillium marneffei

<400> SEQUENCE: 38

Lys Val Asp Ile Val Thr His Gln Lys
1 5

<210> SEQ ID NO 39
<211> LENGTH: 12
<212> TYPE: PRT
<213> ORGANISM: Discula destructiva

<400> SEQUENCE: 39

Lys Leu Glu Glu Asp Ala Ala Tyr His Arg Lys Lys
1 5 10

<210> SEQ ID NO 40
<211> LENGTH: 17
<212> TYPE: PRT
<213> ORGANISM: Ophiostoma mitovirus 3a

<400> SEQUENCE: 40

Lys Val Ile Leu Pro Leu Arg Gly Asn Ile Lys Gly Ile Phe Phe Lys
1 5 10 15

His

<210> SEQ ID NO 41
<211> LENGTH: 11
<212> TYPE: PRT
<213> ORGANISM: Entamoeba invadens

<400> SEQUENCE: 41

Lys Leu Ile Leu Lys Gly Asp Leu Asn Lys His
1               5                   10

<210> SEQ ID NO 42
<211> LENGTH: 8
<212> TYPE: PRT
<213> ORGANISM: Helicobacter pylori

<400> SEQUENCE: 42

Lys Ser Val His Ala Phe Leu Lys
1               5

<210> SEQ ID NO 43
<211> LENGTH: 9
<212> TYPE: PRT
<213> ORGANISM: Legionella sp.

<400> SEQUENCE: 43

Lys Val His Phe Phe Gln Leu Lys Lys
1               5

<210> SEQ ID NO 44
<211> LENGTH: 9
<212> TYPE: PRT
<213> ORGANISM: Arabidopsis thaliana

<400> SEQUENCE: 44

Lys Asp His Asp Phe Asp Gly Asp Lys
1               5

<210> SEQ ID NO 45
<211> LENGTH: 11
<212> TYPE: PRT
<213> ORGANISM: Arabidopsis thaliana

<400> SEQUENCE: 45

Lys Met Lys Gly Leu Lys Gln Lys Lys Ala His
1               5                   10

<210> SEQ ID NO 46
<211> LENGTH: 12
<212> TYPE: PRT
<213> ORGANISM: Arabidopsis thaliana

<400> SEQUENCE: 46

Lys Glu Leu Ser Ser Thr Thr Gln Glu Lys Ser His
1               5                   10

<210> SEQ ID NO 47
<211> LENGTH: 9
<212> TYPE: PRT
<213> ORGANISM: Feline immunodeficiency syndrome virus

<400> SEQUENCE: 47

His Leu Lys Asp Tyr Lys Leu Val Lys
1               5

<210> SEQ ID NO 48
<211> LENGTH: 7
<212> TYPE: PRT
<213> ORGANISM: Rous sarcoma virus

<400> SEQUENCE: 48

Lys Lys Leu Arg His Glu Lys
1               5

<210> SEQ ID NO 49
<211> LENGTH: 7
<212> TYPE: PRT
<213> ORGANISM: Avian sarcoma virus

<400> SEQUENCE: 49

Lys Lys Leu Arg His Asp Lys
1               5

<210> SEQ ID NO 50
<211> LENGTH: 7
<212> TYPE: PRT
<213> ORGANISM: Homo sapiens

<400> SEQUENCE: 50

Lys Lys Leu Arg His Asp Lys
1               5

<210> SEQ ID NO 51
<211> LENGTH: 7
<212> TYPE: PRT
<213> ORGANISM: Avian sarcoma virus

<400> SEQUENCE: 51

Lys Lys Leu Arg His Glu Lys
1               5

<210> SEQ ID NO 52
<211> LENGTH: 7
<212> TYPE: PRT
<213> ORGANISM: Homo sapiens

<400> SEQUENCE: 52

Lys Lys Leu Arg His Glu Lys
1               5

<210> SEQ ID NO 53
<211> LENGTH: 8
<212> TYPE: PRT
<213> ORGANISM: Homo sapiens

<400> SEQUENCE: 53

Lys Gln Ala His Glu Leu Ala Lys
1               5

<210> SEQ ID NO 54
<211> LENGTH: 8
<212> TYPE: PRT
<213> ORGANISM: Polyamavirus sp.

<400> SEQUENCE: 54

Lys Thr His Arg Phe Ser Lys His
1               5

<210> SEQ ID NO 55
<211> LENGTH: 8
<212> TYPE: PRT
<213> ORGANISM: Sindbis virus

<400> SEQUENCE: 55

Lys Asn Leu His Glu Lys Ile Lys
1 5

<210> SEQ ID NO 56
<211> LENGTH: 9
<212> TYPE: PRT
<213> ORGANISM: Human papilloamavirus type 71

<400> SEQUENCE: 56

Lys His Arg Pro Leu Leu Gln Leu Lys
1 5

<210> SEQ ID NO 57
<211> LENGTH: 7
<212> TYPE: PRT
<213> ORGANISM: Homo sapiens

<400> SEQUENCE: 57

Lys Ser Pro Asn His Val Lys
1 5

<210> SEQ ID NO 58
<211> LENGTH: 8
<212> TYPE: PRT
<213> ORGANISM: Feline sarcoma virus

<400> SEQUENCE: 58

Lys Asn Ile His Leu Glu Lys Lys
1 5

<210> SEQ ID NO 59
<211> LENGTH: 8
<212> TYPE: PRT
<213> ORGANISM: Homo sapiens

<400> SEQUENCE: 59

Lys Asn Ile His Leu Glu Lys Lys
1 5

<210> SEQ ID NO 60
<211> LENGTH: 10
<212> TYPE: PRT
<213> ORGANISM: Polyomavirus sp.

<400> SEQUENCE: 60

Lys Pro His Leu Ala Gln Ser Leu Glu Lys
1 5 10

<210> SEQ ID NO 61
<211> LENGTH: 9
<212> TYPE: PRT
<213> ORGANISM: Polyomavirus sp.

<400> SEQUENCE: 61

Lys Gln His Arg Glu Leu Lys Asp Lys
1 5

<210> SEQ ID NO 62
<211> LENGTH: 9

<212> TYPE: PRT
<213> ORGANISM: Polyomavirus sp.

<400> SEQUENCE: 62

Lys Gln His Arg Glu Leu Lys Asp Lys
1               5

<210> SEQ ID NO 63
<211> LENGTH: 12
<212> TYPE: PRT
<213> ORGANISM: Murine acute leukemia virus

<400> SEQUENCE: 63

Lys Val Pro Val Leu Ile Ser Pro Thr Leu Lys His
1               5                   10

<210> SEQ ID NO 64
<211> LENGTH: 13
<212> TYPE: PRT
<213> ORGANISM: Human T cell lymphotropic virus type 2

<400> SEQUENCE: 64

Lys Ser Leu Leu Leu Glu Val Asp Lys Asp Ile Ser His
1               5                   10

<210> SEQ ID NO 65
<211> LENGTH: 13
<212> TYPE: PRT
<213> ORGANISM: Homo sapiens

<400> SEQUENCE: 65

Lys Ala Gly Ile Thr Ile Met Val Lys Arg Glu Tyr His
1               5                   10

<210> SEQ ID NO 66
<211> LENGTH: 8
<212> TYPE: PRT
<213> ORGANISM: Homo sapiens

<400> SEQUENCE: 66

Lys Ser Gly Lys His Leu Gly Lys
1               5

<210> SEQ ID NO 67
<211> LENGTH: 9
<212> TYPE: PRT
<213> ORGANISM: Homo sapiens

<400> SEQUENCE: 67

Lys Arg Arg Glu Gln Leu Lys His Lys
1               5

<210> SEQ ID NO 68
<211> LENGTH: 10
<212> TYPE: PRT
<213> ORGANISM: Homo sapiens

<400> SEQUENCE: 68

Lys Ser Phe Glu Val Ile Lys Val Ile His
1               5                   10

<210> SEQ ID NO 69
<211> LENGTH: 8
<212> TYPE: PRT
<213> ORGANISM: Homo sapiens

<400> SEQUENCE: 69

Lys Lys Lys His Thr Val Lys Lys
1 5

<210> SEQ ID NO 70
<211> LENGTH: 9
<212> TYPE: PRT
<213> ORGANISM: Homo sapiens

<400> SEQUENCE: 70

Lys Ala Gln Lys Asp His Leu Ser Lys
1 5

<210> SEQ ID NO 71
<211> LENGTH: 10
<212> TYPE: PRT
<213> ORGANISM: Homo sapiens

<400> SEQUENCE: 71

His Leu Lys Arg Val Lys Asp Leu Lys Lys
1 5 10

<210> SEQ ID NO 72
<211> LENGTH: 11
<212> TYPE: PRT
<213> ORGANISM: Homo sapiens

<400> SEQUENCE: 72

Lys Tyr Gly Ser Pro Lys His Arg Leu Ile Lys
1 5 10

<210> SEQ ID NO 73
<211> LENGTH: 13
<212> TYPE: PRT
<213> ORGANISM: Homo sapiens

<400> SEQUENCE: 73

Lys Leu Lys His Ile Leu Gly Lys Ala Arg Phe Ile Lys
1 5 10

<210> SEQ ID NO 74
<211> LENGTH: 12
<212> TYPE: PRT
<213> ORGANISM: Homo sapiens

<400> SEQUENCE: 74

Lys Gly Asp His Val Lys His Tyr Lys Ile Arg Lys
1 5 10

<210> SEQ ID NO 75
<211> LENGTH: 13
<212> TYPE: PRT
<213> ORGANISM: Homo sapiens

<400> SEQUENCE: 75

Lys Glu Lys Leu Arg Asp Val Met Val Asp Arg His Lys
1 5 10

<210> SEQ ID NO 76
<211> LENGTH: 15
<212> TYPE: PRT
<213> ORGANISM: Homo sapiens

<400> SEQUENCE: 76

```
Lys Leu Gln Ala Arg Gln Gln Gln Leu Leu Lys Lys Ile Glu His
1               5                   10                  15


<210> SEQ ID NO 77
<211> LENGTH: 14
<212> TYPE: PRT
<213> ORGANISM: Homo sapiens

<400> SEQUENCE: 77

Lys Lys Gly Asn Arg Val Ser Pro Thr Met Lys Val Thr His
1               5                   10


<210> SEQ ID NO 78
<211> LENGTH: 9
<212> TYPE: PRT
<213> ORGANISM: Homo sapiens

<400> SEQUENCE: 78

Lys Glu Ile Pro Leu His Phe Arg Lys
1               5


<210> SEQ ID NO 79
<211> LENGTH: 8
<212> TYPE: PRT
<213> ORGANISM: Homo sapiens

<400> SEQUENCE: 79

Lys Lys Lys Pro His Ile Lys Lys
1               5


<210> SEQ ID NO 80
<211> LENGTH: 9
<212> TYPE: PRT
<213> ORGANISM: Homo sapiens

<400> SEQUENCE: 80

Lys Thr Arg His Asp Pro Leu Ala Lys
1               5


<210> SEQ ID NO 81
<211> LENGTH: 10
<212> TYPE: PRT
<213> ORGANISM: Homo sapiens

<400> SEQUENCE: 81

Lys His His Pro Lys Asp Asn Leu Ile Lys
1               5                   10


<210> SEQ ID NO 82
<211> LENGTH: 10
<212> TYPE: PRT
<213> ORGANISM: Homo sapiens

<400> SEQUENCE: 82

Lys His Lys Arg Lys Lys Phe Arg Gln Lys
1               5                   10


<210> SEQ ID NO 83
<211> LENGTH: 10
<212> TYPE: PRT
<213> ORGANISM: Homo sapiens

<400> SEQUENCE: 83

Lys Ala Gly Val Ala Phe Leu His Lys Lys
```

-continued

```
1               5                   10


<210> SEQ ID NO 84
<211> LENGTH: 10
<212> TYPE: PRT
<213> ORGANISM: Homo sapiens

<400> SEQUENCE: 84

Lys His Lys Arg Lys Lys Phe Arg Gln Lys
1               5                   10


<210> SEQ ID NO 85
<211> LENGTH: 10
<212> TYPE: PRT
<213> ORGANISM: Homo sapiens

<400> SEQUENCE: 85

Lys Lys Lys Ser Lys Lys His Lys Asp Lys
1               5                   10


<210> SEQ ID NO 86
<211> LENGTH: 11
<212> TYPE: PRT
<213> ORGANISM: Homo sapiens

<400> SEQUENCE: 86

His Lys Ser Glu Lys Pro Ala Leu Pro Arg Lys
1               5                   10


<210> SEQ ID NO 87
<211> LENGTH: 14
<212> TYPE: PRT
<213> ORGANISM: Homo sapiens

<400> SEQUENCE: 87

Lys Lys Lys Lys Pro Ser Arg Leu Lys Gly Asp Asn Glu Lys
1               5                   10


<210> SEQ ID NO 88
<211> LENGTH: 16
<212> TYPE: PRT
<213> ORGANISM: Homo sapiens

<400> SEQUENCE: 88

Lys Thr Lys Lys Gly Asn Arg Val Ser Pro Thr Met Lys Val Thr His
1               5                   10                  15


<210> SEQ ID NO 89
<211> LENGTH: 18
<212> TYPE: PRT
<213> ORGANISM: Homo sapiens

<400> SEQUENCE: 89

Lys His Lys Glu Lys Met Ser Lys Asp Gly Lys Lys Lys Lys Lys Lys
1               5                   10                  15

Ser Lys


<210> SEQ ID NO 90
<211> LENGTH: 9
<212> TYPE: PRT
<213> ORGANISM: Bacillus anthracis

<400> SEQUENCE: 90

Lys Ile His Leu Ile Ser Val Lys Lys
```

1 5

<210> SEQ ID NO 91
<211> LENGTH: 10
<212> TYPE: PRT
<213> ORGANISM: Bacillus anthracis

<400> SEQUENCE: 91

His Val Lys Lys Glu Lys Glu Lys Asn Lys
1 5 10

<210> SEQ ID NO 92
<211> LENGTH: 9
<212> TYPE: PRT
<213> ORGANISM: Bacillus anthracis

<400> SEQUENCE: 92

Lys His Ile Val Lys Ile Glu Val Lys
1 5

<210> SEQ ID NO 93
<211> LENGTH: 16
<212> TYPE: PRT
<213> ORGANISM: Bacillus anthracis

<400> SEQUENCE: 93

Lys Lys Lys Lys Ile Lys Asp Ile Tyr Gly Lys Asp Ala Leu Leu His
1 5 10 15

<210> SEQ ID NO 94
<211> LENGTH: 8
<212> TYPE: PRT
<213> ORGANISM: Bacillus anthracis

<400> SEQUENCE: 94

Lys Trp Glu Lys Ile Lys Gln His
1 5

<210> SEQ ID NO 95
<211> LENGTH: 18
<212> TYPE: PRT
<213> ORGANISM: Bacillus anthracis

<400> SEQUENCE: 95

Lys Lys Leu Gln Ile Pro Pro Pro Ile Glu Pro Lys Lys Asp Asp Ile
1 5 10 15

Ile His

<210> SEQ ID NO 96
<211> LENGTH: 31
<212> TYPE: PRT
<213> ORGANISM: Bacillus anthracis

<400> SEQUENCE: 96

His Asn Arg Tyr Ala Ser Asn Ile Val Glu Ser Ala Tyr Leu Leu Ile
1 5 10 15

Leu Asn Glu Trp Lys Asn Asn Ile Gln Ser Asp Leu Ile Lys Lys
20 25 30

<210> SEQ ID NO 97
<211> LENGTH: 24
<212> TYPE: PRT
<213> ORGANISM: Bacillus anthracis

```
<400> SEQUENCE: 97

His Ala Val Asp Asp Tyr Ala Gly Tyr Leu Leu Asp Lys Asn Gln Ser
1               5                   10                  15

Asp Leu Val Thr Asn Ser Lys Lys
            20


<210> SEQ ID NO 98
<211> LENGTH: 13
<212> TYPE: PRT
<213> ORGANISM: Bacillus anthracis

<400> SEQUENCE: 98

His Ala Glu Arg Leu Lys Val Gln Lys Asn Ala Pro Lys
1               5                   10


<210> SEQ ID NO 99
<211> LENGTH: 10
<212> TYPE: PRT
<213> ORGANISM: Smallpox Virus

<400> SEQUENCE: 99

Lys His Tyr Asn Asn Ile Thr Trp Tyr Lys
1               5                   10


<210> SEQ ID NO 100
<211> LENGTH: 12
<212> TYPE: PRT
<213> ORGANISM: Smallpox Virus

<400> SEQUENCE: 100

Lys Tyr Ser Gln Thr Gly Lys Glu Leu Ile Ile His
1               5                   10


<210> SEQ ID NO 101
<211> LENGTH: 17
<212> TYPE: PRT
<213> ORGANISM: Smallpox Virus

<400> SEQUENCE: 101

His Tyr Asp Asp Val Arg Ile Lys Asn Asp Ile Val Val Ser Arg Cys
1               5                   10                  15

Lys


<210> SEQ ID NO 102
<211> LENGTH: 11
<212> TYPE: PRT
<213> ORGANISM: Smallpox Virus

<400> SEQUENCE: 102

His Arg Phe Lys Leu Ile Leu Asp Ser Lys Ile
1               5                   10


<210> SEQ ID NO 103
<211> LENGTH: 11
<212> TYPE: PRT
<213> ORGANISM: Smallpox Virus

<400> SEQUENCE: 103

Lys Glu Arg Gly His Asn Tyr Tyr Phe Glu Lys
1               5                   10


<210> SEQ ID NO 104
<211> LENGTH: 8
```

<212> TYPE: PRT
<213> ORGANISM: Influenza virus

<400> SEQUENCE: 104

Lys Ser His Phe Ala Asn Leu Lys
1               5

<210> SEQ ID NO 105
<211> LENGTH: 11
<212> TYPE: PRT
<213> ORGANISM: Influenza virus

<400> SEQUENCE: 105

Lys Ser His Phe Ala Asn Leu Lys Gly Thr Lys
1               5                   10

<210> SEQ ID NO 106
<211> LENGTH: 19
<212> TYPE: PRT
<213> ORGANISM: Influenza virus

<400> SEQUENCE: 106

Lys Ser His Phe Ala Asn Leu Lys Gly Thr Lys Thr Arg Gly Lys Leu
1               5                   10                  15

Cys Pro Lys

<210> SEQ ID NO 107
<211> LENGTH: 9
<212> TYPE: PRT
<213> ORGANISM: Influenza virus

<400> SEQUENCE: 107

His Glu Lys Tyr Gly Gly Leu Asn Lys
1               5

<210> SEQ ID NO 108
<211> LENGTH: 11
<212> TYPE: PRT
<213> ORGANISM: Influenza virus

<400> SEQUENCE: 108

His Glu Lys Tyr Gly Gly Leu Asn Lys Ser Lys
1               5                   10

<210> SEQ ID NO 109
<211> LENGTH: 20
<212> TYPE: PRT
<213> ORGANISM: Influenza virus

<400> SEQUENCE: 109

His Glu Lys Tyr Gly Gly Leu Asn Lys Ser Lys Pro Tyr Tyr Thr Gly
1               5                   10                  15

Glu His Ala Lys
            20

<210> SEQ ID NO 110
<211> LENGTH: 13
<212> TYPE: PRT
<213> ORGANISM: Influenza virus

<400> SEQUENCE: 110

His Ala Lys Ala Ile Gly Asn Cys Pro Ile Trp Val Lys
1               5                   10

<210> SEQ ID NO 111
<211> LENGTH: 23
<212> TYPE: PRT
<213> ORGANISM: Influenza virus

<400> SEQUENCE: 111

His Ala Lys Ala Ile Gly Asn Cys Pro Ile Trp Val Lys Thr Pro Leu
1 5 10 15

Lys Leu Ala Asn Gly Thr Lys
20

<210> SEQ ID NO 112
<211> LENGTH: 29
<212> TYPE: PRT
<213> ORGANISM: Influenza virus

<400> SEQUENCE: 112

His Ala Lys Ala Ile Gly Asn Cys Pro Ile Trp Val Lys Thr Pro Leu
1 5 10 15

Lys Leu Ala Asn Gly Thr Lys Tyr Arg Pro Pro Ala Lys
20 25

<210> SEQ ID NO 113
<211> LENGTH: 32
<212> TYPE: PRT
<213> ORGANISM: Influenza virus

<400> SEQUENCE: 113

His Ala Lys Ala Ile Gly Asn Cys Pro Ile Trp Val Lys Thr Pro Leu
1 5 10 15

Lys Leu Ala Asn Gly Thr Lys Tyr Arg Pro Pro Ala Lys Leu Leu Lys
20 25 30

<210> SEQ ID NO 114
<211> LENGTH: 13
<212> TYPE: PRT
<213> ORGANISM: Influenza virus

<400> SEQUENCE: 114

His Phe Ala Asn Leu Lys Gly Thr Lys Thr Arg Gly Lys
1 5 10

<210> SEQ ID NO 115
<211> LENGTH: 17
<212> TYPE: PRT
<213> ORGANISM: Influenza virus

<400> SEQUENCE: 115

His Phe Ala Asn Leu Lys Gly Thr Lys Thr Arg Gly Lys Leu Cys Pro
1 5 10 15

Lys

<210> SEQ ID NO 116
<211> LENGTH: 16
<212> TYPE: PRT
<213> ORGANISM: Influenza virus

<400> SEQUENCE: 116

His Ser Asp Asn Glu Ile Gln Met Val Lys Leu Tyr Gly Asp Ser Lys
1 5 10 15

<210> SEQ ID NO 117

-continued

<211> LENGTH: 21
<212> TYPE: PRT
<213> ORGANISM: Influenza virus

<400> SEQUENCE: 117

His Ser Asp Asn Glu Ile Gln Asp Lys Met Val Lys Leu Tyr Gly Asp
1 5 10 15

Ser Lys Pro Gln Lys
20

<210> SEQ ID NO 118
<211> LENGTH: 19
<212> TYPE: PRT
<213> ORGANISM: Influenza virus

<400> SEQUENCE: 118

His Ser Asp Asn Glu Ile Gln Met Val Lys Leu Tyr Gly Asp Ser Lys
1 5 10 15

Pro Gln Lys

<210> SEQ ID NO 119
<211> LENGTH: 9
<212> TYPE: PRT
<213> ORGANISM: Influenza virus
<220> FEATURE:
<221> NAME/KEY: MOD_RES
<222> LOCATION: (2)..(2)
<223> OTHER INFORMATION: Ala or Val

<400> SEQUENCE: 119

Lys Xaa Ser Ile Leu His Glu Val Lys
1 5

<210> SEQ ID NO 120
<211> LENGTH: 15
<212> TYPE: PRT
<213> ORGANISM: Influenza virus

<400> SEQUENCE: 120

Lys Cys Thr Gly Thr Ile Pro Ser Ala Lys Ala Ser Ile Leu His
1 5 10 15

<210> SEQ ID NO 121
<211> LENGTH: 18
<212> TYPE: PRT
<213> ORGANISM: Influenza virus

<400> SEQUENCE: 121

Lys Cys Thr Gly Thr Ile Pro Ser Ala Lys Ala Ser Ile Leu His Glu
1 5 10 15

Val Lys

<210> SEQ ID NO 122
<211> LENGTH: 16
<212> TYPE: PRT
<213> ORGANISM: Influenza virus

<400> SEQUENCE: 122

Lys Tyr Gly Gly Leu Asn Lys Ser Lys Pro Tyr Tyr Thr Gly Glu His
1 5 10 15

<210> SEQ ID NO 123
<211> LENGTH: 26
<212> TYPE: PRT

<213> ORGANISM: Influenza virus

<400> SEQUENCE: 123

Lys Val Trp Cys Ala Ser Gly Arg Ser Lys Val Ile Lys Gly Ser Leu
1 5 10 15

Pro Leu Ile Gly Glu Ala Asp Cys Leu His
20 25

<210> SEQ ID NO 124
<211> LENGTH: 10
<212> TYPE: PRT
<213> ORGANISM: Influenza virus

<400> SEQUENCE: 124

Lys Pro Tyr Tyr Thr Gly Glu His Ala Lys
1 5 10

<210> SEQ ID NO 125
<211> LENGTH: 18
<212> TYPE: PRT
<213> ORGANISM: Influenza virus

<400> SEQUENCE: 125

Lys Cys Met Gly Thr Ile Pro Ser Ala Lys Ala Ser Ile Leu His Glu
1 5 10 15

Val Lys

<210> SEQ ID NO 126
<211> LENGTH: 15
<212> TYPE: PRT
<213> ORGANISM: Influenza virus

<400> SEQUENCE: 126

His Asn Val Ile Asn Ala Glu Lys Ala Pro Gly Gly Pro Tyr Lys
1 5 10 15

<210> SEQ ID NO 127
<211> LENGTH: 16
<212> TYPE: PRT
<213> ORGANISM: Influenza virus

<400> SEQUENCE: 127

His Ser Asp Asn Glu Thr Gln Met Ala Lys Leu Tyr Gly Asp Ser Lys
1 5 10 15

<210> SEQ ID NO 128
<211> LENGTH: 18
<212> TYPE: PRT
<213> ORGANISM: Influenza virus

<400> SEQUENCE: 128

His Gly Val Ala Val Ala Ala Asp Leu Lys Ser Thr Gln Glu Ala Ile
1 5 10 15

Asn Lys

<210> SEQ ID NO 129
<211> LENGTH: 29
<212> TYPE: PRT
<213> ORGANISM: Influenza virus

<400> SEQUENCE: 129

His Gly Val Ala Val Ala Ala Asp Leu Lys Ser Thr Gln Glu Ala Ile
1 5 10 15

Asn Lys Asp Thr Ile Ser Thr Gln Glu Ala Ile Asn Lys
20 25

<210> SEQ ID NO 130
<211> LENGTH: 21
<212> TYPE: PRT
<213> ORGANISM: Influenza virus

<400> SEQUENCE: 130

Lys Leu Tyr Gly Asp Ser Lys Pro Gln Lys Phe Thr Ser Ser Ala Asn
1 5 10 15

Gly Val Thr Thr His
20

<210> SEQ ID NO 131
<211> LENGTH: 19
<212> TYPE: PRT
<213> ORGANISM: Influenza virus

<400> SEQUENCE: 131

His Ser Asp Asn Glu Thr Gln Met Ala Lys Leu Tyr Gly Asp Ser Lys
1 5 10 15

Pro Gln Lys

<210> SEQ ID NO 132
<211> LENGTH: 13
<212> TYPE: PRT
<213> ORGANISM: Influenza virus

<400> SEQUENCE: 132

His Phe Ala Asn Leu Lys Gly Thr Gln Thr Arg Gly Lys
1 5 10

<210> SEQ ID NO 133
<211> LENGTH: 12
<212> TYPE: PRT
<213> ORGANISM: Influenza virus

<400> SEQUENCE: 133

Lys Pro Arg Ser Ala Leu Lys Cys Lys Gly Phe His
1 5 10

<210> SEQ ID NO 134
<211> LENGTH: 22
<212> TYPE: PRT
<213> ORGANISM: Influenza virus
<220> FEATURE:
<221> NAME/KEY: MOD_RES
<222> LOCATION: (15)..(15)
<223> OTHER INFORMATION: Gly or Ala

<400> SEQUENCE: 134

Lys Ser Lys Pro Tyr Tyr Thr Gly Glu His Ala Lys Ala Ile Xaa Asn
1 5 10 15

Cys Pro Ile Trp Val Lys
20

<210> SEQ ID NO 135
<211> LENGTH: 16
<212> TYPE: PRT
<213> ORGANISM: Influenza virus
<220> FEATURE:
<221> NAME/KEY: MOD_RES
<222> LOCATION: (3)..(3)

<223> OTHER INFORMATION: Val or Ile
<220> FEATURE:
<221> NAME/KEY: MOD_RES
<222> LOCATION: (13)..(13)
<223> OTHER INFORMATION: Arg or Lys
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Thr or Ala

<400> SEQUENCE: 135

His Pro Xaa Thr Ile Gly Glu Cys Pro Lys Tyr Val Xaa Xaa Xaa Lys
1               5                   10                  15

<210> SEQ ID NO 136
<211> LENGTH: 21
<212> TYPE: PRT
<213> ORGANISM: Influenza virus
<220> FEATURE:
<221> NAME/KEY: MOD_RES
<222> LOCATION: (10)..(10)
<223> OTHER INFORMATION: Glu or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Asn or Ser
<220> FEATURE:
<221> NAME/KEY: MOD_RES
<222> LOCATION: (17)..(17)
<223> OTHER INFORMATION: Lys or Arg

<400> SEQUENCE: 136

His Asp Ser Asn Val Lys Asn Leu Tyr Xaa Lys Val Xaa Xaa Gln Leu
1               5                   10                  15

Xaa Asn Asn Ala Lys
            20

<210> SEQ ID NO 137
<211> LENGTH: 17
<212> TYPE: PRT
<213> ORGANISM: Influenza virus
<220> FEATURE:
<221> NAME/KEY: MOD_RES
<222> LOCATION: (10)..(10)
<223> OTHER INFORMATION: Glu or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Asn or Ser

<400> SEQUENCE: 137

His Asp Ser Asn Val Lys Asn Leu Tyr Xaa Lys Val Xaa Xaa Gln Leu
1               5                   10                  15

Lys

<210> SEQ ID NO 138
<211> LENGTH: 36
<212> TYPE: PRT
<213> ORGANISM: Influenza virus
<220> FEATURE:
<221> NAME/KEY: MOD_RES
<222> LOCATION: (4)..(5)
<223> OTHER INFORMATION: Xaas can be Asn Asn or Asp Asp
<220> FEATURE:
<221> NAME/KEY: MOD_RES
<222> LOCATION: (6)..(6)
<223> OTHER INFORMATION: Ala, Thr or Glu
<220> FEATURE:
<221> NAME/KEY: MOD_RES
<222> LOCATION: (12)..(12)
<223> OTHER INFORMATION: Arg or Lys
<220> FEATURE:
<221> NAME/KEY: MOD_RES
<222> LOCATION: (31)..(31)
<223> OTHER INFORMATION: Glu or Lys

<400> SEQUENCE: 138

```
His Lys Cys Xaa Xaa Xaa Cys Met Glu Ser Val Xaa Asn Gly Thr Tyr
1               5                   10                  15

Asp Tyr Pro Lys Tyr Ser Glu Glu Ser Lys Leu Asn Arg Glu Xaa Ile
            20                  25                  30

Asp Gly Val Lys
        35
```

<210> SEQ ID NO 139
<211> LENGTH: 26
<212> TYPE: PRT
<213> ORGANISM: Influenza virus
<220> FEATURE:
<221> NAME/KEY: MOD_RES
<222> LOCATION: (4)..(5)
<223> OTHER INFORMATION: Xaas can be Asn Asn or Asp Asp
<220> FEATURE:
<221> NAME/KEY: MOD_RES
<222> LOCATION: (6)..(6)
<223> OTHER INFORMATION: Ala, Thr or Glu
<220> FEATURE:
<221> NAME/KEY: MOD_RES
<222> LOCATION: (12)..(12)
<223> OTHER INFORMATION: Arg or Lys

<400> SEQUENCE: 139

```
His Lys Cys Xaa Xaa Xaa Cys Met Glu Ser Val Xaa Asn Gly Thr Tyr
1               5                   10                  15

Asp Tyr Pro Lys Tyr Ser Glu Glu Ser Lys
            20                  25
```

<210> SEQ ID NO 140
<211> LENGTH: 50
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Glu or Gly
<220> FEATURE:
<221> NAME/KEY: MOD_RES
<222> LOCATION: (21)..(21)
<223> OTHER INFORMATION: Asp or Asn

<400> SEQUENCE: 140

```
His Gln Asn Xaa Gln Gly Ser Gly Tyr Ala Ala Asp Gln Lys Ser Thr
1               5                   10                  15

Gln Asn Ala Ile Xaa Gly Ile Thr Asn Lys Val Asn Ser Val Ile Glu
            20                  25                  30

Lys Met Asn Thr Gln Phe Thr Ala Val Gly Lys Glu Phe Asn Lys Leu
        35                  40                  45
```

-continued

Glu Lys
    50

<210> SEQ ID NO 141
<211> LENGTH: 33
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Glu or Gly
<220> FEATURE:
<221> NAME/KEY: MOD_RES
<222> LOCATION: (21)..(21)
<223> OTHER INFORMATION: Asp or Asn

<400> SEQUENCE: 141

His Gln Asn Xaa Gln Gly Ser Gly Tyr Ala Ala Asp Gln Lys Ser Thr
1               5                   10                  15

Gln Asn Ala Ile Xaa Gly Ile Thr Asn Lys Val Asn Ser Val Ile Glu
            20                  25                  30

Lys

<210> SEQ ID NO 142
<211> LENGTH: 26
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Glu or Gly
<220> FEATURE:
<221> NAME/KEY: MOD_RES
<222> LOCATION: (21)..(21)
<223> OTHER INFORMATION: Asp or Asn

<400> SEQUENCE: 142

His Gln Asn Xaa Gln Gly Ser Gly Tyr Ala Ala Asp Gln Lys Ser Thr
1               5                   10                  15

Gln Asn Ala Ile Xaa Gly Ile Thr Asn Lys
            20                  25

<210> SEQ ID NO 143
<211> LENGTH: 14
<212> TYPE: PRT
<213> ORGANISM: Influenza virus

<400> SEQUENCE: 143

Lys Phe Glu Ile Phe Pro Lys Thr Ser Ser Trp Pro Asn His
1               5                   10

<210> SEQ ID NO 144
<211> LENGTH: 27
<212> TYPE: PRT
<213> ORGANISM: Influenza virus
<220> FEATURE:
<221> NAME/KEY: MOD_RES
<222> LOCATION: (3)..(3)
<223> OTHER INFORMATION: Asn, Ser or Thr
<220> FEATURE:
<221> NAME/KEY: MOD_RES
<222> LOCATION: (9)..(9)
<223> OTHER INFORMATION: Asn or Ser
<220> FEATURE:
<221> NAME/KEY: MOD_RES
<222> LOCATION: (13)..(13)
<223> OTHER INFORMATION: Val or Thr

<400> SEQUENCE: 144

```
Lys Gly Xaa Ser Tyr Pro Lys Leu Xaa Lys Ser Tyr Xaa Asn Asn Lys
1               5                   10                  15

Gly Lys Glu Val Leu Val Leu Trp Gly Val His
            20                  25


<210> SEQ ID NO 145
<211> LENGTH: 18
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Val or Thr

<400> SEQUENCE: 145

Lys Ser Tyr Xaa Asn Asn Lys Gly Lys Glu Val Leu Val Leu Trp Gly
1               5                   10                  15

Val His


<210> SEQ ID NO 146
<211> LENGTH: 36
<212> TYPE: PRT
<213> ORGANISM: Influenza virus

<400> SEQUENCE: 146

His Lys Cys Asn Asn Glu Cys Met Glu Ser Val Lys Asn Gly Thr Tyr
1               5                   10                  15

Asp Tyr Pro Lys Tyr Ser Glu Glu Ser Lys Leu Asn Arg Glu Lys Ile
            20                  25                  30

Asp Gly Val Lys
        35


<210> SEQ ID NO 147
<211> LENGTH: 26
<212> TYPE: PRT
<213> ORGANISM: Influenza virus

<400> SEQUENCE: 147

His Lys Cys Asn Asn Glu Cys Met Glu Ser Val Lys Asn Gly Thr Tyr
1               5                   10                  15

Asp Tyr Pro Lys Tyr Ser Glu Glu Ser Lys
            20                  25


<210> SEQ ID NO 148
<211> LENGTH: 20
<212> TYPE: PRT
<213> ORGANISM: Influenza virus

<400> SEQUENCE: 148

His Lys Cys Asn Asn Glu Cys Met Glu Ser Val Lys Asn Gly Thr Tyr
1               5                   10                  15

Asp Tyr Pro Lys
            20


<210> SEQ ID NO 149
<211> LENGTH: 12
<212> TYPE: PRT
<213> ORGANISM: Influenza virus

<400> SEQUENCE: 149

His Lys Cys Asn Asn Glu Cys Met Glu Ser Val Lys
1               5                   10
```

-continued

<210> SEQ ID NO 150
<211> LENGTH: 34
<212> TYPE: PRT
<213> ORGANISM: Influenza virus
<220> FEATURE:
<221> NAME/KEY: MOD_RES
<222> LOCATION: (9)..(9)
<223> OTHER INFORMATION: Lys or Arg
<220> FEATURE:
<221> NAME/KEY: MOD_RES
<222> LOCATION: (16)..(16)
<223> OTHER INFORMATION: Glu or Gly

<400> SEQUENCE: 150

```
His Asn Gly Lys Ser Ser Phe Tyr Xaa Asn Leu Leu Trp Leu Thr Xaa
1               5                   10                  15

Lys Asn Gly Leu Tyr Pro Asn Leu Ser Lys Ser Tyr Val Asn Asn Lys
            20                  25                  30

Glu Lys
```

<210> SEQ ID NO 151
<211> LENGTH: 32
<212> TYPE: PRT
<213> ORGANISM: Influenza virus
<220> FEATURE:
<221> NAME/KEY: MOD_RES
<222> LOCATION: (9)..(9)
<223> OTHER INFORMATION: Lys or Arg
<220> FEATURE:
<221> NAME/KEY: MOD_RES
<222> LOCATION: (16)..(16)
<223> OTHER INFORMATION: Glu or Gly

<400> SEQUENCE: 151

```
His Asn Gly Lys Ser Ser Phe Tyr Xaa Asn Leu Leu Trp Leu Thr Xaa
1               5                   10                  15

Lys Asn Gly Leu Tyr Pro Asn Leu Ser Lys Ser Tyr Val Asn Asn Lys
            20                  25                  30
```

<210> SEQ ID NO 152
<211> LENGTH: 26
<212> TYPE: PRT
<213> ORGANISM: Influenza virus
<220> FEATURE:
<221> NAME/KEY: MOD_RES
<222> LOCATION: (9)..(9)
<223> OTHER INFORMATION: Lys or Arg
<220> FEATURE:
<221> NAME/KEY: MOD_RES
<222> LOCATION: (16)..(16)
<223> OTHER INFORMATION: Glu or Gly

<400> SEQUENCE: 152

```
His Asn Gly Lys Ser Ser Phe Tyr Xaa Asn Leu Leu Trp Leu Thr Xaa
1               5                   10                  15

Lys Asn Gly Leu Tyr Pro Asn Leu Ser Lys
            20                  25
```

<210> SEQ ID NO 153
<211> LENGTH: 17
<212> TYPE: PRT
<213> ORGANISM: Influenza virus
<220> FEATURE:
<221> NAME/KEY: MOD_RES
<222> LOCATION: (9)..(9)
<223> OTHER INFORMATION: Lys or Arg
<220> FEATURE:

<221> NAME/KEY: MOD_RES
<222> LOCATION: (16)..(16)
<223> OTHER INFORMATION: Glu or Gly

<400> SEQUENCE: 153

His Asn Gly Lys Ser Ser Phe Tyr Xaa Asn Leu Leu Trp Leu Thr Xaa
1 5 10 15

Lys

<210> SEQ ID NO 154
<211> LENGTH: 40
<212> TYPE: PRT
<213> ORGANISM: Influenza virus

<400> SEQUENCE: 154

Lys Ser Ser Phe Tyr Lys Asn Leu Leu Trp Leu Thr Glu Lys Asn Gly
1 5 10 15

Leu Tyr Pro Asn Leu Ser Lys Ser Tyr Val Asn Asn Lys Glu Lys Glu
20 25 30

Val Leu Val Leu Trp Gly Val His
35 40

<210> SEQ ID NO 155
<211> LENGTH: 35
<212> TYPE: PRT
<213> ORGANISM: Influenza virus

<400> SEQUENCE: 155

Lys Asn Leu Leu Trp Leu Thr Glu Lys Asn Gly Leu Tyr Pro Asn Leu
1 5 10 15

Ser Lys Ser Tyr Val Asn Asn Lys Glu Lys Glu Val Leu Val Leu Trp
20 25 30

Gly Val His
35

<210> SEQ ID NO 156
<211> LENGTH: 27
<212> TYPE: PRT
<213> ORGANISM: Influenza virus

<400> SEQUENCE: 156

Lys Asn Gly Leu Tyr Pro Asn Leu Ser Lys Ser Tyr Val Asn Asn Lys
1 5 10 15

Glu Lys Glu Val Leu Val Leu Trp Gly Val His
20 25

<210> SEQ ID NO 157
<211> LENGTH: 18
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Val or Ala
<220> FEATURE:
<221> NAME/KEY: MOD_RES
<222> LOCATION: (12)..(12)
<223> OTHER INFORMATION: May or may not be present
<220> FEATURE:
<221> NAME/KEY: MOD_RES
<222> LOCATION: (13)..(13)
<223> OTHER INFORMATION: May or may not be present

<400> SEQUENCE: 157

```
Lys Ser Tyr Xaa Asn Asn Lys Glu Lys Glu Val Leu Val Leu Trp Gly
1               5                   10                  15

Val His


<210> SEQ ID NO 158
<211> LENGTH: 12
<212> TYPE: PRT
<213> ORGANISM: Influenza virus

<400> SEQUENCE: 158

Lys Glu Ser Ser Trp Pro Asn His Thr Val Thr Lys
1               5                   10


<210> SEQ ID NO 159
<211> LENGTH: 44
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Thr or Asn

<400> SEQUENCE: 159

His Glu Thr Xaa Lys Gly Val Thr Ala Ala Cys Pro Tyr Ala Gly Ala
1               5                   10                  15

Ser Ser Phe Tyr Arg Asn Leu Leu Trp Leu Val Lys Lys Glu Asn Ser
            20                  25                  30

Tyr Pro Lys Leu Ser Lys Ser Tyr Val Asn Asn Lys
        35                  40


<210> SEQ ID NO 160
<211> LENGTH: 38
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Thr or Asn

<400> SEQUENCE: 160

His Glu Thr Xaa Lys Gly Val Thr Ala Ala Cys Pro Tyr Ala Gly Ala
1               5                   10                  15

Ser Ser Phe Tyr Arg Asn Leu Leu Trp Leu Val Lys Lys Glu Asn Ser
            20                  25                  30

Tyr Pro Lys Leu Ser Lys
        35


<210> SEQ ID NO 161
<211> LENGTH: 22
<212> TYPE: PRT
<213> ORGANISM: Influenza virus

<400> SEQUENCE: 161

Lys Phe Glu Ile Phe Pro Lys Thr Ser Ser Trp Pro Asn Glu Val Leu
1               5                   10                  15

Val Leu Trp Gly Val His
            20


<210> SEQ ID NO 162
<211> LENGTH: 8
<212> TYPE: PRT
<213> ORGANISM: Influenza virus

<400> SEQUENCE: 162
```

Lys Glu Arg Ser Trp Pro Lys His
1 5

<210> SEQ ID NO 163
<211> LENGTH: 21
<212> TYPE: PRT
<213> ORGANISM: Influenza virus

<400> SEQUENCE: 163

Lys Leu Ser Lys Ser Tyr Val Asn Asn Lys Glu Lys Glu Val Leu Val
1 5 10 15

Leu Trp Gln Val His
20

<210> SEQ ID NO 164
<211> LENGTH: 15
<212> TYPE: PRT
<213> ORGANISM: Influenza virus

<400> SEQUENCE: 164

Lys Asn Asn Lys Glu Lys Glu Val Leu Val Leu Trp Gln Val His
1 5 10 15

<210> SEQ ID NO 165
<211> LENGTH: 34
<212> TYPE: PRT
<213> ORGANISM: Influenza virus
<220> FEATURE:
<221> NAME/KEY: MOD_RES
<222> LOCATION: (2)..(2)
<223> OTHER INFORMATION: Lys or Asn
<220> FEATURE:
<221> NAME/KEY: MOD_RES
<222> LOCATION: (3)..(3)
<223> OTHER INFORMATION: Gly or Gln
<220> FEATURE:
<221> NAME/KEY: MOD_RES
<222> LOCATION: (9)..(9)
<223> OTHER INFORMATION: Arg or Lys
<220> FEATURE:
<221> NAME/KEY: MOD_RES
<222> LOCATION: (20)..(20)
<223> OTHER INFORMATION: Leu or Ser
<220> FEATURE:
<221> NAME/KEY: MOD_RES
<222> LOCATION: (23)..(23)
<223> OTHER INFORMATION: Asn or Thr

<400> SEQUENCE: 165

His Xaa Xaa Lys Ser Ser Phe Tyr Xaa Asn Leu Leu Trp Leu Thr Glu
1 5 10 15

Lys Asn Gly Xaa Tyr Pro Xaa Leu Ser Lys Ser Tyr Ala Asn Asn Lys
20 25 30

Glu Lys

<210> SEQ ID NO 166
<211> LENGTH: 17
<212> TYPE: PRT
<213> ORGANISM: Influenza virus
<220> FEATURE:
<221> NAME/KEY: MOD_RES
<222> LOCATION: (2)..(2)
<223> OTHER INFORMATION: Lys or Asn
<220> FEATURE:
<221> NAME/KEY: MOD_RES
<222> LOCATION: (3)..(3)
<223> OTHER INFORMATION: Gly or Gln
<220> FEATURE:

-continued

<221> NAME/KEY: MOD_RES
<222> LOCATION: (9)..(9)
<223> OTHER INFORMATION: Arg or Lys

<400> SEQUENCE: 166

His Xaa Xaa Lys Ser Ser Phe Tyr Xaa Asn Leu Leu Trp Leu Thr Glu
1 5 10 15

Lys

<210> SEQ ID NO 167
<211> LENGTH: 9
<212> TYPE: PRT
<213> ORGANISM: Influenza virus

<400> SEQUENCE: 167

His Ala Lys Lys Ser Ser Phe Tyr Lys
1 5

<210> SEQ ID NO 168
<211> LENGTH: 11
<212> TYPE: PRT
<213> ORGANISM: Influenza virus

<400> SEQUENCE: 168

His Asn Gly Lys Leu Cys Arg Leu Lys Gly Lys
1 5 10

<210> SEQ ID NO 169
<211> LENGTH: 9
<212> TYPE: PRT
<213> ORGANISM: Influenza virus
<220> FEATURE:
<221> NAME/KEY: MOD_RES
<222> LOCATION: (7)..(7)
<223> OTHER INFORMATION: Gln or Gly

<400> SEQUENCE: 169

His Tyr Lys Leu Asn Asn Xaa Lys Lys
1 5

<210> SEQ ID NO 170
<211> LENGTH: 25
<212> TYPE: PRT
<213> ORGANISM: Influenza virus

<400> SEQUENCE: 170

His Asp Ile Tyr Arg Asp Glu Ala Ile Asn Asn Arg Phe Gln Ile Gln
1 5 10 15

Gly Val Lys Leu Thr Gln Gly Tyr Lys
20 25

<210> SEQ ID NO 171
<211> LENGTH: 11
<212> TYPE: PRT
<213> ORGANISM: Influenza virus

<400> SEQUENCE: 171

Lys Gly Asn Gly Cys Phe Glu Ile Phe His Lys
1 5 10

<210> SEQ ID NO 172
<211> LENGTH: 18
<212> TYPE: PRT
<213> ORGANISM: Influenza virus

<400> SEQUENCE: 172

Lys Leu Asn Arg Leu Ile Glu Lys Thr Asn Asp Lys Tyr His Gln Ile
1               5                   10                  15

Glu Lys

<210> SEQ ID NO 173
<211> LENGTH: 14
<212> TYPE: PRT
<213> ORGANISM: Influenza virus

<400> SEQUENCE: 173

Lys Leu Asn Arg Leu Ile Glu Lys Thr Asn Asp Lys Tyr His
1               5                   10

<210> SEQ ID NO 174
<211> LENGTH: 13
<212> TYPE: PRT
<213> ORGANISM: Influenza virus

<400> SEQUENCE: 174

Lys Cys His Thr Asp Lys Gly Ser Leu Ser Thr Thr Lys
1               5                   10

<210> SEQ ID NO 175
<211> LENGTH: 16
<212> TYPE: PRT
<213> ORGANISM: Influenza virus

<400> SEQUENCE: 175

Lys Ile Asn Asn Gly Asp Tyr Ala Lys Leu Tyr Ile Trp Gly Val His
1               5                   10                  15

<210> SEQ ID NO 176
<211> LENGTH: 17
<212> TYPE: PRT
<213> ORGANISM: Influenza virus

<400> SEQUENCE: 176

His Asn Gly Lys Leu Cys Arg Lys Gly Ile Ala Pro Leu Gln Leu Gly
1               5                   10                  15

Lys

<210> SEQ ID NO 177
<211> LENGTH: 38
<212> TYPE: PRT
<213> ORGANISM: Influenza virus

<400> SEQUENCE: 177

His Glu Thr Asn Arg Gln Val Thr Ala Ala Cys Pro Tyr Ala Gly Ala
1               5                   10                  15

Asn Ser Phe Phe Arg Asn Leu Ile Trp Leu Val Lys Lys Glu Ser Ser
            20                  25                  30

Tyr Pro Lys Leu Ser Lys
        35

<210> SEQ ID NO 178
<211> LENGTH: 35
<212> TYPE: PRT
<213> ORGANISM: Influenza virus

<400> SEQUENCE: 178

His Glu Thr Asn Arg Gln Val Thr Ala Ala Cys Pro Tyr Ala Gly Ala

-continued 1 5 10 15

Asn Ser Phe Phe Arg Asn Leu Ile Trp Leu Val Lys Lys Glu Ser Ser
20 25 30

Tyr Pro Lys
35

<210> SEQ ID NO 179
<211> LENGTH: 31
<212> TYPE: PRT
<213> ORGANISM: Influenza virus

<400> SEQUENCE: 179

His Pro Pro Thr Ser Thr Asp Gln Gln Ser Leu Tyr Gln Asn Ala Asp
1 5 10 15

Ala Tyr Ile Phe Val Gly Ser Ser Lys Tyr Asn Arg Lys Phe Lys
20 25 30

<210> SEQ ID NO 180
<211> LENGTH: 35
<212> TYPE: PRT
<213> ORGANISM: Influenza virus

<400> SEQUENCE: 180

His Pro Pro Thr Ser Thr Asp Gln Gln Ser Leu Tyr Gln Asn Ala Asp
1 5 10 15

Ala Tyr Ile Phe Val Gly Ser Ser Lys Tyr Asn Arg Lys Phe Lys Pro
20 25 30

Glu Ile Ala
35

<210> SEQ ID NO 181
<211> LENGTH: 25
<212> TYPE: PRT
<213> ORGANISM: Influenza virus

<400> SEQUENCE: 181

His Asp Ile Tyr Arg Asp Glu Ala Ile Asn Asn Arg Phe Gln Ile Gln
1 5 10 15

Gly Val Lys Ile Thr Gln Gly Tyr Lys
20 25

<210> SEQ ID NO 182
<211> LENGTH: 43
<212> TYPE: PRT
<213> ORGANISM: Influenza virus

<400> SEQUENCE: 182

His Gln Asn Glu Gln Gly Ser Gly Tyr Ala Ala Asp Gln Lys Ser Thr
1 5 10 15

Gln Asn Ala Ile Asp Gly Ile Thr Asn Lys Val Asn Ser Val Ile Glu
20 25 30

Lys Met Asn Thr Gln Phe Thr Ala Val Gly Lys
35 40

<210> SEQ ID NO 183
<211> LENGTH: 33
<212> TYPE: PRT
<213> ORGANISM: Influenza virus

<400> SEQUENCE: 183

His Gln Asn Glu Gln Gly Ser Gly Tyr Ala Ala Asp Gln Lys Ser Thr 1 5 10 15

Gln Asn Ala Ile Asp Gly Ile Thr Asn Lys Val Asn Ser Val Ile Glu
20 25 30

Lys

<210> SEQ ID NO 184
<211> LENGTH: 50
<212> TYPE: PRT
<213> ORGANISM: Influenza virus

<400> SEQUENCE: 184

His Gln Asn Glu Gln Gly Ser Gly Tyr Ala Ala Asp Gln Lys Ser Thr
1 5 10 15

Gln Asn Ala Ile Asn Gly Ile Thr Asn Lys Val Asn Ser Val Ile Glu
20 25 30

Lys Met Asn Thr Gln Phe Thr Ala Val Gly Lys Glu Phe Asn Lys Leu
35 40 45

Glu Lys
50

<210> SEQ ID NO 185
<211> LENGTH: 18
<212> TYPE: PRT
<213> ORGANISM: Influenza virus

<400> SEQUENCE: 185

His Asn Gly Lys Leu Cys Arg Leu Lys Gly Ile Ala Pro Leu Gln Leu
1 5 10 15

Gly Lys

<210> SEQ ID NO 186
<211> LENGTH: 12
<212> TYPE: PRT
<213> ORGANISM: Influenza virus

<400> SEQUENCE: 186

His Lys Cys Asn Asn Glu Cys Met Glu Ser Val Lys
1 5 10

<210> SEQ ID NO 187
<211> LENGTH: 14
<212> TYPE: PRT
<213> ORGANISM: Influenza virus

<400> SEQUENCE: 187

Lys Phe Glu Ile Phe Pro Lys Ala Ser Ser Trp Pro Asn His
1 5 10

<210> SEQ ID NO 188
<211> LENGTH: 21
<212> TYPE: PRT
<213> ORGANISM: Influenza virus

<400> SEQUENCE: 188

His Asp Ser Asn Val Lys Asn Leu Tyr Glu Lys Val Arg Ser Gln Leu
1 5 10 15

Arg Asn Asn Ala Lys
20

<210> SEQ ID NO 189
<211> LENGTH: 22

<212> TYPE: PRT
<213> ORGANISM: Influenza virus

<400> SEQUENCE: 189

```
Lys Val Asn Ser Val Ile Lys Lys Met Asn Thr Gln Phe Ala Ala Val
1               5                   10                  15

Gly Lys Glu Phe Asn His
            20
```

<210> SEQ ID NO 190
<211> LENGTH: 8
<212> TYPE: PRT
<213> ORGANISM: Influenza virus

<400> SEQUENCE: 190

```
Lys His Asn Gly Lys Leu Cys Lys
1               5
```

<210> SEQ ID NO 191
<211> LENGTH: 28
<212> TYPE: PRT
<213> ORGANISM: Influenza virus

<400> SEQUENCE: 191

```
Lys Lys Gly Thr Ser Tyr Pro Lys Leu Ser Lys Ser Tyr Thr His Asn
1               5                   10                  15

Lys Gly Lys Glu Val Leu Val Leu Trp Gly Val His
            20                  25
```

<210> SEQ ID NO 192
<211> LENGTH: 27
<212> TYPE: PRT
<213> ORGANISM: Influenza virus

<400> SEQUENCE: 192

```
Lys Gly Thr Ser Tyr Pro Lys Leu Ser Lys Ser Tyr Thr His Asn Lys
1               5                   10                  15

Gly Lys Glu Val Leu Val Leu Trp Gly Val His
            20                  25
```

<210> SEQ ID NO 193
<211> LENGTH: 21
<212> TYPE: PRT
<213> ORGANISM: Influenza virus

<400> SEQUENCE: 193

```
Lys Leu Ser Lys Ser Tyr Thr His Asn Lys Gly Lys Glu Val Leu Val
1               5                   10                  15

Leu Trp Gly Val His
            20
```

<210> SEQ ID NO 194
<211> LENGTH: 18
<212> TYPE: PRT
<213> ORGANISM: Influenza virus

<400> SEQUENCE: 194

```
Lys Ser Tyr Thr His Asn Lys Gly Lys Glu Val Leu Val Leu Trp Gly
1               5                   10                  15

Val His
```

<210> SEQ ID NO 195

<211> LENGTH: 10
<212> TYPE: PRT
<213> ORGANISM: Influenza virus

<400> SEQUENCE: 195

Lys Gly Val Thr Ala Ser Cys Ser His Lys
1 5 10

<210> SEQ ID NO 196
<211> LENGTH: 34
<212> TYPE: PRT
<213> ORGANISM: Influenza virus

<400> SEQUENCE: 196

Lys Gly Val Thr Ala Ser Cys Ser His Lys Gly Arg Ser Ser Phe Tyr
1 5 10 15

Arg Asn Leu Leu Trp Leu Thr Glu Lys Asn Gly Leu Tyr Pro Asn Leu
20 25 30

Ser Lys

<210> SEQ ID NO 197
<211> LENGTH: 27
<212> TYPE: PRT
<213> ORGANISM: Influenza virus

<400> SEQUENCE: 197

Lys Gly Asn Ser Tyr Pro Lys Leu Ser Lys Ser Tyr Val Asn Asn Lys
1 5 10 15

Glu Lys Glu Val Leu Val Leu Trp Gly Ile His
20 25

<210> SEQ ID NO 198
<211> LENGTH: 8
<212> TYPE: PRT
<213> ORGANISM: Influenza virus

<400> SEQUENCE: 198

Lys Glu Phe Asn His Leu Glu Lys
1 5

<210> SEQ ID NO 199
<211> LENGTH: 39
<212> TYPE: PRT
<213> ORGANISM: Influenza virus

<400> SEQUENCE: 199

His Pro Pro Thr Ser Thr Asp Gln Gln Ser Leu Tyr Gln Asn Ala Asp
1 5 10 15

Ala Tyr Val Phe Val Gly Ser Ser Lys Tyr Asn Lys Lys Phe Lys Pro
20 25 30

Glu Ile Ala Thr Arg Pro Lys
35

<210> SEQ ID NO 200
<211> LENGTH: 31
<212> TYPE: PRT
<213> ORGANISM: Influenza virus

<400> SEQUENCE: 200

His Pro Pro Thr Ser Thr Asp Gln Gln Ser Leu Tyr Gln Asn Ala Asp
1 5 10 15

Ala Tyr Val Phe Val Gly Ser Ser Lys Tyr Asn Lys Lys Phe Lys 20 25 30

<210> SEQ ID NO 201
<211> LENGTH: 31
<212> TYPE: PRT
<213> ORGANISM: Influenza virus

<400> SEQUENCE: 201

His Glu Gly Lys Ser Ser Phe Tyr Arg Asn Leu Leu Trp Leu Thr Glu
1 5 10 15

Lys Glu Gly Ser Tyr Pro Lys Leu Lys Asn Ser Tyr Val Asn Lys
20 25 30

<210> SEQ ID NO 202
<211> LENGTH: 23
<212> TYPE: PRT
<213> ORGANISM: Influenza virus

<400> SEQUENCE: 202

His Glu Gly Lys Ser Ser Phe Tyr Arg Asn Leu Leu Trp Leu Thr Glu
1 5 10 15

Lys Glu Gly Ser Tyr Pro Lys
20

<210> SEQ ID NO 203
<211> LENGTH: 26
<212> TYPE: PRT
<213> ORGANISM: Influenza virus

<400> SEQUENCE: 203

His Lys Cys Asp Asn Glu Cys Met Glu Ser Val Arg Asn Gly Thr Tyr
1 5 10 15

Asp Tyr Pro Lys Tyr Ser Glu Glu Ser Lys
20 25

<210> SEQ ID NO 204
<211> LENGTH: 12
<212> TYPE: PRT
<213> ORGANISM: Influenza virus

<400> SEQUENCE: 204

Lys Glu Ser Ser Trp Pro Asn His Thr Val Thr Lys
1 5 10

<210> SEQ ID NO 205
<211> LENGTH: 35
<212> TYPE: PRT
<213> ORGANISM: Influenza virus

<400> SEQUENCE: 205

Lys Asn Leu Leu Trp Leu Thr Glu Lys Asn Gly Leu Tyr Pro Asn Leu
1 5 10 15

Ser Lys Ser Tyr Val Asn Asn Lys Glu Lys Glu Ile Leu Val Leu Trp
20 25 30

Gly Val His
35

<210> SEQ ID NO 206
<211> LENGTH: 27
<212> TYPE: PRT
<213> ORGANISM: Influenza virus
<220> FEATURE:
<221> NAME/KEY: MOD_RES
<222> LOCATION: (9)..(9)
<223> OTHER INFORMATION: Lys or Met
<220> FEATURE:
<221> NAME/KEY: MOD_RES
<222> LOCATION: (10)..(10)
<223> OTHER INFORMATION: May or may not be present
<220> FEATURE:
<221> NAME/KEY: MOD_RES
<222> LOCATION: (16)..(16)
<223> OTHER INFORMATION: Glu or Gly
<220> FEATURE:
<221> NAME/KEY: MOD_RES
<222> LOCATION: (17)..(17)
<223> OTHER INFORMATION: May or may not be present

<400> SEQUENCE: 206

```
His Asn Gly Lys Ser Ser Phe Tyr Xaa Asn Leu Leu Trp Leu Thr Xaa
1               5                   10                  15

Lys Lys Asn Gly Leu Tyr Pro Asn Leu Ser Lys
            20                  25
```

<210> SEQ ID NO 207
<211> LENGTH: 17
<212> TYPE: PRT
<213> ORGANISM: Influenza virus

<400> SEQUENCE: 207

```
His Asn Gly Lys Ser Ser Phe Tyr Lys Asn Leu Leu Trp Leu Thr Glu
1               5                   10                  15

Lys
```

<210> SEQ ID NO 208
<211> LENGTH: 55
<212> TYPE: PRT
<213> ORGANISM: Influenza virus

<400> SEQUENCE: 208

```
His Thr Val Thr Lys Gly Val Thr Ala Ser Cys Ser His Asn Gly Lys
1               5                   10                  15

Ser Ser Phe Tyr Lys Asn Leu Leu Trp Leu Thr Glu Lys Asn Gly Leu
            20                  25                  30

Tyr Pro Asn Leu Ser Lys Ser Tyr Val Asn Asn Lys Glu Lys Glu Val
        35                  40                  45

Leu Val Leu Trp Gly Val His
    50                  55
```

<210> SEQ ID NO 209
<211> LENGTH: 38
<212> TYPE: PRT
<213> ORGANISM: Influenza virus
<220> FEATURE:
<221> NAME/KEY: MOD_RES
<222> LOCATION: (5)..(5)
<223> OTHER INFORMATION: Lys or Gly
<220> FEATURE:
<221> NAME/KEY: MOD_RES
<222> LOCATION: (8)..(8)
<223> OTHER INFORMATION: Thr or Ser
<220> FEATURE:
<221> NAME/KEY: MOD_RES
<222> LOCATION: (21)..(21)
<223> OTHER INFORMATION: Lys or Met
<220> FEATURE:
<221> NAME/KEY: MOD_RES
<222> LOCATION: (22)..(22)
<223> OTHER INFORMATION: May or may not be present
<220> FEATURE:
<221> NAME/KEY: MOD_RES -continued
<222> LOCATION: (28)..(28)
<223> OTHER INFORMATION: Glu or Gly
<220> FEATURE:
<221> NAME/KEY: MOD_RES
<222> LOCATION: (30)..(30)
<223> OTHER INFORMATION: Asn or Lys

<400> SEQUENCE: 209

```
His Thr Val Thr Xaa Gly Val Xaa Ala Ser Cys Ser His Asn Gly Lys
1               5                   10                  15

Ser Ser Phe Tyr Xaa Asn Leu Leu Trp Leu Thr Xaa Lys Xaa Gly Leu
            20                  25                  30

Tyr Pro Asn Leu Ser Lys
        35
```

<210> SEQ ID NO 210
<211> LENGTH: 29
<212> TYPE: PRT
<213> ORGANISM: Influenza virus

<400> SEQUENCE: 210

```
His Thr Val Thr Lys Gly Val Thr Ala Ser Cys Ser His Asn Gly Lys
1               5                   10                  15

Ser Ser Phe Tyr Lys Asn Leu Leu Trp Leu Thr Glu Lys
            20                  25
```

<210> SEQ ID NO 211
<211> LENGTH: 48
<212> TYPE: PRT
<213> ORGANISM: Influenza virus

<400> SEQUENCE: 211

```
Lys Tyr Val Arg Ser Thr Lys Leu Arg Met Val Thr Gly Leu Arg Asn
1               5                   10                  15

Ile Pro Ser Ile Gln Ser Arg Gly Leu Phe Gly Ala Ile Ala Gly Phe
            20                  25                  30

Ile Glu Gly Gly Trp Thr Gly Met Ile Asp Gly Trp Tyr Gly Tyr His
        35                  40                  45
```

<210> SEQ ID NO 212
<211> LENGTH: 43
<212> TYPE: PRT
<213> ORGANISM: Influenza virus

<400> SEQUENCE: 212

```
His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Ile Ile Glu
            20                  25                  30

Lys Met Asn Thr Gln Phe Thr Ala Val Gly Lys
        35                  40
```

<210> SEQ ID NO 213
<211> LENGTH: 33
<212> TYPE: PRT
<213> ORGANISM: Influenza virus

<400> SEQUENCE: 213

```
His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Ile Ile Glu
            20                  25                  30
```

Lys

<210> SEQ ID NO 214
<211> LENGTH: 26
<212> TYPE: PRT
<213> ORGANISM: Influenza virus

<400> SEQUENCE: 214

His Gln Asn Glu Gln Gly Ser Gly Tyr Ala Ala Asp Gln Lys Ser Thr
1 5 10 15

Gln Asn Ala Ile Asn Gly Ile Thr Asn Lys
20 25

<210> SEQ ID NO 215
<211> LENGTH: 23
<212> TYPE: PRT
<213> ORGANISM: Influenza virus

<400> SEQUENCE: 215

His Ser Gly Ala Arg Ser Phe Tyr Arg Asn Leu Leu Trp Ile Val Lys
1 5 10 15

Lys Gly Asn Ser Tyr Pro Lys
20

<210> SEQ ID NO 216
<211> LENGTH: 26
<212> TYPE: PRT
<213> ORGANISM: Influenza virus

<400> SEQUENCE: 216

His Ser Gly Ala Arg Ser Phe Tyr Arg Asn Leu Leu Trp Ile Val Lys
1 5 10 15

Lys Gly Asn Ser Tyr Pro Lys Leu Asn Lys
20 25

<210> SEQ ID NO 217
<211> LENGTH: 32
<212> TYPE: PRT
<213> ORGANISM: Influenza virus

<400> SEQUENCE: 217

His Ser Gly Ala Arg Ser Phe Tyr Arg Asn Leu Leu Trp Ile Val Lys
1 5 10 15

Lys Gly Asn Ser Tyr Pro Lys Leu Asn Lys Ser Tyr Thr Asn Asp Lys
20 25 30

<210> SEQ ID NO 218
<211> LENGTH: 34
<212> TYPE: PRT
<213> ORGANISM: Influenza virus

<400> SEQUENCE: 218

His Ser Gly Ala Arg Ser Phe Tyr Arg Asn Leu Leu Trp Ile Val Lys
1 5 10 15

Lys Gly Asn Ser Tyr Pro Lys Leu Asn Lys Ser Tyr Thr Asn Asp Lys
20 25 30

Gly Lys

<210> SEQ ID NO 219
<211> LENGTH: 16
<212> TYPE: PRT

<213> ORGANISM: Influenza virus

<400> SEQUENCE: 219

His Thr Val Ser Lys Gly Val Thr Thr Ser Cys Ser His Asn Gly Lys
1               5                   10                  15

<210> SEQ ID NO 220
<211> LENGTH: 12
<212> TYPE: PRT
<213> ORGANISM: Influenza virus

<400> SEQUENCE: 220

Lys Ala Thr Ser Trp Pro Asn His Glu Thr Thr Lys
1               5                   10

<210> SEQ ID NO 221
<211> LENGTH: 12
<212> TYPE: PRT
<213> ORGANISM: Influenza virus

<400> SEQUENCE: 221

Lys Gln Val Thr Thr Ser Cys Ser His Asn Gln Lys
1               5                   10

<210> SEQ ID NO 222
<211> LENGTH: 27
<212> TYPE: PRT
<213> ORGANISM: Influenza virus

<400> SEQUENCE: 222

Lys Gly Asn Ser Tyr Pro Lys Leu Asn Lys Ser Tyr Thr Asn Asp Lys
1               5                   10                  15

Gly Lys Glu Val Leu Val Ile Trp Gly Val His
            20                  25

<210> SEQ ID NO 223
<211> LENGTH: 21
<212> TYPE: PRT
<213> ORGANISM: Influenza virus

<400> SEQUENCE: 223

Lys Leu Asn Lys Ser Tyr Thr Asn Asp Lys Gly Lys Glu Val Leu Val
1               5                   10                  15

Ile Trp Gly Val His
            20

<210> SEQ ID NO 224
<211> LENGTH: 18
<212> TYPE: PRT
<213> ORGANISM: Influenza virus

<400> SEQUENCE: 224

Lys Ser Tyr Thr Asn Asp Lys Gly Lys Glu Val Leu Val Ile Trp Gly
1               5                   10                  15

Val His

<210> SEQ ID NO 225
<211> LENGTH: 35
<212> TYPE: PRT
<213> ORGANISM: Influenza virus
<220> FEATURE:
<221> NAME/KEY: MOD_RES
<222> LOCATION: (16)..(16)
<223> OTHER INFORMATION: Glu or Gln
<220> FEATURE:
<221> NAME/KEY: MOD_RES
<222> LOCATION: (29)..(29)
<223> OTHER INFORMATION: Val or Ala

<400> SEQUENCE: 225

His Asn Gln Lys Ser Ser Phe Tyr Arg Asn Leu Leu Trp Leu Thr Xaa
1 5 10 15

Lys Asn Gly Leu Tyr Pro Asn Leu Ser Lys Ser Tyr Xaa Ala Asn Asn
20 25 30

Lys Glu Lys
35

<210> SEQ ID NO 226
<211> LENGTH: 16
<212> TYPE: PRT
<213> ORGANISM: Influenza virus

<400> SEQUENCE: 226

His Pro Ile Thr Ile Gly Glu Cys Pro Lys Tyr Val Arg Ser Ala Lys
1 5 10 15

<210> SEQ ID NO 227
<211> LENGTH: 43
<212> TYPE: PRT
<213> ORGANISM: Influenza virus

<400> SEQUENCE: 227

His Gln Asn Glu Gln Gly Ser Gly Tyr Ala Ala Asp Gln Lys Ser Thr
1 5 10 15

Gln Asn Ala Ile Asn Gly Ile Thr Asn Lys Val Asn Ser Val Ile Glu
20 25 30

Lys Met Asn Thr Gln Phe Thr Ala Val Gly Lys
35 40

<210> SEQ ID NO 228
<211> LENGTH: 33
<212> TYPE: PRT
<213> ORGANISM: Influenza virus

<400> SEQUENCE: 228

His Gln Asn Glu Gln Gly Ser Gly Tyr Ala Ala Asp Gln Lys Ser Thr
1 5 10 15

Gln Asn Ala Ile Asn Gly Ile Thr Asn Lys Val Asn Ser Val Ile Glu
20 25 30

Lys

<210> SEQ ID NO 229
<211> LENGTH: 34
<212> TYPE: PRT
<213> ORGANISM: Influenza virus

<400> SEQUENCE: 229

His Asn Gly Lys Ser Ser Phe Tyr Arg Asn Leu Leu Trp Leu Thr Glu
1 5 10 15

Lys Asn Gly Leu Tyr Pro Asn Leu Ser Lys Ser Tyr Val Asn Asn Lys
20 25 30

Glu Lys

<210> SEQ ID NO 230
<211> LENGTH: 11

<212> TYPE: PRT
<213> ORGANISM: Influenza virus

<400> SEQUENCE: 230

Lys His Phe Glu Lys Val Lys Ile Leu Pro Lys
1 5 10

<210> SEQ ID NO 231
<211> LENGTH: 14
<212> TYPE: PRT
<213> ORGANISM: Influenza virus

<400> SEQUENCE: 231

Lys His Leu Leu Ser Ser Val Lys His Phe Glu Lys Val Lys
1 5 10

<210> SEQ ID NO 232
<211> LENGTH: 13
<212> TYPE: PRT
<213> ORGANISM: Influenza virus
<220> FEATURE:
<221> NAME/KEY: MOD_RES
<222> LOCATION: (3)..(3)
<223> OTHER INFORMATION: Lys, Gln or Met
<220> FEATURE:
<221> NAME/KEY: MOD_RES
<222> LOCATION: (4)..(4)
<223> OTHER INFORMATION: Asp or Asn

<400> SEQUENCE: 232

His Ala Xaa Xaa Ile Leu Glu Lys Thr His Asn Gly Lys
1 5 10

<210> SEQ ID NO 233
<211> LENGTH: 16
<212> TYPE: PRT
<213> ORGANISM: Influenza virus
<220> FEATURE:
<221> NAME/KEY: MOD_RES
<222> LOCATION: (3)..(3)
<223> OTHER INFORMATION: Lys, Gln or Met
<220> FEATURE:
<221> NAME/KEY: MOD_RES
<222> LOCATION: (4)..(4)
<223> OTHER INFORMATION: Asp or Asn
<220> FEATURE:
<221> NAME/KEY: MOD_RES
<222> LOCATION: (16)..(16)
<223> OTHER INFORMATION: Lys or Arg

<400> SEQUENCE: 233

His Ala Xaa Xaa Ile Leu Glu Lys Thr His Asn Gly Lys Leu Cys Xaa
1 5 10 15

<210> SEQ ID NO 234
<211> LENGTH: 19
<212> TYPE: PRT
<213> ORGANISM: Influenza virus

<400> SEQUENCE: 234

His Asn Val His Pro Leu Thr Ile Gly Glu Cys Pro Lys Tyr Val Lys
1 5 10 15

Ser Glu Lys

<210> SEQ ID NO 235
<211> LENGTH: 16
<212> TYPE: PRT
<213> ORGANISM: Influenza virus

<400> SEQUENCE: 235

His Pro Leu Thr Ile Gly Glu Cys Pro Lys Tyr Val Lys Ser Glu Lys
1 5 10 15

<210> SEQ ID NO 236
<211> LENGTH: 18
<212> TYPE: PRT
<213> ORGANISM: Influenza virus

<400> SEQUENCE: 236

Lys His Leu Leu Ser Ser Val Lys His Phe Glu Lys Val Lys Ile Leu
1 5 10 15

Pro Lys

<210> SEQ ID NO 237
<211> LENGTH: 38
<212> TYPE: PRT
<213> ORGANISM: Influenza virus

<400> SEQUENCE: 237

Lys Arg Gln Ser Ser Gly Ile Met Lys Thr Glu Gly Thr Leu Glu Asn
1 5 10 15

Cys Glu Thr Lys Cys Gln Thr Pro Leu Gly Ala Ile Asn Thr Thr Leu
20 25 30

Pro Phe His Asn Val His
35

<210> SEQ ID NO 238
<211> LENGTH: 27
<212> TYPE: PRT
<213> ORGANISM: Influenza virus
<220> FEATURE:
<221> NAME/KEY: MOD_RES
<222> LOCATION: (7)..(7)
<223> OTHER INFORMATION: Val or Ile
<220> FEATURE:
<221> NAME/KEY: MOD_RES
<222> LOCATION: (10)..(10)
<223> OTHER INFORMATION: Gly or Arg
<220> FEATURE:
<221> NAME/KEY: MOD_RES
<222> LOCATION: (26)..(26)
<223> OTHER INFORMATION: Val or Ile

<400> SEQUENCE: 238

Lys Gly Ser Asn Tyr Pro Xaa Ala Lys Xaa Ser Tyr Asn Asn Thr Ser
1 5 10 15

Gly Glu Gln Met Leu Ile Ile Trp Gln Xaa His
20 25

<210> SEQ ID NO 239
<211> LENGTH: 36
<212> TYPE: PRT
<213> ORGANISM: Influenza virus

<400> SEQUENCE: 239

His Thr Thr Leu Gly Gln Ser Arg Ala Cys Ala Val Ser Gly Asn Pro
1 5 10 15

Ser Phe Phe Arg Asn Met Val Trp Leu Thr Glu Lys Gly Ser Asn Tyr
20 25 30

Pro Val Ala Lys
35

<210> SEQ ID NO 240
<211> LENGTH: 7
<212> TYPE: PRT
<213> ORGANISM: Influenza virus

<400> SEQUENCE: 240

Lys His Phe Glu Lys Val Lys
1               5

<210> SEQ ID NO 241
<211> LENGTH: 38
<212> TYPE: PRT
<213> ORGANISM: Influenza virus

<400> SEQUENCE: 241

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 242
<211> LENGTH: 35
<212> TYPE: PRT
<213> ORGANISM: Influenza virus

<400> SEQUENCE: 242

Lys Arg Gly Ser Ser Gly Ile Met Lys Thr Glu Gly Thr Leu Glu Asn
1               5                   10                  15

Cys Glu Thr Lys Cys Gln Thr Pro Leu Gly Ala Ile Asn Thr Thr Leu
            20                  25                  30

Pro Phe His
        35

<210> SEQ ID NO 243
<211> LENGTH: 27
<212> TYPE: PRT
<213> ORGANISM: Influenza virus

<400> SEQUENCE: 243

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His
            20                  25

<210> SEQ ID NO 244
<211> LENGTH: 38
<212> TYPE: PRT
<213> ORGANISM: Influenza virus

<400> SEQUENCE: 244

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 245
<211> LENGTH: 30

-continued

<212> TYPE: PRT
<213> ORGANISM: Influenza virus
<220> FEATURE:
<221> NAME/KEY: MOD_RES
<222> LOCATION: (29)..(29)
<223> OTHER INFORMATION: Val or Ile

<400> SEQUENCE: 245

Lys Thr Glu Gly Thr Leu Glu Asn Cys Glu Thr Lys Cys Gln Thr Pro
1 5 10 15

Leu Gly Ala Ile Asn Thr Thr Leu Pro Phe His Asn Xaa His
20 25 30

<210> SEQ ID NO 246
<211> LENGTH: 38
<212> TYPE: PRT
<213> ORGANISM: Influenza virus

<400> SEQUENCE: 246

Lys Ile Ser Lys Arg Gly Ser Ser Gly Ile Met Lys Thr Glu Gly Thr
1 5 10 15

Leu Glu Asn Cys Glu Thr Lys Cys Gln Thr Pro Leu Gly Ala Ile Asn
20 25 30

Thr Thr Leu Pro Phe His
35

<210> SEQ ID NO 247
<211> LENGTH: 27
<212> TYPE: PRT
<213> ORGANISM: Influenza virus
<220> FEATURE:
<221> NAME/KEY: MOD_RES
<222> LOCATION: (2)..(2)
<223> OTHER INFORMATION: Glu or Gly

<400> SEQUENCE: 247

Lys Xaa Ser Asn Tyr Pro Val Ala Lys Gly Ser Tyr Asn Asn Thr Ser
1 5 10 15

Gly Glu Gln Met Leu Ile Ile Trp Gly Val His
20 25

<210> SEQ ID NO 248
<211> LENGTH: 16
<212> TYPE: PRT
<213> ORGANISM: Influenza virus

<400> SEQUENCE: 248

His Pro Leu Thr Ile Gly Glu Cys Pro Lys Tyr Val Lys Ser Glu Lys
1 5 10 15

<210> SEQ ID NO 249
<211> LENGTH: 16
<212> TYPE: PRT
<213> ORGANISM: Influenza virus

<400> SEQUENCE: 249

Lys Cys Gln Thr Pro Leu Gly Ala Ile Lys Thr Thr Leu Pro Phe His
1 5 10 15

<210> SEQ ID NO 250
<211> LENGTH: 58
<212> TYPE: PRT
<213> ORGANISM: Influenza virus
<220> FEATURE:
<221> NAME/KEY: MOD_RES
<222> LOCATION: (21)..(21)
<223> OTHER INFORMATION: Phe or Ile
<220> FEATURE:
<221> NAME/KEY: MOD_RES
<222> LOCATION: (47)..(47)
<223> OTHER INFORMATION: Asn or Ser

<400> SEQUENCE: 250

His His Ser Asn Asp Gln Gly Ser Gly Tyr Ala Ala Asp Lys Glu Ser
1               5                   10                  15

Thr Gln Lys Ala Xaa Asp Gly Ile Thr Asn Lys Val Asn Ser Val Ile
            20                  25                  30

Glu Lys Met Asn Thr Gln Phe Glu Ala Val Gly Lys Leu Phe Xaa Asn
        35                  40                  45

Leu Glu Lys Leu Glu Asn Leu Asn Lys Lys
    50                  55

<210> SEQ ID NO 251
<211> LENGTH: 57
<212> TYPE: PRT
<213> ORGANISM: Influenza virus
<220> FEATURE:
<221> NAME/KEY: MOD_RES
<222> LOCATION: (20)..(20)
<223> OTHER INFORMATION: Phe or Ile
<220> FEATURE:
<221> NAME/KEY: MOD_RES
<222> LOCATION: (46)..(46)
<223> OTHER INFORMATION: Asn or Ser

<400> SEQUENCE: 251

His Ser Asn Asp Gln Gly Ser Gly Tyr Ala Ala Asp Lys Glu Ser Thr
1               5                   10                  15

Gln Lys Ala Xaa Asp Gly Ile Thr Asn Lys Val Asn Ser Val Ile Glu
            20                  25                  30

Lys Met Asn Thr Gln Phe Glu Ala Val Gly Lys Leu Phe Xaa Asn Leu
        35                  40                  45

Glu Lys Leu Glu Asn Leu Asn Lys Lys
    50                  55

<210> SEQ ID NO 252
<211> LENGTH: 26
<212> TYPE: PRT
<213> ORGANISM: Influenza virus
<220> FEATURE:
<221> NAME/KEY: MOD_RES
<222> LOCATION: (20)..(20)
<223> OTHER INFORMATION: Phe or Ile

<400> SEQUENCE: 252

His Ser Asn Asp Gln Gly Ser Gly Tyr Ala Ala Asp Lys Glu Ser Thr
1               5                   10                  15

Gln Lys Ala Xaa Asp Gly Ile Thr Asn Lys
            20                  25

<210> SEQ ID NO 253
<211> LENGTH: 21
<212> TYPE: PRT
<213> ORGANISM: Influenza virus

<400> SEQUENCE: 253

His Asp Ser Asn Val Arg Asn Leu Tyr Asp Lys Val Arg Met Gln Leu
1               5                   10                  15

Arg Asp Asn Ala Lys

20

<210> SEQ ID NO 254
<211> LENGTH: 30
<212> TYPE: PRT
<213> ORGANISM: Influenza virus

<400> SEQUENCE: 254

His Lys Cys Asp Asp Glu Cys Met Asn Ser Val Lys Asn Gly Thr Tyr
1 5 10 15

Asp Tyr Pro Lys Leu Asn Arg Asn Glu Ile Lys Gly Val Lys
20 25 30

<210> SEQ ID NO 255
<211> LENGTH: 27
<212> TYPE: PRT
<213> ORGANISM: Influenza virus

<400> SEQUENCE: 255

His Lys Cys Asp Asp Glu Cys Met Asn Ser Val Lys Asn Gly Thr Tyr
1 5 10 15

Asp Tyr Pro Lys Leu Asn Arg Asn Glu Ile Lys
20 25

<210> SEQ ID NO 256
<211> LENGTH: 20
<212> TYPE: PRT
<213> ORGANISM: Influenza virus

<400> SEQUENCE: 256

His Lys Cys Asp Asp Glu Cys Met Asn Ser Val Lys Asn Gly Thr Tyr
1 5 10 15

Asp Tyr Pro Lys
20

<210> SEQ ID NO 257
<211> LENGTH: 12
<212> TYPE: PRT
<213> ORGANISM: Influenza virus

<400> SEQUENCE: 257

His Lys Cys Asp Asp Glu Cys Met Asn Ser Val Lys
1 5 10

<210> SEQ ID NO 258
<211> LENGTH: 27
<212> TYPE: PRT
<213> ORGANISM: Influenza virus

<400> SEQUENCE: 258

Lys Gly Ser Asn Tyr Pro Val Ala Lys Gly Ser Tyr Asn Asn Thr Asn
1 5 10 15

Gly Glu Gln Ile Leu Ile Ile Trp Gly Val His
20 25

<210> SEQ ID NO 259
<211> LENGTH: 43
<212> TYPE: PRT
<213> ORGANISM: Influenza virus

<400> SEQUENCE: 259

His Ser Asn Asp Gln Gly Ser Gly Tyr Ala Ala Asp Lys Glu Ser Thr
1 5 10 15

Gln Lys Ala Val Asp Gly Ile Thr Asn Lys Val Asn Ser Val Ile Glu
20 25 30

Lys Met Asn Thr Gln Phe Glu Ala Val Gly Lys
35 40

<210> SEQ ID NO 260
<211> LENGTH: 35
<212> TYPE: PRT
<213> ORGANISM: Influenza virus

<400> SEQUENCE: 260

Lys Arg Gly Ser Ser Gly Ile Met Lys Thr Glu Gly Thr Leu Glu Asn
1 5 10 15

Cys Glu Thr Lys Cys Gln Thr Pro Leu Gly Ala Ile Asn Thr Thr Leu
20 25 30

Pro Phe His
35

<210> SEQ ID NO 261
<211> LENGTH: 16
<212> TYPE: PRT
<213> ORGANISM: Influenza virus

<400> SEQUENCE: 261

His Pro Leu Thr Ile Gly Glu Cys Pro Lys Tyr Val Lys Ser Glu Lys
1 5 10 15

<210> SEQ ID NO 262
<211> LENGTH: 16
<212> TYPE: PRT
<213> ORGANISM: Influenza virus

<400> SEQUENCE: 262

His Ala Lys Asp Ile Leu Glu Lys Thr His Asn Gly Lys Leu Cys Lys
1 5 10 15

<210> SEQ ID NO 263
<211> LENGTH: 25
<212> TYPE: PRT
<213> ORGANISM: Influenza virus

<400> SEQUENCE: 263

His Asp Val Tyr Arg Asp Glu Ala Leu Asn Asn Arg Phe Gln Ile Lys
1 5 10 15

Gly Val Glu Leu Lys Ser Gly Tyr Lys
20 25

<210> SEQ ID NO 264
<211> LENGTH: 19
<212> TYPE: PRT
<213> ORGANISM: Influenza virus

<400> SEQUENCE: 264

His Thr Ile Asp Leu Thr Asp Ser Glu Met Asn Lys Leu Phe Glu Arg
1 5 10 15

Thr Arg Lys

<210> SEQ ID NO 265
<211> LENGTH: 7
<212> TYPE: PRT
<213> ORGANISM: Influenza virus

<400> SEQUENCE: 265

Lys Phe His Gln Ile Glu Lys
1               5

<210> SEQ ID NO 266
<211> LENGTH: 11
<212> TYPE: PRT
<213> ORGANISM: Influenza virus
<220> FEATURE:
<221> NAME/KEY: MOD_RES
<222> LOCATION: (8)..(8)
<223> OTHER INFORMATION: Gly or Gln

<400> SEQUENCE: 266

Lys Thr Asn Glu Lys Phe His Xaa Ile Glu Lys
1               5                   10

<210> SEQ ID NO 267
<211> LENGTH: 14
<212> TYPE: PRT
<213> ORGANISM: Influenza virus
<220> FEATURE:
<221> NAME/KEY: MOD_RES
<222> LOCATION: (5)..(5)
<223> OTHER INFORMATION: Val or Leu

<400> SEQUENCE: 267

Lys Leu Asn Arg Xaa Ile Glu Lys Thr Asn Glu Lys Phe His
1               5                   10

<210> SEQ ID NO 268
<211> LENGTH: 25
<212> TYPE: PRT
<213> ORGANISM: Influenza virus

<400> SEQUENCE: 268

His Gln Ile Glu Lys Glu Phe Ser Glu Val Glu Gly Arg Ile Gln Asp
1               5                   10                  15

Leu Glu Lys Tyr Val Glu Asp Thr Lys
            20                  25

<210> SEQ ID NO 269
<211> LENGTH: 8
<212> TYPE: PRT
<213> ORGANISM: Influenza virus

<400> SEQUENCE: 269

Lys Ile Cys Asn Asn Pro His Lys
1               5

<210> SEQ ID NO 270
<211> LENGTH: 14
<212> TYPE: PRT
<213> ORGANISM: Influenza virus

<400> SEQUENCE: 270

Lys Leu Asn Arg Val Ile Lys Lys Thr Asn Glu Lys Phe His
1               5                   10

<210> SEQ ID NO 271
<211> LENGTH: 24
<212> TYPE: PRT
<213> ORGANISM: Influenza virus
<220> FEATURE:
<221> NAME/KEY: MOD_RES
<222> LOCATION: (3)..(3)

<223> OTHER INFORMATION: Ile or Val
<220> FEATURE:
<221> NAME/KEY: MOD_RES
<222> LOCATION: (17)..(17)
<223> OTHER INFORMATION: Gly or Gln
<220> FEATURE:
<221> NAME/KEY: MOD_RES
<222> LOCATION: (20)..(20)
<223> OTHER INFORMATION: Arg or Lys
<220> FEATURE:
<221> NAME/KEY: MOD_RES
<222> LOCATION: (22)..(22)
<223> OTHER INFORMATION: Gln or Gly

<400> SEQUENCE: 271

His Asp Xaa Tyr Arg Asp Glu Ala Leu Asn Asn Arg Phe Gln Ile Lys
1 5 10 15

Xaa Val Glu Xaa Ser Xaa Tyr Lys
20

<210> SEQ ID NO 272
<211> LENGTH: 25
<212> TYPE: PRT
<213> ORGANISM: Influenza virus

<400> SEQUENCE: 272

His Gln Ile Glu Lys Glu Phe Ser Glu Val Glu Gly Arg Ile Gln Asp
1 5 10 15

Leu Glu Lys Tyr Val Glu Asp Thr Lys
20 25

<210> SEQ ID NO 273
<211> LENGTH: 25
<212> TYPE: PRT
<213> ORGANISM: Influenza virus

<400> SEQUENCE: 273

Lys Tyr Val Glu Asp Thr Lys Ile Asp Leu Trp Ser Tyr Asn Ala Glu
1 5 10 15

Leu Leu Val Ala Leu Glu Asn Gln His
20 25

<210> SEQ ID NO 274
<211> LENGTH: 49
<212> TYPE: PRT
<213> ORGANISM: Influenza virus

<400> SEQUENCE: 274

Lys Tyr Val Lys Gln Asn Ser Leu Lys Leu Ala Thr Gly Met Arg Asn
1 5 10 15

Val Pro Glu Lys Gln Thr Arg Gly Leu Phe Gly Ala Ile Ala Gly Phe
20 25 30

Ile Glu Asn Gly Trp Glu Gly Met Ile Asp Gly Trp Tyr Gly Phe Arg
35 40 45

His

<210> SEQ ID NO 275
<211> LENGTH: 39
<212> TYPE: PRT
<213> ORGANISM: Influenza virus

<400> SEQUENCE: 275

Lys Glu Phe Ser Glu Val Glu Gly Arg Ile Gln Asp Leu Glu Lys Tyr
1 5 10 15

```
Val Glu Asp Thr Lys Ile Asp Leu Trp Ser Tyr Asn Ala Glu Leu Leu
            20                  25                  30

Val Ala Leu Glu Asn Gln His
        35


<210> SEQ ID NO 276
<211> LENGTH: 33
<212> TYPE: PRT
<213> ORGANISM: Influenza virus
<220> FEATURE:
<221> NAME/KEY: MOD_RES
<222> LOCATION: (4)..(4)
<223> OTHER INFORMATION: Ser or Glu
<220> FEATURE:
<221> NAME/KEY: MOD_RES
<222> LOCATION: (5)..(5)
<223> OTHER INFORMATION: Glu or Gln
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (9)..(9)
<223> OTHER INFORMATION: Gln or Tyr
<220> FEATURE:
<221> NAME/KEY: MOD_RES
<222> LOCATION: (13)..(13)
<223> OTHER INFORMATION: Leu or Gln
<220> FEATURE:
<221> NAME/KEY: MOD_RES
<222> LOCATION: (18)..(18)
<223> OTHER INFORMATION: Ala or Asn
<220> FEATURE:
<221> NAME/KEY: MOD_RES
<222> LOCATION: (20)..(20)
<223> OTHER INFORMATION: Ile or Leu
<220> FEATURE:
<221> NAME/KEY: MOD_RES
<222> LOCATION: (22)..(22)
<223> OTHER INFORMATION: Gln or Gly
<220> FEATURE:
<221> NAME/KEY: MOD_RES
<222> LOCATION: (24)..(24)
<223> OTHER INFORMATION: Asn or Thr
<220> FEATURE:
<221> NAME/KEY: MOD_RES
<222> LOCATION: (25)..(25)
<223> OTHER INFORMATION: Gly or Asn
<220> FEATURE:
<221> NAME/KEY: MOD_RES
<222> LOCATION: (27)..(27)
<223> OTHER INFORMATION: Leu or Val
<220> FEATURE:
<221> NAME/KEY: MOD_RES
<222> LOCATION: (29)..(29)
<223> OTHER INFORMATION: Arg or Ser
<220> FEATURE:
<221> NAME/KEY: MOD_RES
<222> LOCATION: (32)..(32)
<223> OTHER INFORMATION: Glu or Cys

<400> SEQUENCE: 276

His Gln Asn Xaa Xaa Gly Xaa Gly Xaa Ala Ala Asp Xaa Lys Ser Thr
1               5                   10                  15

Gln Xaa Ala Xaa Asp Xaa Ile Xaa Xaa Lys Xaa Asn Xaa Val Ile Xaa
            20                  25                  30

Lys


<210> SEQ ID NO 277
<211> LENGTH: 18
<212> TYPE: PRT
```

<213> ORGANISM: Influenza virus
<220> FEATURE:
<221> NAME/KEY: MOD_RES
<222> LOCATION: (4)..(4)
<223> OTHER INFORMATION: Gly or Gln
<220> FEATURE:
<221> NAME/KEY: MOD_RES
<222> LOCATION: (6)..(6)
<223> OTHER INFORMATION: Gln or Arg
<220> FEATURE:
<221> NAME/KEY: MOD_RES
<222> LOCATION: (14)..(14)
<223> OTHER INFORMATION: Val or Ile
<220> FEATURE:
<221> NAME/KEY: MOD_RES
<222> LOCATION: (17)..(17)
<223> OTHER INFORMATION: Ser or Thr

<400> SEQUENCE: 277

His Cys Asp Xaa Phe Xaa Asn Glu Lys Trp Asp Leu Phe Xaa Glu Arg
1               5                   10                  15

Xaa Lys

<210> SEQ ID NO 278
<211> LENGTH: 20
<212> TYPE: PRT
<213> ORGANISM: Influenza virus

<400> SEQUENCE: 278

His Thr Ile Asp Leu Thr Asp Ser Glu Met Asn Lys Lys Leu Phe Glu
1               5                   10                  15

Arg Thr Arg Lys
            20

<210> SEQ ID NO 279
<211> LENGTH: 28
<212> TYPE: PRT
<213> ORGANISM: Influenza virus

<400> SEQUENCE: 279

Lys Ser Gly Ser Thr Tyr Pro Val Leu Lys Val Thr Met Pro Asn Asn
1               5                   10                  15

Asp Asn Phe Asp Lys Leu Tyr Ile Trp Gly Val His
            20                  25

<210> SEQ ID NO 280
<211> LENGTH: 34
<212> TYPE: PRT
<213> ORGANISM: Influenza virus

<400> SEQUENCE: 280

Lys Leu Asn Trp Leu Thr Lys Ser Gly Asn Thr Tyr Pro Val Leu Asn
1               5                   10                  15

Val Thr Met Pro Asn Asn Asp Asn Phe Asp Lys Leu Val Ile Trp Gly
            20                  25                  30

Val His

<210> SEQ ID NO 281
<211> LENGTH: 19
<212> TYPE: PRT
<213> ORGANISM: Influenza virus

<400> SEQUENCE: 281

His Thr Ile Asp Leu Thr Asp Ser Glu Met Asn Lys Leu Phe Glu Lys
1               5                   10                  15

Thr Arg Lys

<210> SEQ ID NO 282
<211> LENGTH: 18
<212> TYPE: PRT
<213> ORGANISM: Influenza virus

<400> SEQUENCE: 282

Lys Leu Asn Arg Leu Ile Glu Lys Thr Asn Glu Lys Phe His Gln Thr
1 5 10 15

Glu Lys

<210> SEQ ID NO 283
<211> LENGTH: 47
<212> TYPE: PRT
<213> ORGANISM: Influenza virus

<400> SEQUENCE: 283

His Thr Gly Lys Ser Ser Val Met Arg Ser Asp Ala Pro Ile Asp Phe
1 5 10 15

Cys Asn Ser Glu Cys Ile Thr Pro Asn Gln Ser Ile Pro Asn Asp Lys
20 25 30

Pro Phe Gln Asn Val Asn Lys Ile Thr Tyr Gly Ala Cys Pro Lys
35 40 45

<210> SEQ ID NO 284
<211> LENGTH: 39
<212> TYPE: PRT
<213> ORGANISM: Influenza virus

<400> SEQUENCE: 284

His Thr Gly Lys Ser Ser Val Met Arg Ser Asp Ala Pro Ile Asp Phe
1 5 10 15

Cys Asn Ser Glu Cys Ile Thr Pro Asn Gln Ser Ile Pro Asn Asp Lys
20 25 30

Pro Phe Gln Asn Val Asn Lys
35

<210> SEQ ID NO 285
<211> LENGTH: 33
<212> TYPE: PRT
<213> ORGANISM: Influenza virus

<400> SEQUENCE: 285

His Pro Ser Thr Asp Ser Asp Gln Thr Ser Leu Tyr Val Arg Ala Ser
1 5 10 15

Gly Arg Val Thr Val Ser Thr Lys Arg Ser Gln Gln Thr Val Ile Pro
20 25 30

Lys

<210> SEQ ID NO 286
<211> LENGTH: 25
<212> TYPE: PRT
<213> ORGANISM: Influenza virus

<400> SEQUENCE: 286

Lys Tyr Val Glu Asp Thr Lys Ile Asp Leu Trp Ser Tyr Asn Ala Glu
1 5 10 15

Leu Leu Val Ala Leu Glu Asn Gln His
20 25

<210> SEQ ID NO 287
<211> LENGTH: 26
<212> TYPE: PRT
<213> ORGANISM: Influenza virus

<400> SEQUENCE: 287

Lys Leu Phe Glu Arg Thr Arg Lys Gln Leu Arg Glu Asn Ala Glu Asp
1 5 10 15

Met Gly Asn Gly Cys Phe Lys Ile Tyr His
20 25

<210> SEQ ID NO 288
<211> LENGTH: 16
<212> TYPE: PRT
<213> ORGANISM: Influenza virus

<400> SEQUENCE: 288

Lys Arg Arg Ser Ile Lys Ser Phe Phe Ser Arg Leu Asn Trp Leu His
1 5 10 15

<210> SEQ ID NO 289
<211> LENGTH: 16
<212> TYPE: PRT
<213> ORGANISM: Influenza virus
<220> FEATURE:
<221> NAME/KEY: MOD_RES
<222> LOCATION: (12)..(12)
<223> OTHER INFORMATION: Val or Arg

<400> SEQUENCE: 289

His Pro Val Thr Ile Gly Glu Cys Pro Lys Tyr Xaa Lys Ser Thr Lys
1 5 10 15

<210> SEQ ID NO 290
<211> LENGTH: 30
<212> TYPE: PRT
<213> ORGANISM: Influenza virus

<400> SEQUENCE: 290

Lys Gly Asn Ser Tyr Pro Lys Leu Ser Lys Leu Ser Lys Ser Tyr Ile
1 5 10 15

Ile Asn Lys Lys Lys Glu Val Leu Val Ile Trp Gly Ile His
20 25 30

<210> SEQ ID NO 291
<211> LENGTH: 24
<212> TYPE: PRT
<213> ORGANISM: Influenza virus
<220> FEATURE:
<221> NAME/KEY: MOD_RES
<222> LOCATION: (9)..(9)
<223> OTHER INFORMATION: Val or Tyr

<400> SEQUENCE: 291

Lys Leu Ser Lys Leu Ser Lys Ser Xaa Ile Ile Asn Lys Lys Lys Glu
1 5 10 15

Val Leu Val Ile Trp Gly Ile His
20

<210> SEQ ID NO 292
<211> LENGTH: 21
<212> TYPE: PRT
<213> ORGANISM: Influenza virus
<220> FEATURE:

<221> NAME/KEY: MOD_RES
<222> LOCATION: (6)..(6)
<223> OTHER INFORMATION: Val or Tyr

<400> SEQUENCE: 292

Lys Leu Ser Lys Ser Xaa Ile Ile Asn Lys Lys Lys Glu Val Leu Val
1 5 10 15

Ile Trp Gly Ile His
20

<210> SEQ ID NO 293
<211> LENGTH: 29
<212> TYPE: PRT
<213> ORGANISM: Influenza virus

<400> SEQUENCE: 293

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 294
<211> LENGTH: 29
<212> TYPE: PRT
<213> ORGANISM: Influenza virus

<400> SEQUENCE: 294

Leu Lys Glu Asp Leu Tyr Pro Lys Leu Arg Lys Ser Val Val His Asn
1 5 10 15

Lys Lys Lys Glu Val Leu Val Ile Trp Gly Ile His His
20 25

<210> SEQ ID NO 295
<211> LENGTH: 29
<212> TYPE: PRT
<213> ORGANISM: Influenza virus

<400> SEQUENCE: 295

Leu Lys Glu Asn Ser Tyr Pro Lys Leu Arg Lys Ser Ile Ile Ile Asn
1 5 10 15

Lys Lys Lys Glu Val Leu Val Ile Trp Gly Ile His His
20 25

<210> SEQ ID NO 296
<211> LENGTH: 29
<212> TYPE: PRT
<213> ORGANISM: Influenza virus

<400> SEQUENCE: 296

Lys Lys Gly Thr Ser Tyr Pro Lys Leu Ser Lys Ser Tyr Thr Asn Asn
1 5 10 15

Lys Lys Lys Glu Val Leu Val Leu Trp Gly Val His His
20 25

<210> SEQ ID NO 297
<211> LENGTH: 29
<212> TYPE: PRT
<213> ORGANISM: Influenza virus

<400> SEQUENCE: 297

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 298
<211> LENGTH: 29
<212> TYPE: PRT
<213> ORGANISM: Human coronavirus

<400> SEQUENCE: 298

Lys Lys Ser Ala Lys Thr Gly Thr Pro Lys Pro Ser Arg Asn Gln Ser
1 5 10 15

Pro Ala Ser Ser Gln Thr Ser Ala Lys Ser Leu Ala His
20 25

<210> SEQ ID NO 299
<211> LENGTH: 29
<212> TYPE: PRT
<213> ORGANISM: Canine coronavirus

<400> SEQUENCE: 299

Lys Lys Leu Gly Val Asp Thr Glu Lys Gln Gln Gln Arg Ser Lys Ser
1 5 10 15

Lys Glu Arg Ser Asn Ser Lys Thr Arg Asp Thr Thr Pro
20 25

<210> SEQ ID NO 300
<211> LENGTH: 28
<212> TYPE: PRT
<213> ORGANISM: Influenza virus

<400> SEQUENCE: 300

Lys Asn Gly Leu Tyr Pro Asn Leu Ser Lys Ser Tyr Ala Asn Asn Lys
1 5 10 15

Glu Lys Glu Val Leu Ile Leu Trp Gly Val His His
20 25

<210> SEQ ID NO 301
<211> LENGTH: 27
<212> TYPE: PRT
<213> ORGANISM: Avian bronchitis coronavirus

<400> SEQUENCE: 301

Lys Lys Ile Asn Ser Pro Gln Pro Lys Phe Glu Gly Ser Gly Val Pro
1 5 10 15

Asp Asn Glu Asn Leu Lys Thr Ser Gln Gln His
20 25

<210> SEQ ID NO 302
<211> LENGTH: 24
<212> TYPE: PRT
<213> ORGANISM: Porcine epidemic diarrhea virus

<400> SEQUENCE: 302

Lys Thr Gly Asn Ala Lys Leu Gln Arg Lys Lys Glu Lys Lys Asn Lys
1 5 10 15

Arg Glu Thr Thr Leu Gln Gln His
20

<210> SEQ ID NO 303
<211> LENGTH: 21
<212> TYPE: PRT
<213> ORGANISM: SARS coronavirus

<400> SEQUENCE: 303

Lys His Leu Asp Ala Tyr Lys Thr Phe Pro Pro Thr Glu Pro Lys Lys
1 5 10 15

Asp Lys Lys Lys Lys
20

<210> SEQ ID NO 304
<211> LENGTH: 18
<212> TYPE: PRT
<213> ORGANISM: SARS coronavirus

<400> SEQUENCE: 304

Lys His Arg Glu Phe Val Phe Lys Asn Lys Asp Gly Phe Leu Tyr Val
1 5 10 15

Tyr Lys

<210> SEQ ID NO 305
<211> LENGTH: 11
<212> TYPE: PRT
<213> ORGANISM: SARS coronavirus

<400> SEQUENCE: 305

Lys Glu Glu Leu Asp Lys Tyr Phe Lys Asn His
1 5 10

<210> SEQ ID NO 306
<211> LENGTH: 9
<212> TYPE: PRT
<213> ORGANISM: SARS coronavirus

<400> SEQUENCE: 306

Lys Tyr Arg Tyr Leu Arg His Gly Lys
1 5

<210> SEQ ID NO 307
<211> LENGTH: 9
<212> TYPE: PRT
<213> ORGANISM: SARS coronavirus

<400> SEQUENCE: 307

Lys Lys Gly Ala Lys Leu Leu His Lys
1 5

<210> SEQ ID NO 308
<211> LENGTH: 7
<212> TYPE: PRT
<213> ORGANISM: SARS coronavirus

<400> SEQUENCE: 308

Lys His Leu Asp Ala Tyr Lys
1 5

<210> SEQ ID NO 309
<211> LENGTH: 16
<212> TYPE: PRT
<213> ORGANISM: Human immunodeficiency virus

<400> SEQUENCE: 309

His Leu Val Cys Gly Lys Lys Gly Leu Gly Leu Ser Gly Arg Lys Lys
1 5 10 15

<210> SEQ ID NO 310
<211> LENGTH: 19

<212> TYPE: PRT
<213> ORGANISM: Monkeypox virus

<400> SEQUENCE: 310

Lys Lys Ile Thr Asn Ile Thr Thr Lys Phe Glu Gln Leu Glu Lys Cys
1 5 10 15

Cys Lys His

<210> SEQ ID NO 311
<211> LENGTH: 17
<212> TYPE: PRT
<213> ORGANISM: African swine fever virus

<400> SEQUENCE: 311

Lys Lys Leu Lys Lys Ser Leu Lys Leu Leu Ser Phe Tyr His Pro Lys
1 5 10 15

Lys

<210> SEQ ID NO 312
<211> LENGTH: 16
<212> TYPE: PRT
<213> ORGANISM: West Nile Virus

<400> SEQUENCE: 312

Lys Asn Arg Ile Glu Arg Leu Lys Lys Glu Tyr Ser Ser Thr Trp His
1 5 10 15

<210> SEQ ID NO 313
<211> LENGTH: 11
<212> TYPE: PRT
<213> ORGANISM: Nipah virus

<400> SEQUENCE: 313

Lys Ser Arg Gly Ile Pro Ile Lys Lys Gly His
1 5 10

<210> SEQ ID NO 314
<211> LENGTH: 11
<212> TYPE: PRT
<213> ORGANISM: Hendra virus

<400> SEQUENCE: 314

Lys Ser Arg Ile Met Pro Ile Lys Lys Gly His
1 5 10

<210> SEQ ID NO 315
<211> LENGTH: 10
<212> TYPE: PRT
<213> ORGANISM: Sindbis virus

<400> SEQUENCE: 315

Lys Lys Phe Leu Asn Gln Phe Lys His His
1 5 10

<210> SEQ ID NO 316
<211> LENGTH: 9
<212> TYPE: PRT
<213> ORGANISM: Smallpox virus

<400> SEQUENCE: 316

Lys Ile His Leu Ile Ser Val Lys Lys
1 5

<210> SEQ ID NO 317
<211> LENGTH: 8
<212> TYPE: PRT
<213> ORGANISM: Smallpox virus

<400> SEQUENCE: 317

Lys Leu Ile Ser Ile His Glu Lys
1               5

<210> SEQ ID NO 318
<211> LENGTH: 8
<212> TYPE: PRT
<213> ORGANISM: Bacillus anthracis

<400> SEQUENCE: 318

Lys Leu Arg Glu Glu His Glu Lys
1               5

<210> SEQ ID NO 319
<211> LENGTH: 8
<212> TYPE: PRT
<213> ORGANISM: Plasmodium falciparum

<400> SEQUENCE: 319

Lys His Lys Lys Gln Ile Val Lys
1               5

<210> SEQ ID NO 320
<211> LENGTH: 8
<212> TYPE: PRT
<213> ORGANISM: Ebola virus

<400> SEQUENCE: 320

Lys Lys His Ala Thr Val Leu Lys
1               5

<210> SEQ ID NO 321
<211> LENGTH: 8
<212> TYPE: PRT
<213> ORGANISM: Plasmodium falciparum

<400> SEQUENCE: 321

Lys Lys Glu Asp Asp Glu Lys His
1               5

<210> SEQ ID NO 322
<211> LENGTH: 8
<212> TYPE: PRT
<213> ORGANISM: Homo sapiens

<400> SEQUENCE: 322

Lys His Lys Glu Lys Met Ser Lys
1               5

<210> SEQ ID NO 323
<211> LENGTH: 29
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (14)..(14)
<223> OTHER INFORMATION: Thr or Val

<400> SEQUENCE: 323

Lys Lys Gly Xaa Ser Tyr Pro Lys Leu Ser Lys Ser Tyr Xaa Asn Asn
1               5                   10                  15

Lys Gly Lys Glu Val Leu Val Leu Trp Gly Val His His
            20                  25

<210> SEQ ID NO 324
<211> LENGTH: 29
<212> TYPE: PRT
<213> ORGANISM: Influenza virus

<400> SEQUENCE: 324

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
            20                  25

<210> SEQ ID NO 325
<211> LENGTH: 5
<212> TYPE: PRT
<213> ORGANISM: Porcine epidemic diarrhea coronavirus

<400> SEQUENCE: 325

Lys Lys Lys Lys Lys
1               5

<210> SEQ ID NO 326
<211> LENGTH: 29
<212> TYPE: PRT
<213> ORGANISM: Influenza virus

<400> SEQUENCE: 326

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25

<210> SEQ ID NO 327
<211> LENGTH: 29
<212> TYPE: PRT
<213> ORGANISM: Influenza virus

<400> SEQUENCE: 327

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
            20                  25

<210> SEQ ID NO 328
<211> LENGTH: 29
<212> TYPE: PRT
<213> ORGANISM: Influenza virus

<400> SEQUENCE: 328

Lys Lys Gly Ser Asn Tyr Pro Val Ala Lys Gly Ser Tyr Asn Asn Thr
1               5                   10                  15

Ser Gly Glu Gln Met Leu Ile Ile Trp Gly Val His His
            20                  25

<210> SEQ ID NO 329
<211> LENGTH: 29
<212> TYPE: PRT
<213> ORGANISM: Influenza virus

<400> SEQUENCE: 329

Lys Lys Gly Pro Asn Tyr Pro Val Ala Lys Gly Ser Tyr Asn Asn Thr
1 5 10 15

Ser Gly Glu Gln Met Leu Ile Ile Trp Gly Val His His
20 25

<210> SEQ ID NO 330
<211> LENGTH: 29
<212> TYPE: PRT
<213> ORGANISM: Influenza virus

<400> SEQUENCE: 330

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 331
<211> LENGTH: 29
<212> TYPE: PRT
<213> ORGANISM: Influenza virus

<400> SEQUENCE: 331

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 332
<211> LENGTH: 29
<212> TYPE: PRT
<213> ORGANISM: Influenza virus

<400> SEQUENCE: 332

Lys Lys Gly Asp Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 333
<211> LENGTH: 29
<212> TYPE: PRT
<213> ORGANISM: Influenza virus

<400> SEQUENCE: 333

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 334
<211> LENGTH: 29
<212> TYPE: PRT
<213> ORGANISM: Influenza virus

<400> SEQUENCE: 334

Lys Lys Gly Asn Ser Tyr Pro Lys Ile Ser Lys Ser Tyr Ile Asn Asn
1 5 10 15

Lys Glu Lys Glu Val Leu Val Leu Trp Gly Ile His His
20 25

<210> SEQ ID NO 335
<211> LENGTH: 29
<212> TYPE: PRT
<213> ORGANISM: Influenza virus

<400> SEQUENCE: 335

Lys Lys Gly Asn Ser Tyr Pro Lys Leu Ser Lys Ser Tyr Ile Asn Asn
1 5 10 15

Lys Lys Lys Glu Val Leu Val Ile Trp Gly Ile His His
20 25

<210> SEQ ID NO 336
<211> LENGTH: 29
<212> TYPE: PRT
<213> ORGANISM: Influenza virus

<400> SEQUENCE: 336

Lys Lys Gly Asn Ser Tyr Pro Lys Leu Ser Lys Ser Tyr Ile Asn Asn
1 5 10 15

Lys Gly Lys Lys Val Leu Val Leu Trp Gly Ile His His
20 25

<210> SEQ ID NO 337
<211> LENGTH: 29
<212> TYPE: PRT
<213> ORGANISM: Influenza virus

<400> SEQUENCE: 337

Lys Lys Gly Thr Ser Tyr Pro Lys Leu Ser Lys Ser Tyr Thr Asn Asn
1 5 10 15

Lys Lys Lys Glu Val Leu Val Leu Trp Gly Val His His
20 25

<210> SEQ ID NO 338
<211> LENGTH: 28
<212> TYPE: PRT
<213> ORGANISM: Influenza virus

<400> SEQUENCE: 338

Lys Asn Gly Leu Tyr Pro Asn Leu Ser Lys Ser Tyr Ala Asn Asn Lys
1 5 10 15

Glu Lys Glu Val Leu Ile Leu Trp Gly Val His His
20 25

<210> SEQ ID NO 339
<211> LENGTH: 21
<212> TYPE: PRT
<213> ORGANISM: SARS coronavirus

<400> SEQUENCE: 339

Lys His Leu Asp Ala Tyr Lys Thr Phe Pro Pro Thr Glu Pro Lys Lys
1 5 10 15

Asp Lys Lys Lys Lys
20

<210> SEQ ID NO 340
<211> LENGTH: 29
<212> TYPE: PRT
<213> ORGANISM: Influenza virus

<400> SEQUENCE: 340

Lys Lys Glu Asn Ser Tyr Pro Lys Leu Arg Lys Ser Ile Ile Ile Asn
1               5                   10                  15

Lys Lys Lys Glu Val Leu Val Ile Trp Gly Ile His His
            20                  25

<210> SEQ ID NO 341
<211> LENGTH: 29
<212> TYPE: PRT
<213> ORGANISM: Influenza virus

<400> SEQUENCE: 341

Lys Leu Glu Tyr Lys Tyr Pro Ala Leu Asn Val Thr Met Pro Asn Asn
1               5                   10                  15

Asp Lys Phe Asp Lys Leu Tyr Ile Trp Gly Val His His
            20                  25

<210> SEQ ID NO 342
<211> LENGTH: 27
<212> TYPE: PRT
<213> ORGANISM: Influenza virus

<400> SEQUENCE: 342

Lys Tyr Lys Tyr Pro Ala Leu Asn Val Thr Met Pro Asn Asn Glu Lys
1               5                   10                  15

Phe Asp Lys Leu Tyr Ile Trp Gly Val His His
            20                  25

<210> SEQ ID NO 343
<211> LENGTH: 24
<212> TYPE: PRT
<213> ORGANISM: Porcine epidemic diarrhea coronavius

<400> SEQUENCE: 343

Lys Thr Gly Asn Ala Lys Leu Gln Arg Lys Lys Glu Lys Lys Asn Lys
1               5                   10                  15

Arg Glu Thr Thr Leu Gln Gln His
            20

<210> SEQ ID NO 344
<211> LENGTH: 27
<212> TYPE: PRT
<213> ORGANISM: Avian bronchitis coronavirus

<400> SEQUENCE: 344

Lys Lys Ile Asn Ser Pro Gly Pro Lys Phe Glu Gly Ser Gly Val Pro
1               5                   10                  15

Asp Asn Glu Asn Leu Lys Thr Ser Gln Gln His
            20                  25

<210> SEQ ID NO 345
<211> LENGTH: 27
<212> TYPE: PRT
<213> ORGANISM: Shrimp white spot syndrome virus

<400> SEQUENCE: 345

Lys Lys Asn Val Lys Ser Ala Lys Gln Leu Pro His Leu Lys Val Leu
1               5                   10                  15

Leu Asp Val Arg Gly Ala Lys Gln Leu Pro His
            20                  25

-continued

<210> SEQ ID NO 346
<211> LENGTH: 27
<212> TYPE: PRT
<213> ORGANISM: Avian bronchitis coronavirus

<400> SEQUENCE: 346

```
Lys Lys Ile Asn Ser Pro Gly Pro Lys Phe Glu Gly Ser Gly Val Pro
1               5                   10                  15

Asp Asn Glu Asn Leu Lys Thr Ser Gln Gln His
            20                  25
```

<210> SEQ ID NO 347
<211> LENGTH: 20
<212> TYPE: PRT
<213> ORGANISM: SARS coronavirus

<400> SEQUENCE: 347

```
Lys His Leu Arg Glu Phe Val Phe Lys Asn Lys Asp Gly Phe Leu Tyr
1               5                   10                  15

Val Tyr Lys Lys
            20
```

<210> SEQ ID NO 348
<211> LENGTH: 14
<212> TYPE: PRT
<213> ORGANISM: SARS coronavirus

<400> SEQUENCE: 348

```
Lys Lys Gly Ala Lys Leu Leu His Lys Pro Ile Val Trp His
1               5                   10
```

<210> SEQ ID NO 349
<211> LENGTH: 20
<212> TYPE: PRT
<213> ORGANISM: SARS coronavirus

<400> SEQUENCE: 349

```
Lys His Leu Arg Glu Phe Val Phe Lys Asn Lys Asp Gly Phe Leu Tyr
1               5                   10                  15

Val Tyr Lys Lys
            20
```

<210> SEQ ID NO 350
<211> LENGTH: 14
<212> TYPE: PRT
<213> ORGANISM: SARS coronavirus

<400> SEQUENCE: 350

```
Lys Lys Gly Ala Lys Leu Leu His Lys Pro Ile Val Trp His
1               5                   10
```

<210> SEQ ID NO 351
<211> LENGTH: 11
<212> TYPE: PRT
<213> ORGANISM: SARS coronavirus

<400> SEQUENCE: 351

```
Lys Glu Glu Leu Asp Lys Tyr Phe Lys Asn His
1               5                   10
```

<210> SEQ ID NO 352
<211> LENGTH: 9
<212> TYPE: PRT

<213> ORGANISM: SARS coronavirus

<400> SEQUENCE: 352

Lys Lys Gly Ala Lys Leu Leu His Lys
1 5

<210> SEQ ID NO 353
<211> LENGTH: 9
<212> TYPE: PRT
<213> ORGANISM: SARS coronavirus

<400> SEQUENCE: 353

Lys Tyr Arg Tyr Leu Arg His Gly Lys
1 5

<210> SEQ ID NO 354
<211> LENGTH: 7
<212> TYPE: PRT
<213> ORGANISM: SARS coronavirus

<400> SEQUENCE: 354

Lys His Leu Asp Ala Tyr Lys
1 5

<210> SEQ ID NO 355
<211> LENGTH: 11
<212> TYPE: PRT
<213> ORGANISM: Nipah virus

<400> SEQUENCE: 355

Lys Ser Arg Gly Ile Pro Ile Lys Lys Gly His
1 5 10

<210> SEQ ID NO 356
<211> LENGTH: 11
<212> TYPE: PRT
<213> ORGANISM: Hendra virus

<400> SEQUENCE: 356

Lys Ser Arg Ile Met Pro Ile Lys Lys Gly His
1 5 10

<210> SEQ ID NO 357
<211> LENGTH: 10
<212> TYPE: PRT
<213> ORGANISM: Sindbis virus

<400> SEQUENCE: 357

Lys Lys Phe Leu Asn Gln Phe Lys His His
1 5 10

<210> SEQ ID NO 358
<211> LENGTH: 10
<212> TYPE: PRT
<213> ORGANISM: Homo sapiens

<400> SEQUENCE: 358

Lys Lys Lys Ser Lys Lys His Lys Asp Lys
1 5 10

<210> SEQ ID NO 359
<211> LENGTH: 10
<212> TYPE: PRT
<213> ORGANISM: Homo sapiens

<400> SEQUENCE: 359

Lys His His Pro Lys Asp Asn Leu Ile Lys
1 5 10

<210> SEQ ID NO 360
<211> LENGTH: 10
<212> TYPE: PRT
<213> ORGANISM: Homo sapiens

<400> SEQUENCE: 360

Lys His Lys Arg Lys Lys Phe Arg Gln Lys
1 5 10

<210> SEQ ID NO 361
<211> LENGTH: 10
<212> TYPE: PRT
<213> ORGANISM: Homo sapiens

<400> SEQUENCE: 361

Lys Ala Gly Val Ala Phe Leu His Lys Lys
1 5 10

<210> SEQ ID NO 362
<211> LENGTH: 9
<212> TYPE: PRT
<213> ORGANISM: Smallpox virus

<400> SEQUENCE: 362

Lys Ile His Leu Ile Ser Val Lys Lys
1 5

<210> SEQ ID NO 363
<211> LENGTH: 9
<212> TYPE: PRT
<213> ORGANISM: Human immunodeficiency virus

<400> SEQUENCE: 363

Lys Arg Phe Ile Leu His Ala Lys Lys
1 5

<210> SEQ ID NO 364
<211> LENGTH: 8
<212> TYPE: PRT
<213> ORGANISM: Smallpox virus

<400> SEQUENCE: 364

Lys Leu Ile Ser Ile His Glu Lys
1 5

<210> SEQ ID NO 365
<211> LENGTH: 8
<212> TYPE: PRT
<213> ORGANISM: Bacillus anthracis

<400> SEQUENCE: 365

Lys Leu Arg Glu Glu His Cys Lys
1 5

<210> SEQ ID NO 366
<211> LENGTH: 8
<212> TYPE: PRT
<213> ORGANISM: Ebola virus

<400> SEQUENCE: 366

Lys Lys His Ala Thr Val Leu Lys
1 5

<210> SEQ ID NO 367
<211> LENGTH: 10
<212> TYPE: PRT
<213> ORGANISM: Influenza virus
<220> FEATURE:
<221> NAME/KEY: MOD_RES
<222> LOCATION: (5)..(5)
<223> OTHER INFORMATION: Ile or Val
<220> FEATURE:
<221> NAME/KEY: MOD_RES
<222> LOCATION: (8)..(8)
<223> OTHER INFORMATION: Val or Ile

<400> SEQUENCE: 367

Lys Glu Val Leu Xaa Trp Gly Xaa His His
1 5 10

<210> SEQ ID NO 368
<211> LENGTH: 29
<212> TYPE: PRT
<213> ORGANISM: Influenza virus

<400> SEQUENCE: 368

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 369
<211> LENGTH: 29
<212> TYPE: PRT
<213> ORGANISM: Influenza virus

<400> SEQUENCE: 369

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 370
<211> LENGTH: 29
<212> TYPE: PRT
<213> ORGANISM: Influenza virus

<400> SEQUENCE: 370

Lys Lys Glu Asn Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 371
<211> LENGTH: 29
<212> TYPE: PRT
<213> ORGANISM: Influenza virus

<400> SEQUENCE: 371

Lys Lys Gly Asp Ser Tyr Pro Lys Leu Thr Asn Ser Tyr Val Asn Asn
1 5 10 15

Lys Gly Lys Glu Val Leu Val Leu Trp Gly Val His His
20 25

<210> SEQ ID NO 372
<211> LENGTH: 29
<212> TYPE: PRT
<213> ORGANISM: Influenza virus

<400> SEQUENCE: 372

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 373
<211> LENGTH: 29
<212> TYPE: PRT
<213> ORGANISM: Influenza virus

<400> SEQUENCE: 373

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 374
<211> LENGTH: 29
<212> TYPE: PRT
<213> ORGANISM: Influenza virus

<400> SEQUENCE: 374

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 375
<211> LENGTH: 29
<212> TYPE: PRT
<213> ORGANISM: Influenza virus

<400> SEQUENCE: 375

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 376
<211> LENGTH: 29
<212> TYPE: PRT
<213> ORGANISM: Influenza virus

<400> SEQUENCE: 376

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 377
<211> LENGTH: 29
<212> TYPE: PRT
<213> ORGANISM: Influenza virus

<400> SEQUENCE: 377

```
Lys Lys Gly Asn Ser Tyr Pro Lys Leu Ser Lys Ser Tyr Thr Asn Asn
1               5                   10                  15
```

Lys Gly Lys Glu Val Leu Val Ile Trp Gly Val His His
20 25

<210> SEQ ID NO 378
<211> LENGTH: 29
<212> TYPE: PRT
<213> ORGANISM: Influenza virus

<400> SEQUENCE: 378

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 379
<211> LENGTH: 29
<212> TYPE: PRT
<213> ORGANISM: Influenza virus

<400> SEQUENCE: 379

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 380
<211> LENGTH: 29
<212> TYPE: PRT
<213> ORGANISM: Influenza virus

<400> SEQUENCE: 380

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 381
<211> LENGTH: 29
<212> TYPE: PRT
<213> ORGANISM: Influenza virus

<400> SEQUENCE: 381

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 382
<211> LENGTH: 29
<212> TYPE: PRT
<213> ORGANISM: Influenza virus

<400> SEQUENCE: 382

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 383
<211> LENGTH: 29
<212> TYPE: PRT
<213> ORGANISM: Influenza virus

<400> SEQUENCE: 383

Lys Lys Gly Asp Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 384
<211> LENGTH: 29
<212> TYPE: PRT
<213> ORGANISM: Influenza virus

<400> SEQUENCE: 384

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 385
<211> LENGTH: 29
<212> TYPE: PRT
<213> ORGANISM: Influenza virus

<400> SEQUENCE: 385

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 386
<211> LENGTH: 29
<212> TYPE: PRT
<213> ORGANISM: Influenza virus

<400> SEQUENCE: 386

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 387
<211> LENGTH: 29
<212> TYPE: PRT
<213> ORGANISM: Influenza virus

<400> SEQUENCE: 387

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 388
<211> LENGTH: 29
<212> TYPE: PRT
<213> ORGANISM: Influenza virus

<400> SEQUENCE: 388

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 389
<211> LENGTH: 29
<212> TYPE: PRT
<213> ORGANISM: Influenza virus

<400> SEQUENCE: 389

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 390
<211> LENGTH: 29
<212> TYPE: PRT
<213> ORGANISM: Influenza virus

<400> SEQUENCE: 390

Lys Lys Gly Asn Ser Tyr Pro Lys Ile Ser Lys Ser Tyr Ile Asn Asn
1 5 10 15

Lys Glu Lys Glu Val Leu Val Leu Trp Gly Ile His His
20 25

<210> SEQ ID NO 391
<211> LENGTH: 29
<212> TYPE: PRT
<213> ORGANISM: Influenza virus

<400> SEQUENCE: 391

Lys Lys Gly Asn Ser Tyr Pro Lys Leu Ser Lys Ser Tyr Ile Asn Asn
1 5 10 15

Lys Lys Lys Glu Val Leu Val Ile Trp Gly Ile His His
20 25

<210> SEQ ID NO 392
<211> LENGTH: 29
<212> TYPE: PRT
<213> ORGANISM: Influenza virus

<400> SEQUENCE: 392

Lys Lys Gly Asn Ser Tyr Pro Lys Leu Ser Lys Ser Tyr Ile Asn Asn
1 5 10 15

Lys Gly Lys Lys Val Leu Val Leu Trp Gly Ile His His
20 25

<210> SEQ ID NO 393
<211> LENGTH: 29
<212> TYPE: PRT
<213> ORGANISM: Influenza virus

<400> SEQUENCE: 393

Lys Lys Gly Thr Ser Tyr Pro Lys Leu Ser Lys Ser Tyr Thr Asn Asn
1 5 10 15

Lys Lys Lys Glu Val Leu Val Leu Trp Gly Val His His
20 25

<210> SEQ ID NO 394
<211> LENGTH: 28
<212> TYPE: PRT
<213> ORGANISM: Influenza virus

<400> SEQUENCE: 394

Lys Asn Gly Leu Tyr Pro Asn Leu Ser Lys Ser Tyr Ala Asn Asn Lys

```
1               5                   10                  15

Glu Lys Glu Val Leu Val Leu Trp Gly Val His His
            20                  25


<210> SEQ ID NO 395
<211> LENGTH: 28
<212> TYPE: PRT
<213> ORGANISM: Influenza virus

<400> SEQUENCE: 395

Lys Asn Gly Leu Tyr Pro Asn Leu Ser Lys Ser Tyr Ala Asn Asn Lys
1               5                   10                  15

Glu Lys Glu Val Leu Ile Leu Trp Gly Val His His
            20                  25


<210> SEQ ID NO 396
<211> LENGTH: 29
<212> TYPE: PRT
<213> ORGANISM: Influenza virus

<400> SEQUENCE: 396

Lys Lys Gly Pro Asn Tyr Pro Val Ala Lys Arg Ser Tyr Asn Asn Thr
1               5                   10                  15

Ser Gly Glu Gln Met Leu Ile Ile Trp Gly Val His His
            20                  25


<210> SEQ ID NO 397
<211> LENGTH: 29
<212> TYPE: PRT
<213> ORGANISM: Influenza virus

<400> SEQUENCE: 397

Lys Lys Gly Pro Asn Tyr Pro Val Ala Lys Arg Ser Tyr Asn Asn Thr
1               5                   10                  15

Ser Gly Glu Gln Met Leu Ile Ile Trp Gly Ile His His
            20                  25


<210> SEQ ID NO 398
<211> LENGTH: 29
<212> TYPE: PRT
<213> ORGANISM: Influenza virus

<400> SEQUENCE: 398

Lys Lys Glu Asn Ser Tyr Pro Lys Leu Arg Lys Ser Ile Ile Ile Asn
1               5                   10                  15

Lys Lys Glu Val Lys Leu Val Ile Trp Gly Ile His His
            20                  25


<210> SEQ ID NO 399
<211> LENGTH: 19
<212> TYPE: PRT
<213> ORGANISM: Influenza virus

<400> SEQUENCE: 399

Lys Ser Tyr Lys Asn Thr Arg Lys Asp Pro Ala Leu Ile Ile Trp Gly
1               5                   10                  15

Ile His His


<210> SEQ ID NO 400
<211> LENGTH: 29
<212> TYPE: PRT
<213> ORGANISM: Influenza virus
```

```
<400> SEQUENCE: 400

Lys Lys Asn Asn Ala Tyr Pro Thr Ile Lys Arg Thr Tyr Asn Asn Thr
1               5                   10                  15

Asn Val Glu Asp Leu Leu Ile Leu Trp Gly Ile His His
            20                  25


<210> SEQ ID NO 401
<211> LENGTH: 29
<212> TYPE: PRT
<213> ORGANISM: Influenza virus

<400> SEQUENCE: 401

Lys Lys Asn Asn Ala Tyr Pro Thr Ile Lys Arg Ser Tyr Ser Asn Thr
1               5                   10                  15

Asn Gln Glu Asp Leu Leu Val Leu Trp Gly Ile His His
            20                  25


<210> SEQ ID NO 402
<211> LENGTH: 29
<212> TYPE: PRT
<213> ORGANISM: Influenza virus

<400> SEQUENCE: 402

Lys Lys Asn Asn Ala Tyr Pro Thr Ile Lys Arg Thr Tyr Asn Asn Thr
1               5                   10                  15

Asn Ile Glu Asp Leu Leu Ile Leu Trp Gly Ile His His
            20                  25


<210> SEQ ID NO 403
<211> LENGTH: 29
<212> TYPE: PRT
<213> ORGANISM: Influenza virus

<400> SEQUENCE: 403

Lys Lys Asn Asn Ala Tyr Pro Thr Ile Lys Arg Thr Tyr Asn Asn Thr
1               5                   10                  15

Asn Met Glu Asp Leu Leu Ile Leu Trp Gly Ile His His
            20                  25


<210> SEQ ID NO 404
<211> LENGTH: 29
<212> TYPE: PRT
<213> ORGANISM: Influenza virus

<400> SEQUENCE: 404

Lys Lys Gly Asn Ala Tyr Pro Thr Ile Lys Arg Thr Tyr Asn Asn Thr
1               5                   10                  15

Asn Val Glu Asp Leu Leu Ile Leu Trp Gly Ile His His
            20                  25


<210> SEQ ID NO 405
<211> LENGTH: 29
<212> TYPE: PRT
<213> ORGANISM: Influenza virus

<400> SEQUENCE: 405

Lys Lys Asn Asn Thr Tyr Pro Thr Ile Lys Arg Ser Tyr Asn Asn Thr
1               5                   10                  15

Asn Gln Glu Asp Leu Leu Ile Leu Trp Gly Ile His His
            20                  25
```

<210> SEQ ID NO 406
<211> LENGTH: 29
<212> TYPE: PRT
<213> ORGANISM: Influenza virus

<400> SEQUENCE: 406

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 407
<211> LENGTH: 29
<212> TYPE: PRT
<213> ORGANISM: Influenza virus

<400> SEQUENCE: 407

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 408
<211> LENGTH: 29
<212> TYPE: PRT
<213> ORGANISM: Influenza virus

<400> SEQUENCE: 408

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 409
<211> LENGTH: 29
<212> TYPE: PRT
<213> ORGANISM: Influenza virus

<400> SEQUENCE: 409

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 410
<211> LENGTH: 29
<212> TYPE: PRT
<213> ORGANISM: Influenza virus

<400> SEQUENCE: 410

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 411
<211> LENGTH: 29
<212> TYPE: PRT
<213> ORGANISM: Influenza virus

<400> SEQUENCE: 411

```
Lys Lys Asn Ser Ala Tyr Pro Thr Ile Lys Arg Ser Tyr Asn Asn Thr
```

```
1               5                   10                  15

Asn Gln Glu Asp Leu Leu Val Leu Trp Gly Ile His His
            20                  25
```

<210> SEQ ID NO 412
<211> LENGTH: 29
<212> TYPE: PRT
<213> ORGANISM: Influenza virus

<400> SEQUENCE: 412

```
Lys Lys Asn Asn Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 413
<211> LENGTH: 29
<212> TYPE: PRT
<213> ORGANISM: Influenza virus

<400> SEQUENCE: 413

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 414
<211> LENGTH: 29
<212> TYPE: PRT
<213> ORGANISM: Influenza virus

<400> SEQUENCE: 414

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 415
<211> LENGTH: 29
<212> TYPE: PRT
<213> ORGANISM: Influenza virus

<400> SEQUENCE: 415

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 416
<211> LENGTH: 29
<212> TYPE: PRT
<213> ORGANISM: Influenza virus

<400> SEQUENCE: 416

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 417
<211> LENGTH: 29
<212> TYPE: PRT

<213> ORGANISM: Influenza virus

<400> SEQUENCE: 417

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 418
<211> LENGTH: 29
<212> TYPE: PRT
<213> ORGANISM: Influenza virus

<400> SEQUENCE: 418

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 419
<211> LENGTH: 29
<212> TYPE: PRT
<213> ORGANISM: Influenza virus

<400> SEQUENCE: 419

```
Lys Lys Asn Asn Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 420
<211> LENGTH: 29
<212> TYPE: PRT
<213> ORGANISM: Influenza virus

<400> SEQUENCE: 420

```
Lys Lys Asn Ser Thr Tyr Pro Thr Ile Lys Arg Ser Tyr Asn Asn Thr
1               5                   10                  15

Asn Gln Glu Asp Leu Leu Val Met Trp Gly Ile His His
            20                  25
```

<210> SEQ ID NO 421
<211> LENGTH: 29
<212> TYPE: PRT
<213> ORGANISM: Influenza virus

<400> SEQUENCE: 421

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 422
<211> LENGTH: 29
<212> TYPE: PRT
<213> ORGANISM: Influenza virus

<400> SEQUENCE: 422

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 423
<211> LENGTH: 29
<212> TYPE: PRT
<213> ORGANISM: Influenza virus

<400> SEQUENCE: 423

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 424
<211> LENGTH: 29
<212> TYPE: PRT
<213> ORGANISM: Influenza virus

<400> SEQUENCE: 424

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile Gln His
            20                  25
```

<210> SEQ ID NO 425
<211> LENGTH: 29
<212> TYPE: PRT
<213> ORGANISM: Influenza virus

<400> SEQUENCE: 425

```
Lys Lys Asn Ser Ala Tyr Pro Ile Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 426
<211> LENGTH: 29
<212> TYPE: PRT
<213> ORGANISM: Influenza virus
<220> FEATURE:
<221> NAME/KEY: MOD_RES
<222> LOCATION: (13)..(13)
<223> OTHER INFORMATION: Variable amino acid

<400> SEQUENCE: 426

```
Lys Lys Asn Ser Ala Tyr Pro Thr Ile Lys Arg Ser Xaa Asn Asn Thr
1               5                   10                  15

Asn His Glu Asp Leu Leu Val Leu Trp Gly Ile His His
            20                  25
```

<210> SEQ ID NO 427
<211> LENGTH: 29
<212> TYPE: PRT
<213> ORGANISM: Influenza virus

<400> SEQUENCE: 427

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 428
<211> LENGTH: 29
<212> TYPE: PRT

<213> ORGANISM: Influenza virus

<400> SEQUENCE: 428

Lys Lys Asn Asn Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 429
<211> LENGTH: 29
<212> TYPE: PRT
<213> ORGANISM: Influenza virus

<400> SEQUENCE: 429

Lys Lys Asn Asn Thr Tyr Pro Thr Ile Lys Lys Ser Tyr Asn Asn Thr
1 5 10 15

Asn Gln Glu Asp Leu Leu Val Leu Trp Gly Ile His His
20 25

<210> SEQ ID NO 430
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 430

Leu Val Leu Trp Gly
1 5

<210> SEQ ID NO 431
<211> LENGTH: 29
<212> TYPE: PRT
<213> ORGANISM: Influenza virus

<400> SEQUENCE: 431

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 432
<211> LENGTH: 29
<212> TYPE: PRT
<213> ORGANISM: Influenza virus

<400> SEQUENCE: 432

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 433
<211> LENGTH: 29
<212> TYPE: PRT
<213> ORGANISM: Shrimp White Spot Syndrome Virus

<400> SEQUENCE: 433

Lys Lys Asn Val Lys Ser Ala Lys Gln Leu Pro His Leu Lys Val Leu
1 5 10 15

Lys Lys Leu Asp Val Arg Gly Ala Lys Gln Leu Pro His
20 25

<210> SEQ ID NO 434
<211> LENGTH: 28
<212> TYPE: PRT
<213> ORGANISM: Shrimp White Spot Syndrome Virus

<400> SEQUENCE: 434

Lys Val His Leu Asp Val Lys Gly Val Lys Gln Leu Leu His Leu Lys
1 5 10 15

Val Arg Leu Asp Val Arg Gly Ala Lys Gln Leu His
20 25

<210> SEQ ID NO 435
<211> LENGTH: 29
<212> TYPE: PRT
<213> ORGANISM: Influenza virus

<400> SEQUENCE: 435

Lys Lys Glu Asn Ser Tyr Pro Lys Leu Arg Lys Ser Ile Ile Ile Asn
1 5 10 15

Lys Lys Glu Val Lys Leu Val Ile Trp Gly Ile His His
20 25

<210> SEQ ID NO 436
<211> LENGTH: 19
<212> TYPE: PRT
<213> ORGANISM: Influenza virus

<400> SEQUENCE: 436

Lys Ser Tyr Lys Asn Thr Arg Lys Asp Pro Ala Leu Ile Ile Trp Gly
1 5 10 15

Ile His His

<210> SEQ ID NO 437
<211> LENGTH: 29
<212> TYPE: PRT
<213> ORGANISM: Influenza virus

<400> SEQUENCE: 437

Lys Lys Gly Pro Asn Tyr Pro Val Ala Lys Arg Ser Tyr Asn Asn Thr
1 5 10 15

Ser Gly Glu Gln Met Leu Ile Ile Trp Gly Val His His
20 25

<210> SEQ ID NO 438
<211> LENGTH: 29
<212> TYPE: PRT
<213> ORGANISM: Influenza virus

<400> SEQUENCE: 438

Lys Lys Gly Pro Asn Tyr Pro Val Ala Lys Arg Ser Tyr Asn Asn Thr
1 5 10 15

Ser Gly Glu Gln Met Leu Ile Ile Trp Gly Ile His His
20 25

<210> SEQ ID NO 439
<211> LENGTH: 29
<212> TYPE: PRT
<213> ORGANISM: Influenza virus

<400> SEQUENCE: 439

Lys Lys Asn Asn Ala Tyr Pro Thr Ile Lys Arg Thr Tyr Asn Asn Thr 1 5 10 15

Asn Val Glu Asp Leu Leu Ile Leu Trp Gly Ile His His
20 25

<210> SEQ ID NO 440
<211> LENGTH: 29
<212> TYPE: PRT
<213> ORGANISM: Influenza virus

<400> SEQUENCE: 440

Lys Lys Asn Asn Ala Tyr Pro Thr Ile Lys Arg Ser Tyr Ser Asn Thr
1 5 10 15

Asn Gln Glu Asp Leu Leu Val Leu Trp Gly Ile His His
20 25

<210> SEQ ID NO 441
<211> LENGTH: 19
<212> TYPE: PRT
<213> ORGANISM: Human immunodeficiency virus type 1

<400> SEQUENCE: 441

His Cys Leu Val Cys Lys Gln Lys Lys Gly Leu Gly Ile Ser Tyr Gly
1 5 10 15

Arg Lys Lys

<210> SEQ ID NO 442
<211> LENGTH: 19
<212> TYPE: PRT
<213> ORGANISM: Human immunodeficiency virus type 1

<400> SEQUENCE: 442

His Cys Leu Val Cys Phe Gln Lys Lys Gly Leu Gly Ile Ser Tyr Gly
1 5 10 15

Arg Lys Lys

<210> SEQ ID NO 443
<211> LENGTH: 23
<212> TYPE: PRT
<213> ORGANISM: Human immunodeficiency virus type 1

<400> SEQUENCE: 443

Lys Cys Ser Tyr His Cys Leu Val Cys Phe Gln Lys Lys Gly Leu Gly
1 5 10 15

Ile Ser Tyr Gly Arg Lys Lys
20

<210> SEQ ID NO 444
<211> LENGTH: 23
<212> TYPE: PRT
<213> ORGANISM: Human immunodeficiency virus type 1

<400> SEQUENCE: 444

His Cys Cys Phe His Cys Gln Ile Cys Leu His Thr Lys Ala Leu Ala
1 5 10 15

Leu Tyr His Gln Arg Lys Lys
20

<210> SEQ ID NO 445
<211> LENGTH: 23
<212> TYPE: PRT
<213> ORGANISM: Human immunodeficiency virus type 1

<400> SEQUENCE: 445

Arg Cys Trp Pro His Cys Leu Leu Cys Phe Ile His Lys Gln Leu Val
1               5                   10                  15

Ile Ser Tyr Gly Arg Lys Lys
            20

<210> SEQ ID NO 446
<211> LENGTH: 23
<212> TYPE: PRT
<213> ORGANISM: Human immunodeficiency virus type 1

<400> SEQUENCE: 446

Tyr Cys Ser Ser His Cys Leu Ser Cys Phe Leu Met Lys Arg Leu Ser
1               5                   10                  15

Ile Ser Tyr Gly Arg Lys Lys
            20

<210> SEQ ID NO 447
<211> LENGTH: 23
<212> TYPE: PRT
<213> ORGANISM: Human immunodeficiency virus type 1

<400> SEQUENCE: 447

Ile Cys Ser Tyr His Cys Leu Ser Cys Phe Met Ser Lys Gly Leu Gly
1               5                   10                  15

Ile Ser Tyr Gly Arg Lys Lys
            20

<210> SEQ ID NO 448
<211> LENGTH: 23
<212> TYPE: PRT
<213> ORGANISM: Human immunodeficiency virus type 1

<400> SEQUENCE: 448

Ser Cys Ser Tyr His Cys Leu Arg Cys Phe Asn Lys Lys Gly Leu Gly
1               5                   10                  15

Ile Ser Tyr Gly Arg Lys Lys
            20

<210> SEQ ID NO 449
<211> LENGTH: 23
<212> TYPE: PRT
<213> ORGANISM: Human immunodeficiency virus type 1

<400> SEQUENCE: 449

Val Cys Ser Tyr His Cys Leu Val Cys Phe Gln Lys Lys Gly Leu Gly
1               5                   10                  15

Ile Ser Tyr Gly Arg Lys Lys
            20

<210> SEQ ID NO 450
<211> LENGTH: 23
<212> TYPE: PRT
<213> ORGANISM: Human immunodeficiency virus type 1

<400> SEQUENCE: 450

Ala Cys Ser Tyr His Cys Leu Val Cys Phe Gln Lys Lys Gly Leu Gly
1               5                   10                  15

Ile Ser Tyr Gly Arg Lys Lys
            20

<210> SEQ ID NO 451
<211> LENGTH: 23
<212> TYPE: PRT
<213> ORGANISM: Human immunodeficiency virus type 1

<400> SEQUENCE: 451

Phe Cys Ser Tyr His Cys Leu Val Cys Phe Gln Lys Lys Gly Leu Gly
1               5                   10                  15

Ile Ser Tyr Gly Arg Lys Lys
            20

<210> SEQ ID NO 452
<211> LENGTH: 23
<212> TYPE: PRT
<213> ORGANISM: Human immunodeficiency virus type 1

<400> SEQUENCE: 452

Pro Cys Ser Tyr His Cys Leu Val Cys Phe Gln Lys Lys Gly Leu Gly
1               5                   10                  15

Ile Ser Tyr Gly Arg Lys Lys
            20

<210> SEQ ID NO 453
<211> LENGTH: 23
<212> TYPE: PRT
<213> ORGANISM: Human immunodeficiency virus type 1

<400> SEQUENCE: 453

Gln Cys Ser Tyr His Cys Leu Val Cys Phe Gln Lys Lys Gly Leu Gly
1               5                   10                  15

Ile Ser Tyr Gly Arg Lys Lys
            20

<210> SEQ ID NO 454
<211> LENGTH: 27
<212> TYPE: PRT
<213> ORGANISM: Triticum sp.

<400> SEQUENCE: 454

His Lys Asp Arg Leu Thr Lys Lys Val Val Asp Ile Ala Arg Glu Val
1               5                   10                  15

Ala Lys Val Asp Val Pro Glu Tyr Arg Arg His
            20                  25

<210> SEQ ID NO 455
<211> LENGTH: 27
<212> TYPE: PRT
<213> ORGANISM: Triticum sp.

<400> SEQUENCE: 455

His Lys Glu Arg Leu Asp Arg Lys Val Val Asp Val Ala Arg Glu Val
1               5                   10                  15

Ala Lys Val Glu Val Pro Ser Tyr Arg Arg His
            20                  25

<210> SEQ ID NO 456
<211> LENGTH: 27
<212> TYPE: PRT
<213> ORGANISM: Triticum sp.

<400> SEQUENCE: 456

His Lys Glu Arg Leu Asp Arg Lys Val Val Asp Val Ala Arg Glu Val
1               5                   10                  15

```
Ala Lys Met Glu Val Pro Ser Tyr Arg Arg His
            20                  25


<210> SEQ ID NO 457
<211> LENGTH: 5
<212> TYPE: PRT
<213> ORGANISM: Influenza virus

<400> SEQUENCE: 457

Lys Lys Lys Lys His
1               5


<210> SEQ ID NO 458
<211> LENGTH: 11
<212> TYPE: PRT
<213> ORGANISM: Influenza virus

<400> SEQUENCE: 458

Lys Lys Lys Lys His Lys Lys Lys Lys Lys His
1               5                   10


<210> SEQ ID NO 459
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Lys Lys Lys Lys His Lys
1               5


<210> SEQ ID NO 460
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Lys Lys Lys His Lys Lys
1               5


<210> SEQ ID NO 461
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Lys Lys His Lys Lys Lys
1               5


<210> SEQ ID NO 462
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462
```

```
Lys His Lys Lys Lys Lys
1               5


<210> SEQ ID NO 463
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Lys Lys Lys Lys Lys Lys His
1               5


<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Lys Lys Lys Lys Lys His Lys
1               5


<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Lys Lys Lys Lys His Lys Lys
1               5


<210> SEQ ID NO 466
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Lys Lys Lys His Lys Lys Lys
1               5


<210> SEQ ID NO 467
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Lys Lys His Lys Lys Lys Lys
1               5


<210> SEQ ID NO 468
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 468

Lys His Lys Lys Lys Lys Lys
1               5

<210> SEQ ID NO 469
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

His Lys Lys Lys Lys Lys Lys
1               5

<210> SEQ ID NO 470
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(18)
<223> OTHER INFORMATION: Variable amino acid and this region may
      encompass 0 to 15 residues

<400> SEQUENCE: 470

His Leu Lys Xaa Xaa Xaa Xaa Xaa Xaa Xaa Xaa Xaa Xaa Xaa Xaa Xaa
1               5                   10                  15

Xaa Xaa His Leu Lys
            20

<210> SEQ ID NO 471
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Tyr Lys Ala Gly Val Ala Phe Leu His Lys Lys Asn Asp Ile Ile Asp
1               5                   10                  15

Glu

<210> SEQ ID NO 472
<211> LENGTH: 422
<212> TYPE: PRT
<213> ORGANISM: Homo sapiens

<400> SEQUENCE: 472

Met Tyr Arg Pro Asp Val Val Arg Ala Arg Lys Arg Val Cys Trp Glu
1               5                   10                  15

Pro Trp Val Ile Gly Leu Val Ile Phe Ile Ser Leu Ile Val Leu Ala
            20                  25                  30

Val Cys Ile Gly Leu Thr Val His Tyr Val Arg Tyr Asn Gln Lys Lys
        35                  40                  45

Thr Tyr Asn Tyr Tyr Ser Thr Leu Ser Phe Thr Thr Asp Lys Leu Tyr
    50                  55                  60

```
Ala Glu Phe Gly Arg Glu Ala Ser Asn Asn Phe Thr Glu Met Ser Gln
65                  70                  75                  80

Arg Leu Glu Ser Met Val Lys Asn Ala Phe Tyr Lys Ser Pro Leu Arg
                85                  90                  95

Glu Glu Phe Val Lys Ser Gln Val Ile Lys Phe Ser Gln Gln Lys His
            100                 105                 110

Gly Val Leu Ala His Met Leu Leu Ile Cys Arg Phe His Ser Thr Glu
        115                 120                 125

Asp Pro Glu Thr Val Asp Lys Ile Val Gln Leu Val Leu His Glu Lys
    130                 135                 140

Leu Gln Asp Ala Val Gly Pro Pro Lys Val Asp Pro His Ser Val Lys
145                 150                 155                 160

Ile Lys Lys Ile Asn Lys Thr Glu Thr Asp Ser Tyr Leu Asn His Cys
                165                 170                 175

Cys Gly Thr Arg Arg Ser Lys Thr Leu Gly Gln Ser Leu Arg Ile Val
            180                 185                 190

Gly Gly Thr Glu Val Glu Glu Gly Glu Trp Pro Trp Gln Ala Ser Leu
        195                 200                 205

Gln Trp Asp Gly Ser His Arg Cys Gly Ala Thr Leu Ile Asn Ala Thr
    210                 215                 220

Trp Leu Val Ser Ala Ala His Cys Phe Thr Thr Tyr Lys Asn Pro Ala
225                 230                 235                 240

Arg Trp Thr Ala Ser Phe Gly Val Thr Ile Lys Pro Ser Lys Met Lys
                245                 250                 255

Arg Gly Leu Arg Arg Ile Ile Val His Glu Lys Tyr Lys His Pro Ser
            260                 265                 270

His Asp Tyr Asp Ile Ser Leu Ala Glu Leu Ser Ser Pro Val Pro Tyr
        275                 280                 285

Thr Asn Ala Val His Arg Val Cys Leu Pro Asp Ala Ser Tyr Glu Phe
    290                 295                 300

Gln Pro Gly Asp Val Met Phe Val Thr Gly Phe Gly Ala Leu Lys Asn
305                 310                 315                 320

Asp Gly Tyr Ser Gln Asn His Leu Arg Gln Ala Gln Val Thr Leu Ile
                325                 330                 335

Asp Ala Thr Thr Cys Asn Glu Pro Gln Ala Tyr Asn Asp Ala Ile Thr
            340                 345                 350

Pro Arg Met Leu Cys Ala Gly Ser Leu Glu Gly Lys Thr Asp Ala Cys
        355                 360                 365

Gln Gly Asp Ser Gly Gly Pro Leu Val Ser Ser Asp Ala Arg Asp Ile
    370                 375                 380

Trp Tyr Leu Ala Gly Ile Val Ser Trp Gly Asp Glu Cys Ala Lys Pro
385                 390                 395                 400

Asn Lys Pro Gly Val Tyr Thr Arg Val Thr Ala Leu Arg Asp Trp Ile
                405                 410                 415

Thr Ser Lys Thr Gly Ile
            420


<210> SEQ ID NO 473
<211> LENGTH: 29
<212> TYPE: PRT
<213> ORGANISM: Influenza virus

<400> SEQUENCE: 473

Lys Lys Gly Thr Ser Tyr Pro Lys Leu Ser Lys Ser Tyr Thr Asn Asn
```

1 5 10 15

Lys Gly Lys Glu Val Leu Val Leu Trp Gly Val His His
20 25

<210> SEQ ID NO 474
<211> LENGTH: 29
<212> TYPE: PRT
<213> ORGANISM: Influenza virus

<400> SEQUENCE: 474

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 475
<211> LENGTH: 29
<212> TYPE: PRT
<213> ORGANISM: Influenza virus

<400> SEQUENCE: 475

Lys Lys Glu Asn Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 476
<211> LENGTH: 29
<212> TYPE: PRT
<213> ORGANISM: Influenza virus

<400> SEQUENCE: 476

Lys Lys Gly Asp Ser Tyr Pro Lys Leu Thr Asn Ser Tyr Val Asn Asn
1 5 10 15

Lys Gly Lys Glu Val Leu Val Leu Trp Gly Val His His
20 25

<210> SEQ ID NO 477
<211> LENGTH: 29
<212> TYPE: PRT
<213> ORGANISM: Influenza virus

<400> SEQUENCE: 477

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 478
<211> LENGTH: 29
<212> TYPE: PRT
<213> ORGANISM: Influenza virus

<400> SEQUENCE: 478

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 479
<211> LENGTH: 29
<212> TYPE: PRT

<213> ORGANISM: Influenza virus

<400> SEQUENCE: 479

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 480
<211> LENGTH: 29
<212> TYPE: PRT
<213> ORGANISM: Influenza virus

<400> SEQUENCE: 480

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 481
<211> LENGTH: 29
<212> TYPE: PRT
<213> ORGANISM: Influenza virus

<400> SEQUENCE: 481

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 482
<211> LENGTH: 29
<212> TYPE: PRT
<213> ORGANISM: Influenza virus

<400> SEQUENCE: 482

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 483
<211> LENGTH: 29
<212> TYPE: PRT
<213> ORGANISM: Influenza virus

<400> SEQUENCE: 483

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 484
<211> LENGTH: 29
<212> TYPE: PRT
<213> ORGANISM: Influenza virus

<400> SEQUENCE: 484

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 485
<211> LENGTH: 29
<212> TYPE: PRT
<213> ORGANISM: Influenza virus

<400> SEQUENCE: 485

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 486
<211> LENGTH: 29
<212> TYPE: PRT
<213> ORGANISM: Influenza virus

<400> SEQUENCE: 486

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 487
<211> LENGTH: 29
<212> TYPE: PRT
<213> ORGANISM: Influenza virus

<400> SEQUENCE: 487

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 488
<211> LENGTH: 29
<212> TYPE: PRT
<213> ORGANISM: Influenza virus

<400> SEQUENCE: 488

Lys Lys Gly Asp Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 489
<211> LENGTH: 29
<212> TYPE: PRT
<213> ORGANISM: Influenza virus

<400> SEQUENCE: 489

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 490
<211> LENGTH: 29
<212> TYPE: PRT
<213> ORGANISM: Influenza virus

<400> SEQUENCE: 490

```
Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
            20                  25


<210> SEQ ID NO 491
<211> LENGTH: 29
<212> TYPE: PRT
<213> ORGANISM: Influenza virus

<400> SEQUENCE: 491

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 492
<211> LENGTH: 29
<212> TYPE: PRT
<213> ORGANISM: Influenza virus

<400> SEQUENCE: 492

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 493
<211> LENGTH: 29
<212> TYPE: PRT
<213> ORGANISM: Influenza virus

<400> SEQUENCE: 493

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 494
<211> LENGTH: 29
<212> TYPE: PRT
<213> ORGANISM: Influenza virus

<400> SEQUENCE: 494

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 495
<211> LENGTH: 29
<212> TYPE: PRT
<213> ORGANISM: Influenza virus

<400> SEQUENCE: 495

Lys Lys Gly Asn Ser Tyr Pro Lys Ile Ser Lys Ser Tyr Ile Asn Asn
1               5                   10                  15

Lys Glu Lys Glu Val Leu Val Leu Trp Gly Ile His His
            20                  25


<210> SEQ ID NO 496
<211> LENGTH: 29
```

<212> TYPE: PRT
<213> ORGANISM: Influenza virus

<400> SEQUENCE: 496

```
Lys Lys Gly Asn Ser Tyr Pro Lys Leu Ser Lys Ser Tyr Ile Asn Asn
1               5                   10                  15

Lys Lys Lys Glu Val Leu Val Ile Trp Gly Ile His His
            20                  25
```

<210> SEQ ID NO 497
<211> LENGTH: 29
<212> TYPE: PRT
<213> ORGANISM: Influenza virus

<400> SEQUENCE: 497

```
Lys Lys Gly Asn Ser Tyr Pro Lys Leu Ser Lys Ser Tyr Ile Asn Asn
1               5                   10                  15

Lys Gly Lys Lys Val Leu Val Leu Trp Gly Ile His His
            20                  25
```

<210> SEQ ID NO 498
<211> LENGTH: 29
<212> TYPE: PRT
<213> ORGANISM: Influenza virus

<400> SEQUENCE: 498

```
Lys Lys Gly Thr Ser Tyr Pro Lys Leu Ser Lys Ser Tyr Thr Asn Asn
1               5                   10                  15

Lys Lys Lys Glu Val Leu Val Leu Trp Gly Val His His
            20                  25
```

<210> SEQ ID NO 499
<211> LENGTH: 28
<212> TYPE: PRT
<213> ORGANISM: Influenza virus

<400> SEQUENCE: 499

```
Lys Asn Gly Leu Tyr Pro Asn Leu Ser Lys Ser Tyr Ala Asn Asn Lys
1               5                   10                  15

Glu Lys Glu Val Leu Val Leu Trp Gly Val His His
            20                  25
```

<210> SEQ ID NO 500
<211> LENGTH: 28
<212> TYPE: PRT
<213> ORGANISM: Influenza virus

<400> SEQUENCE: 500

```
Lys Asn Gly Leu Tyr Pro Asn Leu Ser Lys Ser Tyr Ala Asn Asn Lys
1               5                   10                  15

Glu Lys Glu Val Leu Ile Leu Trp Gly Val His His
            20                  25
```

<210> SEQ ID NO 501
<211> LENGTH: 29
<212> TYPE: PRT
<213> ORGANISM: Influenza virus

<400> SEQUENCE: 501

```
Lys Lys Glu Asn Ser Tyr Pro Lys Leu Arg Lys Ser Ile Ile Ile Asn
1               5                   10                  15

Lys Lys Glu Val Lys Leu Val Ile Trp Gly Ile His His
```

20 25

<210> SEQ ID NO 502
<211> LENGTH: 19
<212> TYPE: PRT
<213> ORGANISM: Influenza virus

<400> SEQUENCE: 502

Lys Ser Tyr Lys Asn Thr Arg Lys Asp Pro Ala Leu Ile Ile Trp Gly
1 5 10 15

Ile His His

<210> SEQ ID NO 503
<211> LENGTH: 29
<212> TYPE: PRT
<213> ORGANISM: Influenza virus

<400> SEQUENCE: 503

Lys Lys Gly Pro Asn Tyr Pro Val Ala Lys Arg Ser Tyr Asn Asn Thr
1 5 10 15

Ser Gly Glu Gln Met Leu Ile Ile Trp Gly Val His His
20 25

<210> SEQ ID NO 504
<211> LENGTH: 29
<212> TYPE: PRT
<213> ORGANISM: Influenza virus

<400> SEQUENCE: 504

Lys Lys Gly Pro Asn Tyr Pro Val Ala Lys Arg Ser Tyr Asn Asn Thr
1 5 10 15

Ser Gly Glu Gln Met Leu Ile Ile Trp Gly Ile His His
20 25

<210> SEQ ID NO 505
<211> LENGTH: 29
<212> TYPE: PRT
<213> ORGANISM: Influenza virus

<400> SEQUENCE: 505

Lys Lys Asn Asn Ala Tyr Pro Thr Ile Lys Arg Thr Tyr Asn Asn Thr
1 5 10 15

Asn Val Glu Asp Leu Leu Ile Leu Trp Gly Ile His His
20 25

<210> SEQ ID NO 506
<211> LENGTH: 29
<212> TYPE: PRT
<213> ORGANISM: Influenza virus

<400> SEQUENCE: 506

Lys Lys Asn Asn Ala Tyr Pro Thr Ile Lys Arg Ser Tyr Ser Asn Thr
1 5 10 15

Asn Gln Glu Asp Leu Leu Val Leu Trp Gly Ile His His
20 25

<210> SEQ ID NO 507
<211> LENGTH: 29
<212> TYPE: PRT
<213> ORGANISM: Influenza virus

<400> SEQUENCE: 507

```
Lys Lys Asn Asn Ala Tyr Pro Thr Ile Lys Arg Thr Tyr Asn Asn Thr
1               5                   10                  15

Asn Ile Glu Asp Leu Leu Ile Leu Trp Gly Ile His His
            20                  25


<210> SEQ ID NO 508
<211> LENGTH: 29
<212> TYPE: PRT
<213> ORGANISM: Influenza virus

<400> SEQUENCE: 508

Lys Lys Asn Asn Ala Tyr Pro Thr Ile Lys Arg Thr Tyr Asn Asn Thr
1               5                   10                  15

Asn Met Glu Asp Leu Leu Ile Leu Trp Gly Ile His His
            20                  25


<210> SEQ ID NO 509
<211> LENGTH: 29
<212> TYPE: PRT
<213> ORGANISM: Influenza virus

<400> SEQUENCE: 509

Lys Lys Gly Asn Ala Tyr Pro Thr Ile Lys Arg Thr Tyr Asn Asn Thr
1               5                   10                  15

Asn Val Glu Asp Leu Leu Ile Leu Trp Gly Ile His His
            20                  25


<210> SEQ ID NO 510
<211> LENGTH: 29
<212> TYPE: PRT
<213> ORGANISM: Influenza virus

<400> SEQUENCE: 510

Lys Lys Asn Asn Thr Tyr Pro Thr Ile Lys Arg Ser Tyr Asn Asn Thr
1               5                   10                  15

Asn Gln Glu Asp Leu Leu Ile Leu Trp Gly Ile His His
            20                  25


<210> SEQ ID NO 511
<211> LENGTH: 29
<212> TYPE: PRT
<213> ORGANISM: Influenza virus

<400> SEQUENCE: 511

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 512
<211> LENGTH: 29
<212> TYPE: PRT
<213> ORGANISM: Influenza virus

<400> SEQUENCE: 512

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 513
<211> LENGTH: 29
```

<212> TYPE: PRT
<213> ORGANISM: Influenza virus

<400> SEQUENCE: 513

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 514
<211> LENGTH: 29
<212> TYPE: PRT
<213> ORGANISM: Influenza virus

<400> SEQUENCE: 514

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 515
<211> LENGTH: 29
<212> TYPE: PRT
<213> ORGANISM: Influenza virus

<400> SEQUENCE: 515

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 516
<211> LENGTH: 29
<212> TYPE: PRT
<213> ORGANISM: Influenza virus

<400> SEQUENCE: 516

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 517
<211> LENGTH: 29
<212> TYPE: PRT
<213> ORGANISM: Influenza virus

<400> SEQUENCE: 517

Lys Lys Asn Asn Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 518
<211> LENGTH: 29
<212> TYPE: PRT
<213> ORGANISM: Influenza virus

<400> SEQUENCE: 518

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His 20 25

<210> SEQ ID NO 519
<211> LENGTH: 29
<212> TYPE: PRT
<213> ORGANISM: Influenza virus

<400> SEQUENCE: 519

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 520
<211> LENGTH: 29
<212> TYPE: PRT
<213> ORGANISM: Influenza virus

<400> SEQUENCE: 520

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 521
<211> LENGTH: 29
<212> TYPE: PRT
<213> ORGANISM: Influenza virus

<400> SEQUENCE: 521

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 522
<211> LENGTH: 29
<212> TYPE: PRT
<213> ORGANISM: Influenza virus

<400> SEQUENCE: 522

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 523
<211> LENGTH: 29
<212> TYPE: PRT
<213> ORGANISM: Influenza virus

<400> SEQUENCE: 523

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 524
<211> LENGTH: 29
<212> TYPE: PRT
<213> ORGANISM: Influenza virus

<400> SEQUENCE: 524

```
Lys Lys Asn Asn Ala Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 525
<211> LENGTH: 29
<212> TYPE: PRT
<213> ORGANISM: Influenza virus

<400> SEQUENCE: 525

Lys Lys Asn Ser Thr Tyr Pro Thr Ile Lys Arg Ser Tyr Asn Asn Thr
1               5                   10                  15

Asn Gln Glu Asp Leu Leu Val Met Trp Gly Ile His His
            20                  25


<210> SEQ ID NO 526
<211> LENGTH: 29
<212> TYPE: PRT
<213> ORGANISM: Influenza virus

<400> SEQUENCE: 526

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 527
<211> LENGTH: 29
<212> TYPE: PRT
<213> ORGANISM: Influenza virus

<400> SEQUENCE: 527

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 528
<211> LENGTH: 29
<212> TYPE: PRT
<213> ORGANISM: Influenza virus

<400> SEQUENCE: 528

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 529
<211> LENGTH: 29
<212> TYPE: PRT
<213> ORGANISM: Influenza virus

<400> SEQUENCE: 529

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile Gln His
            20                  25


<210> SEQ ID NO 530
```

-continued

<211> LENGTH: 29
<212> TYPE: PRT
<213> ORGANISM: Influenza virus

<400> SEQUENCE: 530

Lys Lys Asn Ser Ala Tyr Pro Ile Ile Lys Arg Ser Tyr Asn Asn Thr
1 5 10 15

Asn Gln Glu Asp Leu Leu Val Leu Trp Gly Ile His His
20 25

<210> SEQ ID NO 531
<211> LENGTH: 29
<212> TYPE: PRT
<213> ORGANISM: Influenza virus
<220> FEATURE:
<221> NAME/KEY: MOD_RES
<222> LOCATION: (13)..(13)
<223> OTHER INFORMATION: Variable amino acid

<400> SEQUENCE: 531

Lys Lys Asn Ser Ala Tyr Pro Thr Ile Lys Arg Ser Xaa Asn Asn Thr
1 5 10 15

Asn His Glu Asp Leu Leu Val Leu Trp Gly Ile His His
20 25

<210> SEQ ID NO 532
<211> LENGTH: 40
<212> TYPE: PRT
<213> ORGANISM: Human coronavirus

<400> SEQUENCE: 532

Lys Lys Ser Ala Lys Thr Gly Thr Pro Lys Pro Ser Arg Asn Gln Ser
1 5 10 15

Pro Ala Ser Ser Gln Thr Ser Ala Lys Ser Leu Ala Arg Ser Gln Ser
20 25 30

Ser Glu Thr Lys Glu Gln Lys His
35 40

<210> SEQ ID NO 533
<211> LENGTH: 37
<212> TYPE: PRT
<213> ORGANISM: Canine coronavirus

<400> SEQUENCE: 533

Lys Lys Leu Gly Val Asp Thr Glu Lys Gln Gln Gln Arg Ser Arg Ser
1 5 10 15

Lys Ser Lys Glu Arg Ser Asn Ser Lys Thr Arg Asp Thr Thr Pro Lys
20 25 30

Asn Glu Asn Lys His
35

<210> SEQ ID NO 534
<211> LENGTH: 7
<212> TYPE: PRT
<213> ORGANISM: Shrimp White Spot Syndrome Virus

<400> SEQUENCE: 534

Lys Gln Leu Leu His Leu Lys
1 5

<210> SEQ ID NO 535
<211> LENGTH: 7
<212> TYPE: PRT

<213> ORGANISM: Shrimp White Spot Syndrome Virus

<400> SEQUENCE: 535

Lys Val His Leu Asp Val Lys
1 5

<210> SEQ ID NO 536
<211> LENGTH: 14
<212> TYPE: PRT
<213> ORGANISM: Shrimp White Spot Syndrome Virus

<400> SEQUENCE: 536

Lys Val His Leu Asp Val Lys Gly Val Lys Gln Leu Leu His
1 5 10

<210> SEQ ID NO 537
<211> LENGTH: 12
<212> TYPE: PRT
<213> ORGANISM: Shrimp White Spot Syndrome Virus

<400> SEQUENCE: 537

Lys Lys Asp Val Lys Ser Ala Lys Gln Leu Pro His
1 5 10

<210> SEQ ID NO 538
<211> LENGTH: 10
<212> TYPE: PRT
<213> ORGANISM: Shrimp White Spot Syndrome Virus

<400> SEQUENCE: 538

Lys Ser Ala Lys Gln Leu Pro His Leu Lys
1 5 10

<210> SEQ ID NO 539
<211> LENGTH: 12
<212> TYPE: PRT
<213> ORGANISM: Shrimp White Spot Syndrome Virus

<400> SEQUENCE: 539

Lys Lys Asp Val Lys Ser Ala Lys Gln Leu Pro His
1 5 10

<210> SEQ ID NO 540
<211> LENGTH: 12
<212> TYPE: PRT
<213> ORGANISM: Shrimp White Spot Syndrome Virus

<400> SEQUENCE: 540

Lys Lys Asp Val Lys Ser Ala Lys Gln Leu Pro His
1 5 10

<210> SEQ ID NO 541
<211> LENGTH: 12
<212> TYPE: PRT
<213> ORGANISM: Shrimp White Spot Syndrome Virus

<400> SEQUENCE: 541

Lys Lys Asp Val Lys Ser Ala Lys Gln Leu Pro His
1 5 10

<210> SEQ ID NO 542
<211> LENGTH: 12
<212> TYPE: PRT
<213> ORGANISM: Shrimp White Spot Syndrome Virus -continued

<400> SEQUENCE: 542

```
Lys Lys Asp Val Lys Ser Ala Lys Gln Leu Pro His
1               5                   10
```